United States Patent
Maisch et al.

(10) Patent No.: US 9,745,302 B2
(45) Date of Patent: Aug. 29, 2017

(54) 10H-BENZO[G]PTERIDINE-2,4-DIONE DERIVATIVES, METHOD FOR THE PRODUCTION THEREOF, AND USE THEREOF

(71) Applicant: TriOptoTec GmbH, Regensburg (DE)

(72) Inventors: Tim Maisch, Nürnberg (DE); Andreas Späth, Regensburg (DE)

(73) Assignee: TRIOPTOTEC GMBH (DE)

(*) Notice: Subject to any disclaimer, the term of this patent is extended or adjusted under 35 U.S.C. 154(b) by 0 days.

(21) Appl. No.: 14/982,140

(22) Filed: Dec. 29, 2015

(65) Prior Publication Data

US 2016/0176877 A1    Jun. 23, 2016

Related U.S. Application Data

(63) Continuation of application No. 14/127,464, filed as application No. PCT/EP2012/062172 on Jun. 22, 2012, now Pat. No. 9,241,995.

(30) Foreign Application Priority Data

Jun. 22, 2011  (DE) ..................... 10 2011 105 657

(51) Int. Cl.
| | | |
|---|---|---|
| *A61L 31/08* | (2006.01) | |
| *A61L 31/16* | (2006.01) | |
| *A61Q 17/00* | (2006.01) | |
| *A61K 31/525* | (2006.01) | |
| *A01N 43/90* | (2006.01) | |
| *A61Q 11/02* | (2006.01) | |
| *C11D 3/48* | (2006.01) | |
| *A61Q 11/00* | (2006.01) | |
| *A61K 41/00* | (2006.01) | |
| *A61K 8/49* | (2006.01) | |
| *C07D 475/14* | (2006.01) | |

(52) U.S. Cl.
CPC .......... *C07D 475/14* (2013.01); *A01N 43/90* (2013.01); *A61K 8/4953* (2013.01); *A61K 31/525* (2013.01); *A61K 41/0057* (2013.01); *A61L 31/08* (2013.01); *A61L 31/16* (2013.01); *A61Q 11/00* (2013.01); *A61Q 11/02* (2013.01); *A61Q 17/005* (2013.01); *C11D 3/48* (2013.01); *A61L 2300/404* (2013.01)

(58) Field of Classification Search
CPC .... A61L 2300/404; A61L 31/08; A61L 31/16; A61Q 11/00; A61Q 11/02; A01N 43/90; A61K 31/525; A61K 41/0057; A61K 8/4953; C07D 475/14; C11D 3/48
See application file for complete search history.

(56) References Cited

U.S. PATENT DOCUMENTS

| | | |
|---|---|---|
| 3,822,133 A | 7/1974 | Short et al. |
| 2010/0080781 A1 | 4/2010 | Goodrich et al. |
| 2014/0200220 A1 | 7/2014 | Maisch et al. |

FOREIGN PATENT DOCUMENTS

| | | | |
|---|---|---|---|
| DE | 22 24 371 A1 | 1/1973 | |
| JP | 2008 056585 | 3/2008 | |
| JP | 2008-056585 A | 3/2008 | |
| WO | WO 03/057253 A1 | 7/2003 | |
| WO | WO 2008/114009 | 9/2008 | |
| WO | WO 2008/114009 A1 | 9/2008 | |
| WO | WO 2010/019208 A1 | 2/2010 | |
| WO | WO 2011/008247 A1 | 1/2011 | |
| WO | WO 2011/126567 A1 | 10/2011 | |
| WO | WO 2015/053797 | * 4/2015 | .......... C07C 323/22 |

OTHER PUBLICATIONS

Rand, et al., Structural Characterization and Mapping of the Covalently Linked FAD Cofactor in Choline Oxidase from Arthrobacter globiformis, Biochemistry, 42(23), 7188-7194 (2003).*
Alagaratnam, et al., Probing the reactivity of different forms of azurin by flavin photoreduction, FEBS Journal 278, 1506-12521 (2011).*
International Search Report and Written Opinion in German dated Aug. 9, 2012 issued in corresponding International patent application No. PCT/EP2012/062172.
Alexander Barthel, et al., "Synthesis of Dimeric Quinazolin-2-one, 1,4-Benzodiazepin-2-one, and Isoalloxazine dompounds as Inhibitors of Amyloid Peptides Association," Arch. Pharm. Chem. Life Sci., vol. 342, 2009, pp. 445-452.
Michael C. Falk, et al., "Synthetic Flavinyl Peptides Related to the Active Site of Mitochondrial Monoamine Oxidase. I. Chemical and Spectral Properties," Biochemistry, vol. 15, No. 3, 1976, pp. 639-645.
Jens Butenandt, et al., "A Comparative Repair Study of Thymine- and Uracil-Photodimers With Model Compounds and a Photolyase Repair Enzyme," Chem. Eur. J., vol. 6, No. 1, 2000, pp. 62-72.
Carolina Moura, et al., "Rhenium(v) Oxocomplexes With Novel Pyrazolyl-Based $N_4$- and $N_3S$-Donor Chelators," Dalton Transactions, 2006, pp. 5630-5640.
Marcin Jasiński, "Synthesis of New Bis-imidazole Derivatives," Helvetica Chimica Acta, vol. 90, 2007, pp. 1765-1780.
A. A. Miles, et al., "The Estimation of the Bactericidal Power of the Blood," The Journal of Hygiene, vol. 38, No. 6, Nov. 1938, pp. 732-749.
Richard R. Holmes, et al., "A Simple Method for the Direct Oxidation of Aromatic Amines to Nitroso Compounds," vol. 82, 1960, pp. 3454-3456.
Robert Epple, et al., "Investigation of Flavin-Containing DNA-Repair Model Compounds," J. Am. Chem. Soc., vol. 119, 1997, pp. 7440-7451.
Naomi Sakai, et al., "Electrostatics of Cell Membrane Recognition: Structure and Activity of Neutral and Cationic Rigid Push-Pull Rods in Isoelectric, Anionic, and Polarized Lipid Bilayer Membranes," J. Am. Chem. Soc., vol. 123, 2001, pp. 2517-2524.

(Continued)

Primary Examiner — Erich A Leeser
(74) Attorney, Agent, or Firm — Ostrolenk Faber LLP

(57) ABSTRACT

The invention relates to 10H-benzo[g]pteridine-2,4-dione derivatives, to the production thereof, and to the use thereof.

37 Claims, 23 Drawing Sheets

(56) References Cited

OTHER PUBLICATIONS

Sathya Srinivasachari, et al., "Polycationic β-Cyclodextrin 'Click Clusters'": Monodisperse and Versatile Scaffolds for Nucleic Acid Delivery, J. Am. Chem. Soc., vol. 130, pp. 4618-4627.
Youli Xiao, et al., "Revisiting the IspH Catalytic System in the Deoxyxylulose Phosphate Pathway: Achieving High Activity," J. Am. Chem. Soc., vol. 131, 2009, pp. 9931-9933.
Antonio Monge, et al., "Hypoxia-Selective Agents Derived From Quinoxaline 1,4-Di-N-Oxides," J. Med. Chem., vol. 38, 1995, pp. 1786-1792.
Olaf Wiest, et al., "Design, Synthesis, and Evaluation of a Biomimetic Artificial Photolyase Model," J. Org. Chem., vol. 69, 2004, pp. 8183-8185.
Toru Sugaya, et al., "Improved Synthesis of Thromboxane $A_2$ Receptor Antagonists With a Dibenzoxepin Ring System," Synthesis, Oct. 1995, pp. 1257-1262.
Donald B. McCormick, "Flavin Derivatives via Bromination of the 8-Methyl Substituent (1)," Apr. 1970, pp. 447-450.
John M. Boyce, et al., "Guideline for Hand Hygiene in Health-Care Settings. Recommendations of the Healthcare Infection Control Practices Advisory Committee and the HICPAC/SHEA/APIC/IDSA Hand Hygiene Task Force", Am. J. Infect. Control, vol. 30, No. 8, 2002, pp. S1-S46.
John M. Boyce, et al., "Guideline for Hand Hygiene in Health-Care Settings: Recommendations of the Healthcare Infection Control Practices Advisory Committee and the HICPAC/SHEA/APIC/IDSA Hand Hygiene Task Force," Infection Control and Hospital. Epidemiology, vol. 23, No. S12, Dec. 2002, pp. S3-S40.
Didier Pittet, MD, et al., "The World Health Organization Guidelines on Hand Hygiene in Health Care and Their Consensus Recommendations," Infection Control and Hospital Epidemiology, vol. 30, No. 7, update from Jul. 2009.
Dr. H. F. Rabenau, et al., ("Leitlinie der Deutschen Vereinigung zur Bekämpfung der Viruskrankheiten (DVV) c.V. und des Robert Koch-Instituts (RKI) zur Prüfung von chemischen Desinfektionsmitteln auf Wirksamkeit gegen Viren in der Humanmedizin" Bundesgesundheitsblatt, Gesundheitsforschung, Gesundheitsschutz 51(8), (2008), pp. 937-945) (with English translation)—Guideline of "Deutsche Vereinigung zur Bekämpfung der Viruskrankheiten (DVV; German Association for the Control of Virus Diseases) and Robert Koch Institute (RKI; German Federal Health Authority) for Testing the Virucidal Efficacy of Chemical Disinfectants in the Human Medical Area."
Din EN 14885:Jan. 2007 "Chemische Desinfektionsmittel und Antiseptika-Anwendung Europäischer Normen für chemische Desinfektionsmittel und Antiseptika;" Deutsche Fassung EN 14885:2006—"Chemical disinfectants and antiseptics—Application of European Standards for chemical disinfectants and antiseptics" (an index in German and English is attached).

Jiri Svoboda, et al., "Thiourea-Enhanced Flavin Photooxidation of Benzyl Alcohol," Chemistry—A European Journal, Feb. 18, 2008, vol. 14, No. 6, pp. 1854-1865, XP55034202.
Patrizio Mattei, et al., "A Flavo-thiazolio-cyclophane as a Biomimetic Catalyst for the Preparative-Scale Electro-oxidation of Aromatic Aldehydes to Methyl Esters," Helvetica Chimica Acta, vol. 80, No. 5, Aug. 11, 1997, pp. 1555-1588, XP55034146.
Timothy R. G. Edwards, et al., "Synthesis of Bifunctionalised Flavins for Incorporation Into Well Defined Redox Systems," Tetrahedron, vol. 46, No. 3, Jan. 1, 1990, pp. 935-956, XP55034164.
Howard L. Levine, "Oxidation of Dihydronicotinamides by Flavopapain," Journal of the American Ciiemical Society, vol. 100, No. 24, Nov. 1, 1978, pp. 7670-7677, XP55034166.
William C. Kenney, et al., "Identification and Properties of the Covalently Bound Flavin of β-Cyclopiazonate Oxidocyclase," Biochemistry, vol. 15, No. 22, Nov. 1, 1976, pp. 4931-4935, XP55034169.
Rosemarie F. Hartman, et al., "A Possible Chain Reaction in Photosensitized Splitting of Pyrimidine Dimers by a Protonated, Oxidized Flavin," The Journal of Organic Chemistry, vol. 57, No. 8, Apr. 1, 1992, pp. 2302-2306, XP55034176.
Seiji Shinkai, et al., "Coenzyme Models. Part 23. Formation and Reactivity of the Stable 'Quinone Form' of Flavin in Cationic Polymer Matrices," Journal of the Chemical Society, Perkin Transactions 1, Jan. 1, 1980, pp. 1622-1625, XP55034011.
Yasushi Imada, et al., "Synthesis and electrochemical behavior of clothespin-shaped bisflavin compounds," Tetrahedron Letters, Elsevier, Amsterdam, NL, vol. 49, No. 16, Mar. 4, 2008, pp. 2523-2526, XP022541918.
Takashi Harayama, et al., "Reaction of 6-Ethylamino-3-methyluracil with Nitrobenzenes," Journal of Heterocyclic Chemistry, vol. 23, No. 5, Sep. 1, 1986, pp. 1507-1509, XP55034208.
Christopher Cox, et al., "Strong Hydrogen Bonding to the Amide Nitrogen Atom in an "Amide Proton Sponge": Consequences for Structure and Reactivity," Angewandte Chemie, International Edition, Wiley VCH Verlag, Weinheim, vol. 38, No. 6, Jan. 1, 1999, pp. 798-800, XP008154136.
Edwards, et al., Synthesis of Bifunctionalised Flavins for Incorporation Into Well Defined Redox Systems, Tetrahedron, vol. 46, No. 3, pp. 935-956 (1990).
Svoboda, et al., Thiourea-Enhanced Flavin Photooxidation of Benzyl Alcohol, Chem. Eur. J., 14 pp. 1854-1865 (2008).
Lozovskaya, et al., Photosensitization and Photoprotection by Some Drugs, Metabolites and Other Compounds, Biofizika (1997), 42(3), pp. 549-557.
Levine, et al., Oxidation of Dihydronicotinamides by Flavopapain, J. of the American Chem. Soc., vol. 100, No. 24, pp. 7670-7777 (1978).
Hartman et al., A Possible Chain Reaction in Photosensitized Splitting of Pyrimidine Dimers by a Protonated, Oxidized Flavin, J. Org. Chem., 57, pp. 2302-2306 (1992).
Shinkai, et al., Coenzyme Models Part 23. Formation and Reactivity of the Stable "Quinone Form" of Flavin in Cationic Polymer Matrices, J. of the Chem. Soc., 1, p. 1622 (1980).

* cited by examiner

Flavin Fl-08:

Flavin FL-02:

Flavin FL-06:

Flavin FL-07:

Flavin Fl-13:

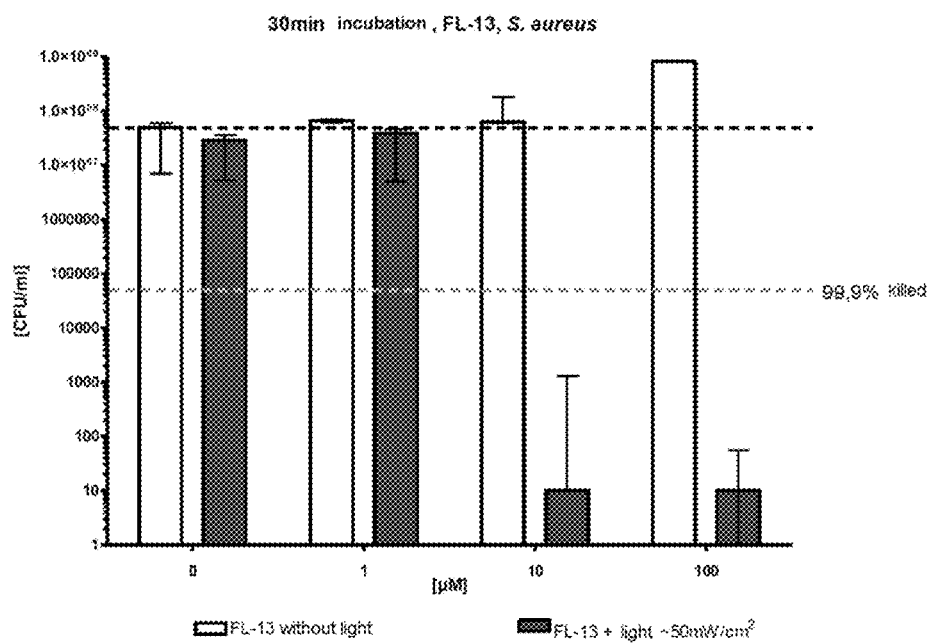

Flavin Fl-15:

Flavin Fl-17:

Flavin Fl-21:

Flavin Fl-24:

Flavin Fl-26:

Flavin Fl-27:

Flavin FL-08b:

10H-BENZO[G]PTERIDINE-2,4-DIONE DERIVATIVES, METHOD FOR THE PRODUCTION THEREOF, AND USE THEREOF

CROSS-REFERENCE TO RELATED APPLICATIONS

The present application is a continuation of prior U.S. patent application Ser. No. 14/127,464, filed Feb. 14, 2014, by Tim Maisch and Andreas Späth, entitled "10H-BENZO [G]PTERIDINE-2,4-DIONE DERIVATIVES, METHOD FOR THE PRODUCTION THEREOF, AND USE THEREOF," which is a 35 U.S.C. §371 National Phase conversion of International Application No. PCT/EP2012/062172, filed Jun. 22, 2012, which claims the benefit of German Patent Application No. 10 2011 105657.6, filed Jun. 22, 2011. The PCT International Application was published in the German language. The contents of each of the patent applications listed above are incorporated in full herein by reference.

TECHNICAL FIELD OF THE INVENTION

The present invention relates to 10H-benzo[g]pteridine-2,4-dione derivatives, and to the preparation and use thereof.

BACKGROUND OF THE INVENTION

The active or passive penetration of pathogens into a host, the inherent presence of these therein and the propagation thereof is referred to as infection. Sources of infectious particles occur everywhere. For example, the human body is colonized by a large number of microorganisms which are generally kept under control by the normal metabolism and an intact immune system. However, a weakened immune system, for example, may result in significant propagation of the pathogens and, according to the type of pathogen, in different disease symptoms. For many pathogen-induced diseases, medicine has specific antidotes at its disposal, for example antibiotics against bacteria or antimycotics against fungi or virustatics against viruses. However, increasing occurrence of resistant pathogens is observed when these antidotes are used, and some of these pathogens have resistances against several antidotes at the same time. The occurrence of these resistant or multiresistant pathogens has made the treatment of infection disorders increasingly difficult.

The clinical consequence of resistance is manifested by a failure of the treatment, particularly in the case of immunosuppressed patients.

New starting points for control of resistant or multiresistant disease pathogens are therefore firstly the search for new antidotes, for example antibiotics or antimycotics, and secondly the search for alternative means of inactivation.

An alternative method which has been found to be useful is the photodynamic inactivation of microorganisms. Two different photooxidative processes play a crucial role in the photodynamic inactivation of microorganisms. Prerequisites for the running of a photooxidative inactivation are firstly the presence of a sufficient amount of oxygen and secondly the localization of a so-called photosensitizer, which is excited by light of an appropriate wavelength. The excited photosensitizer can bring about the formation of reactive oxygen species (ROS), which can form firstly free radicals, for example superoxide anions, hydrogen peroxide or hydroxyl radicals, and/or secondly excited molecular oxygen, for example singlet oxygen.

For both reactions, the photooxidation of specific biomolecules directly adjacent to the reactive oxygen species (ROS) is of primary importance. This involves particularly oxidation of lipids and proteins which occur, for example, as constituents of the cell membrane of microorganisms. The destruction of the cell membrane in turn results in inactivation of the microorganisms in question. For viruses and fungi, a similar elimination process is assumed.

For example, singlet oxygen attacks all molecules. However, unsaturated fatty acids in the membranes of bacteria are particularly prone to damage. Healthy endogenous cells have a cellular defense against attacks by free radicals, called catalases or superoxide dismutases. Therefore, healthy endogenous cells can counteract damage by reactive oxygen species (ROS), for example free radicals or singlet oxygen.

The prior art discloses numerous photosensitizers which come, for example, from the group of the porphyrins and derivatives thereof or phthalocyanines and derivatives thereof or fullerenes and derivatives thereof or derivatives of the phenothiazinium structure, for example methylene blue or toluidine blue, or representatives of the phenoxazinium series, for example Nile blue. The photodynamics of methylene blue or toluidine blue with respect to bacteria have already been used, for example, in dentistry.

The photosensitizers known from the prior art are usually substances having a relatively complex molecular structure and therefore complex purification processes.

The non-patent literature Svoboda et al. (Chem. Eur. J. 2008, 14, pages 1854-1864) describes the influence of thiourea on the photooxidation of benzyl alcohol by flavin and various flavin derivatives, including the compound having the formula (20):

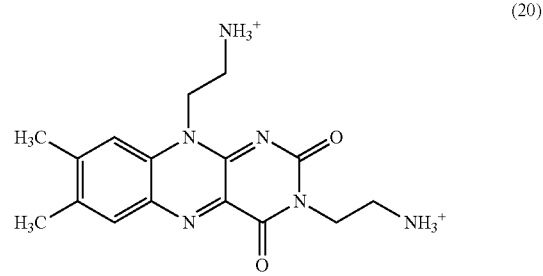

However, Svoboda et al. do not describe any effect of the flavin derivatives examined on the viability of microorganisms.

It is additionally known that 10-methyl-10H-benzo[g] pteridine-2,4-dione derivatives riboflavin and tetraacetylriboflavin have high yields of singlet oxygen, although the affinity for microorganisms is low. It is additionally known that singlet oxygen can diffuse only over a short distance before it reacts or is degraded. Therefore, the inactivation of microorganisms by 10-methyl-10H-benzo[g]pteridine-2,4-dione derivatives riboflavin and tetraacetylriboflavin is inadequate.

Moreover, WO 2010/019208 A1 and WO 2011/008247 A1 disclose numerous flavin, roseoflavin and riboflavin derivatives which can bind to flavin mononucleotide (FMN) riboswitches. Riboswitches are RNA elements in the untranslated regions of the mRNA of prokaryotes, fungi and plants, which bind low molecular weight metabolites, for example FMN, and then regulate gene expression. For example, after binding of FMN to FMN riboswitches of prokaryotes, the expression of enzymes responsible for riboflavin and FMN biosynthesis is repressed, as a result of which riboflavin and FMN biosynthesis stops. Riboflavin assumes a central role in the metabolism, since it serves as a precursor for flavin coenzymes. Therefore, suppressed riboflavin and FMN biosynthesis leads to reduced viability.

However, this form of control of pathogenic microorganisms can likewise result in occurrence of resistances, which can arise, for example, as a result of mutations in the RNA elements in question.

SUMMARY OF THE INVENTION

It is therefore an object of the present invention to provide novel photosensitizers which more efficiently inactivate microorganisms.

The object of the present invention is achieved by the provision of a compound having the formula (1):

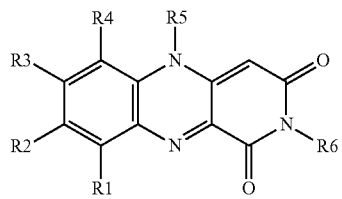

(1)

where I) only 1 R1, R2, R3, R4, R5 or R6 radical is an organic radical having:
a) at least two uncharged, protonatable nitrogen atoms not bonded directly to the isoalloxazine ring, or
a) at least two positively charged, preferably quaternary, nitrogen atoms not bonded directly to the isoalloxazine ring,
and where each of the R1, R2, R3 and R4 radicals which is not an organic radical having a) at least two uncharged, protonatable nitrogen atoms not bonded directly to the isoalloxazine ring, or b) at least two positively charged, preferably quaternary, nitrogen atoms not bonded directly to the isoalloxazine ring, is the same or different and is independently hydrogen, halogen, hydroxyl, thiol, nitro, carboxylate, aldehyde having 1 to 20 carbon atoms, ketone having 2 to 20 carbon atoms, O-alkyl having 1 to 20 carbon atoms, S-alkyl having 1 to 20 carbon atoms, O-alkenyl having 2 to 20 carbon atoms, S-alkenyl having 2 to 20 carbon atoms, O-aryl having 5 to 20 carbon atoms, S-aryl having 5 to 20 carbon atoms, carboxylic ester having 1 to 20 carbon atoms, carboxamide having 1 to 20 carbon atoms, thioester having 1 to 20 carbon atoms, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms or heteroaryl having 4 to 20 carbon atoms, which does not contain any nitrogen atoms, and
where each of the R5 and R6 radicals which is not an organic radical having a) at least two uncharged, protonatable nitrogen atoms not bonded directly to the isoalloxazine ring, or b) at least two positively charged, preferably quaternary, nitrogen atoms not bonded directly to the isoalloxazine ring, is the same or different and is independently hydrogen, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms or heteroaryl having 4 to 20 carbon atoms, which does not contain any nitrogen atoms,
with the proviso that the R3 radical is not an aminomethyl radical, where the nitrogen atom may be unsubstituted or substituted, and
excluding compounds in which the R1, R4 and R10 radicals are hydrogen, the R2 radical is hydrogen, alkyl having 1 to 8 carbon atoms or cycloalkyl having 3 to 7 carbon atoms, the R3 radical is hydrogen, halogen, alkyl having 1 to 8 carbon atoms, O-alkyl having 1 to 8 carbon atoms or a heterocyclic radical having 4 to 7 carbon atoms, and the R5 radical is an alkyl radical which has 1 to 8 carbon atoms and is substituted by at least by a radical of the formula —N($R^{35}$)($R^{36}$) or a radical of the formula —O$R^{35}$, where the $R^{35}$ radical is a radical of the formula —$C_{1-8}$alkyl(amine)-O$R^{37}$ or a 7,8-dimethylisoalloxazin-10-yl-$C_{1-8}$alkyl radical and where the $R^{36}$ radical is hydrogen or a radical of the formula —$C_{1-8}$alkyl, which may be unsubstituted or substituted, and where the $R^{37}$ radical is hydrogen, aryl having 6 to 7 carbon atoms or alkyl which may be unsubstituted or substituted and has 1 to 8 carbon atoms, and
additionally excluding compounds in which the R1 and R4 radicals are hydrogen, the R10 radical is hydrogen or a radical having the general formula —$C_{1-4}$alkyl-OC(O)$CH_3$, the R2 radical is hydrogen or alkyl having 8 to 8 carbon atoms and the R5 radical is a radical having the general formula —$C_{1-6}$alkyl-N($R^{31}$)—$C_{0-3}$ alkyl-($R^{32}$), where $R^{31}$ is hydrogen or a radical having the formula —$C_{1-4}$alkyl and where $R^{32}$ is a radical having the formula —$C_{1-4}$alkyl-N($R^{33}$)($R^{34}$), a radical having the formula —$C_{0-4}$alkyl-aryl, a radical having the formula —$C_{0-4}$alkylheterocycloalkyl or a radical having the formula —$C_{0-4}$alkylheteroaryl, and where the $R^{33}$ and $R^{34}$ radicals are each independently hydrogen or —$C_{1-4}$alkyl, and
additionally excluding 10-butyl-7,8-dimethyl-3-[2-oxo-2-(1,4,7,10-tetrazacyclododec-1-yl)ethyl]benzo[g]pteridine-2,4-dione and 10-[2-(2-methoxyethoxy)ethyl]-7,8-dimethyl-3-[2-oxo-2-(1,4,7,10-tetrazacyclododec-1-yl)ethyl]benzo[g]pteridine-2,4-dione, or
where II) only 1 R1, R2, R3, R4, R5 or R6 radical is an organic radical having:
a) at least one uncharged, protonatable nitrogen atom not bonded directly to the isoalloxazine ring, and
b) at least one positively charged, preferably quaternary, nitrogen atom not bonded directly to the isoalloxazine ring,
and where each of the R1, R2, R3 and R4 radicals which is not an organic radical having a) at least one uncharged, protonatable nitrogen atom not bonded directly to the isoalloxazine ring, or b) at least one positively charged, preferably quaternary, nitrogen atom not bonded directly to the isoalloxazine ring, is the same or different and is independently hydrogen, halogen, hydroxyl, thiol, nitro, carboxylate, aldehyde having 1 to 20 carbon atoms, ketone having 2 to 20 carbon atoms, O-alkyl having 1 to 20 carbon atoms, S-alkyl having 1 to 20 carbon atoms, O-alkenyl having 2 to 20 carbon atoms, S-alkenyl having 2 to 20 carbon atoms, O-aryl having 5 to 20 carbon atoms, S-aryl having 5 to 20 carbon atoms, carboxylic ester having 1 to 20 carbon atoms, carboxamide having 1 to 20 carbon atoms, thioester having 1 to 20 carbon atoms, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms or heteroaryl having 4 to 20 carbon atoms, which does not contain any nitrogen atoms, and where each of the R5 and R6 radicals which is not an organic radical having a) at least one uncharged, protonatable nitrogen atom not bonded directly to the isoalloxazine ring, or b) at least one positively charged, preferably quaternary, nitrogen atom not bonded directly to the isoalloxazine ring, is the same or different and is independently hydrogen, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms or heteroaryl having 4 to 20 carbon atoms, which does not contain any nitrogen atoms, or where III) at least 2 R1, R2, R3, R4, R5 or R6 radicals are an organic radical having:
a) at least one uncharged, protonatable nitrogen atom not bonded directly to the isoalloxazine ring, and/or
b) at least one positively charged, preferably quaternary, nitrogen atom not bonded directly to the isoalloxazine ring, and where each of the R1, R2, R3 and R4 radicals which is not an organic radical having a) at least one uncharged, protonatable nitrogen atom not bonded directly to the isoalloxazine ring, or b) at least one positively charged, preferably quaternary, nitrogen atom not bonded directly to the isoalloxazine ring, is the same or different and is independently hydrogen, halogen, hydroxyl, thiol, nitro, carboxylate, aldehyde having 1 to 20 carbon atoms, ketone having 2 to 20 carbon atoms, O-alkyl having 1 to 20 carbon atoms, S-alkyl having 1 to 20 carbon atoms, O-alkenyl having 2 to 20 carbon atoms, S-alkenyl having 2 to 20 carbon atoms, O-aryl having 5 to 20 carbon atoms, S-aryl having 5 to 20 carbon atoms, carboxylic ester having 1 to 20 carbon atoms, carboxamide having 1 to 20 carbon atoms, thioester having 1 to 20 carbon atoms, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms or heteroaryl having 4 to 20 carbon atoms, which does not contain any nitrogen atoms, and where each of the R5 and R6 radicals which is not an organic radical having a) at least one uncharged, protonatable nitrogen atom not bonded directly to the isoalloxazine ring, or b) at least one positively charged, preferably quaternary, nitrogen atom not bonded directly to the isoalloxazine ring, is the same or different and is independently hydrogen, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms or heteroaryl having 4 to 20 carbon atoms, which does not contain any nitrogen atoms, and excluding the compound having the formula (20):

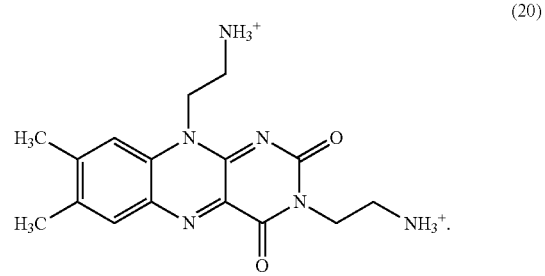

The object of the present invention is likewise achieved by the use of a compound having the formula (1):

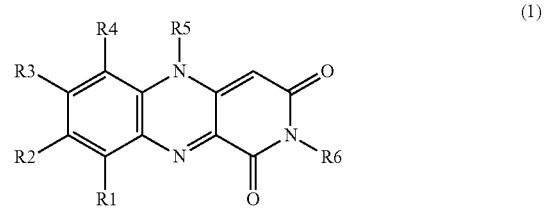

as a photosensitizer, preferably in the photodynamic inactivation of microorganisms, further preferably in photodynamic therapy, where I) only 1 R1, R2, R3, R4, R5 or R6 radical is an organic radical having:
a) at least two uncharged, protonatable nitrogen atoms not bonded directly to the isoalloxazine ring, or
a) at least two positively charged, preferably quaternary, nitrogen atoms not bonded directly to the isoalloxazine ring, and where each of the R1, R2, R3 and R4 radicals which is not an organic radical having a) at least two uncharged, protonatable nitrogen atoms not bonded directly to the isoalloxazine ring, or b) at least two positively charged, preferably quaternary, nitrogen atoms not bonded directly to the isoalloxazine ring, is the same or different and is independently hydrogen, halogen, hydroxyl, thiol, nitro, carboxylate, aldehyde having 1 to 20 carbon atoms, ketone having 2 to 20 carbon atoms, O-alkyl having 1 to 20 carbon atoms, S-alkyl having 1 to 20 carbon atoms, O-alkenyl having 2 to 20 carbon atoms, S-alkenyl having 2 to 20 carbon atoms, O-aryl having 5 to 20 carbon atoms, S-aryl having 5 to 20 carbon atoms, carboxylic ester having 1 to 20 carbon atoms, carboxamide having 1 to 20 carbon atoms, thioester having 1 to 20 carbon atoms, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms or heteroaryl having 4 to 20 carbon atoms, which does not contain any nitrogen atoms, and where each of the R5 and R6 radicals which is not an organic radical having a) at least two uncharged, protonatable nitrogen atoms not bonded directly to the isoalloxazine ring, or b) at least two positively charged, preferably quaternary, nitrogen atoms not bonded directly to the isoalloxazine ring, is the same or different and is independently hydrogen, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms or heteroaryl having 4 to 20 carbon atoms, which does not contain any nitrogen atoms, or where II) only 1 R1, R2, R3, R4, R5 or R6 radical is an organic radical having:
a) at least one uncharged, protonatable nitrogen atom not bonded directly to the isoalloxazine ring, and
b) at least one positively charged, preferably quaternary, nitrogen atom not bonded directly to the isoalloxazine ring, and where each of the R1, R2, R3 and R4 radicals which is not an organic radical having a) at least one uncharged, protonatable nitrogen atom not bonded directly to the isoalloxazine ring, or b) at least one positively charged, preferably quaternary, nitrogen atom not bonded directly to the isoalloxazine ring, is the same or different and is independently hydrogen, halogen, hydroxyl, thiol, nitro, carboxylate, aldehyde having 1 to 20 carbon atoms, ketone having 2 to 20 carbon atoms, O-alkyl having 1 to 20 carbon atoms, S-alkyl having 1 to 20 carbon atoms, O-alkenyl having 2 to 20 carbon atoms, S-alkenyl having 2 to 20 carbon atoms, O-aryl having 5 to 20 carbon atoms, S-aryl having 5 to 20 carbon atoms, carboxylic ester having 1 to 20 carbon atoms, carboxamide having 1 to 20 carbon atoms, thioester having 1 to 20 carbon atoms, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms or heteroaryl having 4 to 20 carbon atoms, which does not contain any nitrogen atoms, or where each of the R5 and R6 radicals which is not an organic radical having a) at least one uncharged, protonatable nitrogen atom not bonded directly to the isoalloxazine ring, or b) at least one positively charged, preferably quaternary, nitrogen atom not bonded directly to the isoalloxazine ring, is the same or different and is independently hydrogen, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms or heteroaryl having 4 to 20 carbon atoms, which does not contain any nitrogen atoms, or where III) at least 2 R1, R2, R3, R4, R5 or R6 radicals are an organic radical having:
a) at least one uncharged, protonatable nitrogen atom not bonded directly to the isoalloxazine ring, and/or
b) at least one positively charged, preferably quaternary, nitrogen atom not bonded directly to the isoalloxazine ring, and where each of the R1, R2, R3 and R4 radicals which is not an organic radical having a) at least one uncharged, protonatable nitrogen atom not bonded directly to the isoalloxazine ring, or b) at least one positively charged, preferably quaternary, nitrogen atom not bonded directly to the isoalloxazine ring, is the same or different and is independently hydrogen, halogen, hydroxyl, thiol, nitro, carboxylate, aldehyde having 1 to 20 carbon atoms, ketone having 2 to 20 carbon atoms, O-alkyl having 1 to 20 carbon atoms, S-alkyl having 1 to 20 carbon atoms, O-alkenyl having 2 to 20 carbon atoms, S-alkenyl having 2 to 20 carbon atoms, O-aryl having 5 to 20 carbon atoms, S-aryl having 5 to 20 carbon atoms, carboxylic ester having 1 to 20 carbon atoms, carboxamide having 1 to carbon atoms, thioester having 1 to 20 carbon atoms, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms or heteroaryl having 4 to 20 carbon atoms, which does not contain any nitrogen atoms, and where each of the R5 and R6 radicals which is not an organic radical having a) at least one uncharged, protonatable nitrogen atom not bonded directly to the isoalloxazine ring, or b) at least one positively charged, preferably quaternary, nitrogen atom not bonded directly to the isoalloxazine ring, is the same or different and is independently hydrogen, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms or heteroaryl having 4 to 20 carbon atoms, which does not contain any nitrogen atoms.

The compound having the formula (1) is a 10H-benzo[g]pteridine-2,4-dione or flavin derivative, which is also referred to as such hereinafter.

The counterion used for at least one positively charged, preferably quaternary, nitrogen atom may be any suitable anion. Preferably, the counterion(s) used for the positively charged, preferably quaternary, nitrogen atom(s) are anions which enable the provision of a pharmacologically acceptable salt.

BRIEF DESCRIPTION OF THE DRAWINGS

FIG. 5b) shows the results of incubation of *Staphylococcus aureus* samples with FL-13 for 30 minutes.

DESCRIPTION OF PREFERRED EMBODIMENTS

Figure 1:
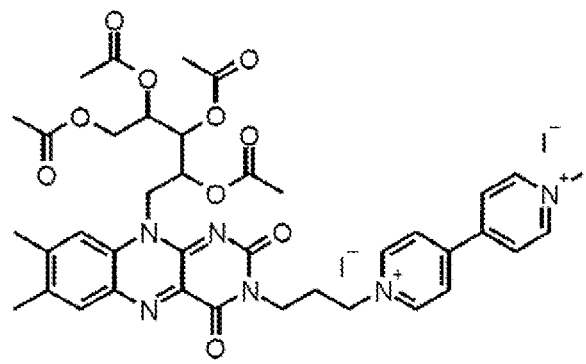
FIG. 1 shows the structural formula of Flavin FL-08.

In a preferred embodiment of the present invention, positively charged, preferably quaternary, nitrogen atoms have, as counterion, fluoride, chloride, bromide, iodide, sulfate, hydrogensulfate, phosphate, dihydrogenphosphate, hydrogenphosphate, tosylate, mesylate, formate, acetate, oxalate, benzoate, citrate and/or mixtures thereof.

The object of the present invention is likewise achieved by the provision of a process for preparing the inventive 10H-benzo[g]pteridine-2,4-dione derivatives of the formula (1) as claimed in either of claims 15 and 16.

Further preferred embodiments of the present invention are described in the dependent claims.

According to the invention, "photosensitizer" is understood to mean compounds which absorb electromagnetic radiation, preferably visible light, UV light and/or infrared light, and then generate reactive oxygen species (ROS), preferably free radicals and/or singlet oxygen, from triplet oxygen.

According to the invention, the term "photodynamic therapy" is understood to mean the light-induced, photodynamic inactivation of cells or microorganisms.

According to the invention, the term "inactivation" is understood to mean the reduction of the viability or the destruction of a microorganism, preferably the destruction thereof. A light-induced inactivation can be determined, for example, via reduction in the number of microorganisms after irradiation of a defined starting amount of these microorganisms in the presence of at least one compound having the formula (1) used in accordance with the invention.

According to the invention, a reduction in viability is understood to mean that the number of microorganisms is reduced by at least 99.0%, preferably by at least 99.9%, further preferably by at least 99.99%, further preferably by at least 99.999%, even further preferably by at least 99.9999%. Exceptionally preferably, the number of microorganisms is reduced by more than 99.9 to 100%, preferably by more than 99.99 to 100%.

Preferably, the reduction in the number of microorganisms is reported as the $\log_{10}$ reduction factor according to Boyce, J. M. and Pittet, D. ("Guidelines for hand hygiene in healthcare settings. Recommendations of the Healthcare Infection Control Practices Advisory Committee and the HIPAC/SHEA/APIC/IDSA Hand Hygiene Task Force", Am. J. Infect. Control 30 (8), 2002, pages 1-46).

According to the invention, the term "$\log_{10}$ reduction factor" is understood to mean the difference between the decadic logarithm of the number of microorganisms before and the decadic logarithm of the number of microorganisms after an irradiation of these microorganisms with electromagnetic radiation in the presence of at least one compound having the formula (1) used in accordance with the invention.

Suitable methods for determining the $\log_{10}$ reduction factor are described, for example, in DIN EN 14885:2007-01 "Chemical disinfectants and antiseptics—Application of European Standards for chemical disinfectants and antiseptics" or in Rabenau, H. F. and Schwebke, I. ("Leitlinie der Deutschen Vereinigung zur Bekämpfung der Viruskrankheiten (DVV) e.V. und des Robert Koch-Instituts (RKI) zur Prüfung von chemischen Desinfektionsmitteln auf Wirksamkeit gegen Viren in der Humanmedizin" Bundesgesundheitsblatt, Gesundheitsforschung, Gesundheitsschutz 51(8), (2008), pages 937-945).

Preferably, the $\log_{10}$ reduction factor after irradiation of microorganisms with electromagnetic radiation in the presence of at least one compound having the formula (1) used in accordance with the invention is at least 2 $\log_{10}$, preferably at least 3 $\log_{10}$, further preferably at least 4 $\log_{10}$, further preferably at least 4.5 $\log_{10}$, further preferably at least 5 $\log_{10}$, further preferably at least 6 $\log_{10}$, even further preferably at least 7 $\log_{10}$, even further preferably at least 7.5 $\log_{10}$.

For example, a reduction in the number of microorganisms after irradiation of these microorganisms with electromagnetic radiation in the presence of at least one compound having the formula (1) used in accordance with the invention by 2 orders of magnitude, based on the starting amount of these microorganisms, means a $\log_{10}$ reduction factor of 2 $\log_{10}$.

Further preferably, the number of microorganisms after irradiation of these microorganisms with electromagnetic radiation in the presence of at least one compound having the formula (1) used in accordance with the invention is reduced by at least 1 order of magnitude, further preferably by at least 2 orders of magnitude, preferably by at least 4 orders of magnitude, further preferably by at least 5 orders of magnitude, further preferably by at least 6 orders of magnitude, even further preferably by at least 7 orders of magnitude, based in each case on the starting amount of these microorganisms.

The term "microorganisms" in the context of the invention is understood to mean especially viruses, archaea, prokaryotic microorganisms such as bacteria and bacterial spores, and eukaryotic microorganisms such as fungi, protozoa, fungal spores, unicellular algae. The microorganisms may occur in unicellular or multicellular form, for example as a fungal mycelium.

An inventive 10H-benzo[g]pteridine-2,4-dione derivative has the formula (1)

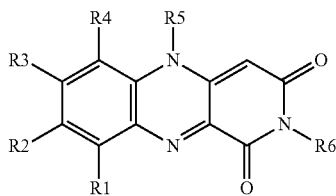

where I) only 1 R1, R2, R3, R4, R5 or R6 radical is an organic radical having:
a) at least two, preferably at least three, preferably at least four, further preferably at least five, uncharged, protonatable nitrogen atoms not bonded directly to the isoalloxazine ring, or
b) at least two, preferably at least three, preferably at least four, further preferably at least five, positively charged, preferably quaternary, nitrogen atoms not bonded directly to the isoalloxazine ring, or where II) only 1 R1, R2, R3, R4, R5 or R6 radical is an organic radical having:
a) at least one, preferably at least two, preferably at least three, preferably at least four, further preferably at least five, uncharged, protonatable nitrogen atom(s) not bonded directly to the isoalloxazine ring, and
b) at least one, preferably at least two, preferably at least three, preferably at least four, further preferably at least five, positively charged, preferably quaternary, nitrogen atom(s) not bonded directly to the isoalloxazine ring, or where III) at least 2 R1, R2, R3, R4, R5 or R6 radicals are an organic radical having:
a) at least one, preferably at least two, preferably at least three, preferably at least four, further preferably at least five, uncharged, protonatable nitrogen atom(s) not bonded directly to the isoalloxazine ring, and
b) at least one, preferably at least two, preferably at least three, preferably at least four, further preferably at least five, positively charged, preferably quaternary, nitrogen atom(s).

In a preferred embodiment, an inventive 10H-benzo[g]pteridine-2,4-dione derivative of the formula (1) does not have any uncharged, protonatable nitrogen atom bonded directly to the isoalloxazine ring, for example in the form of an amino radical, methylamino radical or dimethylamino radical, or any positively charged nitrogen atom bonded directly to the isoalloxazine ring, for example in the form of a pyridin-1-ium-1-yl radical or trimethylammonio radical.

In variant I) of the inventive 10H-benzo[g]pteridine-2,4-dione derivative of the formula (1)

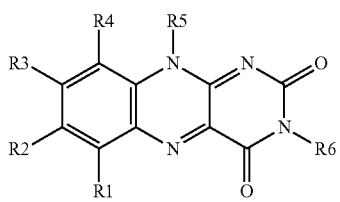

only 1 R1, R2, R3, R4, R5 or R6 radical is an organic radical having:
a) at least two, preferably at least three, preferably at least four, further preferably at least five, uncharged, protonatable nitrogen atoms not bonded directly to the isoalloxazine ring, or
b) at least two, preferably at least three, preferably at least four, further preferably at least five, positively charged, preferably quaternary, nitrogen atoms not bonded directly to the isoalloxazine ring, and where each of the R1, R2, R3 and R4 radicals which is not an organic radical having a) at least two, preferably at least three, preferably at least four, further preferably at least five, uncharged, protonatable nitrogen atoms not bonded directly to the isoalloxazine ring, or b) at least two, preferably at least three, preferably at least four, further preferably at least five, positively charged, preferably quaternary, nitrogen atoms not bonded directly to the isoalloxazine ring, is the same or different and is independently hydrogen, halogen, hydroxyl, thiol, nitro, carboxylate, aldehyde having 1 to 20 carbon atoms, ketone having 2 to 20 carbon atoms, O-alkyl having 1 to 20 carbon atoms, S-alkyl having 1 to 20 carbon atoms, O-alkenyl having 2 to 20 carbon atoms, S-alkenyl having 2 to 20 carbon atoms, O-aryl having 5 to 20 carbon atoms, S-aryl having 5 to 20 carbon atoms, carboxylic ester having 1 to 20 carbon atoms, carboxamide having 1 to 20 carbon atoms, thioester having 1 to 20 carbon atoms, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms or heteroaryl having 4 to 20 carbon atoms, which does not contain any nitrogen atoms, and where each of the R5 and R6 radicals which is not an organic radical having a) at least two, preferably at least three, preferably at least four, further preferably at least five, uncharged, protonatable nitrogen atoms not bonded directly to the isoalloxazine ring, or b) at least two, preferably at least three, preferably at least four, further preferably at least five, positively charged, preferably quaternary, nitrogen atoms not bonded directly to the isoalloxazine ring, is the same or different and is independently hydrogen, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms or heteroaryl having 4 to 20 carbon atoms, which does not contain any nitrogen atoms, with the proviso that the R3 radical is not an aminomethyl radical, where the nitrogen atom may be unsubstituted or substituted, and excluding compounds in which the R1, R4 and R10 radicals are hydrogen, the R2 radical is hydrogen, alkyl having 1 to 8 carbon atoms or cycloalkyl having 3 to 7 carbon atoms, the R3 radical is hydrogen, halogen, alkyl having 1 to 8 carbon atoms, O-alkyl having 1 to 8 carbon atoms or a heterocyclic radical having 4 to 7 carbon atoms, and the R5 radical is an alkyl radical which has 1 to 8 carbon atoms and is substituted by at least by a radical of the formula —N($R^{35}$)($R^{36}$) or a radical of the formula —O$R^{35}$, where the $R^{35}$ radical is a radical of the formula —$C_{1-8}$alkyl(amine)-O$R^{37}$ or a 7,8-dimethylisoalloxazin-10-yl-$C_{1-8}$alkyl radical and where the $R^{36}$ radical is hydrogen or a radical of the formula —$C_{1-8}$alkyl, which may be unsubstituted or substituted, and where the $R^{37}$ radical is hydrogen, aryl having 6 to 7 carbon atoms or alkyl which may be unsubstituted or substituted and has 1 to 8 carbon atoms, and additionally excluding compounds in which the R1 and R4 radicals are hydrogen, the R10 radical is hydrogen or a radical having the general formula —C$_{1-4}$alkyl-OC(O)CH$_3$, the R2 radical is hydrogen or alkyl having 8 to 8 carbon atoms and the R5 radical is a radical having the general formula —C$_{1-6}$alkyl-N(R$^{31}$)—C$_{0-3}$alkyl-(R$^{32}$), where R$^{31}$ is hydrogen or a radical having the formula —C$_{1-4}$alkyl and where R$^{32}$ is a radical having the formula —C$_{1-4}$alkyl-N(R$^{33}$)(R$^{34}$), a radical having the formula —C$_{0-4}$alkyl-aryl, a radical having the formula —C$_{0-4}$alkylheterocycloalkyl or a radical having the formula —C$_{0-4}$alkylheteroaryl, and where the R$^{33}$ and R$^{34}$ radicals are each independently hydrogen or —C$_{1-4}$alkyl, and excluding 10-butyl-7,8-dimethyl-3-[2-oxo-2-(1,4,7,10-tetrazacyclododec-1-yl)ethyl]benzo[g]pteridine-2,4-dione and 10-[2-(2-methoxyethoxy)ethyl]-7,8-dimethyl-3-[2-oxo-2-(1,4,7,10-tetrazacyclododec-1-yl)ethyl]benzo[g]pteridine-2,4-dione.

In a preferred embodiment of variant I) of the 10H-benzo[g]pteridine-2,4-dione derivative of the formula (1), the R5 radical is an acyclic polyol radical of the general formula —CH$_2$(CH(OH))$_g$CH$_2$OH or an ether, ester or acetal thereof, where g is an integer from 1 to 10, preferably 1 to 4, and where A) only 1 R1, R2, R3 or R4 radical is an organic radical having:
  a) at least two, preferably at least three, preferably at least four, further preferably at least five, uncharged, protonatable nitrogen atoms not bonded directly to the isoalloxazine ring, or
  b) at least two, preferably at least three, preferably at least four, further preferably at least five, positively charged, preferably quaternary, nitrogen atoms not bonded directly to the isoalloxazine ring,
  where each of the R1, R2, R3 and R4 radicals which is not an organic radical having a) at least two, preferably at least three, preferably at least four, further preferably at least five, uncharged, protonatable nitrogen atoms not bonded directly to the isoalloxazine ring, or b) at least two, preferably at least three, preferably at least four, further preferably at least five, positively charged, preferably quaternary, nitrogen atoms not bonded directly to the isoalloxazine ring, is the same or different and is independently hydrogen, halogen, hydroxyl, thiol, nitro, carboxylate, aldehyde having 1 to 20 carbon atoms, ketone having 2 to 20 carbon atoms, O-alkyl having 1 to 20 carbon atoms, S-alkyl having 1 to 20 carbon atoms, O-alkenyl having 2 to 20 carbon atoms, S-alkenyl having 2 to 20 carbon atoms, O-aryl having 5 to 20 carbon atoms, S-aryl having 5 to 20 carbon atoms, carboxylic ester having 1 to 20 carbon atoms, carboxamide having 1 to 20 carbon atoms, thioester having 1 to 20 carbon atoms, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms or heteroaryl having 4 to 20 carbon atoms, which does not contain any nitrogen atoms, and
  where the R6 radical is hydrogen, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms or heteroaryl having 4 to 20 carbon atoms, which does not contain any nitrogen atoms, or
B) only the R6 radical is in organic radical having:
  a) at least two, preferably at least three, preferably at least four, further preferably at least five, uncharged, protonatable nitrogen atoms not bonded directly to the isoalloxazine ring, or
  b) at least two, preferably at least three, preferably at least four, further preferably at least five, positively charged, preferably quaternary, nitrogen atoms not bonded directly to the isoalloxazine ring,
  where the R1 to R4 radicals are the same or different and are each independently hydrogen, halogen, hydroxyl, thiol, nitro, carboxylate, aldehyde having 1 to 20 carbon atoms, ketone having 2 to 20 carbon atoms, O-alkyl having 1 to 20 carbon atoms, S-alkyl having 1 to 20 carbon atoms, O-alkenyl having 1 to 20 carbon atoms, S-alkenyl having 1 to 20 carbon atoms, O-aryl having 5 to 20 carbon atoms, S-aryl having 5 to 20 carbon atoms, ether having 2 to 20 carbon atoms, thioether having 2 to 20 carbon atoms, carboxylic ester having 1 to 20 carbon atoms, carboxamide having 1 to 20 carbon atoms, thioester having 1 to 20 carbon atoms, alkyl having 1 to 20 carbon atoms, alkenyl having 1 to 20 carbon atoms, cycloalkyl having 3 to 20 carbon atoms, cycloalkenyl having 3 to 20 carbon atoms, aryl having 5 to 20 carbon atoms, heteroaryl which does not contain any nitrogen atom and has 4 to 20 carbon atoms.

Further preferably, the R5 radical is an acyclic polyol radical selected from the group consisting of arabityl, ribityl, xylityl, erythrityl, threityl, lactityl, mannityl and sorbityl, further preferably D-ribityl and D-arabityl, or an ether, ester or acetal thereof.

In a further preferred embodiment of variant I) of the inventive 10H-benzo[g]pteridine-2,4-dione derivative of the formula (1),
A) only 1 R1, R2, R3 or R4 radical is an organic radical of the general formula (2), (3) or (4):

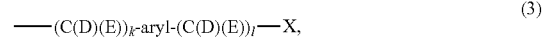

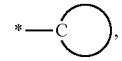

where h is an integer from 1 to 20, preferably from 1 to 19, preferably from 1 to 17, further preferably from 1 to 13, further preferably from 1 to 9, further preferably from 1 to 6, further preferably from 1 to 4, and k, l are each independently an integer from 0 to 6, preferably from 1 to 5, where D and E are each independently hydrogen, halogen, preferably chlorine, bromine, iodine or fluorine, hydroxyl, O—R$^{(VIII)}$ where R$^{(VIII)}$ is methyl, ethyl, n-propyl, n-butyl, phenyl or benzyl, O—C(=O)—R$^{(IX)}$ where R$^{(IX)}$ is hydrogen, methyl, ethyl, n-propyl, n-butyl, phenyl or benzyl, or thiol, further preferably hydrogen or hydroxyl, and where X is an organic radical having a) at least two, preferably at least three, preferably at least four, further preferably at least five, uncharged, protonatable nitrogen atoms not bonded directly to the isoalloxazine ring, or
b) at least two, preferably at least three, preferably at least four, further preferably at least five, positively charged, preferably quaternary, nitrogen atoms not bonded directly to the isoalloxazine ring, preferably with the proviso that the R3 radical is not an aminomethyl radical, where the nitrogen atom may be unsubstituted or substituted, and where aryl is a substituted or unsubstituted aromatic system having 5 to 20 carbon atoms or a substituted or unsubstituted heteroaromatic system which does not contain any nitrogen atom and has 4 to 20 carbon atoms, and where the radical having the formula (4) is a heteroaromatic system which is bonded to the isoalloxazine ring via a carbon atom in the heteroaromatic system and which contains a) at least two, preferably at least three, uncharged, protonatable nitrogen atoms not bonded directly to the isoalloxazine ring, or b) at least two, preferably at least three, positively charged, preferably quaternary, nitrogen atoms not bonded directly to the isoalloxazine ring, where the R1, R2, R3 or R4 radicals which are not an organic radical of the general formula (2), (3) or (4) are the same or different and are each independently hydrogen, halogen, hydroxyl, thiol, nitro, carboxylate, aldehyde having 1 to 20 carbon atoms, ketone having 2 to 20 carbon atoms, O-alkyl having 1 to 20 carbon atoms, S-alkyl having 1 to 20 carbon atoms, O-alkenyl having 2 to 20 carbon atoms, S-alkenyl having 2 to 20 carbon atoms, O-aryl having 5 to 20 carbon atoms, S-aryl having 5 to 20 carbon atoms, ether having 2 to 20 carbon atoms, thioether having 2 to 20 carbon atoms, carboxylic ester having 1 to 20 carbon atoms, carboxamide having 1 to 20 carbon atoms, thioester having 1 to 20 carbon atoms, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms, heteroaryl which does not contain any nitrogen atom and has 4 to 20 carbon atoms, and where each of the R5 and R6 radicals is the same or different and is independently hydrogen, alkyl having 1 to 20 carbon atoms, alkenyl having 2 to 20 carbon atoms, ether having 2 to 20 carbon atoms, thioether having 2 to 20 carbon atoms, cycloalkyl having 3 to 20 carbon atoms, cycloalkenyl having 3 to 20 carbon atoms, aryl having 5 to 20 carbon atoms or heteroaryl which does not contain any nitrogen atom and has 4 to 20 carbon atoms, or B) only 1 R5 or R6 radical is an organic radical of the general formula (2), (3) or (4):

(2)

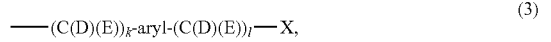
(3)

(4)

where h is an integer from 1 to 20, preferably from 1 to 19, preferably from 1 to 17, further preferably from 1 to 13, further preferably from 1 to 9, further preferably from 1 to 6, further preferably from 1 to 4, and k, l are each independently an integer from 0 to 6, preferably from 1 to 5, where D and E are each independently hydrogen, halogen, preferably chlorine, bromine, iodine or fluorine, hydroxyl, O—R$^{(VIII)}$ where R$^{(VIII)}$ is methyl, ethyl, n-propyl, n-butyl, phenyl or benzyl, O—C(=O)—R$^{(IX)}$ where R$^{(IX)}$ is hydrogen, methyl, ethyl, n-propyl, n-butyl, phenyl or benzyl, or thiol, further preferably hydrogen or hydroxyl, and where X is an organic radical having a) at least two, preferably at least three, preferably at least four, further preferably at least five, uncharged, protonatable nitrogen atoms not bonded directly to the isoalloxazine ring, or b) at least two, preferably at least three, preferably at least four, further preferably at least five, positively charged, preferably quaternary, nitrogen atoms not bonded directly to the isoalloxazine ring, where aryl is a substituted or unsubstituted aromatic system having 5 to 20 carbon atoms or a substituted or unsubstituted heteroaromatic system which does not contain any nitrogen atom and has 4 to 20 carbon atoms, and where the radical having the formula (4) is a heteroaromatic system which is bonded to the isoalloxazine ring via a carbon atom in the heteroaromatic system and which contains a) at least two, preferably at least three, uncharged, protonatable nitrogen atoms not bonded directly to the isoalloxazine ring, or b) at least two, preferably at least three, positively charged, preferably quaternary, nitrogen atoms not bonded directly to the isoalloxazine ring, and where the R5 and R6 radical which is not an organic radical of the general formula (2), (3) or (4) is hydrogen, alkyl having 1 to 20 carbon atoms, alkenyl having 2 to 20 carbon atoms, ether having 2 to 20 carbon atoms, thioether having 2 to 20 carbon atoms, cycloalkyl having 3 to 20 carbon atoms, cycloalkenyl having 3 to 20 carbon atoms, aryl having 5 to 20 carbon atoms or heteroaryl which does not contain any nitrogen atom and has 4 to 20 carbon atoms, and where the R1 to R4 radicals are the same or different and are each independently hydrogen, halogen, hydroxyl, thiol, nitro, carboxylate, aldehyde having 1 to 20 carbon atoms, ketone having 2 to 20 carbon atoms, O-alkyl having 1 to 20 carbon atoms, S-alkyl having 1 to 20 carbon atoms, O-alkenyl having 1 to 20 carbon atoms, S-alkenyl having 1 to 20 carbon atoms, O-aryl having 5 to 20 carbon atoms, S-aryl having 5 to 20 carbon atoms, ether having 2 to 20 carbon atoms, thioether having 2 to 20 carbon atoms, carboxylic ester having 1 to 20 carbon atoms, carboxamide having 1 to 20 carbon atoms, thioester having 1 to 20 carbon atoms, alkyl having 1 to 20 carbon atoms, alkenyl having 1 to 20 carbon atoms, cycloalkyl having 3 to 20 carbon atoms, cycloalkenyl having 3 to 20 carbon atoms, aryl having 5 to 20 carbon atoms, heteroaryl which does not contain any nitrogen atom and has 4 to 20 carbon atoms, and in each case excluding compounds in which the R1, R4 and R10 radicals are hydrogen, the R2 radical is hydrogen, alkyl having 1 to 8 carbon atoms or cycloalkyl having 3 to 7 carbon atoms, the R3 radical is hydrogen, halogen, alkyl having 1 to 8 carbon atoms, O-alkyl having 1 to 8 carbon atoms or a heterocyclic radical having 4 to 7 carbon atoms, and the R5 radical is an alkyl radical which has 1 to 8 carbon atoms and is substituted by a radical of the formula —N(R$^{35}$)(R$^{36}$) or a radical of the formula —OR$^{35}$, where the R$^{35}$ radical is a radical of the formula —C$_{1-8}$alkyl(amine)-OR$^{37}$ or a 7,8-dimethylisoalloxazin-10-yl-C$_{1-8}$alkyl radical and where the R$^{36}$ radical is hydrogen or a radical of the formula —C$_{1-8}$alkyl, which may be unsubstituted or substituted, and where the $R^{37}$ radical is hydrogen, aryl having 6 to 7 carbon atoms or alkyl which may be unsubstituted or substituted and has 1 to 8 carbon atoms, and in each case additionally excluding compounds in which the R1 and R4 radicals are hydrogen, the R10 radical is hydrogen or a radical having the general formula $-C_{1-4}$alkyl-OC(O)CH$_3$, the R2 radical is hydrogen or alkyl having 8 to 8 carbon atoms and the R5 radical is a radical having the general formula $-C_{1-6}$alkyl-N($R^{31}$)—$C_{0-3}$alkyl-($R^{32}$), where $R^{31}$ is hydrogen or a radical having the formula $-C_{1-4}$alkyl and where $R^{32}$ is a radical having the formula $-C_{1-4}$alkyl-N($R^{33}$)($R^{34}$), a radical having the formula $-C_{0-4}$alkyl-aryl, a radical having the formula $-C_{0-4}$alkylheterocycloalkyl or a radical having the formula $-C_{0-4}$alkylheteroaryl, and where the $R^{33}$ and $R^{34}$ radicals are each independently hydrogen or $-C_{1-4}$alkyl.

In a further-preferred embodiment, the organic radical having a) at least two, preferably at least three, preferably at least four, further preferably at least five, uncharged, protonatable nitrogen atoms not bonded directly to the isoalloxazine ring, or b) at least two, preferably at least three, preferably at least four, further preferably at least five, positively charged, preferably quaternary, nitrogen atoms not bonded directly to the isoalloxazine ring, is a radical of the formula (2) or (3):

(2)

(3)

where h is an integer from 6 to 20, preferably from 6 to 19, preferably from 8 to 17, further preferably from 8 to 15, further preferably from 8 to 13, and k, l are each independently an integer from 0 to 6, preferably from 1 to 5, where D and E are each independently hydrogen, halogen, preferably chlorine, bromine, iodine or fluorine, hydroxyl, O—$R^{(VIII)}$ where $R^{(VIII)}$ is methyl, ethyl, n-propyl, n-butyl, phenyl or benzyl, O—C(=O)—$R^{(IX)}$ where $R^{(IX)}$ is hydrogen, methyl, ethyl, n-propyl, n-butyl, phenyl or benzyl, or thiol, further preferably hydrogen or hydroxyl, and where X is an organic radical containing a) at least two, preferably at least three, preferably at least four, further preferably at least five, uncharged, protonatable nitrogen atoms, or b) at least two, preferably at least three, preferably at least four, further preferably at least five, positively charged, preferably quaternary, nitrogen atoms, and the aryl radical is a substituted or unsubstituted aromatic system having 5 to 20 carbon atoms or a substituted or unsubstituted heteroaromatic system which does not contain any nitrogen atom and has 4 to 20 carbon atoms, where the R3 radical is preferably not an aminomethyl radical, where the nitrogen atom may be unsubstituted or substituted, and in each case excluding compounds in which the R1, R4 and R10 radicals are hydrogen, the R2 radical is hydrogen, alkyl having 1 to 8 carbon atoms or cycloalkyl having 3 to 7 carbon atoms, the R3 radical is hydrogen, halogen, alkyl having 1 to 8 carbon atoms, O-alkyl having 1 to 8 carbon atoms or a heterocyclic radical having 4 to 7 carbon atoms and the R5 radical is an alkyl radical which has 1 to 8 carbon atoms and is substituted by at least by one radical of the formula —N($R^{35}$)($R^{36}$) or a radical of the formula —O$R^{35}$, where the $R^{35}$ radical is a radical of the formula —$C_{1-8}$alkyl(amine)-O$R^{37}$ or a 7,8-dimethyl-isoalloxazin-10-yl-$C_{1-8}$alkyl radical and where the $R^{36}$ radical is hydrogen or a radical of the formula —$C_{1-8}$ alkyl which may be unsubstituted or substituted, and where the $R^{37}$ radical is hydrogen, aryl having 6 to 7 carbon atoms or alkyl which may be unsubstituted or substituted and has 1 to 8 carbon atoms, and additionally in each case excluding compounds in which the R1 and R4 radicals are hydrogen, the R10 radical is hydrogen or a radical having the general formula —$C_{1-4}$alkyl-OC(O)CH$_3$, the R2 radical is hydrogen or alkyl having 8 to 8 carbon atoms and the R5 radical is a radical having the general formula —$C_{1-6}$alkyl-N($R^{31}$)—$C_{0-3}$alkyl-($R^{32}$), where $R^{31}$ is hydrogen or a radical having the formula —$C_{1-4}$alkyl and where $R^{32}$ is a radical having the formula —$C_{1-4}$alkyl-N($R^{33}$)($R^{34}$), a radical having the formula —$C_{0-4}$alkyl-aryl, a radical having the formula —$C_{0-4}$alkylheterocycloalkyl or a radical having the formula —$C_{0-4}$alkyl-heteroaryl, and where the $R^{33}$ and $R^{34}$ radicals are each independently hydrogen or —$C_{1-4}$alkyl.

In a further preferred embodiment of variant I) of the 10H-benzo[g]pteridine-2,4-dione derivative of the formula (1), the R5 radical is an acyclic polyol radical of the general formula —CH$_2$(CH(OH))$_g$CH$_2$OH or an ether, ester or acetal thereof, where g is an integer from 1 to 10, preferably 1 to 4, and where either A) only 1 R1, R2, R3 or R4 radical is an organic radical of the general formula (2), (3) or (4):

(2)

(3)

(4)

where h is an integer from 1 to 20, preferably from 1 to 19, preferably from 1 to 17, further preferably from 1 to 13, further preferably from 1 to 9, further preferably from 1 to 6, further preferably from 1 to 4, and k, l are each independently an integer from 0 to 6, preferably from 1 to 5, where D and E are each independently hydrogen, halogen, preferably chlorine, bromine, iodine or fluorine, hydroxyl, O—$R^{(VIII)}$ where $R^{(VIII)}$ is methyl, ethyl, n-propyl, n-butyl, phenyl or benzyl, O—C(=O)—$R^{(IX)}$ where $R^{(IX)}$ is hydrogen, methyl, ethyl, n-propyl, n-butyl, phenyl or benzyl, or thiol, further preferably hydrogen or hydroxyl, and where X is an organic radical having a) at least two, preferably at least three, preferably at least four, further preferably at least five, uncharged, protonatable nitrogen atoms not bonded directly to the isoalloxazine ring, or b) at least two, preferably at least three, preferably at least four, further preferably at least five, positively charged, preferably quaternary, nitrogen atoms not bonded directly to the isoalloxazine ring, preferably with the proviso that the R3 radical is not an aminomethyl radical, where the nitrogen atom may be unsubstituted or substituted, and where aryl is a substituted or unsubstituted aromatic system having 5 to 20 carbon atoms or a substituted or unsubstituted heteroaromatic system which does not contain any nitrogen atom and has 4 to 20 carbon atoms, and where the radical having the formula (4) is a heteroaromatic system which is bonded to the isoalloxazine ring via a carbon atom in the heteroaromatic system and which contains a) at least two, preferably at least three, uncharged, protonatable nitrogen atoms not bonded directly to the isoalloxazine ring, or b) at least two, preferably at least three, positively charged, preferably quaternary, nitrogen atoms not bonded directly to the isoalloxazine ring, where the R1, R2, R3 or R4 radicals which are not an organic radical of the general formula (2), (3) or (4) are the same or different and are each independently hydrogen, halogen, hydroxyl, thiol, nitro, carboxylate, aldehyde having 1 to 20 carbon atoms, ketone having 2 to 20 carbon atoms, O-alkyl having 1 to 20 carbon atoms, S-alkyl having 1 to 20 carbon atoms, O-alkenyl having 2 to 20 carbon atoms, S-alkenyl having 2 to 20 carbon atoms, O-aryl having 5 to 20 carbon atoms, S-aryl having 5 to 20 carbon atoms, ether having 2 to 20 carbon atoms, thioether having 2 to 20 carbon atoms, carboxylic ester having 1 to 20 carbon atoms, carboxamide having 1 to 20 carbon atoms, thioester having 1 to 20 carbon atoms, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms or heteroaryl which does not contain any nitrogen atom and has 4 to 20 carbon atoms, and where the R6 radical is hydrogen, alkyl having 1 to 20 carbon atoms, alkenyl having 2 to 20 carbon atoms, ether having 2 to 20 carbon atoms, thioether having 2 to 20 carbon atoms, cycloalkyl having 3 to 20 carbon atoms, cycloalkenyl having 3 to 20 carbon atoms, aryl having 5 to 20 carbon atoms or heteroaryl which does not contain any nitrogen atom and has 4 to 20 carbon atoms, or B) only the R6 radical is an organic radical of the general formula (2), (3) or (4):

  (2)

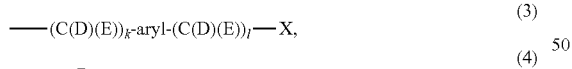  (3)

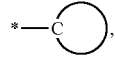  (4)

where h is an integer from 1 to 20, preferably from 1 to 19, preferably from 1 to 17, further preferably from 1 to 13, further preferably from 1 to 9, further preferably from 1 to 6, further preferably from 1 to 4, and k, l are each independently an integer from 0 to 6, preferably from 1 to 5, where D and E are each independently hydrogen, halogen, preferably chlorine, bromine, iodine or fluorine, hydroxyl, O—$R^{(VIII)}$ where $R^{(VIII)}$ is methyl, ethyl, n-propyl, n-butyl, phenyl or benzyl, O—C(=O)—$R^{(IX)}$ where $R^{(IX)}$ is hydrogen, methyl, ethyl, n-propyl, n-butyl, phenyl or benzyl, or thiol, further preferably hydrogen or hydroxyl, and where X is an organic radical having a) at least two, preferably at least three, preferably at least four, further preferably at least five, uncharged, protonatable nitrogen atoms not bonded directly to the isoalloxazine ring, or b) at least two, preferably at least three, preferably at least four, further preferably at least five, positively charged, preferably quaternary, nitrogen atoms not bonded directly to the isoalloxazine ring, and where aryl is a substituted or unsubstituted aromatic system having 5 to 20 carbon atoms or a substituted or unsubstituted heteroaromatic system which does not contain any nitrogen atom and has 4 to 20 carbon atoms, and where the radical having the formula (4) is a heteroaromatic system which is bonded to the isoalloxazine ring via a carbon atom in the heteroaromatic system and which contains a) at least two, preferably at least three, uncharged, protonatable nitrogen atoms not bonded directly to the isoalloxazine ring, or b) at least two, preferably at least three, positively charged, preferably quaternary, nitrogen atoms not bonded directly to the isoalloxazine ring, and where the R1 to R4 radicals are the same or different and are each independently hydrogen, halogen, hydroxyl, thiol, nitro, carboxylate, aldehyde having 1 to 20 carbon atoms, ketone having 2 to 20 carbon atoms, O-alkyl having 1 to 20 carbon atoms, S-alkyl having 1 to 20 carbon atoms, O-alkenyl having 1 to 20 carbon atoms, S-alkenyl having 1 to 20 carbon atoms, O-aryl having 5 to 20 carbon atoms, S-aryl having 5 to 20 carbon atoms, ether having 2 to 20 carbon atoms, thioether having 2 to 20 carbon atoms, carboxylic ester having 1 to 20 carbon atoms, carboxamide having 1 to 20 carbon atoms, thioester having 1 to 20 carbon atoms, alkyl having 1 to 20 carbon atoms, alkenyl having 1 to 20 carbon atoms, cycloalkyl having 3 to 20 carbon atoms, cycloalkenyl having 3 to 20 carbon atoms, aryl having 5 to 20 carbon atoms or heteroaryl which does not contain any nitrogen atom and has 4 to 20 carbon atoms.

In a further-preferred embodiment of variant I) of the 10H-benzo[g]pteridine-2,4-dione derivative of the formula (1), the R5 radical is an acyclic polyol radical of the general formula —$CH_2(CH(OH))_gCH_2OH$ or an ether, ester or acetal thereof, where g is an integer from 1 to 10, preferably 1 to 4, and where either A) only 1 R1, R2, R3 or R4 radical is an organic radical of the general formula —$(C(D)(E))_h$-X or —$(C(D)(E))_k$-aryl-$(C(D)(E))_l$-X, where h is an integer from 1 to 20, preferably from 1 to 19, preferably from 1 to 17, further preferably from 1 to 13, further preferably from 1 to 9, further preferably from 1 to 6, further preferably from 1 to 4, and k, l are each independently an integer from 0 to 6, preferably from 1 to 5, where D and E are each independently hydrogen, halogen, preferably chlorine, bromine, iodine or fluorine, hydroxyl, O—$R^{(VIII)}$ where $R^{(VIII)}$ is methyl, ethyl, n-propyl, n-butyl, phenyl or benzyl, O—C(=O)—$R^{(IX)}$ where $R^{(IX)}$ is hydrogen, methyl, ethyl, n-propyl, n-butyl, phenyl or benzyl, or thiol, further preferably hydrogen or hydroxyl, where X is an organic radical containing a) at least two, preferably at least three, preferably at least four, further preferably at least five, uncharged, protonatable nitrogen atoms not bonded directly to the isoalloxazine ring, or b) at least two, preferably at least three, preferably at least four, further preferably at least five, positively charged, preferably quaternary, nitrogen atoms not bonded directly to the isoalloxazine ring, and aryl is a substituted or unsubstituted aromatic system having 5 to 20 carbon atoms or a substituted or unsubstituted heteroaromatic system which does not contain any nitrogen atom and has 4 to 20 carbon atoms, and where the R1, R2, R3 or R4 radicals which are not an organic radical of the general formula —(C(D)(E))$_h$-X or —(C(D)(E))$_k$-aryl-(C(D)(E))$_l$-X are the same or different and are each independently hydrogen, halogen, hydroxyl, thiol, nitro, carboxylate, aldehyde having 1 to 20 carbon atoms, ketone having 2 to 20 carbon atoms, O-alkyl having 1 to 20 carbon atoms, S-alkyl having 1 to 20 carbon atoms, O-alkenyl having 2 to 20 carbon atoms, S-alkenyl having 2 to 20 carbon atoms, O-aryl having 5 to 20 carbon atoms, S-aryl having 5 to 20 carbon atoms, ether having 2 to 20 carbon atoms, thioether having 2 to 20 carbon atoms, carboxylic ester having 1 to 20 carbon atoms, carboxamide having 1 to 20 carbon atoms, thioester having 1 to 20 carbon atoms, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms or heteroaryl which does not contain any nitrogen atom and has 4 to 20 carbon atoms, and where R6 is hydrogen, alkyl having 1 to 20 carbon atoms, alkenyl having 2 to 20 carbon atoms, ether having 2 to 20 carbon atoms, thioether having 2 to 20 carbon atoms, cycloalkyl having 3 to 20 carbon atoms, cycloalkenyl having 3 to 20 carbon atoms, aryl having 5 to 20 carbon atoms or heteroaryl which does not contain any nitrogen atom and has 4 to 20 carbon atoms, or B) only the R6 radical is an organic radical of the general formula —(C(D)(E))$_h$-X or —(C(D)(E))$_k$-aryl-(C(D)(E))$_l$-X, where h is an integer from 1 to 20, preferably from 1 to 19, preferably from 1 to 17, further preferably from 1 to 13, further preferably from 1 to 9, further preferably from 1 to 6, further preferably from 1 to 4, and k, l are each independently an integer from 0 to 6, preferably from 1 to 5, where D and E are each independently hydrogen, halogen, preferably chlorine, bromine, iodine or fluorine, hydroxyl, O—R$^{(VIII)}$ where R$^{(VIII)}$ is methyl, ethyl, n-propyl, n-butyl, phenyl or benzyl, O—C(=O)—R$^{(IX)}$ where R$^{(IX)}$ is hydrogen, methyl, ethyl, n-propyl, n-butyl, phenyl or benzyl, or thiol, further preferably hydrogen or hydroxyl, where X is an organic radical containing a) at least two, preferably at least three, preferably at least four, further preferably at least five, uncharged, protonatable nitrogen atoms not bonded directly to the isoalloxazine ring, or b) at least two, preferably at least three, preferably at least four, further preferably at least five, positively charged, preferably quaternary, nitrogen atoms not bonded directly to the isoalloxazine ring, and aryl is a substituted or unsubstituted aromatic system having 5 to 20 carbon atoms or a substituted or unsubstituted heteroaromatic system which does not contain any nitrogen atom and has 4 to 20 carbon atoms, and where the R1 to R4 radicals are the same or different and are each independently hydrogen, halogen, hydroxyl, thiol, nitro, carboxylate, aldehyde having 1 to 20 carbon atoms, ketone having 2 to 20 carbon atoms, O-alkyl having 1 to 20 carbon atoms, S-alkyl having 1 to 20 carbon atoms, O-alkenyl having 1 to 20 carbon atoms, S-alkenyl having 1 to 20 carbon atoms, O-aryl having 5 to 20 carbon atoms, S-aryl having 5 to 20 carbon atoms, ether having 2 to 20 carbon atoms, thioether having 2 to 20 carbon atoms, carboxylic ester having 1 to 20 carbon atoms, carboxamide having 1 to 20 carbon atoms, thioester having 1 to 20 carbon atoms, alkyl having 1 to 20 carbon atoms, alkenyl having 1 to 20 carbon atoms, cycloalkyl having 3 to 20 carbon atoms, cycloalkenyl having 3 to 20 carbon atoms, aryl having 5 to 20 carbon atoms or heteroaryl which does not contain any nitrogen atom and has 4 to 20 carbon atoms.

Further preferably, the R5 radical is an acyclic polyol radical selected from the group consisting of arabityl, ribityl, xylityl, erythrityl, threityl, lactityl, mannityl and sorbityl, further preferably D-ribityl and D-arabityl, or an ether, ester or acetal thereof.

In a further preferred embodiment of variant I) of the 10H-benzo[g]pteridine-2,4-dione derivative of the formula (1), only the R5 radical is an acyclic polyol radical of the general formula —CH$_2$(CH(OZ))$_f$CH$_{(3-e)}$(OZ)$_e$ where e is 0, 1 or 2 and f is an integer from 1 to 10, preferably 1 to 4, and where Z is hydrogen, alkyl having 1 to 20 carbon atoms, carboxylic ester having 1 to 20 carbon atoms or an X radical, where X is an organic radical containing a) at least one, preferably at least two, preferably at least three, preferably at least four, further preferably at least five, uncharged, protonatable nitrogen atoms or b) at least two, preferably at least three, preferably at least four, further preferably at least five, positively charged, preferably quaternary, nitrogen atoms, when at least two of the Z radicals are an X radical, or where X is an organic radical containing a) at least two, preferably at least three, preferably at least four, further preferably at least five, uncharged, protonatable nitrogen atoms or b) at least two, preferably at least three, preferably at least four, further preferably at least five, positively charged, preferably quaternary, nitrogen atoms, when only 1 Z radical is an X radical, where R6 is hydrogen, alkyl having 1 to 20 carbon atoms, alkenyl having 2 to 20 carbon atoms, ether having 2 to 20 carbon atoms, thioether having 2 to 20 carbon atoms, cycloalkyl having 3 to 20 carbon atoms, cycloalkenyl having 3 to 20 carbon atoms, aryl having 5 to 20 carbon atoms or heteroaryl which does not contain any nitrogen atom and has 4 to 20 carbon atoms, and where the R1 to R4 radicals are the same or different and are each independently hydrogen, halogen, hydroxyl, thiol, nitro, carboxylate, aldehyde having 1 to 20 carbon atoms, ketone having 2 to 20 carbon atoms, O-alkyl having 1 to 20 carbon atoms, S-alkyl having 1 to 20 carbon atoms, O-alkenyl having 1 to 20 carbon atoms, S-alkenyl having 1 to 20 carbon atoms, O-aryl having 5 to 20 carbon atoms, S-aryl having 5 to 20 carbon atoms, ether having 2 to 20 carbon atoms, thioether having 2 to 20 carbon atoms, carboxylic ester having 1 to 20 carbon atoms, carboxamide having 1 to 20 carbon atoms, thioester having 1 to 20 carbon atoms, alkyl having 1 to 20 carbon atoms, alkenyl having 1 to 20 carbon atoms, cycloalkyl having 3 to 20 carbon atoms, cycloalkenyl having 3 to 20 carbon atoms, aryl having 5 to 20 carbon atoms or heteroaryl which does not contain any nitrogen atom and has 4 to 20 carbon atoms.

Further preferably, the R5 radical is an acyclic polyol radical of the general formula —$CH_2(CH(OZ))_fCH_{(3-e)}(OZ)_e$ where e is 1, or 2 and f is an integer from 1 to 10, preferably 1 to 4, and where Z is an ester of an aminocarboxylic acid which derives from an aminocarboxylic acid, preferably alpha-aminocarboxylic acid, having 1 to 20 carbon atoms, preferably selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, L-homoserine, ornithine, N5-(aminocarbonyl)-L-ornithine, L-(−)-carnitine, alpha-phenylglycine, L-3,4-dihydroxyphenylalanine, 3,6-diaminohexanoic acid, N-(aminoiminomethyl)-N-methylglycine, gamma-aminobutyric acid, L-5-hydroxytryptophan, norleucine and 2,6-diaminopimelic acid, further preferably arginine, glycine, lysine, ornithine, 3,6-diaminohexanoic acid and gamma-aminobutyric acid, even further preferably glycine and lysine, where preferably at least one amino group in each case may be substituted by methyl radicals.

In a further-preferred embodiment of variant I) of the 10H-benzo[g]pteridine-2,4-dione derivative, the organic radical having a) at least two, preferably at least three, preferably at least four, further preferably at least five, uncharged, protonatable nitrogen atoms not bonded directly to the isoalloxazine ring, or b) at least two, preferably at least three, preferably at least four, further preferably at least five, positively charged, preferably quaternary, nitrogen atoms not bonded directly to the isoalloxazine ring, is a radical of the formula (2), (3) or (4):

  (2)

  (3)

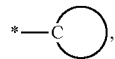  (4)

where h is an integer from 6 to 20, preferably from 6 to 19, preferably from 8 to 17, further preferably from 8 to 15, further preferably from 8 to 13, and k, l are each independently an integer from 0 to 6, preferably from 1 to 5, where D and E are each independently hydrogen, halogen, preferably chlorine, bromine, iodine or fluorine, hydroxyl, O—$R^{(VIII)}$ where $R^{(VIII)}$ is methyl, ethyl, n-propyl, n-butyl, phenyl or benzyl, O—C(=O)—$R^{(IX)}$ where R(IX) is hydrogen, methyl, ethyl, n-propyl, n-butyl, phenyl or benzyl, or thiol, further preferably hydrogen or hydroxyl, and where X is an organic radical containing a) at least two, preferably at least three, preferably at least four, further preferably at least five, uncharged, protonatable nitrogen atoms, or b) at least two, preferably at least three, preferably at least four, further preferably at least five, positively charged, preferably quaternary, nitrogen atoms, and the aryl radical is a substituted or unsubstituted aromatic system having 5 to 20 carbon atoms or a substituted or unsubstituted heteroaromatic system which does not contain any nitrogen atom and has 4 to 20 carbon atoms, and where the radical having the formula (4) is a heteroaromatic system which is bonded to the isoalloxazine ring via a carbon atom in the heteroaromatic system and which contains a) at least two, preferably at least three, uncharged, protonatable nitrogen atoms, or b) at least two, preferably at least three, positively charged, preferably quaternary, nitrogen atoms.

In a further-preferred embodiment of variant I) of the 10H-benzo[g]pteridine-2,4-dione derivative of the formula (1), the organic X radical having a) at least two, preferably at least three, preferably at least four, further preferably at least five, uncharged, protonatable nitrogen atoms, or b) at least two, preferably at least three, preferably at least four, further preferably at least five, positively charged, preferably quaternary, nitrogen atoms, is a radical of the general formula (2):

  (2)

where A is an oxygen or sulfur atom and where n is an integer from 1 to 8 and m is an integer from 0 to 100, and where B is a radical of the formula (3a), (3b), (4a), (4b), (5a) or (5b):

  (3a)

  (3b)

  (4a)

  (4b)

  (5a)

  (5b)

and where the $R^{(I)}$ radical is an aryl radical having 5 to 20 carbon atoms, a heterocyclic radical having 5 to 20 carbon atoms, an alkyl radical, which may be straight-chain or branched, having 1 to 20 carbon atoms, an alkenyl radical, which may be straight-chain or branched, having 2 to 20 carbon atoms, a hydroxyalkyl radical, which may be straight-chain or branched, having 1 to 20 carbon atoms, an ether radical, which may be straight-chain or branched, having 2 to 20 carbon atoms, a thioether radical, which may be straight-chain or branched, having 2 to 20 carbon atoms, or an alkylamino radical, which may be straight-chain or branched, having 1 to 20 carbon atoms, where each of the $R^{(II)}$, $R^{(III)}$, $R^{(IV)}$, $R^{(V)}$ and $R^{(VI)}$ radicals is independently hydrogen, an aryl radical having 5 to 20 carbon atoms, a heterocyclic radical having 5 to 20 carbon atoms, an alkyl radical, which may be straight-chain or branched, having 1 to 20 carbon atoms, an alkenyl radical, which may be straight-chain or branched, having 2 to 20 carbon atoms, a hydroxyalkyl radical, which may be straight-chain or branched, having 1 to 20 carbon atoms, an ether radical, which may be straight-chain or branched, having 2 to 20 carbon atoms, a thioether radical, which may be straight-chain or branched, having 2 to 20 carbon atoms, or an alkylamino radical, which may be straight-chain or branched, having 1 to 20 carbon atoms and where each of the aforementioned aryl radicals, heterocyclic radicals, alkyl radicals, alkenyl radicals, hydroxyalkyl radicals, ether radicals, thioether radicals and alkylamino radicals is substituted at least by one, preferably at least two, preferably at least three, preferably at least four, further preferably at least five, amino radical(s) and/or alkylamino radical(s), which may be straight-chain or branched, having 1 to 20 carbon atoms, for example aminomethyl, 2-aminoethyl, dimethylaminomethyl or (trimethylammonio)methyl, and/or guanidino radical, and where the radical having the formula (4a) and the radical having the formula (5a):

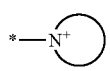

(4a)

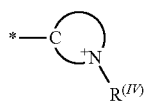

(5a)

is a substituted or unsubstituted heterocyclic radical having 5 to 7 ring atoms including 2 to 4 nitrogen atoms and at least 1 carbon atom and optionally 1 or 2 oxygen or sulfur atoms, where 1 nitrogen atom forms a double bond, and where the radical having the formula (4b) and the radical having the formula (5b):

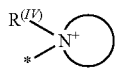

(4b)

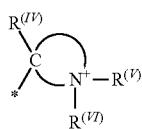

(5b)

is a substituted or unsubstituted heterocyclic radical having 5 to 7 ring atoms including 2 to 4 nitrogen atoms and at least 1 carbon atom and optionally 1 or 2 oxygen or sulfur atoms.

In a further-preferred embodiment of variant I) of the 10H-benzo[g]pteridine-2,4-dione derivative of the formula (1), the radical of the formula (5a) is selected from the group consisting of radicals of the formulae (22a), (22b) and (22c)

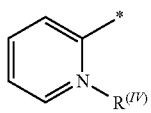

(22a)

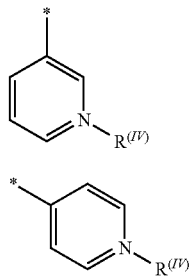

(22b)

(22c)

where each $R^{(IV)}$ is selected from the group consisting of aryl radicals having 5 to 20 carbon atoms, for example phenyl or benzyl, heterocyclic radicals having 5 to 20 carbon atoms, for example 2-pyridyl, 3-pyridyl, 4-pyridyl, 1-methylpyridin-1-ium-2-yl, 1-methylpyridin-1-ium-3-yl or 1-methylpyridin-1-ium-4-yl, alkyl radicals which may be straight-chain or branched and have 1 to 20 carbon atoms, for example methyl, ethyl, n-propyl, i-propyl, n-butyl or t-butyl, alkenyl radicals which may be straight-chain or branched and have 2 to 20 carbon atoms, hydroxyalkyl radicals which may be straight-chain or branched and have 1 to 20 carbon atoms, for example hydroxymethyl, 2-hydroxyethyl, 3-hydroxypropyl or 1-hydroxy-1-methylethyl, ether radicals which may be straight-chain or branched and have 2 to 20 carbon atoms, for example methoxymethyl, methoxyethyl, methoxypropyl, ethoxymethyl, ethoxyethyl, ethoxypropyl, propoxymethyl, propoxyethyl or propoxypropyl, thioether radicals which may be straight-chain or branched and have 2 to 20 carbon atoms, for example methylsulfanylmethyl, ethylsulfanylmethyl, 2-ethylsulfanylethyl or 3-methylsulfanylpropyl, and alkylamino radicals which may be straight-chain or branched and have 1 to 20 carbon atoms, for example aminomethyl, 2-aminoethyl, dimethylaminomethyl or (trimethylammonio)methyl.

In a preferred embodiment of variant I) of the 10H-benzo[g]pteridine-2,4-dione derivative of the formula (1), the radical of the formula (4a) is selected from the group consisting of radicals of the formulae (23a), (23b) and (23c):

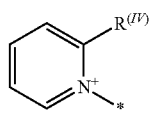

(23a)

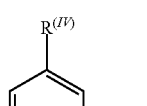

(23b)

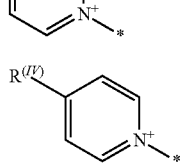

(23c)

where each $R^{(IV)}$ is selected from the group consisting of hydrogen, aryl radicals having 5 to 20 carbon atoms, for example phenyl or benzyl, heterocyclic radicals having 5 to 20 carbon atoms, for example 2-pyridyl, 3-pyridyl, 4-pyridyl, 1-methylpyridin-1-ium-2-yl, 1-methylpyridin-1-ium-3-yl or 1-methylpyridin-1-ium-4-yl, alkyl radicals which may be straight-chain or branched and have 1 to 20 carbon atoms, for example methyl, ethyl, n-propyl, i-propyl, n-butyl or t-butyl, alkenyl radicals which may be straight-chain or branched and have 2 to 20 carbon atoms, hydroxyalkyl radicals which may be straight-chain or branched and have 1 to 20 carbon atoms, for example hydroxymethyl, 2-hydroxyethyl, 3-hydroxypropyl or 1-hydroxy-1-methylethyl, ether radicals which may be straight-chain or branched and have 2 to 20 carbon atoms, for example methoxymethyl, methoxyethyl, methoxypropyl, ethoxymethyl, ethoxyethyl, ethoxypropyl, propoxymethyl, propoxyethyl or propoxypropyl, thioether radicals which may be straight-chain or branched and have 2 to 20 carbon atoms, for example methylsulfanylmethyl, ethylsulfanylmethyl, 2-ethylsulfanylethyl or 3-methylsulfanylpropyl, and alkylamino radicals which may be straight-chain or branched and have 1 to 20 carbon atoms, for example aminomethyl, 2-aminoethyl, dimethylaminomethyl or (trimethylammonio)methyl.

In a preferred embodiment of variant I) of the 10H-benzo[g]pteridine-2,4-dione derivative of the formula (1), the $R^{(II)}$, $R^{(III)}$, $R^{(IV)}$, $R^{(V)}$ and $R^{(VI)}$ radicals are each independently hydrogen or an alkyl radical of the general formula $-(CH_2)_n-CH_3$ and the $R^{(I)}$ radical is an alkyl radical of the general formula $-(CH_2)_n-CH_3$, where each n is an integer from 0 to 19, preferably from 1 to 17, where the aforementioned alkyl radicals are substituted at least by one, preferably at least two, preferably at least three, preferably at least four, further preferably at least five, amino radical(s) and/or alkylamino radical(s) which may be straight-chain or branched and have 1 to 20 carbon atoms, preferably 1 to 4 carbon atoms, for example aminomethyl, 2-aminoethyl, dimethylaminomethyl or (trimethylammonio)methyl, and/or guanidino radical.

In a preferred embodiment of variant I) of the 10H-benzo[g]pteridine-2,4-dione derivative of the formula (1), the $R^{(II)}$, $R^{(III)}$, $R^{(IV)}$, $R^{(V)}$ and $R^{(VI)}$ radicals are each independently hydrogen, methyl, ethyl, prop-1-yl, prop-2-yl, but-1-yl, but-2-yl, 2-methylprop-1-yl, 2-methylprop-2-yl, pent-1-yl, pent-2-yl, pent-3-yl, 2-methylbut-1-yl, 2-methylbut-2-yl, 2-methylbut-3-yl, 2-methylbut-4-yl, 2,2-dimethylprop-1-yl, hex-1-yl, hex-2-yl, hex-3-yl, hept-1-yl, oct-1-yl, 2-methylpent-1-yl, 2-methylpent-2-yl, 2-methylpent-3-yl, 2-methylpent-4-yl, 2-methylpent-5-yl, 3-methylpent-1-yl, 3-methylpent-2-yl, 3-methylpent-3-yl, 2,2-dimethylbut-1-yl, 2,2-dimethylbut-3-yl, 2,2-dimethylbut-4-yl, 2,3-dimethylbut-1-yl or 2,3-dimethylbut-2-yl, and the $R^{(I)}$ radical is methyl, ethyl, prop-1-yl, prop-2-yl, but-1-yl, but-2-yl, 2-methylprop-1-yl, 2-methyl-prop-2-yl, pent-1-yl, pent-2-yl, pent-3-yl, 2-methylbut-1-yl, 2-methylbut-2-yl, 2-methylbut-3-yl, 2-methylbut-4-yl, 2,2-dimethylprop-1-yl, hex-1-yl, hex-2-yl, hex-3-yl, hept-1-yl, oct-1-yl, 2-methylpent-1-yl, 2-methylpent-2-yl, 2-methylpent-3-yl, 2-methylpent-4-yl, 2-methylpent-5-yl, 3-methylpent-1-yl, 3-methylpent-2-yl, 3-methylpent-3-yl, 2,2-dimethylbut-1-yl, 2,2-dimethylbut-3-yl, 2,2-dimethylbut-4-yl, 2,3-dimethylbut-1-yl or 2,3-dimethylbut-2-yl, where the aforementioned alkyl radicals are substituted at least by one, preferably at least two, preferably at least three, preferably at least four, further preferably at least five, amino radical(s) and/or alkylamino radical(s) which may be straight-chain or branched and have 1 to 20 carbon atoms, preferably 1 to 4 carbon atoms, for example aminomethyl, 2-aminoethyl, dimethylaminomethyl or (trimethylammonio)methyl, and/or guanidino radical.

In a particularly preferred embodiment, the $R^{(I)}$, $R^{(II)}$, $R^{(III)}$, $R^{(IV)}$, $R^{(V)}$ and $R^{(VI)}$ radicals may each independently be methyl, ethyl, prop-1-yl, but-1-yl, pent-1-yl, hex-1-yl, hept-1- or oct-1-yl, where the aforementioned alkyl radicals are substituted at least by one, preferably at least two, preferably at least three, preferably at least four, further preferably at least five, amino radical(s) and/or alkylamino radical(s) which may be straight-chain or branched and have 1 to 20 carbon atoms, for example aminomethyl, 2-aminoethyl, dimethylaminomethyl or (trimethylammonio)methyl, and/or guanidino radical.

In a preferred embodiment of variant I) of the 10H-benzo[g]pteridine-2,4-dione derivative of the formula (1), the $R^{(II)}$, $R^{(III)}$, $R^{(IV)}$, $R^{(V)}$ and $R^{(VI)}$ radicals are each independently hydrogen or a radical of the formula (6) to (9):

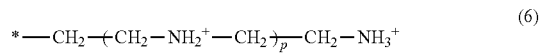

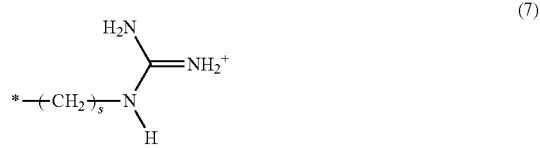

and the $R^{(I)}$ radical is a radical of the formula (6) to (9), where each p is an integer from 1 to 10, preferably from 1 to 7, further preferably from 1 to 3, and where s, r, q are each independently an integer from 1 to 20, preferably from 1 to 8, further preferably from 1 to 4, selected.

In a further-preferred embodiment of variant I) of the 10H-benzo[g]pteridine-2,4-dione derivative of the formula (1), the $R^{(II)}$, $R^{(III)}$, $R^{(IV)}$, $R^{(V)}$ and $R^{(VI)}$ radicals are each independently hydrogen or a polyamine radical of the general formula $-[(CH_2)_a-N(R^{(VII)})-(CH_2)_b-]_cNH_{(3-g)}(R^{(VIII)})_g^+$, and the $R^{(I)}$ radical is a polyamine radical of the general formula $-[(CH_2)_a-N(R^{(VII)})-(CH_2)_b-]_cNH_{(3-g)}(R^{(VIII)})_g^+$, where each c is an integer from 1 to 10, preferably from 1 to 7, further preferably from 1 to 3, a and b are each independently an integer from 1 to 10, preferably from 1 to 4, further preferably from 2 to 3, g is 0, 1, 2 or 3 and $R^{(VII)}$ and $R^{(VIII)}$ are each independently hydrogen, methyl or ethyl.

In variant II) of the inventive 10H-benzo[g]pteridine-2,4-dione derivative of the formula (1)

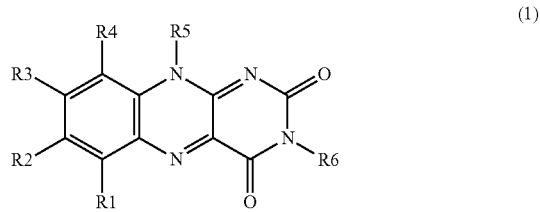

only 1 R1, R2, R3, R4, R5 or R6 radical is an organic radical having:
a) at least one, preferably at least two, preferably at least three, preferably at least four, further preferably at least five, uncharged, protonatable nitrogen atom(s) not bonded directly to the isoalloxazine ring, and
b) at least one, preferably at least two, preferably at least three, preferably at least four, further preferably at least five, positively charged, preferably quaternary, nitrogen atom(s) not bonded directly to the isoalloxazine ring, and where each of the R1, R2, R3 and R4 radicals which is not an organic radical having a) at least one, preferably at least two, preferably at least three, preferably at least four, further preferably at least five, uncharged, protonatable nitrogen atom(s) not bonded directly to the isoalloxazine ring, or b) at least one, preferably at least two, preferably at least three, preferably at least four, further preferably at least five, positively charged, preferably quaternary, nitrogen atom(s) not bonded directly to the isoalloxazine ring, is the same or different and is independently hydrogen, halogen, hydroxyl, thiol, nitro, carboxylate, aldehyde having 1 to 20 carbon atoms, ketone having 2 to 20 carbon atoms, O-alkyl having 1 to 20 carbon atoms, S-alkyl having 1 to 20 carbon atoms, O-alkenyl having 2 to 20 carbon atoms, S-alkenyl having 2 to 20 carbon atoms, O-aryl having 5 to 20 carbon atoms, S-aryl having 5 to 20 carbon atoms, carboxylic ester having 1 to 20 carbon atoms, carboxamide having 1 to 20 carbon atoms, thioester having 1 to 20 carbon atoms, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms or heteroaryl having 4 to 20 carbon atoms, which does not contain any nitrogen atoms, and where each of the R5 and R6 radicals which is not an organic radical having a) at least one, preferably at least two, preferably at least three, preferably at least four, further preferably at least five, uncharged, protonatable nitrogen atom(s) not bonded directly to the isoalloxazine ring, or b) at least one, preferably at least two, preferably at least three, preferably at least four, further preferably at least five, positively charged, preferably quaternary, nitrogen atom(s) not bonded directly to the isoalloxazine ring, is the same or different and is independently hydrogen, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms or heteroaryl having 4 to 20 carbon atoms, which does not contain any nitrogen atoms.

In a preferred embodiment of variant II) of the 10H-benzo[g]pteridine-2,4-dione derivative of the formula (1), the R5 radical is an acyclic polyol radical of the general formula —$CH_2(CH(OH))_gCH_2OH$ or an ether, ester or acetal thereof, where g is an integer from 1 to 10, preferably 1 to 4, and where A) only 1 R1, R2, R3 or R4 radical is an organic radical having:
a) at least one, preferably at least two, preferably at least three, preferably at least four, further preferably at least five, uncharged, protonatable nitrogen atom(s) not bonded directly to the isoalloxazine ring, and
b) at least one, preferably at least two, preferably at least three, preferably at least four, further preferably at least five, positively charged, preferably quaternary, nitrogen atom(s) not bonded directly to the isoalloxazine ring,
where each of the R1, R2, R3 and R4 radicals which is not an organic radical having a) at least one, preferably at least two, preferably at least three, preferably at least four, further preferably at least five, uncharged, protonatable nitrogen atom(s) not bonded directly to the isoalloxazine ring, or b) at least one, preferably at least two, preferably at least three, preferably at least four, further preferably at least five, positively charged, preferably quaternary, nitrogen atom(s) not bonded directly to the isoalloxazine ring, is the same or different and is independently hydrogen, halogen, hydroxyl, thiol, nitro, carboxylate, aldehyde having 1 to 20 carbon atoms, ketone having 2 to 20 carbon atoms, O-alkyl having 1 to 20 carbon atoms, S-alkyl having 1 to 20 carbon atoms, O-alkenyl having 2 to 20 carbon atoms, S-alkenyl having 2 to 20 carbon atoms, O-aryl having 5 to 20 carbon atoms, S-aryl having 5 to 20 carbon atoms, carboxylic ester having 1 to 20 carbon atoms, carboxamide having 1 to 20 carbon atoms, thioester having 1 to 20 carbon atoms, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms or heteroaryl having 4 to 20 carbon atoms, which does not contain any nitrogen atoms, and
where the R6 radical is hydrogen, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms or heteroaryl having 4 to 20 carbon atoms, which does not contain any nitrogen atoms, or B) only the R6 radical is in organic radical having:
a) at least one, preferably at least two, preferably at least three, preferably at least four, further preferably at least five, uncharged, protonatable nitrogen atom(s) not bonded directly to the isoalloxazine ring, and
b) at least one, preferably at least two, preferably at least three, preferably at least four, further preferably at least five, positively charged, preferably quaternary, nitrogen atom(s) not bonded directly to the isoalloxazine ring,
where the R1 to R4 radicals are the same or different and are each independently hydrogen, halogen, hydroxyl, thiol, nitro, carboxylate, aldehyde having 1 to 20 carbon atoms, ketone having 2 to 20 carbon atoms, O-alkyl having 1 to 20 carbon atoms, S-alkyl having 1 to 20 carbon atoms, O-alkenyl having 1 to 20 carbon atoms, S-alkenyl having 1 to 20 carbon atoms, O-aryl having 5 to 20 carbon atoms, S-aryl having 5 to 20 carbon atoms, ether having 2 to 20 carbon atoms, thioether having 2 to 20 carbon atoms, carboxylic ester having 1 to 20 carbon atoms, carboxamide having 1 to 20 carbon atoms, thioester having 1 to 20 carbon atoms, alkyl having 1 to 20 carbon atoms, alkenyl having 1 to 20 carbon atoms, cycloalkyl having 3 to 20 carbon atoms, cycloalkenyl having 3 to 20 carbon atoms, aryl having 5 to 20 carbon atoms or heteroaryl which does not contain any nitrogen atom and has 4 to 20 carbon atoms.

Further preferably, the R5 radical is an acyclic polyol radical selected from the group consisting of arabityl, ribityl, xylityl, erythrityl, threityl, lactityl, mannityl and sorbityl, further preferably D-ribityl and D-arabityl, or an ether, ester or acetal thereof.

In a preferred embodiment of variant II) of the 10H-benzo[g]pteridine-2,4-dione derivative of the formula (1), the organic radical having a) at least one, preferably at least two, preferably at least three, preferably at least four, further preferably at least five, uncharged, protonatable nitrogen atom(s) not bonded directly to the isoalloxazine ring, and b) at least one, preferably at least two, preferably at least three, preferably at least four, further preferably at least five, positively charged, preferably quaternary, nitrogen atom(s) not bonded directly to the isoalloxazine ring, is a radical of the formula (2), (3) or (4):

 (2)

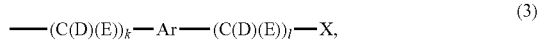 (3)

 (4)

where h is an integer from 1 to 20, preferably from 1 to 19, preferably from 1 to 17, further preferably from 1 to 13, further preferably from 1 to 9, further preferably from 1 to 6, further preferably from 1 to 4, and k, l are each independently an integer from 0 to 6, preferably from 1 to 5, where D and E are each independently hydrogen, halogen, preferably chlorine, bromine, iodine or fluorine, hydroxyl, O—$R^{(VIII)}$ where $R^{(VIII)}$ is methyl, ethyl, n-propyl, n-butyl, phenyl or benzyl, O—C(=O)—$R^{(IX)}$ where $R^{(IX)}$ is hydrogen, methyl, ethyl, n-propyl, n-butyl, phenyl or benzyl, or thiol, further preferably hydrogen or hydroxyl, and where X is an organic radical containing a) at least one, preferably at least two, preferably at least three, preferably at least four, further preferably at least five, uncharged, protonatable nitrogen atom(s), and b) at least one, preferably at least two, preferably at least three, preferably at least four, further preferably at least five, positively charged, preferably quaternary, nitrogen atom(s), and the aryl radical is a substituted or unsubstituted aromatic system having 5 to 20 carbon atoms or a substituted or unsubstituted heteroaromatic system which does not contain any nitrogen atom and has 4 to 20 carbon atoms, and where the radical having the formula (4) is a heteroaromatic system which is bonded to the isoalloxazine ring via a carbon atom in the heteroaromatic system and which contains a) at least one, preferably at least two, preferably at least three, uncharged, protonatable nitrogen atom(s), or b) at least one, preferably at least two, preferably at least three, positively charged, preferably quaternary, nitrogen atom(s).

In a further-preferred embodiment of variant II) of the 10H-benzo[g]pteridine-2,4-dione derivative, the organic radical having a) at least one, preferably at least two, preferably at least three, preferably at least four, further preferably at least five, uncharged, protonatable nitrogen atom(s) not bonded directly to the isoalloxazine ring, and b) at least one, preferably at least two, preferably at least three, preferably at least four, further preferably at least five, positively charged, preferably quaternary, nitrogen atom(s) not bonded directly to the isoalloxazine ring, is a radical of the formula (2) or (3):

 (2)

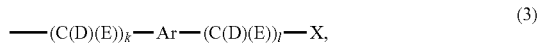 (3)

where h is an integer from 1 to 20, preferably from 1 to 19, preferably from 1 to 17, further preferably from 1 to 13, further preferably from 1 to 9, further preferably from 1 to 6, further preferably from 1 to 4, and k, l are each independently an integer from 0 to 6, preferably from 1 to 5, where D and E are each independently hydrogen, halogen, preferably chlorine, bromine, iodine or fluorine, hydroxyl, O—$R^{(VIII)}$ where $R^{(VIII)}$ is methyl, ethyl, n-propyl, n-butyl, phenyl or benzyl, O—C(=O)—$R^{(IX)}$ where $R^{(IX)}$ is hydrogen, methyl, ethyl, n-propyl, n-butyl, phenyl or benzyl, or thiol, further preferably hydrogen or hydroxyl, and where X is an organic radical containing a) at least one, preferably at least two, preferably at least three, preferably at least four, further preferably at least five, uncharged, protonatable nitrogen atom(s), and b) at least one, preferably at least two, preferably at least three, preferably at least four, further preferably at least five, positively charged, preferably quaternary, nitrogen atom(s), and the aryl radical is a substituted or unsubstituted aromatic system having 5 to 20 carbon atoms or a substituted or unsubstituted heteroaromatic system which does not contain any nitrogen atom and has 4 to 20 carbon atoms.

In a further preferred embodiment of variant II) of the 10H-benzo[g]pteridine-2,4-dione derivative of the formula (1), the R5 radical is an acyclic polyol radical of the formula —$CH_2(CH(OH))_gCH_2OH$ or an ether, ester or acetal thereof, where g is an integer from 1 to 10, preferably 1 to 4, and where either A) only 1 R1, R2, R3 or R4 radical is an organic radical of the general formula (2), (3) or (4):

 (2)

 (3)

 (4)

where h is an integer from 1 to 20 and k and l are each independently an integer from 0 to 6, where D and E are each independently hydrogen, halogen, preferably chlorine, bromine, iodine or fluorine, hydroxyl, O—$R^{(VIII)}$ where $R^{(VIII)}$ is methyl, ethyl, n-propyl, n-butyl, phenyl or benzyl, O—C(=O)—$R^{(IX)}$ where $R^{(IX)}$ is hydrogen, methyl, ethyl, n-propyl, n-butyl, phenyl or benzyl, or thiol, further preferably hydrogen or hydroxyl, and where X is an organic radical having a) at least one, preferably at least two, preferably at least three, preferably at least four, further preferably at least five, uncharged, protonatable nitrogen atom(s), and b) at least one, preferably at least two, preferably at least three, preferably at least four, further preferably at least five, positively charged, preferably quaternary, nitrogen atom(s), and where aryl is a substituted or unsubstituted aromatic system having 5 to 20 carbon atoms or a substituted or unsubstituted heteroaromatic system which does not contain any nitrogen atom and has 4 to 20 carbon atoms, and where the radical having the formula (4) is a heteroaromatic system which is bonded to the isoalloxazine ring via a carbon atom in the heteroaromatic system and which contains a) at least one, preferably at least two, preferably at least three, uncharged, protonatable nitrogen atom(s), and b) at least one, preferably at least two, preferably at least three, positively charged, preferably quaternary, nitrogen atom(s), and where the R1, R2, R3 or R4 radicals which are not an organic radical of the general formula (2), (3) or (4) are the same or different and are each independently hydrogen, halogen, hydroxyl, thiol, nitro, carboxylate, aldehyde having 1 to 20 carbon atoms, ketone having 2 to 20 carbon atoms, O-alkyl having 1 to 20 carbon atoms, S-alkyl having 1 to 20 carbon atoms, O-alkenyl having 2 to 20 carbon atoms, S-alkenyl having 2 to 20 carbon atoms, O-aryl having 5 to 20 carbon atoms, S-aryl having 5 to 20 carbon atoms, ether having 2 to 20 carbon atoms, thioether having 2 to 20 carbon atoms, carboxylic ester having 1 to 20 carbon atoms, carboxamide having 1 to 20 carbon atoms, thioester having 1 to 20 carbon atoms, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms or heteroaryl which does not contain any nitrogen atom and has 4 to 20 carbon atoms, and where the R6 radical is hydrogen, alkyl having 1 to 20 carbon atoms, alkenyl having 2 to 20 carbon atoms, ether having 2 to 20 carbon atoms, thioether having 2 to 20 carbon atoms, cycloalkyl having 3 to 20 carbon atoms, cycloalkenyl having 3 to 20 carbon atoms, aryl having 5 to 20 carbon atoms or heteroaryl which does not contain any nitrogen atom and has 4 to 20 carbon atoms, or B) only the R6 radical is an organic radical of the general formula (2), (3) or (4):

—(C(D)(E))$_h$—X,    (2)

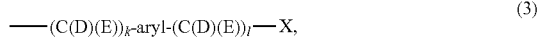

—(C(D)(E))$_k$-aryl-(C(D)(E))$_l$—X,    (3)

(4)

where h is an integer from 1 to 20 and k and l are each independently an integer from 0 to 6, where D and E are each independently hydrogen, halogen, preferably chlorine, bromine, iodine or fluorine, hydroxyl, O—R$^{(VIII)}$ where R$^{(VIII)}$ is methyl, ethyl, n-propyl, n-butyl, phenyl or benzyl, O—C(=O)—R$^{(IX)}$ where R$^{(IX)}$ is hydrogen, methyl, ethyl, n-propyl, n-butyl, phenyl or benzyl, or thiol, further preferably hydrogen or hydroxyl, and where X is an organic radical having a) at least one, preferably at least two, preferably at least three, preferably at least four, further preferably at least five, uncharged, protonatable nitrogen atom(s), and b) at least one, preferably at least two, preferably at least three, preferably at least four, further preferably at least five, positively charged, preferably quaternary, nitrogen atom(s) not bonded directly to the isoalloxazine ring, and where aryl is a substituted or unsubstituted aromatic system having 5 to 20 carbon atoms or a substituted or unsubstituted heteroaromatic system which does not contain any nitrogen atom and has 4 to 20 carbon atoms, and where the radical having the formula (4) is a heteroaromatic system which is bonded to the isoalloxazine ring via a carbon atom in the heteroaromatic system and which contains a) at least one, preferably at least two, preferably at least three, uncharged, protonatable nitrogen atom(s), and b) at least one, preferably at least two, preferably at least three, positively charged, preferably quaternary, nitrogen atom(s), and where the R1 to R4 radicals are the same or different and are each independently hydrogen, halogen, hydroxyl, thiol, nitro, carboxylate, aldehyde having 1 to 20 carbon atoms, ketone having 2 to 20 carbon atoms, O-alkyl having 1 to 20 carbon atoms, S-alkyl having 1 to 20 carbon atoms, O-alkenyl having 1 to 20 carbon atoms, S-alkenyl having 1 to 20 carbon atoms, O-aryl having 5 to 20 carbon atoms, S-aryl having 5 to 20 carbon atoms, ether having 2 to 20 carbon atoms, thioether having 2 to 20 carbon atoms, carboxylic ester having 1 to 20 carbon atoms, carboxamide having 1 to 20 carbon atoms, thioester having 1 to 20 carbon atoms, alkyl having 1 to 20 carbon atoms, alkenyl having 1 to 20 carbon atoms, cycloalkyl having 3 to 20 carbon atoms, cycloalkenyl having 3 to 20 carbon atoms, aryl having 5 to 20 carbon atoms or heteroaryl which does not contain any nitrogen atom and has 4 to 20 carbon atoms.

In a further-preferred embodiment of variant II) of the 10H-benzo[g]pteridine-2,4-dione derivative of the formula (1), the R5 radical is an acyclic polyol radical of the formula —CH$_2$(CH(OH))$_g$CH$_2$OH or an ether, ester or acetal thereof, where g is an integer from 1 to 10, preferably 1 to 4, and where either A) only 1 R1, R2, R3 or R4 radical is an organic radical of the general formula —(C(D)(E))$_h$-X or —(C(D)(E))$_k$-aryl-(C(D)(E))$_l$-X, where h is an integer from 1 to 20, preferably from 1 to 19, preferably from 1 to 17, further preferably from 1 to 13, further preferably from 1 to 9, further preferably from 1 to 6, further preferably from 1 to 4, and k, l are each independently an integer from 0 to 6, preferably from 1 to 5, where D and E are each independently hydrogen, halogen, preferably chlorine, bromine, iodine or fluorine, hydroxyl, O—R$^{(VIII)}$ where R$^{(VIII)}$ is methyl, ethyl, n-propyl, n-butyl, phenyl or benzyl, O—C(=O)—R$^{(IX)}$ where R$^{(IX)}$ is hydrogen, methyl, ethyl, n-propyl, n-butyl, phenyl or benzyl, or thiol, further preferably hydrogen or hydroxyl, where X is an organic radical having a) at least one, preferably at least two, preferably at least three, preferably at least four, further preferably at least five, uncharged, protonatable nitrogen atom(s), and b) at least one, preferably at least two, preferably at least three, preferably at least four, further preferably at least five, positively charged, preferably quaternary, nitrogen atom(s), and where aryl is a substituted or unsubstituted aromatic system having 5 to 20 carbon atoms or a substituted or unsubstituted heteroaromatic system which does not contain any nitrogen atom and has 4 to 20 carbon atoms, and where the R1, R2, R3 or R4 radicals which are not an organic radical of the general formula —(C(D)(E))$_h$-X or —(C(D)(E))$_k$-aryl-(C(D)(E))$_l$-X are the same or different and are each independently hydrogen, halogen, hydroxyl, thiol, nitro, carboxylate, aldehyde having 1 to 20 carbon atoms, ketone having 2 to 20 carbon atoms, O-alkyl having 1 to 20 carbon atoms, S-alkyl having 1 to 20 carbon atoms, O-alkenyl having 2 to 20 carbon atoms, S-alkenyl having 2 to 20 carbon atoms, O-aryl having 5 to 20 carbon atoms, S-aryl having 5 to 20 carbon atoms, ether having 2 to 20 carbon atoms, thioether having 2 to 20 carbon atoms, carboxylic ester having 1 to 20 carbon atoms, carboxamide having 1 to 20 carbon atoms, thioester having 1 to 20 carbon atoms, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms or heteroaryl which does not contain any nitrogen atom and has 4 to 20 carbon atoms, and where R6 is hydrogen, alkyl having 1 to 20 carbon atoms, alkenyl having 2 to 20 carbon atoms, ether having 2 to 20 carbon atoms, thioether having 2 to 20 carbon atoms, cycloalkyl having 3 to 20 carbon atoms, cycloalkenyl having 3 to 20 carbon atoms, aryl having 5 to 20 carbon atoms or heteroaryl which does not contain any nitrogen atom and has 4 to 20 carbon atoms, or B) only the R6 radical is an organic radical of the general formula $-(C(D)(E))_h$-X or $-(C(D)(E))_k$-aryl-$(C(D)(E))_l$-X, where h is an integer from 1 to 20, preferably from 1 to 19, preferably from 1 to 17, further preferably from 1 to 13, further preferably from 1 to 9, further preferably from 1 to 6, further preferably from 1 to 4, and k, l are each independently an integer from 0 to 6, preferably from 1 to 5, where D and E are each independently hydrogen, halogen, preferably chlorine, bromine, iodine or fluorine, hydroxyl, O—$R^{(VIII)}$ where $R^{(VIII)}$ is methyl, ethyl, n-propyl, n-butyl, phenyl or benzyl, O—C(=O)—$R^{(IX)}$ where $R^{(IX)}$ is hydrogen, methyl, ethyl, n-propyl, n-butyl, phenyl or benzyl, or thiol, further preferably hydrogen or hydroxyl, where X is an organic radical having a) at least one, preferably at least two, preferably at least three, preferably at least four, further preferably at least five, uncharged, protonatable nitrogen atom(s), and b) at least one, preferably at least two, preferably at least three, preferably at least four, further preferably at least five, positively charged, preferably quaternary, nitrogen atom(s), and where aryl is a substituted or unsubstituted aromatic system having 5 to 20 carbon atoms or a substituted or unsubstituted heteroaromatic system which does not contain any nitrogen atom and has 4 to 20 carbon atoms, and where the R1 to R4 radicals are the same or different and are each independently hydrogen, halogen, hydroxyl, thiol, nitro, carboxylate, aldehyde having 1 to 20 carbon atoms, ketone having 2 to 20 carbon atoms, O-alkyl having 1 to 20 carbon atoms, S-alkyl having 1 to 20 carbon atoms, O-alkenyl having 1 to 20 carbon atoms, S-alkenyl having 1 to 20 carbon atoms, O-aryl having 5 to 20 carbon atoms, S-aryl having 5 to 20 carbon atoms, ether having 2 to 20 carbon atoms, thioether having 2 to 20 carbon atoms, carboxylic ester having 1 to 20 carbon atoms, carboxamide having 1 to 20 carbon atoms, thioester having 1 to 20 carbon atoms, alkyl having 1 to 20 carbon atoms, alkenyl having 1 to 20 carbon atoms, cycloalkyl having 3 to 20 carbon atoms, cycloalkenyl having 3 to 20 carbon atoms, aryl having 5 to 20 carbon atoms or heteroaryl which does not contain any nitrogen atom and has 4 to 20 carbon atoms.

Further preferably, the R5 radical is an acyclic polyol radical selected from the group consisting of arabityl, ribityl, xylityl, erythrityl, threityl, lactityl, mannityl and sorbityl, further preferably D-ribityl and D-arabityl, or an ether, ester or acetal thereof.

In a further preferred embodiment of variant II) of the 10H-benzo[g]pteridine-2,4-dione derivative of the formula (1), only the R5 radical is an acyclic polyol radical of the general formula —$CH_2(CH(OZ))_fCH_{(3-e)}(OZ)_e$ where e is 0, 1 or 2 and f is an integer from 1 to 10, preferably 1 to 4, and where Z is hydrogen, alkyl having 1 to 20 carbon atoms, carboxylic ester having 1 to 20 carbon atoms or an X radical, where X is an organic radical containing a) at least one, preferably at least two, preferably at least three, preferably at least four, further preferably at least five, uncharged, protonatable nitrogen atom(s), and b) at least one, preferably at least two, preferably at least three, preferably at least four, further preferably at least five, positively charged, preferably quaternary, nitrogen atom(s), and where R6 is hydrogen, alkyl having 1 to 20 carbon atoms, alkenyl having 2 to 20 carbon atoms, ether having 2 to 20 carbon atoms, thioether having 2 to 20 carbon atoms, cycloalkyl having 3 to 20 carbon atoms, cycloalkenyl having 3 to 20 carbon atoms, aryl having 5 to 20 carbon atoms or heteroaryl which does not contain any nitrogen atom and has 4 to 20 carbon atoms, and where the R1 to R4 radicals are the same or different and are each independently hydrogen, halogen, hydroxyl, thiol, nitro, carboxylate, aldehyde having 1 to 20 carbon atoms, ketone having 2 to 20 carbon atoms, O-alkyl having 1 to 20 carbon atoms, S-alkyl having 1 to 20 carbon atoms, O-alkenyl having 1 to 20 carbon atoms, S-alkenyl having 1 to 20 carbon atoms, O-aryl having 5 to 20 carbon atoms, S-aryl having 5 to 20 carbon atoms, ether having 2 to 20 carbon atoms, thioether having 2 to 20 carbon atoms, carboxylic ester having 1 to 20 carbon atoms, carboxamide having 1 to 20 carbon atoms, thioester having 1 to 20 carbon atoms, alkyl having 1 to 20 carbon atoms, alkenyl having 1 to 20 carbon atoms, cycloalkyl having 3 to 20 carbon atoms, cycloalkenyl having 3 to 20 carbon atoms, aryl having 5 to 20 carbon atoms or heteroaryl which does not contain any nitrogen atom and has 4 to 20 carbon atoms.

Further preferably, the R5 radical is an acyclic polyol radical of the general formula —$CH_2(CH(OZ))_fCH_{(3-e)}(OZ)_e$ where e is 1, or 2 and f is an integer from 1 to 10, preferably 1 to 4, and where Z is an ester of an aminocarboxylic acid which derives from an aminocarboxylic acid, preferably alpha-aminocarboxylic acid, having 1 to 20 carbon atoms, preferably selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, L-homoserine, ornithine, N5-(aminocarbonyl)-L-ornithine, L-(−)-carnitine, alpha-phenylglycine, L-3,4-dihydroxyphenylalanine, 3,6-diaminohexanoic acid, N-(aminoiminomethyl)-N-methylglycine, gamma-aminobutyric acid, L-5-hydroxytryptophan, norleucine and 2,6-diaminopimelic acid, further preferably arginine, glycine, lysine, ornithine, 3,6-diaminohexanoic acid and gamma-aminobutyric acid, even further preferably glycine and lysine, where preferably at least one amino group in each case may be substituted by methyl radicals.

In a further-preferred embodiment of variant II) of the 10H-benzo[g]pteridine-2,4-dione derivative of the formula (1), the organic radical X having a) at least one, preferably at least two, preferably at least three, preferably at least four, further preferably at least five, uncharged, protonatable nitrogen atom(s), and
b) at least one, preferably at least two, preferably at least three, preferably at least four, further preferably at least five, positively charged, preferably quaternary, nitrogen atom(s), is a radical of the general formula (2):

(2)

where A is an oxygen or sulfur atom and where n is an integer from 1 to 8 and m is an integer from 0 to 100, and where B is a radical of the formula (3a), (3b), (4a), (4b), (5a) or (5b):

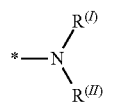

(3a)

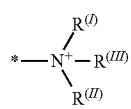

(3b)

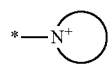

(4a)

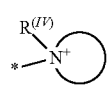

(4b)

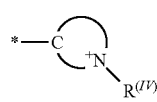

(5a)

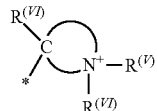

(5b)

and where the $R^{(I)}$ radical is an aryl radical having 5 to 20 carbon atoms, a heterocyclic radical having 5 to 20 carbon atoms, an alkyl radical, which may be straight-chain or branched, having 1 to 20 carbon atoms, an alkenyl radical, which may be straight-chain or branched, having 2 to 20 carbon atoms, a hydroxyalkyl radical, which may be straight-chain or branched, having 1 to 20 carbon atoms, an ether radical, which may be straight-chain or branched, having 2 to 20 carbon atoms, a thioether radical, which may be straight-chain or branched, having 2 to 20 carbon atoms, or an alkylamino radical, which may be straight-chain or branched, having 1 to 20 carbon atoms, where each of the $R^{(II)}$, $R^{(III)}$, $R^{(IV)}$, $R^{(V)}$ and $R^{(VI)}$ radicals is independently hydrogen, an aryl radical having 5 to 20 carbon atoms, a heterocyclic radical having 5 to 20 carbon atoms, an alkyl radical, which may be straight-chain or branched, having 1 to 20 carbon atoms, an alkenyl radical, which may be straight-chain or branched, having 2 to 20 carbon atoms, a hydroxyalkyl radical, which may be straight-chain or branched, having 1 to 20 carbon atoms, an ether radical, which may be straight-chain or branched, having 2 to 20 carbon atoms, a thioether radical, which may be straight-chain or branched, having 2 to 20 carbon atoms, or an alkylamino radical, which may be straight-chain or branched, having 1 to 20 carbon atoms and where each of the aforementioned aryl radicals, heterocyclic radicals, alkyl radicals, alkenyl radicals, hydroxyalkyl radicals, ether radicals, thioether radicals and alkylamino radicals is substituted at least by one, preferably at least two, preferably at least three, preferably at least four, further preferably at least five, amino radical(s) and/or alkylamino radical(s), which may be straight-chain or branched, having 1 to 20 carbon atoms, for example aminomethyl, 2-aminoethyl, dimethylaminomethyl or (trimethylammonio)methyl, and/or guanidino radical, and where the radical having the formula (4a) and the radical having the formula (5a):

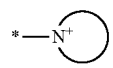

(4a)

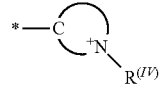

(5a)

is a substituted or unsubstituted heterocyclic radical having 5 to 7 ring atoms including 2 to 4 nitrogen atoms and at least 1 carbon atom and optionally 1 or 2 oxygen or sulfur atoms, where 1 nitrogen atom forms a double bond, and where the radical having the formula (4b) and the radical having the formula (5b):

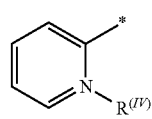

(4b)

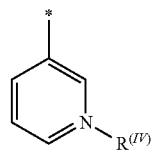

(5b)

is a substituted or unsubstituted heterocyclic radical having 5 to 7 ring atoms including 2 to 4 nitrogen atoms and at least 1 carbon atom and optionally 1 or 2 oxygen or sulfur atoms.

In a further-preferred embodiment of variant II) of the 10H-benzo[g]pteridine-2,4-dione derivative of the formula (1), the radical of the formula (5a) is selected from the group consisting of radicals of the formulae (22a), (22b) and (22c):

(22a)

(22b)

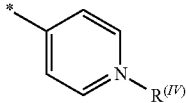

where each $R^{(IV)}$ is selected from the group consisting of aryl radicals having 5 to 20 carbon atoms, for example phenyl or benzyl, heterocyclic radicals having 5 to 20 carbon atoms, for example 2-pyridyl, 3-pyridyl, 4-pyridyl, 1-methylpyridin-1-ium-2-yl, 1-methylpyridin-1-ium-3-yl or 1-methylpyridin-1-ium-4-yl, alkyl radicals which may be straight-chain or branched and have 1 to 20 carbon atoms, for example methyl, ethyl, n-propyl, i-propyl, n-butyl or t-butyl, alkenyl radicals which may be straight-chain or branched and have 2 to 20 carbon atoms, hydroxyalkyl radicals which may be straight-chain or branched and have 1 to 20 carbon atoms, for example hydroxymethyl, 2-hydroxyethyl, 3-hydroxypropyl or 1-hydroxy-1-methylethyl, ether radicals which may be straight-chain or branched and have 2 to 20 carbon atoms, for example methoxymethyl, methoxyethyl, methoxypropyl, ethoxymethyl, ethoxyethyl, ethoxypropyl, propoxymethyl, propoxyethyl or propoxypropyl, thioether radicals which may be straight-chain or branched and have 2 to 20 carbon atoms, for example methylsulfanylmethyl, ethylsulfanylmethyl, 2-ethylsulfanylethyl or 3-methylsulfanylpropyl, and alkylamino radicals which may be straight-chain or branched and have 1 to 20 carbon atoms, for example aminomethyl, 2-aminoethyl, dimethylaminomethyl or (trimethylammonio)methyl.

In a preferred embodiment of variant II) of the 10H-benzo[g]pteridine-2,4-dione derivative of the formula (1), the radical of the formula (4a) is selected from the group consisting of radicals of the formulae (23a), (23b) and (23c):

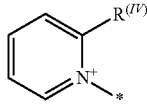
(23a)

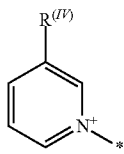
(23b)

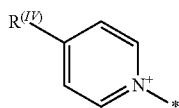
(23c)

where each $R^{(IV)}$ is selected from the group consisting of hydrogen, aryl radicals having 5 to 20 carbon atoms, for example phenyl or benzyl, heterocyclic radicals having 5 to 20 carbon atoms, for example 2-pyridyl, 3-pyridyl, 4-pyridyl, 1-methylpyridin-1-ium-2-yl, 1-methylpyridin-1-ium-3-yl or 1-methylpyridin-1-ium-4-yl, alkyl radicals which may be straight-chain or branched and have 1 to 20 carbon atoms, for example methyl, ethyl, n-propyl, i-propyl, n-butyl or t-butyl, alkenyl radicals which may be straight-chain or branched and have 2 to 20 carbon atoms, hydroxyalkyl radicals which may be straight-chain or branched and have 1 to 20 carbon atoms, for example hydroxymethyl, 2-hydroxyethyl, 3-hydroxypropyl or 1-hydroxy-1-methylethyl, ether radicals which may be straight-chain or branched and have 2 to 20 carbon atoms, for example methoxymethyl, methoxyethyl, methoxypropyl, ethoxymethyl, ethoxyethyl, ethoxypropyl, propoxymethyl, propoxyethyl or propoxypropyl, thioether radicals which may be straight-chain or branched and have 2 to 20 carbon atoms, for example methylsulfanylmethyl, ethylsulfanylmethyl, 2-ethylsulfanylethyl or 3-methylsulfanylpropyl, and alkylamino radicals which may be straight-chain or branched and have 1 to 20 carbon atoms, for example aminomethyl, 2-aminoethyl, dimethylaminomethyl or (trimethylammonio)methyl.

In a preferred embodiment of variant II) of the 10H-benzo[g]pteridine-2,4-dione derivative of the formula (1), the $R^{(II)}$, $R^{(III)}$, $R^{(IV)}$, $R^{(V)}$ and $R^{(VI)}$ radicals are each independently hydrogen or an alkyl radical of the general formula —(CH$_2$)$_n$—CH$_3$ and the $R^{(I)}$ radical is an alkyl radical of the general formula —(CH$_2$)$_n$—CH$_3$, where each n is an integer from 0 to 19, preferably from 1 to 17, where the aforementioned alkyl radicals are substituted at least by one, preferably at least two, preferably at least three, preferably at least four, further preferably at least five, amino radical(s) and/or alkylamino radical(s) which may be straight-chain or branched and have 1 to 20 carbon atoms, preferably 1 to 4 carbon atoms, for example aminomethyl, 2-aminoethyl, dimethylaminomethyl or (trimethylammonio)methyl, and/or guanidino radical.

In a preferred embodiment of variant II) of the 10H-benzo[g]pteridine-2,4-dione derivative of the formula (1), the $R^{(II)}$, $R^{(III)}$, $R^{(IV)}$, $R^{(V)}$ and $R^{(VI)}$ radicals are each independently hydrogen, methyl, ethyl, prop-1-yl, prop-2-yl, but-1-yl, but-2-yl, 2-methylprop-1-yl, 2-methyl-prop-2-yl, pent-1-yl, pent-2-yl, pent-3-yl, 2-methylbut-1-yl, 2-methylbut-2-yl, 2-methylbut-3-yl, 2-methylbut-4-yl, 2,2-dimethylprop-1-yl, hex-1-yl, hex-2-yl, hex-3-yl, hept-1-yl, oct-1-yl, 2-methylpent-1-yl, 2-methylpent-2-yl, 2-methylpent-3-yl, 2-methylpent-4-yl, 2-methylpent-5-yl, 3-methylpent-1-yl, 3-methylpent-2-yl, 3-methylpent-3-yl, 2,2-dimethylbut-1-yl, 2,2-dimethylbut-3-yl, 2,2-dimethylbut-4-yl, 2,3-dimethylbut-1-yl or 2,3-dimethylbut-2-yl, and the $R^{(I)}$ radical is methyl, ethyl, prop-1-yl, prop-2-yl, but-1-yl, but-2-yl, 2-methylprop-1-yl, 2-methyl-prop-2-yl, pent-1-yl, pent-2-yl, pent-3-yl, 2-methylbut-1-yl, 2-methylbut-2-yl, 2-methylbut-3-yl, 2-methylbut-4-yl, 2,2-dimethylprop-1-yl, hex-1-yl, hex-2-yl, hex-3-yl, hept-1-yl, oct-1-yl, 2-methylpent-1-yl, 2-methylpent-2-yl, 2-methylpent-3-yl, 2-methylpent-4-yl, 2-methylpent-5-yl, 3-methylpent-1-yl, 3-methylpent-2-yl, 3-methylpent-3-yl, 2,2-dimethylbut-1-yl, 2,2-dimethylbut-3-yl, 2,2-dimethylbut-4-yl, 2,3-dimethylbut-1-yl or 2,3-dimethylbut-2-yl, where the aforementioned alkyl radicals are substituted at least by one, preferably at least two, preferably at least three, preferably at least four, further preferably at least five, amino radical(s) and/or alkylamino radical(s) which may be straight-chain or branched and have 1 to 20 carbon atoms, preferably 1 to 4 carbon atoms, for example aminomethyl, 2-aminoethyl, dimethylaminomethyl or (trimethylammonio)methyl, and/or guanidino radical.

In a particularly preferred embodiment, the $R^{(I)}$, $R^{(II)}$, $R^{(III)}$, $R^{(IV)}$, $R^{(V)}$ and $R^{(VI)}$ radicals may each independently be methyl, ethyl, prop-1-yl, but-1-yl, pent-1-yl, hex-1-yl, hept-1- or oct-1-yl, where the aforementioned alkyl radicals are substituted at least by one, preferably at least two, preferably at least three, preferably at least four, further preferably at least five, amino radical(s) and/or alkylamino radical(s) which may be straight-chain or branched and have 1 to 20 carbon atoms, for example aminomethyl, 2-aminoethyl, dimethylaminomethyl or (trimethylammonio)methyl, and/or guanidino radical.

In a preferred embodiment of variant II) of the 10H-benzo[g]pteridine-2,4-dione derivative of the formula (1), the $R^{(II)}$, $R^{(III)}$, $R^{(IV)}$, $R^{(V)}$ and $R^{(VI)}$ radicals are each independently hydrogen or a radical of the formula (6) to (9):

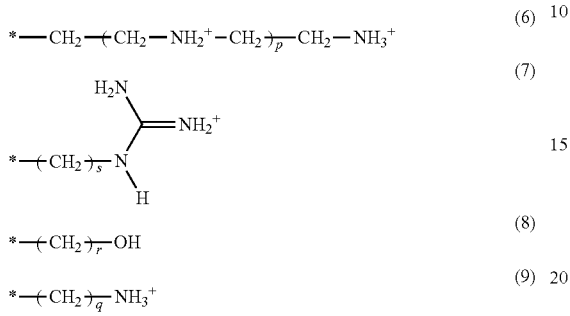

and the $R^{(I)}$ radical is a radical of the formula (6) to (9), where each p is an integer from 1 to 10, preferably from 1 to 7, further preferably from 1 to 3, and where s, r, q are each independently an integer from 1 to 20, preferably from 1 to 8, further preferably from 1 to 4, selected.

In a further-preferred embodiment of variant II) of the 10H-benzo[g]pteridine-2,4-dione derivative of the formula (1), the $R^{(II)}$, $R^{(III)}$, $R^{(IV)}$, $R^{(V)}$ and $R^{(VI)}$ radicals are each independently hydrogen or a polyamine radical of the general formula $-[(CH_2)_a-N(R^{(VII)})-(CH_2)_b-]_cNH_{(3-g)}(R^{(VIII)})_g^+$, and the $R^{(I)}$ radical is a polyamine radical of the general formula $-[(CH_2)_a-N(R^{(VII)})-(CH_2)_b-]_cNH_{3-g}(R^{(VIII)})_g^+$, where each c is an integer from 1 to 10, preferably from 1 to 7, further preferably from 1 to 3, a and b are each independently an integer from 1 to 10, preferably from 1 to 4, further preferably from 2 to 3, g is 0, 1, 2 or 3 and $R^{(VII)}$ and $R^{(VIII)}$ are each independently hydrogen, methyl or ethyl.

In variant III) of the inventive 10H-benzo[g]pteridine-2,4-dione derivative of the formula (1)

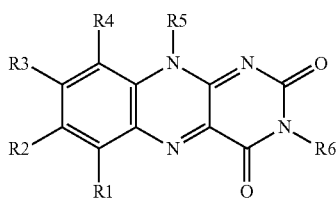

at least 2 R1, R2, R3, R4, R5 or R6 radicals are an organic radical having:
  a) at least one uncharged, protonatable nitrogen atom not bonded directly to the isoalloxazine ring, and/or
  b) at least one positively charged, preferably quaternary, nitrogen atom not bonded directly to the isoalloxazine ring, and
  where each of the R1, R2, R3 and R4 radicals which is not an organic radical having a) at least one uncharged, protonatable nitrogen atom not bonded directly to the isoalloxazine ring, or b) at least one positively charged nitrogen atom not bonded directly to the isoalloxazine ring, is the same or different and is independently hydrogen, halogen, hydroxyl, thiol, nitro, carboxylate, aldehyde having 1 to 20 carbon atoms, ketone having 2 to 20 carbon atoms, O-alkyl having 1 to 20 carbon atoms, S-alkyl having 1 to 20 carbon atoms, O-alkenyl having 2 to 20 carbon atoms, S-alkenyl having 2 to 20 carbon atoms, O-aryl having 5 to 20 carbon atoms, S-aryl having 5 to 20 carbon atoms, carboxylic ester having 1 to 20 carbon atoms, carboxamide having 1 to 20 carbon atoms, thioester having 1 to 20 carbon atoms, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms or heteroaryl having 4 to 20 carbon atoms, which does not contain any nitrogen atoms, and
  where each of the R5 and R6 radicals which is not an organic radical having a) at least one uncharged, protonatable nitrogen atom not bonded directly to the isoalloxazine ring, or b) at least one positively charged, preferably quaternary, nitrogen atom not bonded directly to the isoalloxazine ring, is hydrogen, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms or heteroaryl having 4 to 20 carbon atoms, which does not contain any nitrogen atoms,
  and excluding the compound having the formula (20):

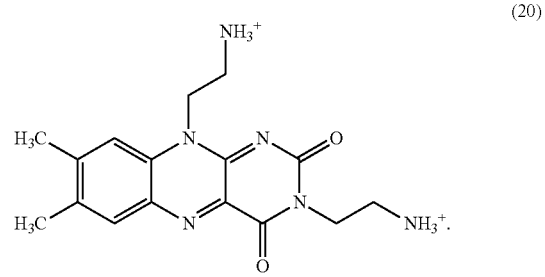

Preferably, the R3 radical is not a heterocyclic radical having 4 to 7 carbon atoms and at least one nitrogen atom.

In a preferred embodiment of variant III) of the 10H-benzo[g]pteridine-2,4-dione derivative of the formula (1), the R5 radical is an acyclic polyol radical of the general formula $-CH_2(CH(OH))_gCH_2OH$ or an ether, ester or acetal thereof, where g is an integer from 1 to 10, preferably 1 to 4, and where
  at least 2 R1, R2, R3, R4 or R6 radicals are an organic radical having:
  a) at least one, preferably at least two, preferably at least three, preferably at least four, further preferably at least five, uncharged, protonatable nitrogen atom(s) not bonded directly to the isoalloxazine ring, and/or
  b) at least one, preferably at least two, preferably at least three, preferably at least four, further preferably at least five, permanently positively charged, preferably quaternary, nitrogen atom(s) not bonded directly to the isoalloxazine ring,
  and where each of the R1, R2, R3 and R4 radicals which is not an organic radical having a) at least one uncharged, protonatable nitrogen atom not bonded directly to the isoalloxazine ring, or b) at least one permanently positively charged, preferably quaternary, nitrogen atom not bonded directly to the isoalloxazine ring, is the same or different and is independently hydrogen, halogen, hydroxyl, thiol, nitro, carboxylate, aldehyde having 1 to 20 carbon atoms, ketone having 2 to 20 carbon atoms, O-alkyl having 1 to 20 carbon atoms, S-alkyl having 1 to 20 carbon atoms, O-alkenyl having 2 to 20 carbon atoms, S-alkenyl having 2 to 20 carbon atoms, O-aryl having 5 to 20 carbon atoms, S-aryl having 5 to 20 carbon atoms, carboxylic ester having 1 to 20 carbon atoms, carboxamide having 1 to 20 carbon atoms, thioester having 1 to 20 carbon atoms, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms or heteroaryl having 4 to 20 carbon atoms, which does not contain any nitrogen atoms, and where the R6 radical, when R6 is not an organic radical having a) at least one uncharged, protonatable nitrogen atom not bonded directly to the isoalloxazine ring, or b) at least one permanently positively charged, preferably quaternary, nitrogen atom not bonded directly to the isoalloxazine ring, is hydrogen, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms or heteroaryl having 4 to 20 carbon atoms, which does not contain any nitrogen atoms.

Further preferably, the R5 radical is an acyclic polyol radical selected from the group consisting of arabityl, ribityl, xylityl, erythrityl, threityl, lactityl, mannityl and sorbityl, further preferably D-ribityl and D-arabityl, or an ether, ester or acetal thereof.

In a further preferred embodiment of variant III) of the 10H-benzo[g]pteridine-2,4-dione derivative of the formula (1), at least 2 R1, R2, R3 or R4 radicals are independently an organic radical of the general formula (2), (3) or (4):

  (2)

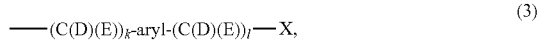  (3)

  (4)

where h is an integer from 1 to 20 and k and l are each independently an integer from 0 to 6, where D and E are each independently hydrogen, halogen, preferably chlorine, bromine, iodine or fluorine, hydroxyl, O—$R^{(VIII)}$ where $R^{(VIII)}$ is methyl, ethyl, n-propyl, n-butyl, phenyl or benzyl, O—C(=O)—$R^{(IX)}$ where $R^{(IX)}$ is hydrogen, methyl, ethyl, n-propyl, n-butyl, phenyl or benzyl, or thiol, further preferably hydrogen or hydroxyl, and where X is an organic radical having a) at least one, preferably at least two, preferably at least three, preferably at least four, further preferably at least five, uncharged, protonatable nitrogen atom(s), and/or
b) at least one, preferably at least two, preferably at least three, preferably at least four, further preferably at least five, positively charged, preferably quaternary, nitrogen atom(s), and where aryl is a substituted or unsubstituted aromatic system having 5 to 20 carbon atoms or a substituted or unsubstituted heteroaromatic system which does not contain any nitrogen atom and has 4 to 20 carbon atoms, and where the radical having the formula (4) is a heteroaromatic system which is bonded to the isoalloxazine ring via a carbon atom in the heteroaromatic system and which contains a) at least one, preferably at least two, preferably at least three, uncharged, protonatable nitrogen atom(s), and/or b) at least one, preferably at least two, preferably at least three, positively charged, preferably quaternary, nitrogen atom(s), and where the R1, R2, R3 or R4 radicals which are not an organic radical of the general formula (2), (3) or (4) are the same or different and are each independently hydrogen, halogen, hydroxyl, thiol, nitro, carboxylate, aldehyde having 1 to 20 carbon atoms, ketone having 2 to 20 carbon atoms, O-alkyl having 1 to 20 carbon atoms, S-alkyl having 1 to 20 carbon atoms, O-alkenyl having 2 to 20 carbon atoms, S-alkenyl having 2 to 20 carbon atoms, O-aryl having 5 to 20 carbon atoms, S-aryl having 5 to 20 carbon atoms, ether having 2 to 20 carbon atoms, thioether having 2 to 20 carbon atoms, carboxylic ester having 1 to 20 carbon atoms, carboxamide having 1 to 20 carbon atoms, thioester having 1 to 20 carbon atoms, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms or heteroaryl which does not contain any nitrogen atom and has 4 to 20 carbon atoms, and where each of the R5 and R6 radicals is the same or different and is independently hydrogen, alkyl having 1 to 20 carbon atoms, alkenyl having 2 to 20 carbon atoms, ether having 2 to 20 carbon atoms, thioether having 2 to 20 carbon atoms, cycloalkyl having 3 to 20 carbon atoms, cycloalkenyl having 3 to 20 carbon atoms, aryl having 5 to 20 carbon atoms or heteroaryl which does not contain any nitrogen atom and has 4 to 20 carbon atoms.

In a further-preferred embodiment, at least 2 R1, R2, R3 or R4 radicals are independently an organic radical of the general formula (2) or (3).

In a further preferred embodiment of variant III) of the 10H-benzo[g]pteridine-2,4-dione derivative of the formula (1), both R5 and R6 radicals are independently an organic radical of the general formula (2), (3) or (4):

  (2)

  (3)

  (4)

where h is an integer from 1 to 20 and k and l are each independently an integer from 0 to 6, where D and E are each independently hydrogen, halogen, preferably chlorine, bromine, iodine or fluorine, hydroxyl, O—$R^{(VIII)}$ where $R^{(VIII)}$ is methyl, ethyl, n-propyl, n-butyl, phenyl or benzyl, O—C(=O)—$R^{(IX)}$ where $R^{(IX)}$ is hydrogen, methyl, ethyl, n-propyl, n-butyl, phenyl or benzyl, or thiol, further preferably hydrogen or hydroxyl, and where X is an organic radical having a) at least one, preferably at least two, preferably at least three, preferably at least four, further preferably at least five, uncharged, protonatable nitrogen atom(s), and/or b) at least one, preferably at least two, preferably at least three, preferably at least four, further preferably at least five, positively charged, preferably quaternary, nitrogen atom(s), and where aryl is a substituted or unsubstituted aromatic system having 5 to 20 carbon atoms or a substituted or unsubstituted heteroaromatic system which does not contain any nitrogen atom and has 4 to 20 carbon atoms, and where the radical having the formula (4) is a heteroaromatic system which is bonded to the isoalloxazine ring via a carbon atom in the heteroaromatic system and which contains a) at least one, preferably at least two, preferably at least three, uncharged, protonatable nitrogen atom(s), and/or b) at least one, preferably at least two, preferably at least three, positively charged, preferably quaternary, nitrogen atom(s) not bonded directly to the isoalloxazine ring, and where the R1 to R4 radicals are the same or different and are each independently hydrogen, halogen, hydroxyl, thiol, nitro, carboxylate, aldehyde having 1 to 20 carbon atoms, ketone having 2 to 20 carbon atoms, O-alkyl having 1 to 20 carbon atoms, S-alkyl having 1 to 20 carbon atoms, O-alkenyl having 1 to 20 carbon atoms, S-alkenyl having 1 to 20 carbon atoms, O-aryl having 5 to 20 carbon atoms, S-aryl having 5 to 20 carbon atoms, ether having 2 to 20 carbon atoms, thioether having 2 to 20 carbon atoms, carboxylic ester having 1 to 20 carbon atoms, carboxamide having 1 to 20 carbon atoms, thioester having 1 to 20 carbon atoms, alkyl having 1 to 20 carbon atoms, alkenyl having 1 to 20 carbon atoms, cycloalkyl having 3 to 20 carbon atoms, cycloalkenyl having 3 to 20 carbon atoms, aryl having 5 to 20 carbon atoms or heteroaryl which does not contain any nitrogen atom and has 4 to 20 carbon atoms.

In a further-preferred embodiment, both R5 and R6 radicals are independently an organic radical of the general formula (2) or (3).

In a further preferred embodiment of variant III) of the 10H-benzo[g]pteridine-2,4-dione derivative of the formula (1), at least 1 R1, R2, R3 or R4 radical is independently an organic radical of the general formula (2), (3) or (4) and at least 1 R5 or R6 radical is independently an organic radical of the general formula (2), (3) or (4):

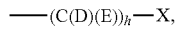  (2)

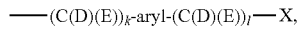  (3)

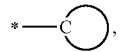  (4)

where h is an integer from 1 to 20 and k and l are each independently an integer from 0 to 6, where D and E are each independently hydrogen, halogen, preferably chlorine, bromine, iodine or fluorine, hydroxyl, O—$R^{(VIII)}$ where $R^{(VIII)}$ is methyl, ethyl, n-propyl, n-butyl, phenyl or benzyl, O—C(=O)—$R^{(IX)}$ where $R^{(IX)}$ is hydrogen, methyl, ethyl, n-propyl, n-butyl, phenyl or benzyl, or thiol, further preferably hydrogen or hydroxyl, and where X is an organic radical having a) at least one, preferably at least two, preferably at least three, preferably at least four, further preferably at least five, uncharged, protonatable nitrogen atom(s), and/or b) at least one, preferably at least two, preferably at least three, preferably at least four, further preferably at least five, positively charged, preferably quaternary, nitrogen atom(s), and where aryl is a substituted or unsubstituted aromatic system having 5 to 20 carbon atoms or a substituted or unsubstituted heteroaromatic system which does not contain any nitrogen atom and has 4 to 20 carbon atoms, and where the radical having the formula (4) is a heteroaromatic system which is bonded to the isoalloxazine ring via a carbon atom in the heteroaromatic system and which contains a) at least one, preferably at least two, preferably at least three, uncharged, protonatable nitrogen atom(s), and/or b) at least one, preferably at least two, preferably at least three, positively charged, preferably quaternary, nitrogen atom(s), and where the R1, R2, R3 or R4 radicals which are not an organic radical of the general formula (2), (3) or (4) are the same or different and are each independently hydrogen, halogen, hydroxyl, thiol, nitro, carboxylate, aldehyde having 1 to 20 carbon atoms, ketone having 2 to 20 carbon atoms, O-alkyl having 1 to 20 carbon atoms, S-alkyl having 1 to 20 carbon atoms, O-alkenyl having 2 to 20 carbon atoms, S-alkenyl having 2 to 20 carbon atoms, O-aryl having 5 to 20 carbon atoms, S-aryl having 5 to 20 carbon atoms, ether having 2 to 20 carbon atoms, thioether having 2 to 20 carbon atoms, carboxylic ester having 1 to 20 carbon atoms, carboxamide having 1 to 20 carbon atoms, thioester having 1 to 20 carbon atoms, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms or heteroaryl which does not contain any nitrogen atom and has 4 to 20 carbon atoms, and where the R5 or R6 radical which is not an organic radical of the general formula (2), (3) or (4) is hydrogen, alkyl having 1 to 20 carbon atoms, alkenyl having 2 to 20 carbon atoms, ether having 2 to 20 carbon atoms, thioether having 2 to 20 carbon atoms, cycloalkyl having 3 to 20 carbon atoms, cycloalkenyl having 3 to 20 carbon atoms, aryl having 5 to 20 carbon atoms or heteroaryl which does not contain any nitrogen atom and has 4 to 20 carbon atoms.

In a further-preferred embodiment, at least 1 R1, R2, R3 or R4 radical is independently an organic radical of the general formula (2) or (3) and at least 1 R5 or R6 radical is independently an organic radical of the general formula (2), (3) or (4), preferably an organic radical of the general formula (2) or (3).

In a further preferred embodiment of variant III) of the 10H-benzo[g]pteridine-2,4-dione derivative of the formula (1), at least 1 R1, R2, R3 or R4 radical and the R6 radical are each independently an organic radical of the general formula (2), (3) or (4):

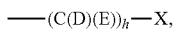

—(C(D)(E))$_h$—X,  (2)

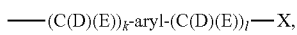

—(C(D)(E))$_k$-aryl-(C(D)(E))$_l$—X,  (3)

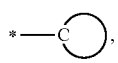

(4)

and where the R5 radical is an acyclic polyol radical of the general formula —CH$_2$(CH(OH))$_g$CH$_2$OH or an ether, ester or acetal thereof, where g is an integer from 1 to 10, preferably 1 to 4.

In a further-preferred embodiment of variant III) of the 10H-benzo[g]pteridine-2,4-dione derivative of the formula (1), at least 2 R1, R2, R3 or R4 radicals are independently an organic radical of the general formula (2), (3) or (4):

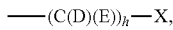

—(C(D)(E))$_h$—X,  (2)

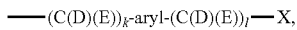

—(C(D)(E))$_k$-aryl-(C(D)(E))$_l$—X,  (3)

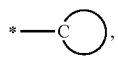

4)

and where the R5 radical is an acyclic polyol radical of the general formula —CH$_2$(CH(OH))$_g$CH$_2$OH or an ether, ester or acetal thereof, where g is an integer from 1 to 10, preferably 1 to 4, and where the R6 radical is hydrogen, alkyl having 1 to 20 carbon atoms, alkenyl having 2 to 20 carbon atoms, ether having 2 to 20 carbon atoms, thioether having 2 to 20 carbon atoms, cycloalkyl having 3 to 20 carbon atoms, cycloalkenyl having 3 to 20 carbon atoms, aryl having 5 to 20 carbon atoms or heteroaryl which does not contain any nitrogen atom and has 4 to 20 carbon atoms, and where the R1, R2, R3 or R4 radicals which are not an organic radical of the general formula (2), (3) or (4) are the same or different and are each independently hydrogen, halogen, hydroxyl, thiol, nitro, carboxylate, aldehyde having 1 to 20 carbon atoms, ketone having 2 to 20 carbon atoms, O-alkyl having 1 to 20 carbon atoms, S-alkyl having 1 to 20 carbon atoms, O-alkenyl having 2 to 20 carbon atoms, S-alkenyl having 2 to 20 carbon atoms, O-aryl having 5 to 20 carbon atoms, S-aryl having 5 to 20 carbon atoms, ether having 2 to 20 carbon atoms, thioether having 2 to 20 carbon atoms, carboxylic ester having 1 to 20 carbon atoms, carboxamide having 1 to 20 carbon atoms, thioester having 1 to 20 carbon atoms, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms or heteroaryl which does not contain any nitrogen atom and has 4 to 20 carbon atoms.

Further preferably, the R5 radical is an acyclic polyol radical selected from the group consisting of arabityl, ribityl, xylityl, erythrityl, threityl, lactityl, mannityl and sorbityl, further preferably D-ribityl and D-arabityl, or an ether, ester or acetal thereof.

In a further preferred embodiment of variant III) of the 10H-benzo[g]pteridine-2,4-dione derivative of the formula (1), only the R5 radical is an acyclic polyol radical of the general formula —CH$_2$(CH(OZ))$_f$CH$_{(3-e)}$(OZ)$_e$ where e is 0, 1 or 2 and f is an integer from 1 to 10, preferably 1 to 4, and where Z is hydrogen, alkyl having 1 to 20 carbon atoms, carboxylic ester having 1 to 20 carbon atoms or an X radical, where X is an organic radical containing a) at least one, preferably at least two, preferably at least three, preferably at least four, further preferably at least five, uncharged, protonatable nitrogen atom(s), and b) at least one, preferably at least two, preferably at least three, preferably at least four, further preferably at least five, positively charged, preferably quaternary, nitrogen atom(s), and where R6 is hydrogen, alkyl having 1 to 20 carbon atoms, alkenyl having 2 to 20 carbon atoms, ether having 2 to 20 carbon atoms, thioether having 2 to 20 carbon atoms, cycloalkyl having 3 to 20 carbon atoms, cycloalkenyl having 3 to 20 carbon atoms, aryl having 5 to 20 carbon atoms or heteroaryl which does not contain any nitrogen atom and has 4 to 20 carbon atoms, and where the R1 to R4 radicals are the same or different and are each independently hydrogen, halogen, hydroxyl, thiol, nitro, carboxylate, aldehyde having 1 to 20 carbon atoms, ketone having 2 to 20 carbon atoms, O-alkyl having 1 to 20 carbon atoms, S-alkyl having 1 to 20 carbon atoms, O-alkenyl having 1 to 20 carbon atoms, S-alkenyl having 1 to 20 carbon atoms, O-aryl having 5 to 20 carbon atoms, S-aryl having 5 to 20 carbon atoms, ether having 2 to 20 carbon atoms, thioether having 2 to 20 carbon atoms, carboxylic ester having 1 to 20 carbon atoms, carboxamide having 1 to 20 carbon atoms, thioester having 1 to 20 carbon atoms, alkyl having 1 to 20 carbon atoms, alkenyl having 1 to 20 carbon atoms, cycloalkyl having 3 to 20 carbon atoms, cycloalkenyl having 3 to 20 carbon atoms, aryl having 5 to 20 carbon atoms or heteroaryl which does not contain any nitrogen atom and has 4 to 20 carbon atoms.

Further preferably, the R5 radical is an acyclic polyol radical of the general formula —CH$_2$(CH(OZ))$_f$CH$_{(3-e)}$(OZ)$_e$ where e is 1, or 2 and f is an integer from 1 to 10, preferably 1 to 4, and where Z is an ester of an aminocarboxylic acid which derives from an aminocarboxylic acid, preferably alpha-aminocarboxylic acid, having 1 to 20 carbon atoms, preferably selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, L-homoserine, ornithine, N5-(aminocarbonyl)-L-ornithine, L-(−)-carnitine, alpha-phenylglycine, L-3,4-dihydroxyphenylalanine, 3,6-diaminohexanoic acid, N-(aminoiminomethyl)-N-methylglycine, gamma-aminobutyric acid, L-5-hydroxytryptophan, norleucine and 2,6-diaminopimelic acid, further preferably arginine, glycine, lysine, ornithine, 3,6-diaminohexanoic acid and gamma-aminobutyric acid, even further preferably glycine and lysine, where preferably at least one amino group in each case may be substituted by methyl radicals.

In a further-preferred embodiment of variant III) of the 10H-benzo[g]pteridine-2,4-dione derivative of the formula (1), the organic radical X having a) at least one, preferably at least two, preferably at least three, preferably at least four, further preferably at least five, uncharged, protonatable nitrogen atom(s), and/or b) at least one, preferably at least two, preferably at least three, preferably at least four, further preferably at least five, positively charged, preferably quaternary, nitrogen atom(s), is a radical of the general formula (2):

 (2)

where A is an oxygen or sulfur atom and where n is an integer from 1 to 8 and m is an integer from 0 to 100, and where B is a radical of the formula (3a), (3b), (4a), (4b), (5a) or (5b):

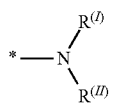 (3a)

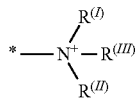 (3b)

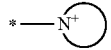 (4a)

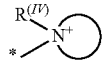 (4b)

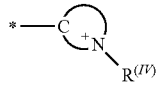 (5a)

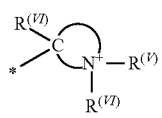 (5b)

and where the $R^{(I)}$ radical is an aryl radical having 5 to 20 carbon atoms, a heterocyclic radical having 5 to 20 carbon atoms, an alkyl radical, which may be straight-chain or branched, having 1 to 20 carbon atoms, an alkenyl radical, which may be straight-chain or branched, having 2 to 20 carbon atoms, a hydroxyalkyl radical, which may be straight-chain or branched, having 1 to 20 carbon atoms, an ether radical, which may be straight-chain or branched, having 2 to 20 carbon atoms, a thioether radical, which may be straight-chain or branched, having 2 to 20 carbon atoms, or an alkylamino radical, which may be straight-chain or branched, having 1 to 20 carbon atoms, where each of the $R^{(II)}$, $R^{(III)}$, $R^{(IV)}$, $R^{(V)}$ and $R^{(VI)}$ radicals is independently hydrogen, an aryl radical having 5 to 20 carbon atoms, a heterocyclic radical having 5 to 20 carbon atoms, an alkyl radical, which may be straight-chain or branched, having 1 to 20 carbon atoms, an alkenyl radical, which may be straight-chain or branched, having 2 to 20 carbon atoms, a hydroxyalkyl radical, which may be straight-chain or branched, having 1 to 20 carbon atoms, an ether radical, which may be straight-chain or branched, having 2 to 20 carbon atoms, a thioether radical, which may be straight-chain or branched, having 2 to 20 carbon atoms, or an alkylamino radical, which may be straight-chain or branched, having 1 to 20 carbon atoms and where each of the aforementioned aryl radicals, heterocyclic radicals, alkyl radicals, alkenyl radicals, hydroxyalkyl radicals, ether radicals, thioether radicals and alkylamino radicals is substituted at least by one, preferably at least two, preferably at least three, preferably at least four, further preferably at least five, amino radical(s) and/or alkylamino radical(s), which may be straight-chain or branched, having 1 to 20 carbon atoms, for example aminomethyl, 2-aminoethyl, dimethylaminomethyl or (trimethylammonio)methyl, and/or guanidino radical, and where the radical having the formula (4a) and the radical having the formula (5a):

 (4a)

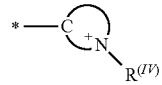 (5a)

is a substituted or unsubstituted heterocyclic radical having 5 to 7 ring atoms including 2 to 4 nitrogen atoms and at least 1 carbon atom and optionally 1 or 2 oxygen or sulfur atoms, where 1 nitrogen atom forms a double bond, and where the radical having the formula (4b) and the radical having the formula (5b):

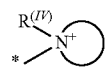 (4b)

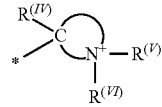 (5b)

is a substituted or unsubstituted heterocyclic radical having 5 to 7 ring atoms including 2 to 4 nitrogen atoms and at least 1 carbon atom and optionally 1 or 2 oxygen or sulfur atoms.

In a further-preferred embodiment of variant III) of the 10H-benzo[g]pteridine-2,4-dione derivative of the formula (1), the radical of the formula (5a) is selected from the group consisting of radicals of the formulae (22a), (22b) and (22c):

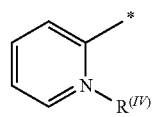 (22a)

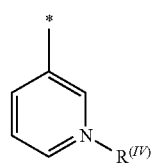 (22b)

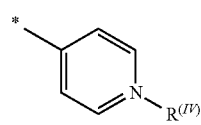 (22c)

where each $R^{(IV)}$ is selected from the group consisting of aryl radicals having 5 to 20 carbon atoms, for example phenyl or benzyl, heterocyclic radicals having 5 to 20 carbon atoms, for example 2-pyridyl, 3-pyridyl, 4-pyridyl, 1-methylpyridin-1-ium-2-yl, 1-methylpyridin-1-ium-3-yl or 1-methylpyridin-1-ium-4-yl, alkyl radicals which may be straight-chain or branched and have 1 to 20 carbon atoms, for example methyl, ethyl, n-propyl, i-propyl, n-butyl or t-butyl, alkenyl radicals which may be straight-chain or branched and have 2 to 20 carbon atoms, hydroxyalkyl radicals which may be straight-chain or branched and have 1 to 20 carbon atoms, for example hydroxymethyl, 2-hydroxyethyl, 3-hydroxypropyl or 1-hydroxy-1-methylethyl, ether radicals which may be straight-chain or branched and have 2 to 20 carbon atoms, for example methoxymethyl, methoxyethyl, methoxypropyl, ethoxymethyl, ethoxyethyl, ethoxypropyl, propoxymethyl, propoxyethyl or propoxypropyl, thioether radicals which may be straight-chain or branched and have 2 to 20 carbon atoms, for example methylsulfanylmethyl, ethylsulfanylmethyl, 2-ethylsulfanylethyl or 3-methylsulfanylpropyl, and alkylamino radicals which may be straight-chain or branched and have 1 to 20 carbon atoms, for example aminomethyl, 2-aminoethyl, dimethylaminomethyl or (trimethylammonio)methyl.

In a preferred embodiment of variant III) of the 10H-benzo[g]pteridine-2,4-dione derivative of the formula (1), the radical of the formula (4a) is selected from the group consisting of radicals of the formulae (23a), (23b) and (23c):

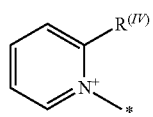

(23a)

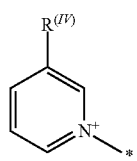

(23b)

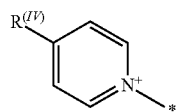

(23c)

where each $R^{(IV)}$ is selected from the group consisting of hydrogen, aryl radicals having 5 to 20 carbon atoms, for example phenyl or benzyl, heterocyclic radicals having 5 to 20 carbon atoms, for example 2-pyridyl, 3-pyridyl, 4-pyridyl, 1-methylpyridin-1-ium-2-yl, 1-methylpyridin-1-ium-3-yl or 1-methylpyridin-1-ium-4-yl, alkyl radicals which may be straight-chain or branched and have 1 to 20 carbon atoms, for example methyl, ethyl, n-propyl, i-propyl, n-butyl or t-butyl, alkenyl radicals which may be straight-chain or branched and have 2 to 20 carbon atoms, hydroxyalkyl radicals which may be straight-chain or branched and have 1 to 20 carbon atoms, for example hydroxymethyl, 2-hydroxyethyl, 3-hydroxypropyl or 1-hydroxy-1-methylethyl, ether radicals which may be straight-chain or branched and have 2 to 20 carbon atoms, for example methoxymethyl, methoxyethyl, methoxypropyl, ethoxymethyl, ethoxyethyl, ethoxypropyl, propoxymethyl, propoxyethyl or propoxypropyl, thioether radicals which may be straight-chain or branched and have 2 to 20 carbon atoms, for example methylsulfanylmethyl, ethylsulfanylmethyl, 2-ethylsulfanylethyl or 3-methylsulfanylpropyl, and alkylamino radicals which may be straight-chain or branched and have 1 to 20 carbon atoms, for example aminomethyl, 2-aminoethyl, dimethylaminomethyl or (trimethylammonio)methyl.

In a preferred embodiment of variant III) of the 10H-benzo[g]pteridine-2,4-dione derivative of the formula (1), the $R^{(II)}$, $R^{(III)}$, $R^{(IV)}$, $R^{(V)}$ and $R^{(VI)}$ radicals are each independently hydrogen or an alkyl radical of the general formula —$(CH_2)_n$—$CH_3$ and the $R^{(I)}$ radical is an alkyl radical of the general formula —$(CH_2)_n$—$CH_3$, where each n is an integer from 0 to 19, preferably from 1 to 17, where the aforementioned alkyl radicals are substituted at least by one, preferably at least two, preferably at least three, preferably at least four, further preferably at least five, amino radical(s) and/or alkylamino radical(s) which may be straight-chain or branched and have 1 to 20 carbon atoms, preferably 1 to 4 carbon atoms, for example aminomethyl, 2-aminoethyl, dimethylaminomethyl or (trimethylammonio)methyl, and/or guanidino radical.

In a preferred embodiment of variant III) of the 10H-benzo[g]pteridine-2,4-dione derivative of the formula (1), the $R^{(II)}$, $R^{(III)}$, $R^{(IV)}$, $R^{(V)}$ and $R^{(VI)}$ radicals are each independently hydrogen, methyl, ethyl, prop-1-yl, prop-2-yl, but-1-yl, but-2-yl, 2-methylprop-1-yl, 2-methyl-prop-2-yl, pent-1-yl, pent-2-yl, pent-3-yl, 2-methylbut-1-yl, 2-methylbut-2-yl, 2-methylbut-3-yl, 2-methylbut-4-yl, 2,2-dimethylprop-1-yl, hex-1-yl, hex-2-yl, hex-3-yl, hept-1-yl, oct-1-yl, 2-methylpent-1-yl, 2-methylpent-2-yl, 2-methylpent-3-yl, 2-methylpent-4-yl, 2-methylpent-5-yl, 3-methylpent-1-yl, 3-methylpent-2-yl, 3-methylpent-3-yl, 2,2-dimethylbut-1-yl, 2,2-dimethylbut-3-yl, 2,2-dimethylbut-4-yl, 2,3-dimethylbut-1-yl or 2,3-dimethylbut-2-yl, and the $R^{(I)}$ radical is methyl, ethyl, prop-1-yl, prop-2-yl, but-1-yl, but-2-yl, 2-methylprop-1-yl, 2-methyl-prop-2-yl, pent-1-yl, pent-2-yl, pent-3-yl, 2-methylbut-1-yl, 2-methylbut-2-yl, 2-methylbut-3-yl, 2-methylbut-4-yl, 2,2-dimethylprop-1-yl, hex-1-yl, hex-2-yl, hex-3-yl, hept-1-yl, oct-1-yl, 2-methylpent-1-yl, 2-methylpent-2-yl, 2-methylpent-3-yl, 2-methylpent-4-yl, 2-methylpent-5-yl, 3-methylpent-1-yl, 3-methylpent-2-yl, 3-methylpent-3-yl, 2,2-dimethylbut-1-yl, 2,2-dimethylbut-3-yl, 2,2-dimethylbut-4-yl, 2,3-dimethylbut-1-yl or 2,3-dimethylbut-2-yl, where the aforementioned alkyl radicals are substituted at least by one, preferably at least two, preferably at least three, preferably at least four, further preferably at least five, amino radical(s) and/or alkylamino radical(s) which may be straight-chain or branched and have 1 to 20 carbon atoms, preferably 1 to 4 carbon atoms, for example aminomethyl, 2-aminoethyl, dimethylaminomethyl or (trimethylammonio)methyl, and/or guanidino radical.

In a particularly preferred embodiment, the $R^{(I)}$, $R^{(II)}$, $R^{(III)}$, $R^{(IV)}$, $R^{(V)}$ and $R^{(VI)}$ radicals may each independently be methyl, ethyl, prop-1-yl, but-1-yl, pent-1-yl, hex-1-yl, hept-1- or oct-1-yl, where the aforementioned alkyl radicals are substituted at least by one, preferably at least two, preferably at least three, preferably at least four, further preferably at least five, amino radical(s) and/or alkylamino radical(s) which may be straight-chain or branched and have 1 to 20 carbon atoms, for example aminomethyl, 2-aminoethyl, dimethylaminomethyl or (trimethylammonio)methyl, and/or guanidino radical.

In a preferred embodiment of variant III) of the 10H-benzo[g]pteridine-2,4-dione derivative of the formula (1), the $R^{(II)}$, $R^{(III)}$, $R^{(IV)}$, $R^{(V)}$ and $R^{(VI)}$ radicals are each independently hydrogen or a radical of the formulae (6) to (9):

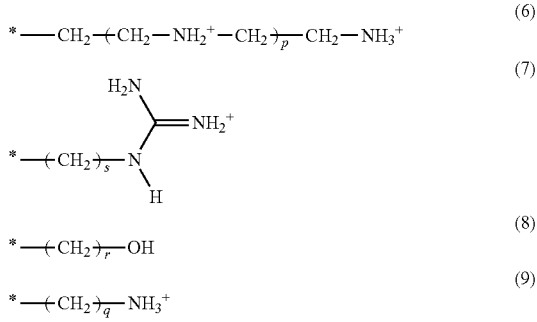

and the R$^{(I)}$ radical is a radical of the formulae (6) to (9), where each p is an integer from 1 to 10, preferably from 1 to 7, further preferably from 1 to 3, and where s, r, q are each independently an integer from 1 to 20, preferably from 1 to 8, further preferably from 1 to 4, selected.

In a further-preferred embodiment of variant III) of the 10H-benzo[g]pteridine-2,4-dione derivative of the formula (1), the R$^{(II)}$, R$^{(III)}$, R$^{(IV)}$, R$^{(V)}$ and R$^{(VI)}$ radicals are each independently hydrogen or a polyamine radical of the general formula —[(CH$_2$)$_a$—N(R$^{(VII)}$)—(CH$_2$)$_b$—]$_c$NH$_{(3-g)}$ (R$^{(VIII)}$)$_g^+$, and the R$^{(I)}$ radical is a polyamine radical of the general formula —[(CH$_2$)$_a$—N(R$^{(VII)}$)—(CH$_2$)$_b$—]$_c$NH$_{(3-g)}$ (R$^{(VIII)}$)$_g^+$, where each c is an integer from 1 to 10, preferably from 1 to 7, further preferably from 1 to 3, a and b are each independently an integer from 1 to 10, preferably from 1 to 4, further preferably from 2 to 3, g is 0, 1, 2 or 3 and R$^{(VII)}$ and R$^{(VIII)}$ are each independently hydrogen, methyl or ethyl.

In a further-preferred embodiment of variants I), II) and III) of the compound of the formula (1), the aforementioned alkyl radicals and alkenyl radicals may be straight-chain or branched, preferably straight-chain, and be either unsubstituted or substituted by at least one radical selected from the group consisting of hydroxyl, sulfanyl, alkyloxy, preferably methoxy, ethoxy, n-propyloxy, i-propyloxy, n-butyloxy and n-pentyloxy, alkylsulfanyl, preferably methylsulfanyl, ethylsulfanyl, n-propylsulfanyl, i-propylsulfanyl, n-butylsulfanyl and n-pentylsulfanyl, alkanoyloxy, preferably formyloxy, acetoxy and n-propanoyloxy, amino, alkylamino having 1 to 4 carbon atoms, preferably methylamino, ethylamino, n-propylamino, i-propylamino and n-butylamino, dialkylamino having 2 to 8 carbon atoms, preferably dimethylamino, ethylmethylamino, diethylamino and di-n-propylamino, trialkylammonio having 3 to 12 carbon atoms, preferably trimethylammonio, triethylammonio, methyldiethylammonio, ethyldimethylammonio and tri-n-propylammonio, and guanidino.

In a further-preferred embodiment, the aforementioned alkyl radicals are each selected from methyl, ethyl, n-propyl, n-butyl, n-pentyl, n-hexyl, n-heptyl and n-octyl.

In a further-preferred embodiment of variants I), II) and III) of the compound of the formula (1), the aforementioned cycloalkyl radicals and cycloalkenyl radicals may have oxygen and/or sulfur atoms as ring atoms and be either unsubstituted or substituted by at least one radical selected from the group consisting of hydroxyl, sulfanyl, alkyloxy, preferably methoxy, ethoxy, n-propyloxy, i-propyloxy, n-butyloxy and n-pentyloxy, alkylsulfanyl, preferably methylsulfanyl, ethylsulfanyl, n-propylsulfanyl, i-propylsulfanyl, n-butylsulfanyl and n-pentylsulfanyl, alkanoyloxy, preferably formyloxy, acetoxy and n-propanoyloxy, amino, alkylamino having 1 to 4 carbon atoms, preferably methylamino, ethylamino, n-propylamino, i-propylamino and n-butylamino, dialkylamino having 2 to 8 carbon atoms, preferably dimethylamino, ethylmethylamino, diethylamino and di-n-propylamino, trialkylammonio having 3 to 12 carbon atoms, preferably trimethylammonio, triethylammonio, methyldiethylammonio, ethyldimethylammonio and tri-n-propylammonio, and guanidino.

In a further-preferred embodiment, the aforementioned cycloalkyl radicals and cycloalkenyl radicals having oxygen and/or sulfur atoms as ring atoms are each selected from the group consisting of tetrahydrofuranyl, tetrahydrothiophenyl, tetrahydropyranyl, tetrahydrothiopyranyl, dioxolanyl and dioxanyl.

In a preferred embodiment of variants I), II) and III) of the compound of the formula (1), the aforementioned aryl radicals each have not more than 4, further preferably not more than 3, further preferably not more than 2, fused rings. Even further preferably, the aryl radicals each have 1 ring.

In a preferred embodiment of variants I), II) and III) of the compound of the formula (1), the aforementioned aryl radicals are selected from the group consisting of phenyl, benzyl, naphthyl, anthracenyl, phenanthenyl and pyrenyl.

In a further preferred embodiment of variants I), II) and III) of the compound of the formula (1), the aforementioned alkenyl radicals have 2 to 17 carbon atoms, further preferably 2 to 13 carbon atoms, further preferably 2 to 9 carbon atoms, further preferably 2 to 5 carbon atoms. In a further-preferred embodiment, the aforementioned alkenyl radicals are selected from the group consisting of ethenyl, n-propenyl and n-butenyl.

In a further preferred embodiment of variants I), II) and III) of the compound of the formula (1), the aforementioned aldehydes have 1 to 17 carbon atoms, further preferably 1 to 13 carbon atoms, further preferably 1 to 9 carbon atoms, further preferably 1 to 5 carbon atoms. In a further-preferred embodiment, the aforementioned aldehydes are selected from the group consisting of methanal-1-yl (formyl), ethanal-1-yl (2-oxoethyl), n-propanal-1-yl (3-oxopropyl) and n-butanal-1-yl (4-oxobutyl).

In a further preferred embodiment of variants I), II) and III) of the compound of the formula (1), the aforementioned ketones have 2 to 17 carbon atoms, further preferably 3 to 14 carbon atoms, further preferably 3 to 9 carbon atoms. In a further-preferred embodiment, the aforementioned ketones are selected from the group consisting of dimethyl ketyl, methyl ethyl ketyl, ethyl methyl ketyl, diethyl ketyl, methyl propyl ketyl, ethyl propyl ketyl, propyl methyl ketyl, propyl ethyl ketyl and dipropyl ketyl, which may be straight-chain or branched. In a further-preferred embodiment, the aforementioned aldehyde radicals and/or ketone radicals may be monosaccharide radicals, preferably pentose or ketose radicals.

Preferably, suitable monosaccharide radicals have 3 to 7 carbon atoms, preferably 5 to 6 carbon atoms, and have one carbonyl group, preferably aldehyde group or keto group, and at least one hydroxyl group and may be open-chain or cyclic, preferably in the form of furanose or pyranose.

Preferably, suitable monosaccharide radicals derive from monosaccharides selected from the group consisting of D-glyceraldehyde, L-glyceraldehyde, D-erythrose, L-erythrose, D-threose, L-threose, D-ribose, L-ribose, D-arabinose, L-arabinose, D-xylose, L-xylose, D-lyxose, L-lyxose, D-allose, L-allose, D-altrose, L-altrose, D-glucose, L-glucose, D-mannose, L-mannose, D-gulose, L-gulose, D-idose, L-idose, D-galactose, L-galactose, D-talose, L-talose, dihydroxyacetone, D-erythrulose, L-erythrulose, D-ribulose, L-ribulose, D-xylulose, L-xylulose, D-psicose, L-psicose, D-fructose, L-fructose, D-sorbose, L-sorbose, D-tagatose and L-tagatose. Further preferably, suitable monosaccharides are selected from the group consisting of D-ribose, L-ribose, D-arabinose, L-arabinose, D-xylose, L-xylose, D-lyxose, L-lyxose, D-allose, L-allose, D-altrose, L-altrose, D-glucose, L-glucose, D-mannose, L-mannose, D-gulose, L-gulose, D-idose, L-idose, D-galactose, L-galactose, D-talose, L-talose, D-ribulose, L-ribulose, D-xylulose, L-xylulose, D-psicose, L-psicose, D-fructose, L-fructose, D-sorbose, L-sorbose, D-tagatose and L-tagatose.

In a further preferred embodiment of variants I), II) and III) of the compound of the formula (1), the aforementioned carboxylic esters have 1 to 17 carbon atoms, further preferably 1 to 20 carbon atoms, further preferably 1 to 12 carbon atoms. In a further-preferred embodiment, the aforementioned carboxylic esters are selected from the group consisting of ethyl esters, n-propyl esters, i-propyl esters, n-butyl esters, sec-butyl esters, tert-butyl esters and benzyl esters.

In a further preferred embodiment of variants I), II) and III) of the compound of the formula (1), the aforementioned carboxamides have 1 to 17 carbon atoms, further preferably 1 to 15 carbon atoms, further preferably 1 to 12 carbon atoms. In a further-preferred embodiment, the aforementioned carboxamides are selected from the group consisting of amide, N-methylamide, N-ethylamide, N-(n-propyl)amide, N-(i-propyl)amide, N-(n-butyl)amide, N-(sec-butyl)amide, N-(tert-butyl)amide, N-phenylamide, N-benzylamide, N,N-dimethylamide, N-methyl-N-ethylamide, N,N-diethylamide, N-methyl-N-(n-propyl)amide, N-methyl-N-(i-propyl)amide, N-methyl-N-(n-butyl)amide, N-methyl-N-(sec-butyl)amide, N-methyl-N-(tert-butyl)amide, N-ethyl-N-(n-propyl)amide, N-ethyl-N-(i-propyl)amide, N-ethyl-N-(n-butyl)amide, N-ethyl-N-(sec-butyl)amide, N-ethyl-N-(tert-butyl)amide, N-(n-propyl)-N-(n-propyl)amide, N-(n-propyl)-N-(i-propyl)amide, N-(n-propyl)-N-(n-butyl)amide, N-(n-propyl)-N-(sec-butyl)amide, N-(n-propyl)-N-(tert-butyl)amide, N-(i-propyl)-N-(n-propyl)amide, N-(i-propyl)-N-(i-propyl)amide, N-(i-propyl)-N-(n-butyl)amide, N-(i-propyl)-N-(sec-butyl)amide, N-(i-propyl)-N-(tert-butyl)amide, N-(n-butyl)-N-(n-propyl)amide, N-(n-butyl)-N-(i-propyl)amide, N-(n-butyl)-N-(n-butyl)amide, N-(n-butyl)-N-(sec-butyl)amide, N-(n-butyl)-N-(tert-butyl)amide, N-(sec-butyl)-N-(n-propyl)amide, N-(sec-butyl)-N-(i-propyl)amide, N-(sec-butyl)-N-(n-butyl)amide, N-(sec-butyl)-N-(sec-butyl)amide, N-(sec-butyl)-N-(tert-butyl)amide, N-(tert-butyl)-N-(n-propyl)amide, N-(tert-butyl)-N-(i-propyl)amide, N-(tert-butyl)-N-(n-butyl)amide, N-(tert-butyl)-N-(sec-butyl)amide, N-(tert-butyl)-N-(tert-butyl)amide, N,N-diphenylamide, N,N-dibenzylamide, N-phenyl-N-benzylamide, N-methyl-N-phenylamide, N-methyl-N-benzylamide, N-ethyl-N-phenylamide, N-ethyl-N-benzylamide, N-phenyl-N-(n-propyl)amide, N-phenyl-N-(i-propyl)amide, N-phenyl-N-(n-butyl)amide, N-phenyl-N-(sec-butyl)amide, N-phenyl-N-(tert-butyl)amide, N-benzyl-N-(n-propyl)amide, N-benzyl-N-(i-propyl)amide, N-benzyl-N-(n-butyl)amide, N-benzyl-N-(sec-butyl)amide and N-benzyl-N-(tert-butyl)amide.

In a further preferred embodiment of variants I), II) and III) of the compound of the formula (1), the aforementioned heteroaryl radical which does not contain any nitrogen atom and has 4 to 20 carbon atoms is selected from the group consisting of thiophenyl, furanyl, benzothiofuranyl and benzofuranyl.

In a further preferred embodiment of variants I), II) and III) of the compound of the formula (1), the aforementioned ether radicals have 2 to 17 carbon atoms, further preferably 2 to 13 carbon atoms, further preferably 2 to 9 carbon atoms. In a further-preferred embodiment, the aforementioned ether radicals are selected, for example, from the group consisting of methoxymethyl, methoxyethyl, methoxy-n-propyl, ethoxymethyl, n-propoxymethyl, 2-ethoxyethoxymethyl, 2-(2-ethoxyethoxy)ethyl, i-propoxymethyl, tert-butyloxymethyl, dioxa-3,6-heptyl and benzyloxymethyl. In a further-preferred embodiment, the aforementioned ether radicals may be simple ether radicals, oligoether radicals, polyether radicals or mixtures thereof.

In a further preferred embodiment of variants I), II) and III) of the compound of the formula (1), the aforementioned thioether radicals have 2 to 17 carbon atoms, further preferably 2 to 13 carbon atoms, further preferably 2 to 9 carbon atoms. In a further-preferred embodiment, the aforementioned thioether radicals are selected, for example, from the group methylsulfanylmethyl, methylsulfanylethyl, 3-methylsulfanyl-n-propyl, ethylsulfanylmethyl, n-propylsulfanylmethyl, 2-ethylsulfanylethylsulfanylmethyl, 2-(2-ethylsulfanylethylsulfanyl)ethyl, 2-methylsulfanylpropyl, tert-butylsulfanylmethyl and benzylsulfanylmethyl consists.

In a further preferred embodiment of variants I), II) and III), the compound of the formula (1) has a molecular weight of less than 1300 g/mol, preferably less than 990 g/mol, further preferably less than 810 g/mol, further preferably less than 690 g/mol, even further preferably less than 610 g/mol, even further preferably less than 600 g/mol, even further preferably less than 570 g/mol.

Chiral centers, unless stated otherwise, may be in the R or S configuration. The invention relates both to the optically pure compounds and to stereoisomer mixtures, such as enantiomer mixtures and diastereomer mixtures, in any ratio.

The invention preferably also relates to mesomers and/or tautomers of the compound having the formula (1), both the pure compounds and the isomer mixtures in any ratio.

In a further preferred embodiment of variant III) of the compound of the formula (1), the organic radical having:
a) at least two uncharged, protonatable nitrogen atoms not bonded directly to the isoalloxazine ring, or
b) at least two positively charged, preferably quaternary, nitrogen atoms not bonded directly to the isoalloxazine ring, is in each case selected from the radicals of the formulae (30a) to (37b)

(30a)

(30b)

(31a)

(31b)

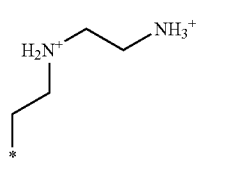 (32a)

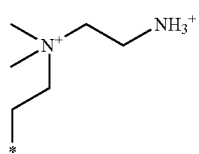 (32b)

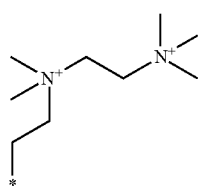 (32c)

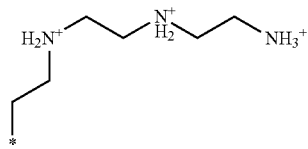 (37a)

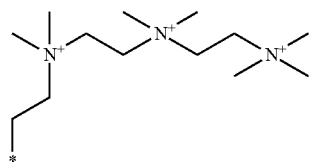 (37b)

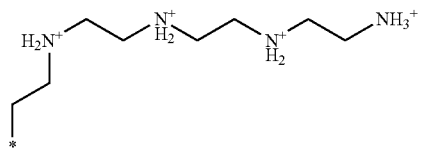 (33a)

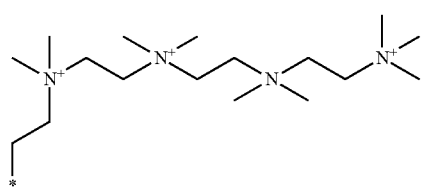 (33b)

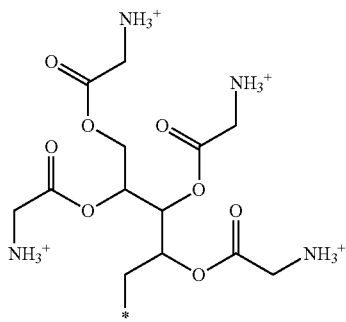 (34a)

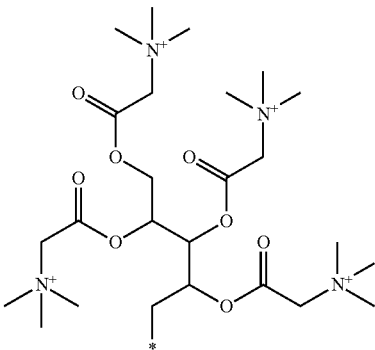 (34b)

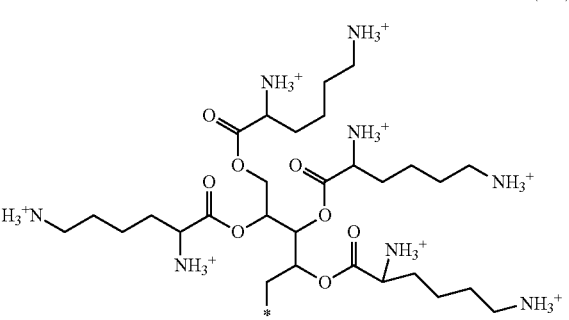 (35a)

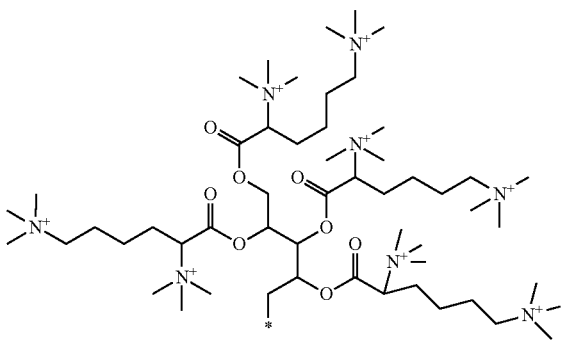 (35b)

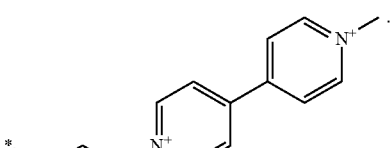 (36)

In a further preferred embodiment of variant II) of the compound of the formula (1), the organic radical having:

a) at least two uncharged, protonatable nitrogen atoms not bonded directly to the isoalloxazine ring, or a) at least two positively charged, preferably quaternary, nitrogen atoms not bonded directly to the isoalloxazine ring, is a radical of the formula (32b):

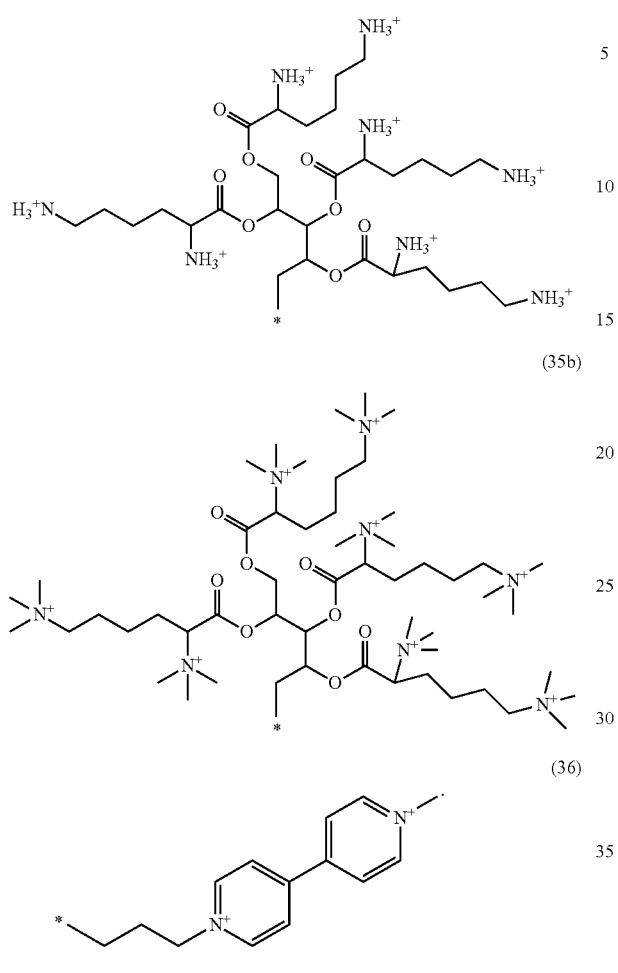

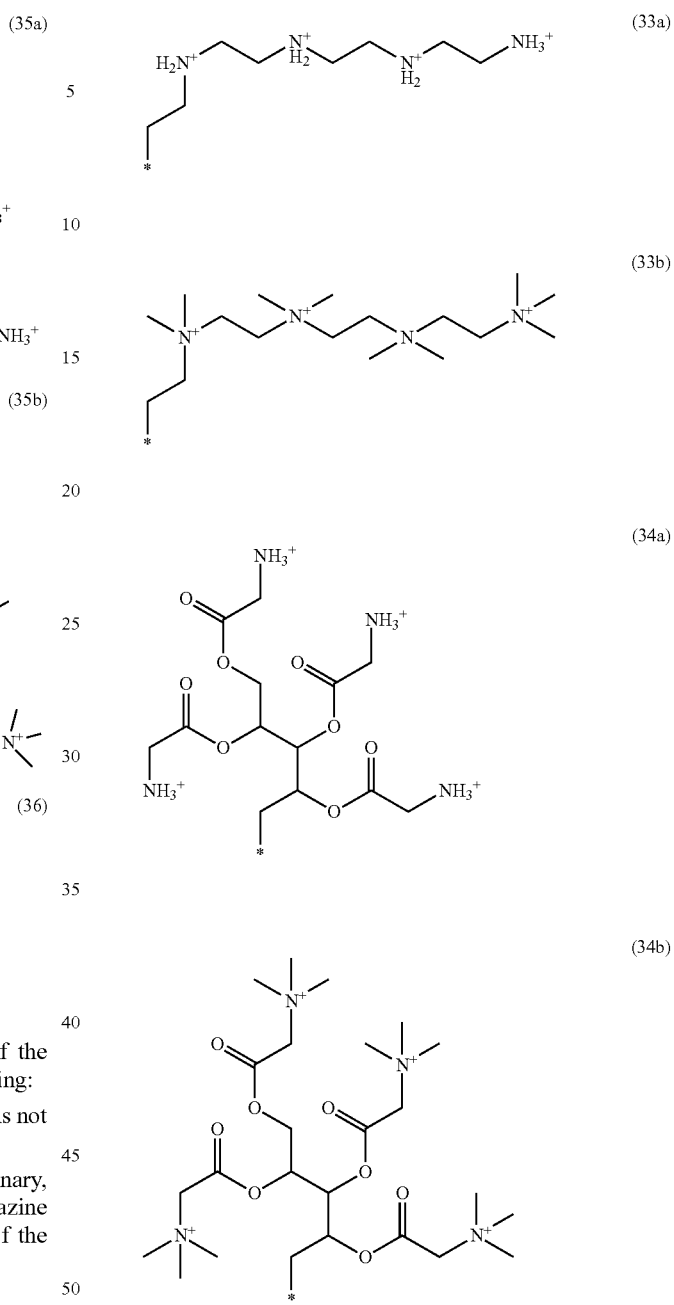

In a further preferred embodiment of variant I) of the compound of the formula (1), the organic radical having:

a) at least two uncharged, protonatable nitrogen atoms not bonded directly to the isoalloxazine ring, or
b) at least two positively charged, preferably quaternary, nitrogen atoms not bonded directly to the isoalloxazine ring, is in each case selected from the radicals of the formulae (32a), (32c), (33a), (33b) to (37b)

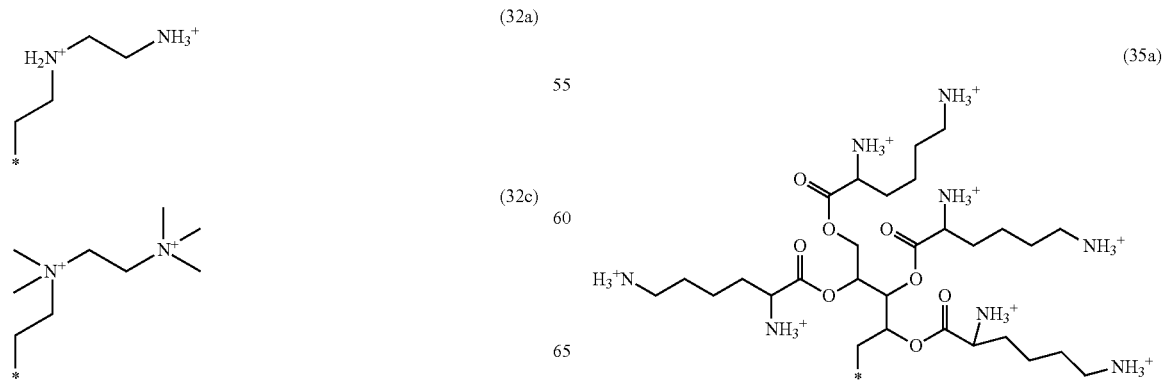

(35b)
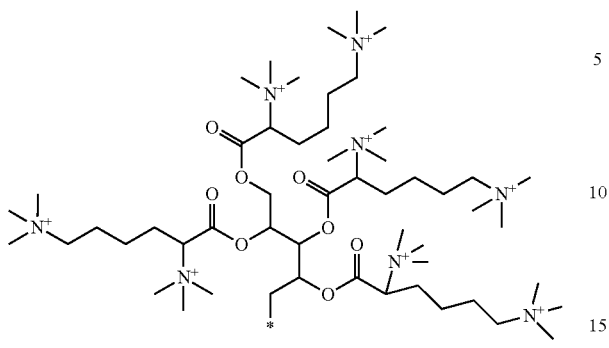

(36)
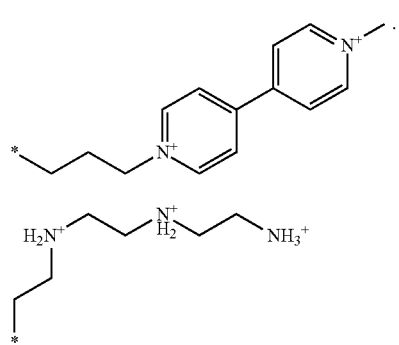

(37a)
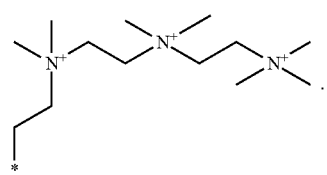

(37b)
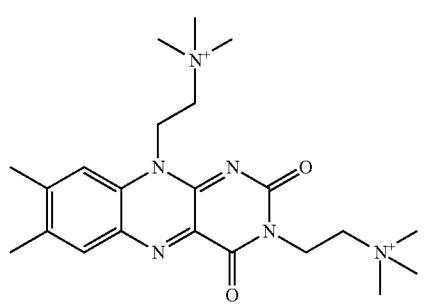

In a further preferred embodiment of variant III), the inventive 10H-benzo[g]pteridine-2,4-dione derivative of the formula (1) is selected from the group consisting of compounds having the formulae (40) to (44):

(40)
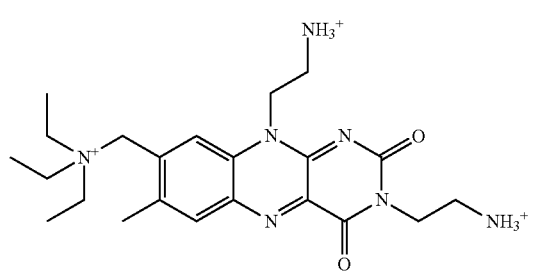

(42)
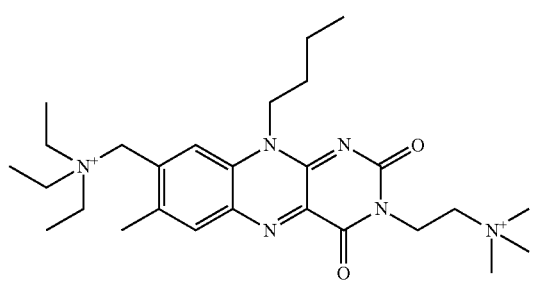

(43)
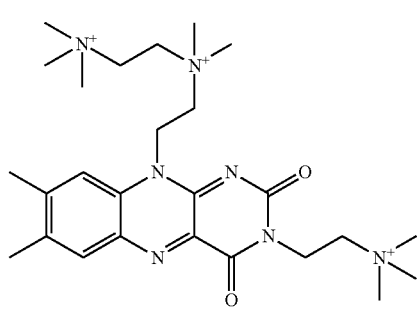

(44)
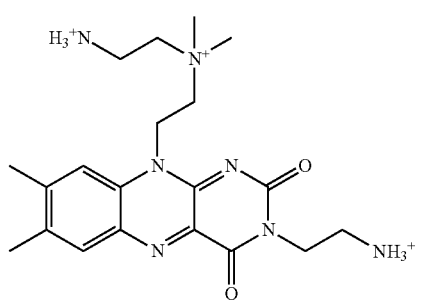

In a further preferred embodiment of variant I), the inventive 10H-benzo[g]pteridine-2,4-dione derivative of the formula (1) is selected from the group consisting of compounds having the formulae (45) to (49) and (115) to (117):

(45)
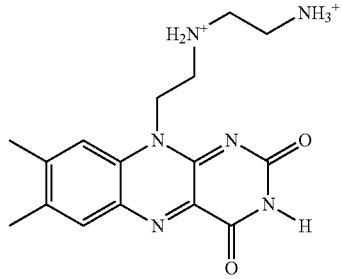

(46)
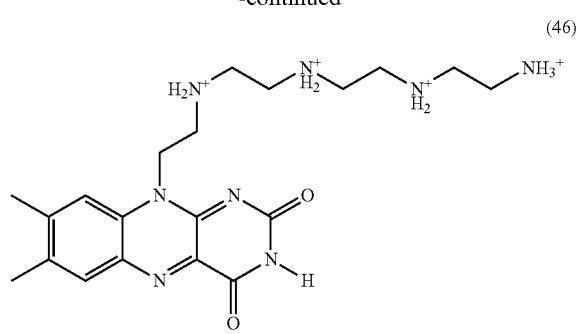

(47)
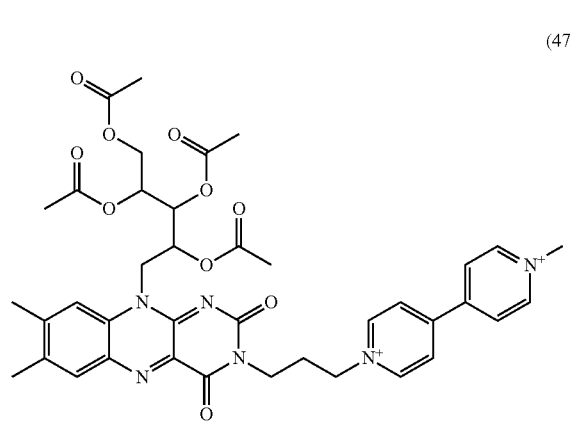

(48)
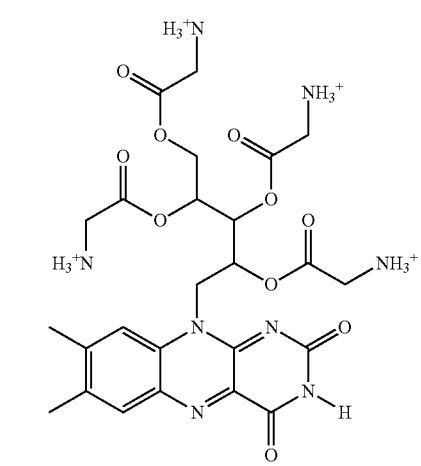

(49)
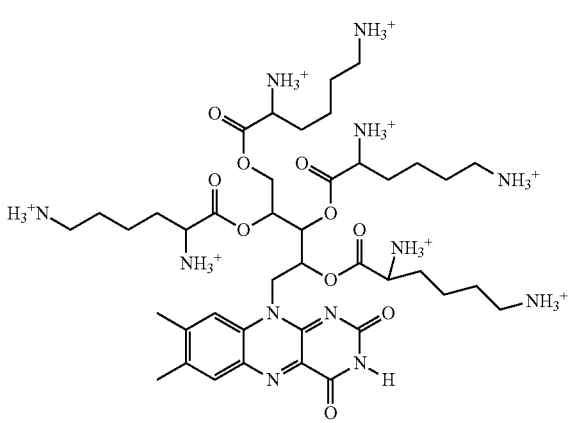

(115)
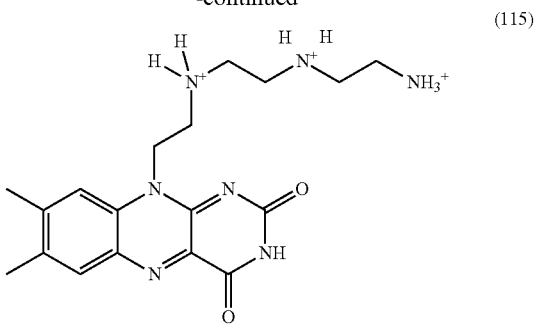

(116)
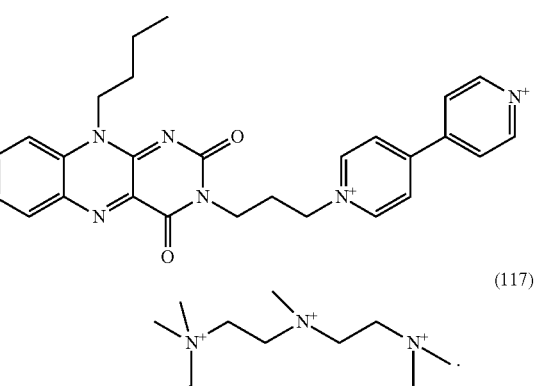

(117)
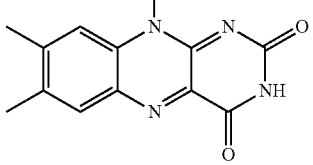

One variant of the process for preparing a compound as claimed in claim 1 comprises the following steps:
(A) reducing a substituted nitroaniline of the formula (9) to a substituted o-phenylenediamine of the formula (10)

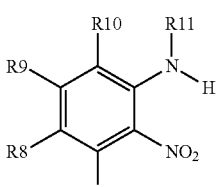

(9)

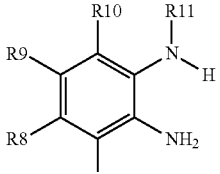

(10)

where each of the R7 to R10 radicals is the same or different and is independently hydrogen, halogen, hydroxyl, thiol, nitro, carboxylate, aldehyde having 1 to 20 carbon atoms, ketone having 2 to 20 carbon atoms, O-alkyl having 1 to 20 carbon atoms, S-alkyl having 1 to 20 carbon atoms, O-alkenyl having 2 to 20 carbon atoms, S-alkenyl having 2 to 20 carbon atoms, O-aryl having 5 to 20 carbon atoms, S-aryl having 5 to 20 carbon atoms, carboxylic ester having 1 to 20 carbon atoms, carboxamide having 1 to 20 carbon atoms, thioester having 1 to 20 carbon atoms, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms, heteroaryl which does not contain any nitrogen atom and has 4 to 20 carbon atoms, —(C(D)(E))$_h$-OH, —(C(D)(E))$_k$-aryl-(C(D)(E))$_l$-OH or an organic radical containing a) at least one uncharged, protonatable nitrogen atom not bonded directly to the isoalloxazine ring, and/or b) at least one positively charged nitrogen atom not bonded directly to the isoalloxazine ring, and where the R11 radical is hydrogen, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms, heteroaryl which does not contain any nitrogen atom and has 4 to 20 carbon atoms, —(C(D)(E))$_h$-OH, —(C(D)(E))$_k$-aryl-(C(D)(E))$_l$-OH or an organic radical containing a) at least one uncharged, protonatable nitrogen atom not bonded directly to the isoalloxazine ring, and/or b) at least one positively charged nitrogen atom not bonded directly to the isoalloxazine ring, and (B) condensing the substituted o-phenylenediamine of the formula (10) obtained in step (A) with alloxane or the hydrate thereof to obtain a compound having the formula (11):

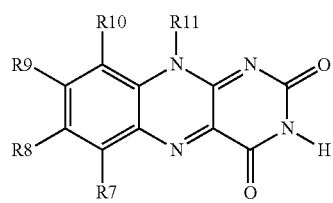

(C) optionally reacting the compound of the formula (11) obtained in step (B) with an alkylating agent of the general formula T-alkyl, T-alkenyl, T-cycloalkyl, T-cycloalkenyl, T-(C(D)(E))$_h$-OH, T-(C(D)(E))$_k$-aryl-(C(D)(E))$_l$-OH, T-aryl, T-(C(D)(E))$_h$-X or T-(C(D)(E))$_k$-aryl-(C(D)(E))$_l$-X, where the T radical is hydrogen, chlorine, bromine, iodine, p-toluenesulfonyl (OTs), methanesulfonyl (OMs), OH or R$_2$S$^+$, where each R may independently be the same or different and is preferably methyl, ethyl, propyl or butyl, to obtain a compound having the formula (12):

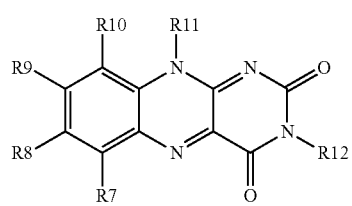

where the R12 radical is hydrogen, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms, heteroaryl which has 4 to 20 carbon atoms and does not contain any nitrogen atom, —(C(D)(E))$_h$-OH, —(C(D)(E))$_k$-aryl-(C(D)(E))$_l$-OH or an organic radical containing a) at least one uncharged, protonatable nitrogen atom not bonded directly to the isoalloxazine ring, and/or b) at least one positively charged nitrogen atom not bonded directly to the isoalloxazine ring, and (D) optionally reacting the compound of the formula (11) obtained in step (B) or the compound of the formula (12) obtained in step (C) with tosyl chloride, mesyl chloride or iodine, optionally in the presence of a catalyst, and subsequently with an organic compound containing at least one uncharged, protonatable nitrogen atom and/or b) at least one positively charged nitrogen atom, when at least 1 R7, R8, R9, R10, R11 or R12 radical is —(C(D)(E))$_h$-OH or —(C(D)(E))$_k$-aryl-(C(D)(E))$_l$-OH, to obtain the inventive 10H-benzo[g]pteridine-2,4-dione derivative of the formula (1), where D and E are each independently hydrogen, halogen, preferably chlorine, bromine, iodine or fluorine, hydroxyl, O—R$^{(VIII)}$ where R$^{(VIII)}$ is methyl, ethyl, n-propyl, n-butyl, phenyl or benzyl, O—C—(=O)—R$^{(IX)}$ where R$^{(IX)}$ is hydrogen, methyl, ethyl, n-propyl, n-butyl, phenyl or benzyl, or thiol, further preferably hydrogen or hydroxyl, and with the proviso that I) only 1 R1, R2, R3, R4, R5 or R6 radical is an organic radical having:
a) at least two, preferably at least three, preferably at least four, further preferably at least five, uncharged, protonatable nitrogen atoms not bonded directly to the isoalloxazine ring, or
b) at least two, preferably at least three, preferably at least four, further preferably at least five, positively charged, preferably quaternary, nitrogen atoms not bonded directly to the isoalloxazine ring,
or II) only 1 R1, R2, R3, R4, R5 or R6 radical is an organic radical having:
a) at least one, preferably at least two, preferably at least three, preferably at least four, further preferably at least five, uncharged, protonatable nitrogen atom(s) not bonded directly to the isoalloxazine ring, and
b) at least one, preferably at least two, preferably at least three, preferably at least four, further preferably at least five, positively charged, preferably quaternary, nitrogen atom(s) not bonded directly to the isoalloxazine ring,
or III) at least 2 R1, R2, R3, R4, R5 or R6 radicals are an organic radical having:
a) at least one, preferably at least two, preferably at least three, preferably at least four, further preferably at least five, uncharged, protonatable nitrogen atom(s) not bonded directly to the isoalloxazine ring, and
b) at least one, preferably at least two, preferably at least three, preferably at least four, further preferably at least five, positively charged, preferably quaternary, nitrogen atom(s) not bonded directly to the isoalloxazine ring.

A further variant of the process for preparing a compound as claimed in claim 1 comprises the following steps:
(A) condensing an amine having the formula R11-NH$_2$ with a chlorouracil derivative of the formula (13), optionally in the presence of a catalyst, preferably Lewis acid or Brønsted acid, to obtain a compound having the formula (14):

(13)

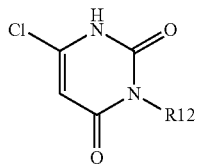

(14)

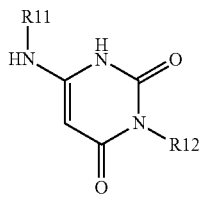

where each of the R11 and R12 radicals is the same or different and is independently hydrogen, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms, heteroaryl which does not contain any nitrogen atom and has 4 to 20 carbon atoms, —(C(D)(E))$_h$-OH, —(C(D)(E))$_k$-aryl-(C(D)(E))$_l$-OH or an organic radical containing a) at least one uncharged, protonatable nitrogen atom not bonded directly to the isoalloxazine ring, and/or b) at least one positively charged nitrogen atom not bonded directly to the isoalloxazine ring, (B) reacting the compound of the formula (14) obtained in step (A) with a nitroso compound of the formula (15) to obtain a compound of the formula (12):

(15)

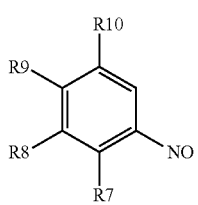

(12)

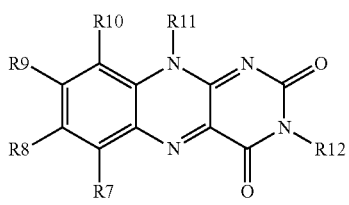

where each of the R7 to R10 radicals, which may independently be the same or different, is hydrogen, halogen, hydroxyl, thiol, nitro, carboxylate, aldehyde having 1 to 20 carbon atoms, ketone having 2 to 20 carbon atoms, O-alkyl having 1 to 20 carbon atoms, S-alkyl having 1 to 20 carbon atoms, O-alkenyl having 2 to 20 carbon atoms, S-alkenyl having 2 to 20 carbon atoms, O-aryl having 5 to 20 carbon atoms, S-aryl having 5 to 20 carbon atoms, carboxylic ester having 1 to 20 carbon atoms, carboxamide having 1 to 20 carbon atoms, thioester having 1 to 20 carbon atoms, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms, heteroaryl which does not contain any nitrogen atom and has 4 to 20 carbon atoms, —(C(D)(E))$_h$-OH, —(C(D)(E))$_k$-aryl-(C(D)(E))$_l$-OH or an organic radical containing a) at least one uncharged, protonatable nitrogen atom not bonded directly to the isoalloxazine ring, and/or b) at least one positively charged nitrogen atom not bonded directly to the isoalloxazine ring, and (C) optionally reacting the compound of the formula (12) obtained in step (B) with tosyl chloride, mesyl chloride or iodine, optionally in the presence of a catalyst, and subsequently with an organic compound containing at least one tertiary nitrogen atom is reacted, when at least 1 R7, R8, R9, R10, R11 or R12 radical is —(C(D)(E))$_h$-OH or —(C(D)(E))$_k$-aryl-(C(D)(E))$_l$-OH, to obtain the inventive 10H-benzo[g]pteridine-2,4-dione derivative of the formula (1), where D and E are each independently hydrogen, halogen, preferably chlorine, bromine, iodine or fluorine, hydroxyl, O—R$^{(VIII)}$ where R$^{(VIII)}$ is methyl, ethyl, n-propyl, n-butyl, phenyl or benzyl, O—C(=O)—R$^{(IX)}$ where R(IX) is hydrogen, methyl, ethyl, n-propyl, n-butyl, phenyl or benzyl, or thiol, further preferably hydrogen or hydroxyl, and with the proviso that I) only 1 R1, R2, R3, R4, R5 or R6 radical is an organic radical having:
 a) at least two, preferably at least three, preferably at least four, further preferably at least five, uncharged, protonatable nitrogen atoms not bonded directly to the isoalloxazine ring, or
 b) at least two, preferably at least three, preferably at least four, further preferably at least five, positively charged, preferably quaternary, nitrogen atoms not bonded directly to the isoalloxazine ring, or II) only 1 R1, R2, R3, R4, R5 or R6 radical is an organic radical having:
 a) at least one, preferably at least two, preferably at least three, preferably at least four, further preferably at least five, uncharged, protonatable nitrogen atom(s) not bonded directly to the isoalloxazine ring, and
 b) at least one, preferably at least two, preferably at least three, preferably at least four, further preferably at least five, positively charged, preferably quaternary, nitrogen atom(s) not bonded directly to the isoalloxazine ring, or III) at least 2 R1, R2, R3, R4, R5 or R6 radicals are an organic radical having:
 a) at least one, preferably at least two, preferably at least three, preferably at least four, further preferably at least five, uncharged, protonatable nitrogen atom(s) not bonded directly to the isoalloxazine ring, and/or
 b) at least one, preferably at least two, preferably at least three, preferably at least four, further preferably at least five, positively charged, preferably quaternary, nitrogen atom(s) not bonded directly to the isoalloxazine ring.

A further variant of the process according to the invention for preparing a 10H-benzo[g]pteridine-2,4-dione derivative of the formula (1) comprises the following steps:

(A) preparing a substituted aniline having the formula (122a) or (122b) by (a) peptide coupling/reduction to an aniline having the formula (121) or (b) reductive amination of an aniline having the formula (121) with aldehydes or (c) Pd-catalyzed coupling of a halide of the formula (124) to an amine of the formula R11-NH₂ or (d) Pd-catalyzed coupling of an amine of the formula (120) to a halide of the formula R11-NH₂

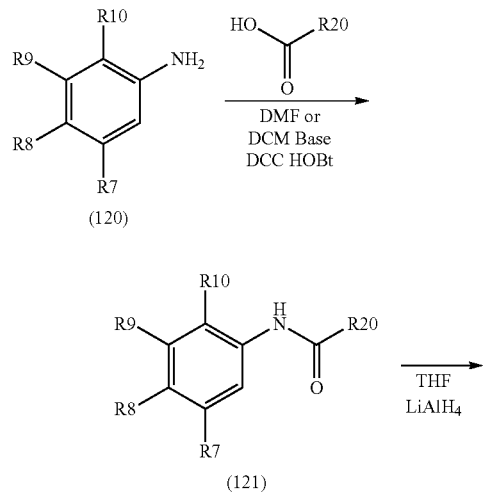
(120)

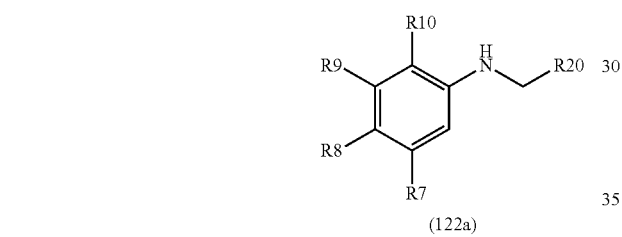
(121)

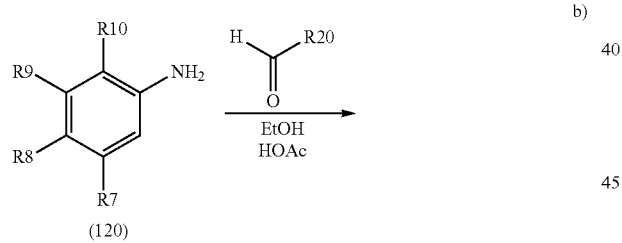
(122a)

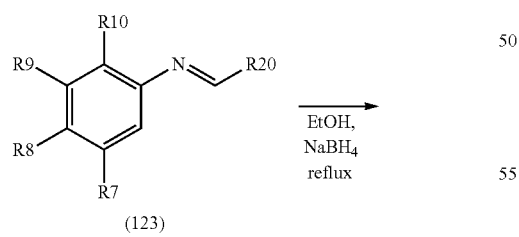
(120)

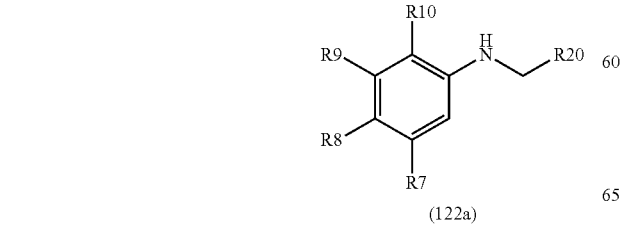
(123)

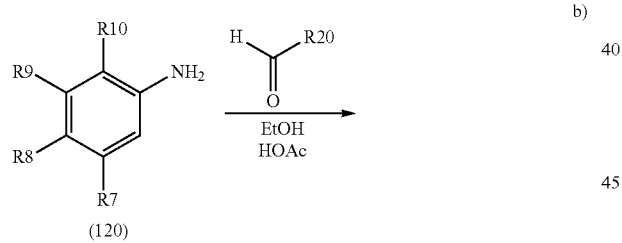
(122a)

-continued

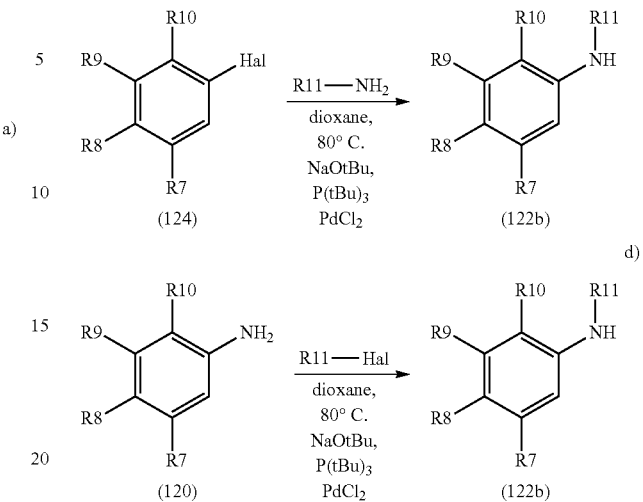
(124) → (122b)  c)

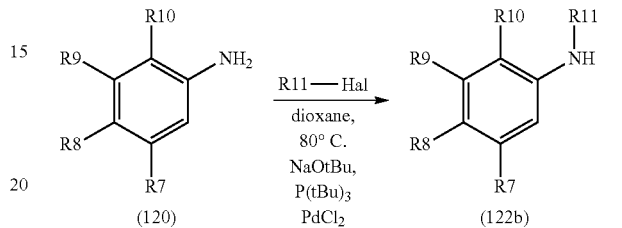
(120) → (122b)  d)

where each of the R7 to R10 radicals, which may independently be the same or different, is hydrogen, halogen, hydroxyl, thiol, nitro, carboxylate, aldehyde having 1 to 20 carbon atoms, ketone having 2 to 20 carbon atoms, O-alkyl having 1 to 20 carbon atoms, S-alkyl having 1 to 20 carbon atoms, O-alkenyl having 2 to 20 carbon atoms, S-alkenyl having 2 to 20 carbon atoms, O-aryl having 5 to 20 carbon atoms, S-aryl having 5 to 20 carbon atoms, carboxylic ester having 1 to 20 carbon atoms, carboxamide having 1 to 20 carbon atoms, thioester having 1 to 20 carbon atoms, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms, heteroaryl which does not contain any nitrogen atom and has 4 to 20 carbon atoms, —(C(D)(E))$_h$-OH, —(C(D)(E))$_k$-aryl-(C(D)(E))$_l$-OH or an organic radical containing a) at least one uncharged, protonatable nitrogen atom not bonded directly to the isoalloxazine ring, and/or b) at least one positively charged nitrogen atom not bonded directly to the isoalloxazine ring, and where the R11 radical is hydrogen, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms, heteroaryl which does not contain any nitrogen atom and has 4 to 20 carbon atoms, —(C(D)(E))$_h$-OH, —(C(D)(E))$_k$-aryl-(C(D)(E))$_l$-OH or an organic radical containing a) at least one uncharged, protonatable nitrogen atom not bonded directly to the isoalloxazine ring, and/or b) at least one positively charged nitrogen atom not bonded directly to the isoalloxazine ring, and where the R20 radical is hydrogen, alkyl having 1 to 19 carbon atoms, alkenyl having 2 to 19 carbon atoms, ether having 1 to 19 carbon atoms, thioether having 1 to 19 carbon atoms, cycloalkyl having 3 to 19 carbon atoms, cycloalkenyl having 3 to 19 carbon atoms, aryl having 5 to 19 carbon atoms, heteroaryl which has 4 to 19 carbon atoms and does not contain any nitrogen atoms, —(C(D)(E))$_{h-1}$-OH, —(C(D)(E))$_{k-1}$-aryl-(C(D)(E))$_{l-1}$-OH or an organic radical containing a) at least one uncharged, protonatable nitrogen atom not bonded directly to the isoalloxazine ring, and/or b) at least one positively charged nitrogen atom not bonded directly to the isoalloxazine ring, and where the Hal radical is fluorine, chlorine, bromine or iodine, (B) reacting the substituted aniline having the formula (122a) obtained in step (A) with violuric acid to obtain a compound of the formula (11z):

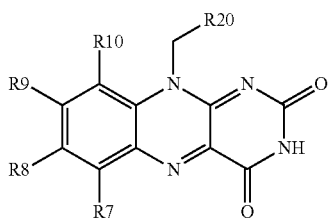

(11z)

reacting the substituted aniline having the formula (122b) obtained in step (A) with violuric acid to obtain a compound of the formula (11):

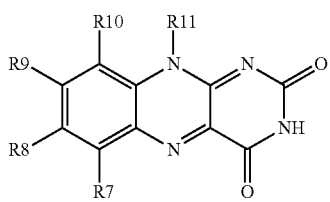

(11)

(C) optionally reacting the compound of the formula (11z) obtained in step (B) with tosyl chloride, mesyl chloride or iodine, optionally in the presence of a catalyst, and subsequently with an organic compound containing at least one tertiary nitrogen atom is reacted, when at least 1 R7, R8, R9, R10, R11 or R20 radical is —(C(D)(E))$_h$-OH or —(C(D)(E))$_k$-aryl-(C(D)(E))$_l$-OH, to obtain the inventive 10H-benzo[g]pteridine-2,4-dione derivative of the formula (12z):

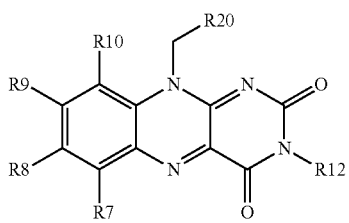

(12z)

where D and E are each independently hydrogen, halogen, preferably chlorine, bromine, iodine or fluorine, hydroxyl, O—R$^{(VIII)}$ where R$^{(VIII)}$ is methyl, ethyl, n-propyl, n-butyl, phenyl or benzyl, O—C(=O)—R$^{(IX)}$ where R(IX) is hydrogen, methyl, ethyl, n-propyl, n-butyl, phenyl or benzyl, or thiol, further preferably hydrogen or hydroxyl, or reacting the compound of the formula (11) obtained in step (B) with tosyl chloride, mesyl chloride or iodine, optionally in the presence of a catalyst, and subsequently with an organic compound containing at least one tertiary nitrogen atom is reacted, when at least 1 R7, R8, R9, R10, R11 or R20 radical is —(C(D)(E))$_h$-OH or —(C(D)(E))$_k$-aryl-(C(D)(E))$_l$-OH, to obtain the inventive 10H-benzo[g]pteridine-2,4-dione derivative of the formula (12):

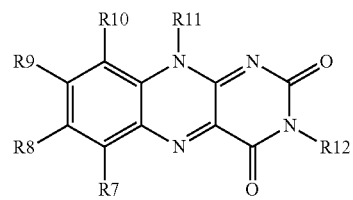

(12)

where D and E are each independently hydrogen, halogen, preferably chlorine, bromine, iodine or fluorine, hydroxyl, O—R$^{(VIII)}$ where R$^{(VIII)}$ is methyl, ethyl, n-propyl, n-butyl, phenyl or benzyl, O—C(=O)—R$^{(IX)}$ where R(IX) is hydrogen, methyl, ethyl, n-propyl, n-butyl, phenyl or benzyl, or thiol, further preferably hydrogen or hydroxyl, and with the proviso that I) only 1 R1, R2, R3, R4, R5 or R6 radical is an organic radical having:
  a) at least two, preferably at least three, preferably at least four, further preferably at least five, uncharged, protonatable nitrogen atoms not bonded directly to the isoalloxazine ring, or
  b) at least two, preferably at least three, preferably at least four, further preferably at least five, positively charged, preferably quaternary, nitrogen atoms not bonded directly to the isoalloxazine ring, or II) only 1 R1, R2, R3, R4, R5 or R6 radical is an organic radical having:
  a) at least one, preferably at least two, preferably
  b) at least three, preferably at least four, further preferably at least five, uncharged, protonatable nitrogen atom(s) not bonded directly to the isoalloxazine ring, and
  b) at least one, preferably at least two, preferably at least three, preferably at least four, further preferably at least five, positively charged, preferably quaternary, nitrogen atom(s) not bonded directly to the isoalloxazine ring, or III) at least 2 R1, R2, R3, R4, R5 or R6 radicals are an organic radical having:
  a) at least one, preferably at least two, preferably at least three, preferably at least four, further preferably at least five, uncharged, protonatable nitrogen atom(s) not bonded directly to the isoalloxazine ring, and/or
  b) at least one, preferably at least two, preferably at least three, preferably at least four, further preferably at least five, positively charged, preferably quaternary, nitrogen atom(s) not bonded directly to the isoalloxazine ring.

In a preferred embodiment of the two process variants, none of the R7 to R12 or R7 to R11 and R20 radicals is an organic radical of the general formula —(C(D)(E))$_h$-X or —(C(D)(E))$_k$-aryl-(C(D)(E))$_l$-X, where D and E are each independently hydrogen, halogen, preferably chlorine, bromine, iodine or fluorine, hydroxyl, O—R$^{(VIII)}$ where R$^{(VIII)}$ is methyl, ethyl, n-propyl, n-butyl, phenyl or benzyl, O—C(=O)—R$^{(IX)}$ where R(IX) is hydrogen, methyl, ethyl, n-propyl, n-butyl, phenyl or benzyl, or thiol, further preferably hydrogen or hydroxyl, and 1 R7 to R10 radical is methyl, in which case the process may comprise the following steps:

(A) free-radically halogenating the compound (11) or (12) in the presence of a free-radical initiator, preferably of a peroxide or of an azo compound, to obtain a compound having the formula (11a-11d) or (12a-12d):

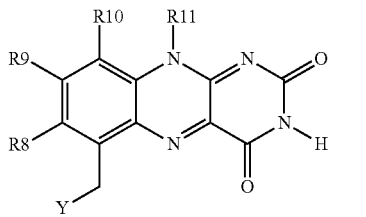
(11a)

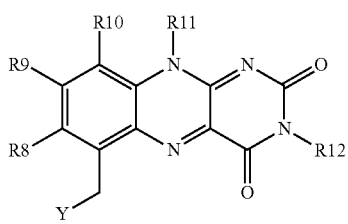
(12a)

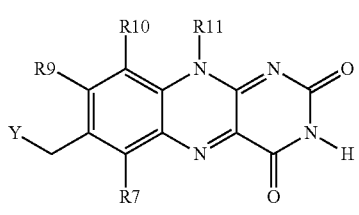
(11b)

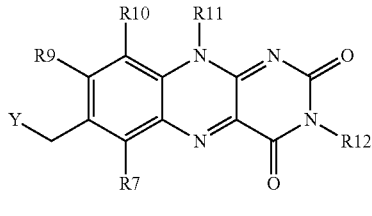
(12b)

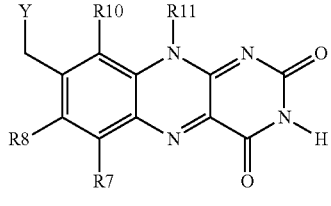
(11c)

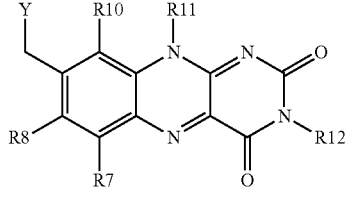
(12c)

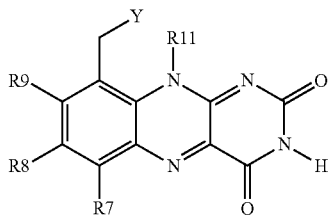
(11d)

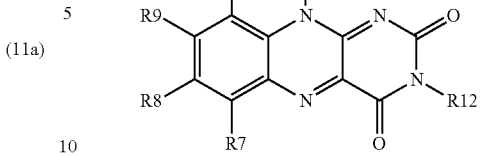
(12d)

where the Y radical is Cl, Br or I, and

B) reacting the compound obtained in step (A) and having the formula (11a-11d) or (12a-12d) with an organic compound containing at least one tertiary nitrogen atom to obtain the inventive 10H-benzo[g]pteridine-2,4-dione derivative of the formula (1).

When different amino protecting groups PG are used in a synthesis, there is the option of an orthogonal protecting group strategy, in which case different amino functions in one molecule can be selectively released and reacted in succession.

Suitable methods for removing the amino protecting group PG are known from the prior art. For example, benzyloxycarbonyl (Cbz) can be removed again by catalytic hydrogenation with hydrogenolytic scission of the benzyl-heteroatom bond with subsequent decarboxylation of the unstable carbamic acid thus formed or treatment with acids. Di-tert-butyloxycarbonyl (Boc) can be removed, for example, by acidic hydrolysis. Allyloxycarbonyl (Alloc) can be removed, for example, by the action of tetrakis(triphenylphosphine)palladium(0) and a nucleophile.

In a further preferred embodiment, steps (B) and/or (C) take place in the presence of one or more solvents. Step (B) can be performed, for example, in the presence of dichloromethane (DCM), dimethylformamide (DMF) or acetonitrile (MeCN). Step (C) can be performed, for example, in the presence of water/dichloromethane or toluene/tetrabutylammonium iodide (TBAI). Preferably, step (C) is performed in the presence of a base, for example LiOH, NaOH or an organic nitrogen base, for example triethylamine.

Unicellular or multicellular microorganisms may be triggers for infectious diseases. Administration of at least one pathogen-specific antidote, for example antibiotic, antimycotic or virustat can reduce the number of pathogens and/or inactivate the pathogen. A pathogen-specific antidote can be administered systemically and/or topically.

In the case of systemic administration, the pathogen-specific antidote is transferred to the blood system and/or lymph system of the body to be treated and is distributed over the entire body in this way. In the case of systemic administration of the pathogen-specific antidote, there may be degradation of the antidote and/or side effects, for example as a result of a biochemical transformation (metabolization) of the antidote.

In the case of topical administration of pathogen-specific antidote, the antidote is applied where it is to act therapeutically, for example on an infected part of the skin, while the healthy skin is not stressed. Thus, systemic side effects can be substantially avoided.

Superficial skin or soft tissue infections need not necessarily be treated by a systemic administration of pathogen-specific antidote, since the antidote can be applied directly to the infected part of the skin.

The pathogen-specific antidotes known to date, both in the case of systemic and topical administration, have side effects and interactions, some of them severe. Furthermore, in the case of topical administration, unreliable taking of medicaments (compliance) on the part of the patient, especially in the case of use of antibiotics, can result in development of resistance.

An alternative here is the photodynamic inactivation of microorganisms, where resistances to photodynamic inactivation are unknown. Irrespective of the nature of the microorganisms to be controlled and the associated infectious diseases, the number of pathogens is reduced and/or the pathogens are killed. For example, mixtures of various microorganisms, for example fungi and bacteria or different bacterial strains, can be controlled.

A compound used in accordance with the invention as a photosensitizer, preferably for photodynamic inactivation of microorganisms, has the formula (1):

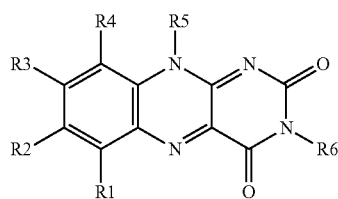

(1)

where I) only 1 R1, R2, R3, R4, R5 or R6 radical is an organic radical having:
a) at least two uncharged, protonatable nitrogen atoms not bonded directly to the isoalloxazine ring, or
a) at least two positively charged nitrogen atoms not bonded directly to the isoalloxazine ring,
and where each of the R1, R2, R3 and R4 radicals which is not an organic radical having a) at least two uncharged, protonatable nitrogen atoms not bonded directly to the isoalloxazine ring, or b) at least two positively charged nitrogen atoms not bonded directly to the isoalloxazine ring, is the same or different and is independently hydrogen, halogen, hydroxyl, thiol, nitro, carboxylate, aldehyde having 1 to 20 carbon atoms, ketone having 2 to 20 carbon atoms, O-alkyl having 1 to 20 carbon atoms, S-alkyl having 1 to 20 carbon atoms, O-alkenyl having 2 to 20 carbon atoms, S-alkenyl having 2 to 20 carbon atoms, O-aryl having 5 to 20 carbon atoms, S-aryl having 5 to 20 carbon atoms, carboxylic ester having 1 to 20 carbon atoms, carboxamide having 1 to 20 carbon atoms, thioester having 1 to 20 carbon atoms, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms or heteroaryl having 4 to 20 carbon atoms, which does not contain any nitrogen atoms, and
where each of the R5 and R6 radicals which is not an organic radical having a) at least two uncharged, protonatable nitrogen atoms not bonded directly to the isoalloxazine ring, or b) at least two positively charged nitrogen atoms not bonded directly to the isoalloxazine ring, is the same or different and is independently hydrogen, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms or heteroaryl having 4 to 20 carbon atoms, which does not contain any nitrogen atoms, or where II) only 1 R1, R2, R3, R4, R5 or R6 radical is an organic radical having:
a) at least one uncharged, protonatable nitrogen atom not bonded directly to the isoalloxazine ring, and
b) at least one positively charged nitrogen atom not bonded directly to the isoalloxazine ring,
and where each of the R1, R2, R3 and R4 radicals which is not an organic radical having a) at least one uncharged, protonatable nitrogen atom not bonded directly to the isoalloxazine ring, or b) at least one positively charged nitrogen atom not bonded directly to the isoalloxazine ring, is the same or different and is independently hydrogen, halogen, hydroxyl, thiol, nitro, carboxylate, aldehyde having 1 to 20 carbon atoms, ketone having 2 to 20 carbon atoms, O-alkyl having 1 to 20 carbon atoms, S-alkyl having 1 to 20 carbon atoms, O-alkenyl having 2 to 20 carbon atoms, S-alkenyl having 2 to 20 carbon atoms, O-aryl having 5 to 20 carbon atoms, S-aryl having 5 to 20 carbon atoms, carboxylic ester having 1 to 20 carbon atoms, carboxamide having 1 to 20 carbon atoms, thioester having 1 to 20 carbon atoms, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms or heteroaryl having 4 to 20 carbon atoms, which does not contain any nitrogen atoms, and
where each of the R5 and R6 radicals which is not an organic radical having a) at least one uncharged, protonatable nitrogen atom not bonded directly to the isoalloxazine ring, or b) at least one positively charged nitrogen atom not bonded directly to the isoalloxazine ring, is the same or different and is independently hydrogen, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms or heteroaryl having 4 to 20 carbon atoms, which does not contain any nitrogen atoms, or where III) at least 2 R1, R2, R3, R4, R5 or R6 radicals are an organic radical having:
a) at least one uncharged, protonatable nitrogen atom not bonded directly to the isoalloxazine ring, and/or
b) at least one positively charged nitrogen atom not bonded directly to the isoalloxazine ring, and
where each of the R1, R2, R3 and R4 radicals which is not an organic radical having a) at least one uncharged, protonatable nitrogen atom not bonded directly to the isoalloxazine ring, or b) at least one positively charged nitrogen atom not bonded directly to the isoalloxazine ring, is the same or different and is independently hydrogen, halogen, hydroxyl, thiol, nitro, carboxylate, aldehyde having 1 to 20 carbon atoms, ketone having 2 to 20 carbon atoms, O-alkyl having 1 to 20 carbon atoms, S-alkyl having 1 to 20 carbon atoms, O-alkenyl having 2 to 20 carbon atoms, S-alkenyl having 2 to 20 carbon atoms, O-aryl having 5 to 20 carbon atoms, S-aryl having 5 to 20 carbon atoms, carboxylic ester having 1 to 20 carbon atoms, carboxamide having 1 to 20 carbon atoms, thioester having 1 to 20 carbon atoms, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms or heteroaryl having 4 to 20 carbon atoms, which does not contain any nitrogen atoms, and where each of the R5 and R6 radicals which is not an organic radical having a) at least one uncharged, protonatable nitrogen atom not bonded directly to the isoalloxazine ring, or b) at least one positively charged nitrogen atom not bonded directly to the isoalloxazine ring, is the same or different and is independently hydrogen, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms or heteroaryl having 4 to 20 carbon atoms, which does not contain any nitrogen atoms.

In a preferred embodiment, a 10H-benzo[g]pteridine-2,4-dione derivative of the formula (1) used in accordance with the invention does not have any uncharged, protonatable nitrogen atom bonded directly to the isoalloxazine ring, for example in the form of an amino radical, methylamino radical or dimethylamino radical, or any positively charged nitrogen atom bonded directly to the isoalloxazine ring, for example in the form of a pyridin-1-ium-1-yl radical or trimethylammonio radical.

In a preferred embodiment of the present invention, at least one 10H-benzo[g]pteridine-2,4-dione derivative as claimed in any of claims 1 to 5 or a pharmacologically compatible salt and/or ester and/or complex thereof is used as a photosensitizer, preferably in the photodynamic inactivation of microorganisms.

In a further-preferred embodiment of the present invention, at least one 10H-benzo[g]pteridine-2,4-dione derivative of the formula (40) to (49) and (115) to (117) or a pharmacologically compatible salt and/or ester and/or complex thereof is used as a photosensitizer, preferably in the photodynamic inactivation of microorganisms:

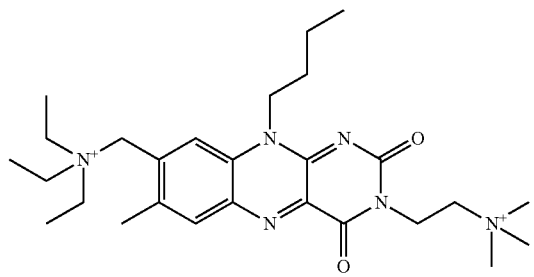
(42)

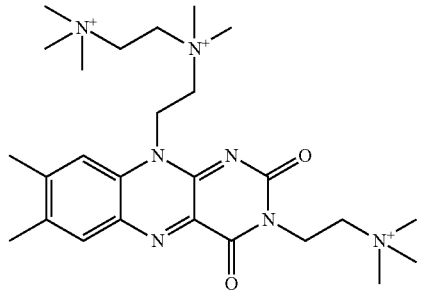
(43)

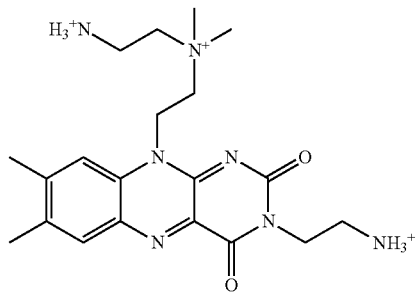
(44)

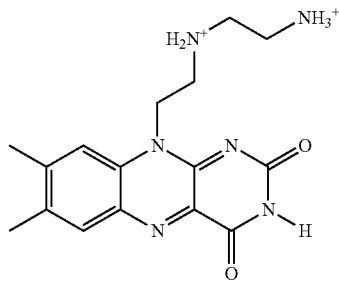
(45)

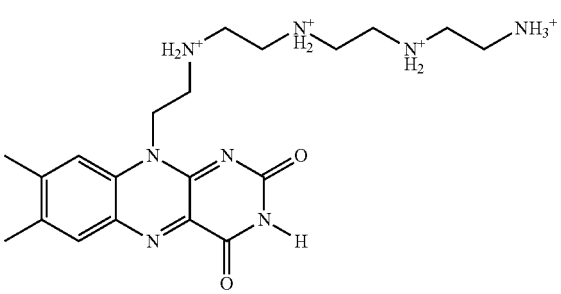
(46)

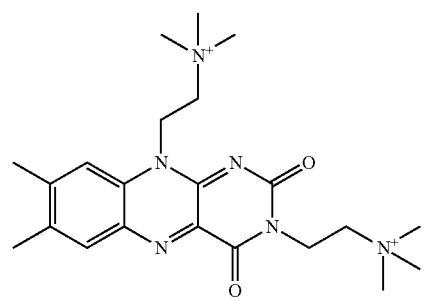
(40)

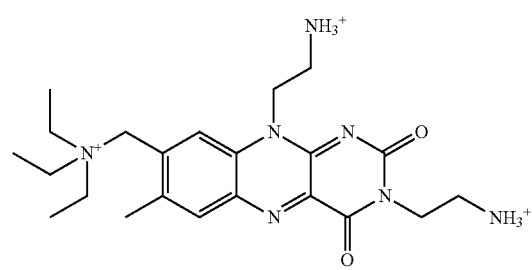
(41)

(47)
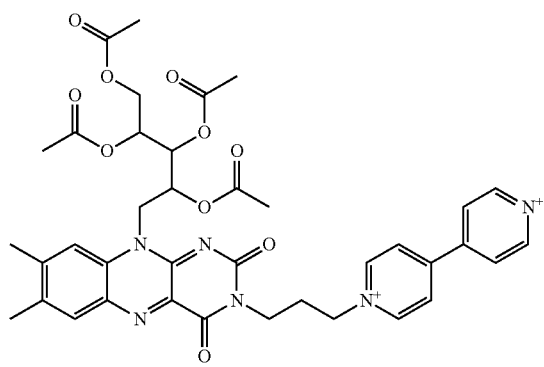
(116)
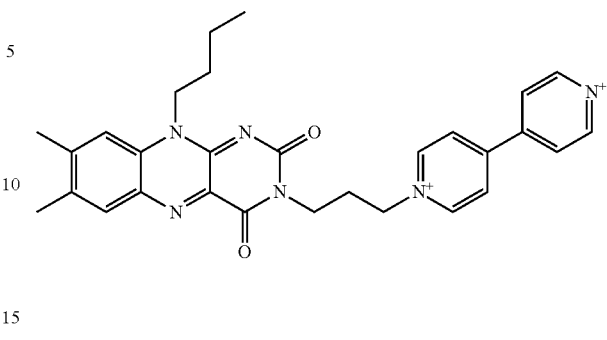
(48)
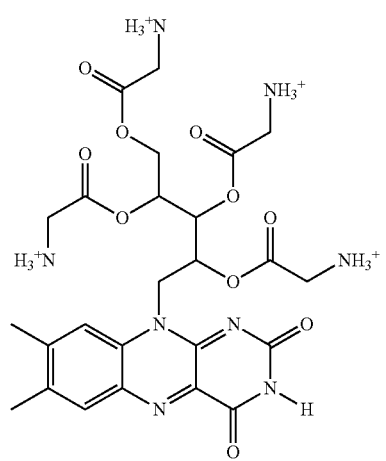
(117)
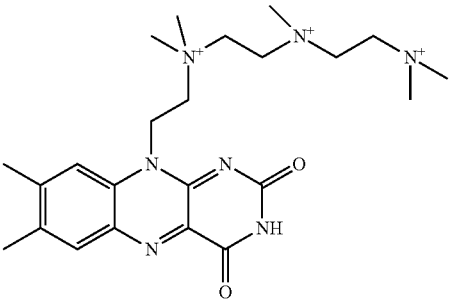
In a further-preferred embodiment of the present invention, at least one 10H-benzo[g]pteridine-2,4-dione derivative of the formulae (90) to (102) or a pharmacologically compatible salt and/or ester and/or complex thereof is used as a photosensitizer, preferably in the photodynamic inactivation of microorganisms:
(49)
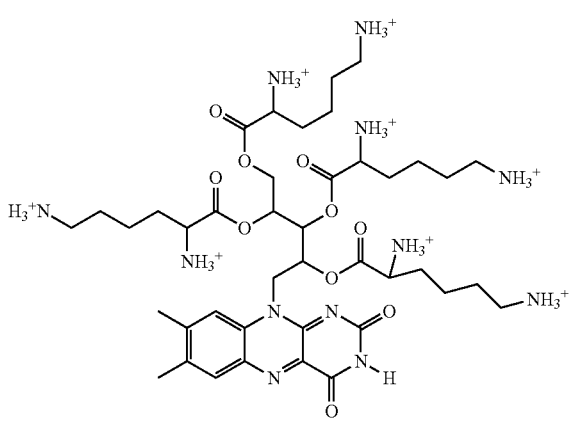
(90)
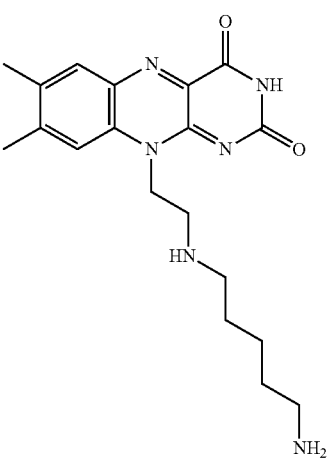
(115)
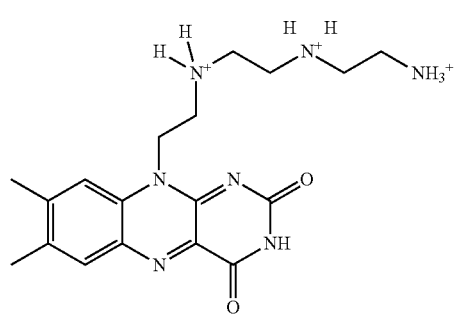

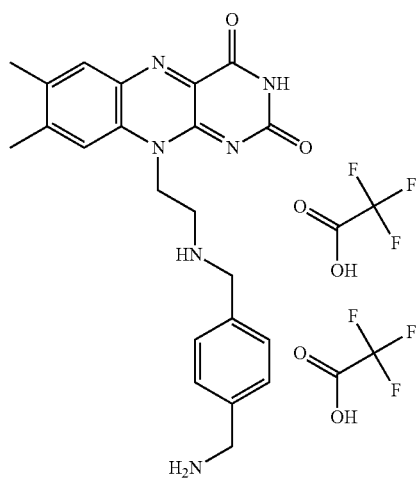
(91)
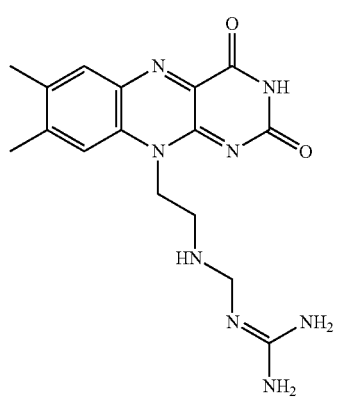
(92)
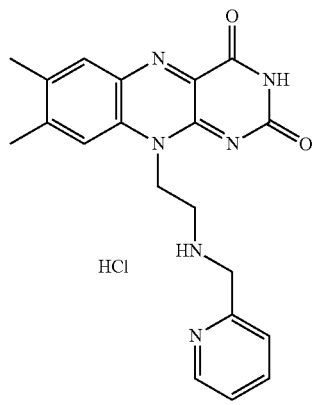
(93)
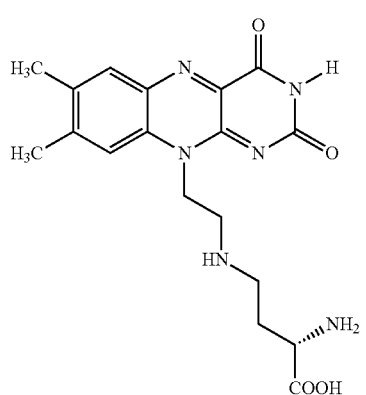
(94)
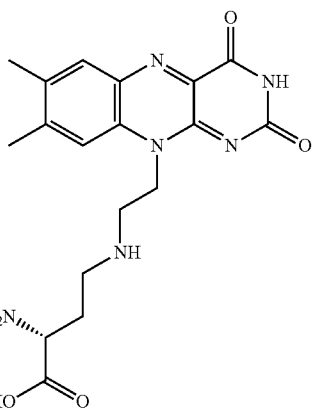
(95)
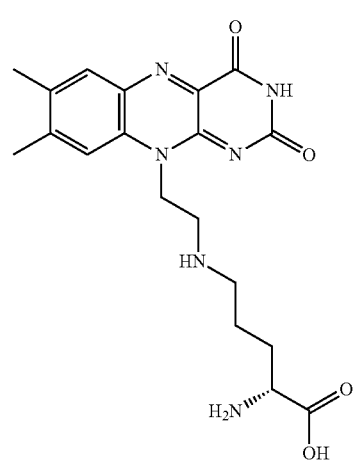
(96)
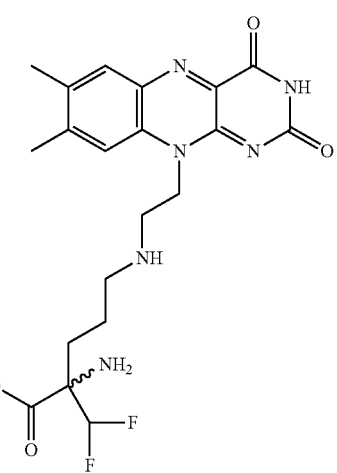
(97)

(98)

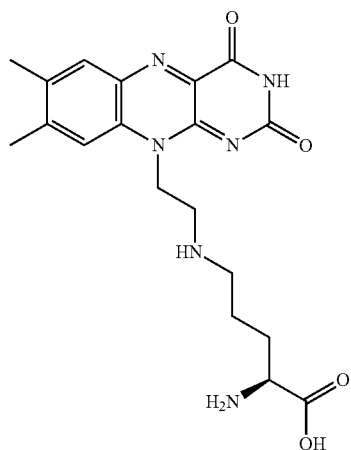

(99)

(100)

(101)

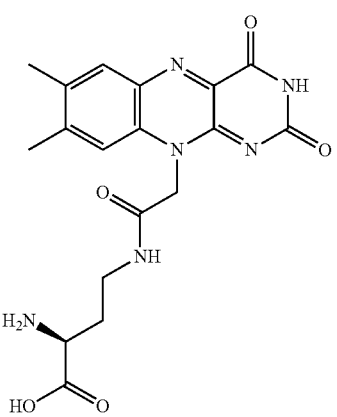

(102)

The preparation of the 10H-benzo[g]pteridine-2,4-dione derivatives of the formula (90) to (102) is described in WO 2010/019208 A1, which is hereby incorporated by reference. In a further-preferred embodiment of the present invention, at least one 10H-benzo[g]pteridine-2,4-dione derivative of the formula (103) to (114) or a pharmacologically compatible salt and/or ester and/or complex thereof is used as a photosensitizer, preferably in the photodynamic inactivation of microorganisms:

(103)

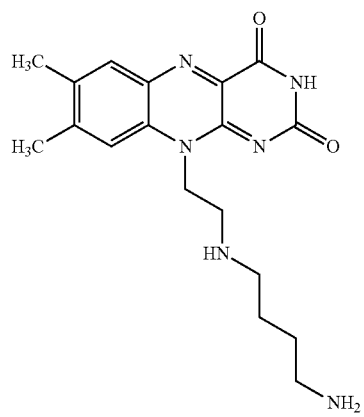
(104)
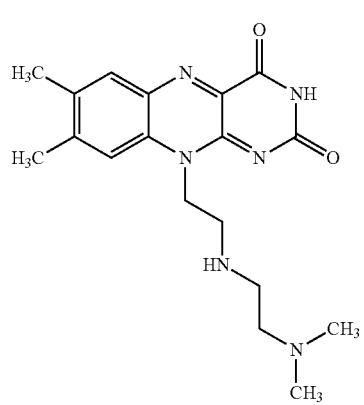
(105)
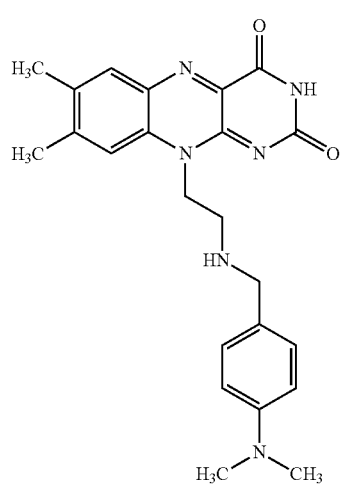
(106)
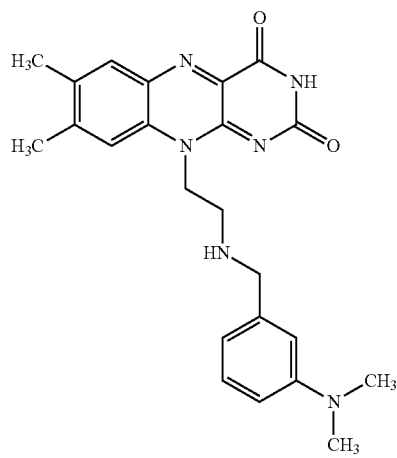
(107)
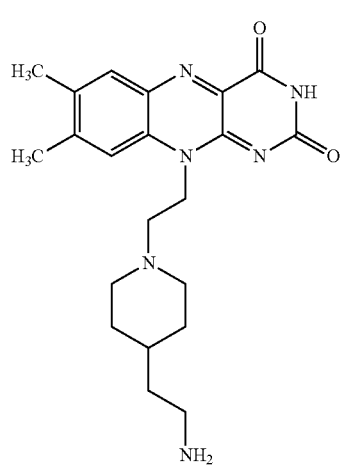
(108)
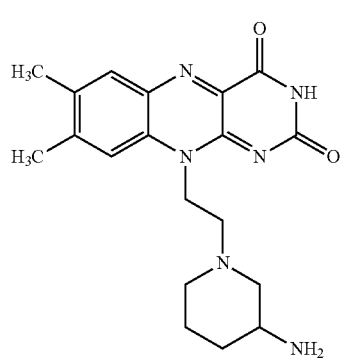
(109)
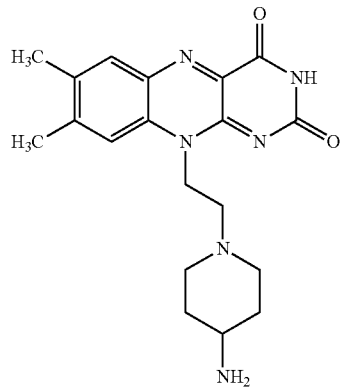
(110)

-continued (111) 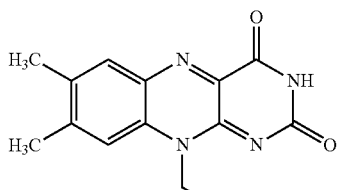

(112) 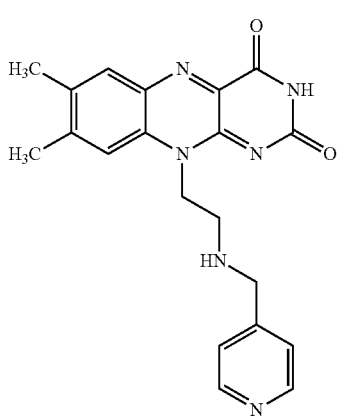

(113) 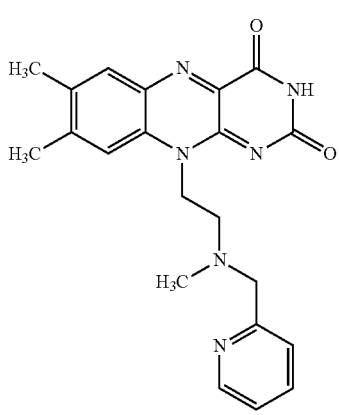

(114) 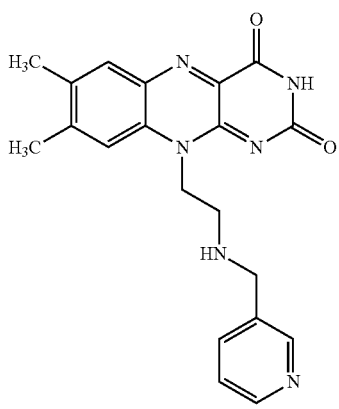

The preparation of the 10H-benzo[g]pteridine-2,4-dione derivatives of the formulae (103) to (114) is described in WO 2011/008247 A1, which is hereby incorporated by reference.

In a preferred embodiment of the present invention, at least one 10H-benzo[g]pteridine-2,4-dione derivative of the formula (1) or a pharmacologically compatible salt and/or ester and/or complex thereof is used as a photosensitizer in the photodynamic inactivation of microorganisms, preferably in photodynamic therapy.

The 10H-benzo[g]pteridine-2,4-dione derivative used in accordance with the invention, after irradiation with electromagnetic radiation of suitable wavelength and energy density, has a high yield of singlet oxygen.

The electromagnetic radiation is preferably in the visible spectral region, ultraviolet region and/or infrared region. Further preferably, the electromagnetic radiation has a wavelength from a range from 280 to 1000 nm, further preferably from 380 to 1000 nm.

Further preferably, the electromagnetic radiation has an energy density from a range from 1 µW/cm$^2$ to 1 MW/cm$^2$, further preferably from 1 mW/cm$^2$ to 1 kW/cm$^2$.

The irradiation time can be varied as a function of the nature of the microorganisms and/or the severity of the infection. The irradiation time is preferably within a range from 1 ρs to 1 h, further preferably from 1 ms to 1000 s.

Preferably, the electromagnetic radiation is generated by a radiation source selected from the group consisting of the sun and artificial radiation sources, for example UV lamp, IR lamp, phosphor lamps, light-emitting diodes, lasers or chemical light.

Furthermore, the inventors have found that, surprisingly, the 10H-benzo[g]pteridine-2,4-dione derivative used in accordance with the invention or pharmacologically acceptable salts and/or esters and/or complexes thereof preferably has a high affinity for microorganisms.

On account of the affinity, the 10H-benzo[g]pteridine-2,4-dione derivative of the formula (1) used in accordance with the invention can bind effectively to microorganisms and produce sufficient singlet oxygen locally to inactivate, preferably kill, the microorganisms.

In this preferred use as a photosensitizer, at least one 10H-benzo[g]pteridine-2,4-dione derivative used in accordance with the invention is bound by microorganisms. After irradiation with electromagnetic radiation of suitable wavelength and energy density, microorganisms are inactivated, preferably killed, by the reactive oxygen species (ROS) formed, preferably oxygen radicals and/or singlet oxygen.

Preferably, the binding of at least one 10H-benzo[g]pteridine-2,4-dione derivative used in accordance with the invention or of a pharmacologically compatible salt and/or ester and/or complex thereof to microorganisms likewise allows staining or localization of microorganisms. In this way, it is preferably also possible to monitor the progress of the inactivation of microorganisms or of the decolonization.

According to the invention, the term "decolonization" is understood to mean the removal, preferably complete removal, of microorganisms.

In a further preferred embodiment, at least one 10H-benzo[g]pteridine-2,4-dione derivative used in accordance with the invention or a pharmacologically acceptable salt and/or ester and/or complex thereof is used in the inactivation of unicellular or multicellular microorganisms, preferably selected from the group consisting of viruses, archaea, bacteria, bacterial spores, fungi, for example mycelium fungi and yeasts, fungal spores, protozoa, algae and blood-transmissible parasites.

It is possible with preference to treat surfaces of the body, for example the skin or mucous membrane, of humans and animals, preferably mammals. In this preferred embodiment, at least one 10H-benzo[g]pteridine-2,4-dione derivative used in accordance with the invention or a pharmacologically acceptable salt and/or ester and/or complex thereof, preferably in a pharmaceutical formulation, is used in the disinfection and/or decolonization of surfaces of skin or soft tissue, preferably with preservation of skin integrity.

In a further preferred embodiment, at least one 10H-benzo[g]pteridine-2,4-dione derivative used in accordance with the invention or a pharmacologically acceptable salt and/or ester and/or complex thereof is present in a pharmaceutical formulation for topical, preferably nasal, oral, anal, vaginal or dermal, administration.

Topical administration is also understood to mean application on or in the ear, preferably the outer ear. The outer ear comprises the ear cartilage, the pinna, the earlobe and the outer auditory canal or else ear canal, and the outside of the eardrum.

In a further preferred embodiment, at least one 10H-benzo[g]pteridine-2,4-dione derivative used in accordance with the invention or a pharmacologically acceptable salt and/or ester and/or complex thereof is used for production of a pharmaceutical formulation in the prophylaxis and/or treatment of an infectious, preferably viral, bacterial and/or mycotic, skin disease which is preferably selected from the group consisting of staphylococcal scalded skin syndrome, impetigo, skin abscess, furuncle, carbuncle, phlegmon, cellulitis, acute lymphadenitis, pilonidal cysts, pyoderma, purulent dermatitis, septic dermatitis, suppurative dermatitis, erythrasma, erysipelas, acne vulgaris and fungal infection.

In a further preferred embodiment, at least one 10H-benzo[g]pteridine-2,4-dione derivative used in accordance with the invention or a pharmacologically acceptable salt and/or ester and/or complex thereof is used for production of a pharmaceutical formulation in wound healing, for example in the event of disrupted healing after surgical interventions.

Preferably, at least one 10H-benzo[g]pteridine-2,4-dione derivative used in accordance with the invention or a pharmacologically acceptable salt and/or ester and/or complex thereof, or a pharmaceutical formulation comprising at least one inventive 10H-benzo[g]pteridine-2,4-dione derivative or a pharmacologically acceptable salt and/or ester and/or complex thereof is used in the disinfection and/or reduction of the microbe count in infected wounds.

In a further preferred embodiment, at least one 10H-benzo[g]pteridine-2,4-dione derivative used in accordance with the invention or a pharmacologically acceptable salt and/or ester and/or complex thereof is used for production of a pharmaceutical formulation in the prophylaxis and/or treatment of infectious, preferably viral, bacterial and/or mycotic, disorders of the ear, of the upper respiratory pathway, of the oral cavity, of the throat, of the larynx, of the lower respiratory pathway and/or of the esophagus.

The prevalence of pathogenic microorganisms is, for example, the main cause of infections in the oral cavity. The problem occurs that the microorganisms are organised synergetically in biofilms of extremely complex structure. These biofilms, for example plaque or dental deposits, consist of several layers of complex structure and contain proteins, carbohydrates, phosphates and microorganisms. Dental deposits arise particularly where tooth surfaces cannot be kept free of deposits by natural or artificial cleaning. This fact makes it difficult to find access to the microorganisms incorporated within the biofilm.

Conventional treatments, for example antibiotics and rinse solutions or mechanical tooth cleaning, can be used only to a limited degree, since they do not directly affect the bacteria, for example in the case of tooth cleaning, can be dosed and applied only with difficulty, for example in the case of antibiotics and rinse solutions, or general application is unjustified because of adverse accompanying phenomena.

In a preferred embodiment, at least one 10H-benzo[g]pteridine-2,4-dione derivative used in accordance with the invention or a pharmacologically acceptable salt and/or ester and/or complex thereof is used as a photosensitizer in the photodynamic inactivation of microorganisms in the oral cavity.

In a further preferred embodiment, at least one 10H-benzo[g]pteridine-2,4-dione derivative used in accordance with the invention or a pharmacologically acceptable salt and/or ester and/or complex thereof is used for production of a pharmaceutical formulation in the treatment and/or prophylaxis of an infectious, preferably viral, bacterial and/or mycotic, disorder of the dental tissue, preferably plaque, caries or pulpitis, and/or infectious, preferably viral, bacterial and/or mycotic, disorder of the periodontium, preferably gingivitis, paradontitis, endodontitis or periimplantitis.

In a further preferred embodiment, at least one 10H-benzo[g]pteridine-2,4-dione derivative used in accordance with the invention or a pharmacologically acceptable salt and/or ester and/or complex thereof, or a pharmaceutical formulation comprising at least one 10H-benzo[g]pteridine-2,4-dione derivative used in accordance with the invention or a pharmacologically acceptable salt and/or ester and/or complex thereof, is used in the cleaning of teeth, dentures and/or dental braces.

In a further preferred embodiment, the 10H-benzo[g]pteridine-2,4-dione derivative used in accordance with the invention or a pharmacologically acceptable salt and/or ester and/or complex thereof, or a pharmaceutical formulation comprising at least one inventive 10H-benzo[g]pteridine-2,4-dione derivative or a pharmacologically acceptable salt and/or ester and/or complex thereof, is used in the nasal decolonization of microorganisms.

For example, methicillin-resistant *Staphylococcus aureus* (MRSA) strains persist for months in the event of nasal colonization, and have a high environmental resistance. Therefore, nasal decolonization, i.e. removal of the microorganisms, generally also reduces colonization in other parts of the body.

The present invention further relates to a pharmaceutical composition comprising at least one 10H-benzo[g]pteridine-2,4-dione derivative used in accordance with the invention of the formula (1) or a pharmacologically acceptable salt and/or ester and/or complex thereof, preferably at least one inventive 10H-benzo[g]pteridine-2,4-dione derivative of the formula (1) or a pharmacologically acceptable salt and/or ester and/or complex thereof.

The pharmaceutical composition is preferably produced by mixing at least one compound of the formula (1) or a pharmacologically acceptable salt and/or ester and/or complex thereof with one or more physiologically acceptable excipient(s) and converted to a suitable administration form.

A suitable administration form of the inventive pharmaceutical composition is preferably selected from the group consisting of ointment, cream, gel, lotion, shake lotion, solution, for example in droplet or spray form, powder, microcapsule and paste.

The inventive pharmaceutical formulation can be applied topically, preferably nasally, orally, anally, vaginally or dermally.

Useful physiologically acceptable excipients include the pharmaceutically customary liquid or solid fillers and extenders, solvents, emulsifiers, glidants, flavor correctors, dyes and/or buffer substances.

In a further preferred embodiment, the pharmaceutical composition comprises an effective amount of at least one 10H-benzo[g]pteridine-2,4-dione derivative used in accordance with the invention or of a pharmacologically acceptable salt and/or ester and/or complex thereof, the effective amount being from 0.01 µg to 1000 µg per gram of the composition, preferably from 0.1 µg to 500 µg per gram of the composition.

In a preferred embodiment of the invention, the pharmaceutical composition comprises at least one 10H-benzo[g]pteridine-2,4-dione derivative used in accordance with the invention or a pharmacologically acceptable salt and/or ester and/or complex thereof and at least one further pharmaceutically active constituent.

Preferably, the at least one further pharmaceutically active constituent is selected from the group consisting of antibiotics, antimycotics, virustatics, antihistamines, sympathomimetics, antihemorrhagics, emollients and skin protection agents, analgesics, disinfectants, immunosera and immunoglobulins, antiparasitic substances, insecticides, repellents and corticosteroids.

In a further preferred embodiment, at least one 10H-benzo[g]pteridine-2,4-dione derivative used in accordance with the invention or a pharmacologically acceptable salt and/or ester and/or complex thereof, or a pharmaceutical formulation comprising at least one 10H-benzo[g]pteridine-2,4-dione derivative used in accordance with the invention or a pharmacologically acceptable salt and/or ester and/or complex thereof, is applied by the user him/herself and, optionally, irradiated subsequently with a suitable radiation source which generates electromagnetic radiation of suitable wavelength and energy density.

In a further preferred embodiment, at least one 10H-benzo[g]pteridine-2,4-dione derivative used in accordance with the invention or a pharmacologically acceptable salt and/or ester and/or complex thereof, or a formulation comprising at least one 10H-benzo[g]pteridine-2,4-dione derivative used in accordance with the invention or a pharmacologically acceptable salt and/or ester and/or complex thereof, is used in the inactivation of microorganisms in medical blood products.

In a preferred embodiment, at least one 10H-benzo[g]pteridine-2,4-dione derivative used in accordance with the invention or a pharmacologically acceptable salt and/or ester and/or complex thereof is used for inactivation of microorganisms on surfaces of all kinds. Further preferably, the 10H-benzo[g]pteridine-2,4-dione derivative used in accordance with the invention or a pharmacologically acceptable salt and/or ester and/or complex thereof is used in surface cleaning and/or coating, preferably of medical products, food and drink packaging or hygiene articles.

Further preferably, at least one 10H-benzo[g]pteridine-2,4-dione derivative used in accordance with the invention or a pharmacologically acceptable salt and/or ester and/or complex thereof is applied to and/or introduced onto surfaces and, optionally, subsequently irradiated with a suitable radiation source which generates electromagnetic irradiation of suitable wavelength and energy density. Preferably, the at least one 10H-benzo[g]pteridine-2,4-dione derivative used in accordance with the invention or a pharmacologically acceptable salt and/or ester and/or complex thereof brings about "self-disinfection" of the surface during the irradiation.

The irradiation may directly follow the treatment of the surface with at least one 10H-benzo[g]pteridine-2,4-dione derivative used in accordance with the invention or a pharmacologically acceptable salt and/or ester and/or complex thereof, preferably the application of the at least one 10H-benzo[g]pteridine-2,4-dione derivative used in accordance with the invention or of a pharmacologically acceptable salt and/or ester and/or complex thereof to the surface and/or introduction of the at least one 10H-benzo[g]pteridine-2,4-dione derivative used in accordance with the invention or of a pharmacologically acceptable salt and/or ester and/or complex thereof into the surface, and/or be effected at a later juncture.

Further preferably, articles having thermally limited shelf life are treated, for example articles made from thermoplastics, or articles which are attacked by disinfectants. Articles having a thermally limited shelf life can, for example, be only inadequately sterilized, since they lose shape or become brittle at relatively high temperatures.

Furthermore, in the event of improper and/or excessive use of disinfectants, development of resistance can result from selection of robust microorganisms when, for example, the active ingredient concentration and contact time and hence the microbe-reducing effect is low.

In a further-preferred embodiment, at least one 10H-benzo[g]pteridine-2,4-dione derivative used in accordance with the invention or a pharmacologically acceptable salt and/or ester and/or complex thereof is used for inactivation of microorganisms on surfaces of medical products, preferably invasive medical implements, for example catheters, hollow probes, tubes or needles.

The medical products are preferably selected from wound dressings, bandages, catheters, hollow probes, tubes and needles.

Further preferably, medical products are also understood to mean dental impressions or dentures, for example prostheses, crowns or implants.

Preferably, a treatment of the surface of medical products with at least one 10H-benzo[g]pteridine-2,4-dione used in accordance with the invention or a pharmacologically acceptable salt and/or ester and/or complex thereof and/or coating and/or immobilization of at least one 10H-benzo[g]pteridine-2,4-dione derivative used in accordance with the invention or of a pharmacologically acceptable salt and/or ester and/or complex thereof on the surface of medical products and subsequent irradiation with electromagnetic radiation of suitable wavelength and energy density reduces, preferably prevents, the colonization of microorganisms on the surfaces treated.

The irradiation may directly follow the treatment of the surface with at least one 10H-benzo[g]pteridine-2,4-dione derivative used in accordance with the invention or a pharmacologically acceptable salt and/or ester and/or complex thereof, preferably the application of the at least one 10H-benzo[g]pteridine-2,4-dione derivative used in accordance with the invention or of a pharmacologically acceptable salt and/or ester and/or complex thereof to the surface and/or introduction of the at least one 10H-benzo[g]pteridine-2,4-dione derivative used in accordance with the invention or of a pharmacologically acceptable salt and/or ester and/or complex thereof into the surface, and/or be effected at a later juncture, before or during the use of the treated medical product.

In a further-preferred use of the at least one 10H-benzo[g]pteridine-2,4-dione derivative used in accordance with the invention or of a pharmacologically acceptable salt and/or ester and/or complex thereof in wound dressings and/or bandages, for example cotton gauze, irradiation with electromagnetic radiation of suitable wavelength and energy density can be effected during or after the application of a wound dressing and/or bandage comprising the at least one 10H-benzo[g]pteridine-2,4-dione derivative used in accordance with the invention or a pharmacologically acceptable salt and/or ester and/or complex thereof, as a result of which there is a subsequent reduction, preferably inactivation, of microorganisms in the wound region or treated parts of the skin.

In a further preferred embodiment, the wound dressing and/or bandage comprises, as well as at least one 10H-benzo[g]pteridine-2,4-dione derivative used in accordance with the invention or a pharmacologically acceptable salt and/or ester and/or complex thereof, further constituents, preferably absorbents, for example calcium alginate or polyurethane foam, or further pharmaceutically active substances.

In a further preferred embodiment, at least one 10H-benzo[g]pteridine-2,4-dione derivative used in accordance with the invention or a pharmacologically acceptable salt and/or ester and/or complex thereof is used for inactivation of microorganisms on surfaces of food and drink packaging.

In a further preferred embodiment, at least one 10H-benzo[g]pteridine-2,4-dione derivative used in accordance with the invention or a pharmacologically acceptable salt and/or ester and/or complex thereof is used for inactivation of microorganisms in a liquid or a liquid, preferably aqueous, formulation, for example emulsion paint.

The liquid is preferably water.

In this case, at least one 10H-benzo[g]pteridine-2,4-dione derivative used in accordance with the invention or a pharmacologically acceptable salt and/or ester and/or complex thereof can be used for treatment of water for the drinks and food industry, the pharmaceutical, chemical and cosmetics industry, the electrical industry. In addition, at least one 10H-benzo[g]pteridine-2,4-dione derivative used in accordance with the invention or a pharmacologically acceptable salt and/or ester and/or complex thereof can be used in drinking water and rainwater treatment, the treatment of wastewater, or in the treatment of water for use in air conditioning.

In this preferred use of at least one 10H-benzo[g]pteridine-2,4-dione derivative used in accordance with the invention or of a pharmacologically acceptable salt and/or ester and/or complex thereof, the liquid or the liquid formulation can subsequently be irradiated with a suitable radiation source which generates electromagnetic radiation of suitable wavelength and energy density. Preferably, the 10H-benzo[g]pteridine-2,4-dione derivative used in accordance with the invention or a pharmacologically acceptable salt and/or ester and/or complex thereof brings about "self-disinfection" of the liquid or of the liquid formulation during the irradiation.

In a further preferred use of the at least one 10H-benzo[g]pteridine-2,4-dione derivative used in accordance with the invention or of a pharmacologically acceptable salt and/or esters and/or complex thereof, the 10H-benzo[g]pteridine-2,4-dione derivative may be bound to a solid carrier and thus be used as part of a solid matrix. More preferably, at least one 10H-benzo[g]pteridine-2,4-dione derivative used in accordance with the invention or a pharmacologically acceptable salt and/or ester and/or complex thereof bound to a solid carrier is introduced into the liquid to be treated, preferably water or blood.

A particularly preferred carrier is a polymer which carries at least one 10H-benzo[g]pteridine-2,4-dione derivative used in accordance with the invention or a pharmacologically acceptable salt and/or ester and/or complex thereof in a covalently bonded manner. This composition, comprising the carrier and at least one 10H-benzo[g]pteridine-2,4-dione derivative used in accordance with the invention or a pharmacologically acceptable salt and/or ester and/or complex thereof, develops antimicrobial activity as soon as it is exposed to electromagnetic radiation of suitable wavelength and energy density.

The present invention further relates to a coated article which comprises and/or has been coated with at least one 10H-benzo[g]pteridine-2,4-dione derivative used in accordance with the invention or a pharmacologically acceptable salt and/or ester and/or complex thereof.

The surface of the coated article preferably comprises at least one 10H-benzo[g]pteridine-2,4-dione derivative used in accordance with the invention or a pharmacologically acceptable salt and/or ester and/or complex thereof.

The coated article can subsequently be irradiated with a suitable radiation source which generates the automatic radiation of suitable wavelength and energy density. Preferably, the 10H-benzo[g]pteridine-2,4-dione derivative used in accordance with the invention or a pharmacologically acceptable salt and/or ester and/or complex thereof brings about "self-disinfection" of the surface of the coated article.

The irradiation may directly follow the treatment of the coated article with at least one 10H-benzo[g]pteridine-2,4-dione derivative used in accordance with the invention or a pharmacologically acceptable salt and/or ester and/or complex thereof, preferably the application of the at least one 10H-benzo[g]pteridine-2,4-dione derivative used in accordance with the invention to the surface of the coated article and/or introduction of the at least one 10H-benzo[g]pteridine-2,4-dione derivative used in accordance with the invention into the surface of the coated article, and/or be effected at a later juncture, preferably before or during the use of the coated article.

Suitable articles are preferably selected from the group consisting of medical products, food and drink packaging, and hygiene articles.

In a further preferred embodiment of the coated article, particles coated with at least one 10H-benzo[g]pteridine-2,4-dione derivative used in accordance with the invention or a pharmacologically acceptable salt and/or ester and/or complex thereof are, for example, inorganic or organic particles.

Further preferably, the particles comprise at least one 10H-benzo[g]pteridine-2,4-dione derivative used in accordance with the invention or a pharmacologically acceptable salt and/or ester and/or complex thereof, which is covalently bonded to the particles.

The invention is illustrated hereinafter by figures and examples, without being restricted thereto.

Example 1) Preparation of Various 10H-benzo[g]pteridine-2,4-dione Derivatives

Overview of the Syntheses:

Scheme 1: Synthesis of compounds (62), (63) (64) and (152); conditions: a) EtOH, NEt$_3$, reflux, 2 d; b) Pd/C, H$_2$, HOAc, 14 h, then alloxane monohydrate, H$_3$BO$_3$, HOAc, RT, 2 d; c) bromocholine hydrobromide, Cs$_2$CO$_3$, DMF, RT, 2 d; d) Br$_2$, dioxane, benzoyl peroxide, 90° C., 1 h; e) NEt$_3$, DMF, 50° C., overnight; f) HCl in Et$_2$O, DCM, RT, overnight;

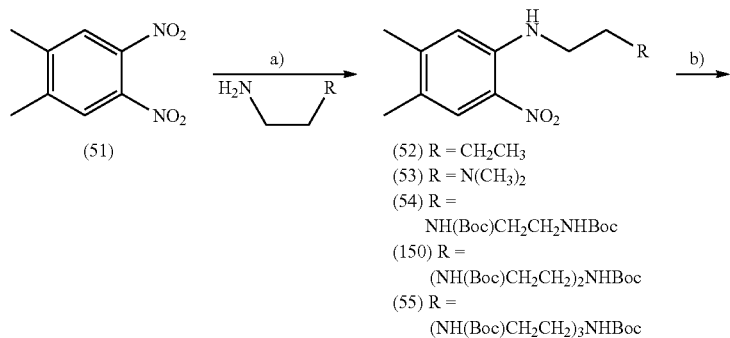

(52) R = CH$_2$CH$_3$
(53) R = N(CH$_3$)$_2$
(54) R = NH(Boc)CH$_2$CH$_2$NHBoc
(150) R = (NH(Boc)CH$_2$CH$_2$)$_2$NHBoc
(55) R = (NH(Boc)CH$_2$CH$_2$)$_3$NHBoc

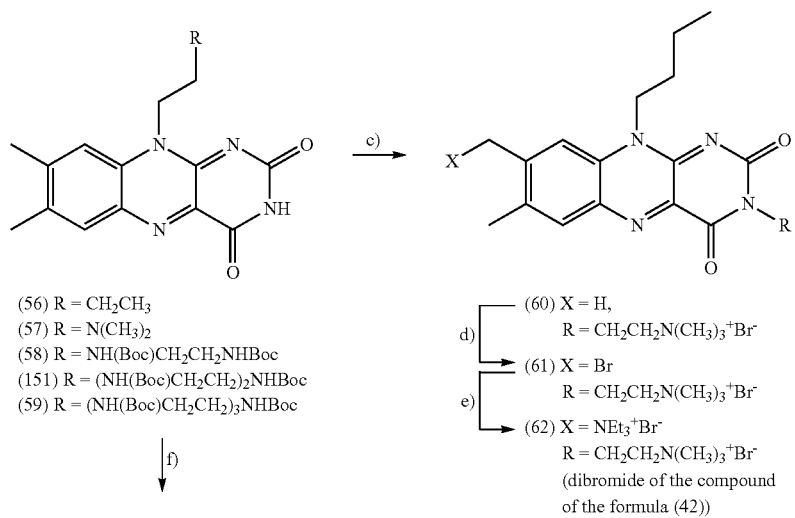

(56) R = CH$_2$CH$_3$
(57) R = N(CH$_3$)$_2$
(58) R = NH(Boc)CH$_2$CH$_2$NHBoc
(151) R = (NH(Boc)CH$_2$CH$_2$)$_2$NHBoc
(59) R = (NH(Boc)CH$_2$CH$_2$)$_3$NHBoc

(60) X = H, R = CH$_2$CH$_2$N(CH$_3$)$_3^+$Br$^-$
(61) X = Br, R = CH$_2$CH$_2$N(CH$_3$)$_3^+$Br$^-$
(62) X = NEt$_3^+$Br$^-$, R = CH$_2$CH$_2$N(CH$_3$)$_3^+$Br$^-$ (dibromide of the compound of the formula (42))

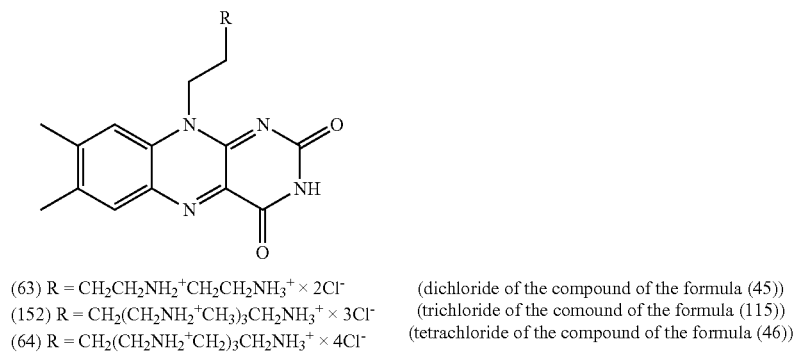

(63) R = CH$_2$CH$_2$NH$_2^+$CH$_2$CH$_2$NH$_3^+$ × 2Cl$^-$ (dichloride of the compound of the formula (45))
(152) R = CH$_2$(CH$_2$NH$_2^+$CH$_3$)$_2$CH$_2$NH$_3^+$ × 3Cl$^-$ (trichloride of the comound of the formula (115))
(64) R = CH$_2$(CH$_2$NH$_2^+$CH$_2$)$_3$CH$_2$NH$_3^+$ × 4Cl$^-$ (tetrachloride of the compound of the formula (46))

Scheme 2: Synthesis of compounds (67) and (68); reaction conditions: a) Br$_2$, dioxane benzoyl peroxide, 90° C., 1 h; e) NEt$_3$, DMF, 50° C., overnight; c) MeI, K$_2$CO$_3$, DMF, RT, 20 h;
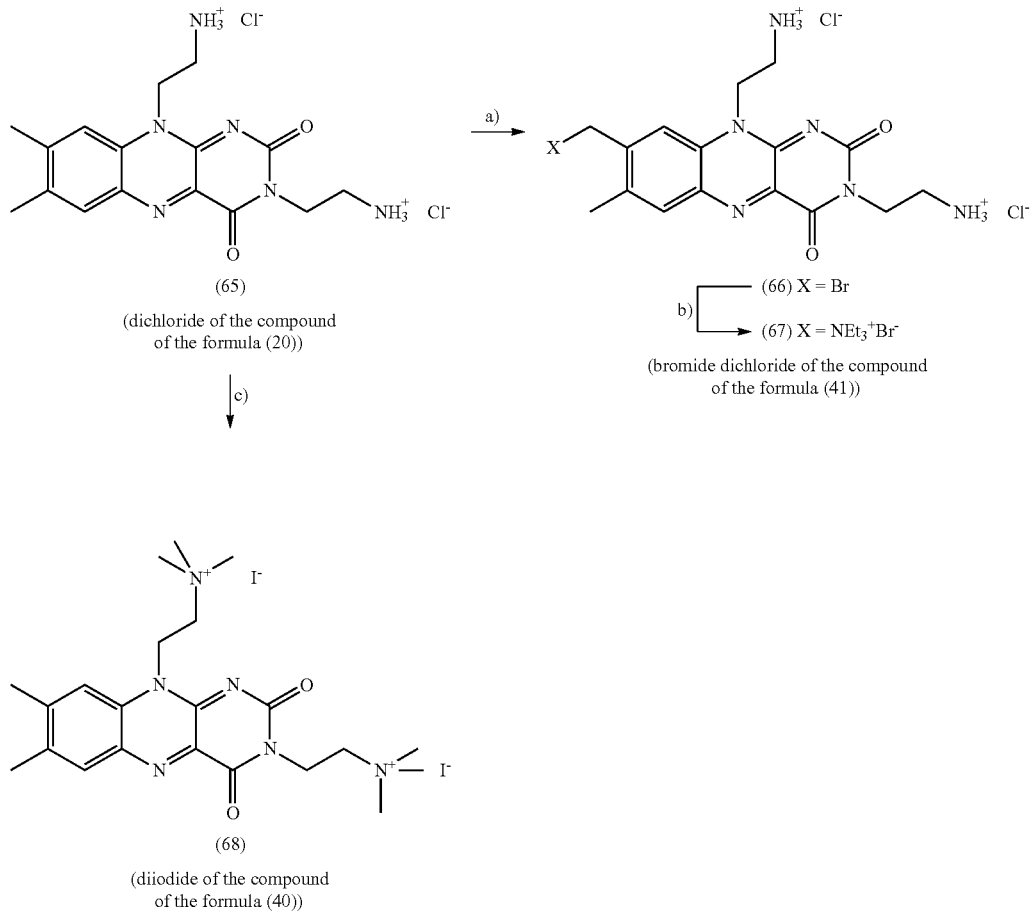
Scheme 3: Synthesis of compounds (70) and (71); reaction conditions: a) 2-N-Boc-aminoethyl bromide, Cs$_2$CO$_3$, DMF, RT, 2d; b) HCl in Et$_2$O, DCM, RT, overnight; c) bromocholine hydrobromide, Cs$_2$CO$_3$, DMF, RT, 2d
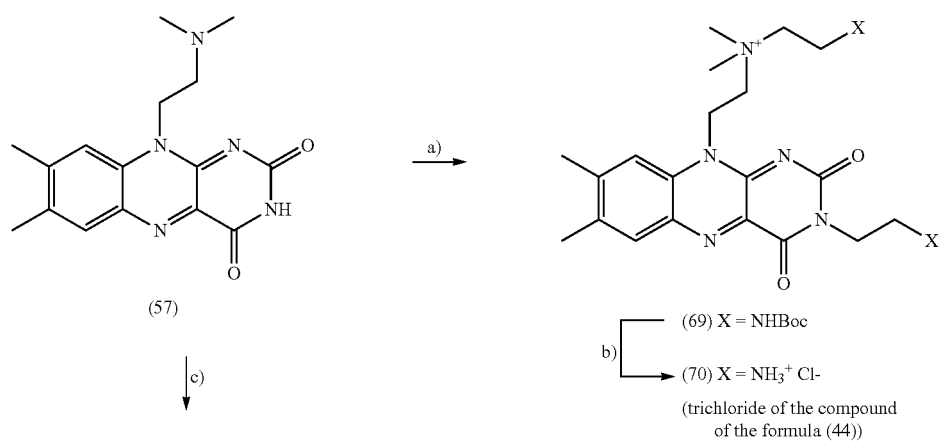

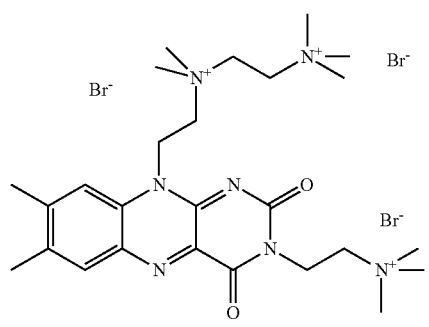
(71)
(tribromide of the compound of the formula (43))
Scheme 4: Synthesis of compounds (74) and (76); reaction conditions: a) N-Boc-glycine or α, ε-N, N'-di-Boc-lysine, DMAP, NEt₃, DCC, DMF, 80° C. → 0° C. → RT, 10 min, then 2 h, then overnight under N₂; b) HCl in Et₂O, DCM, RT, overnight;
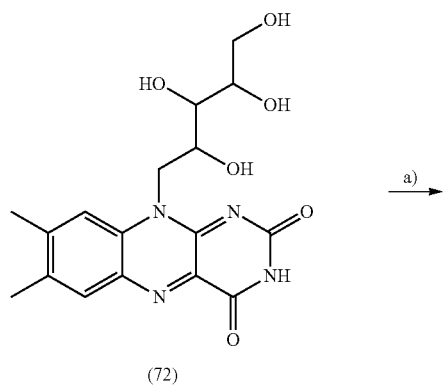
(72)
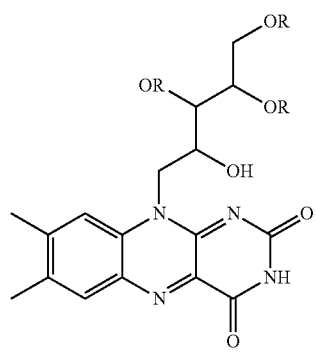
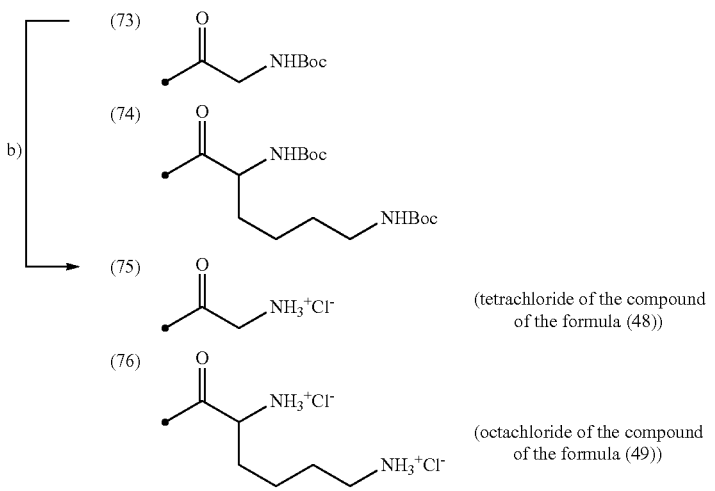
(73)
(74)
(75) (tetrachloride of the compound of the formula (48))
(76) (octachloride of the compound of the formula (49))

Scheme 5: Synthesis of compound (80); reaction conditions: a) HOAc, Ac₂O, HClO₄, 50° C., 2 h; b) 1,3-diiodopropane, K₂CO₃, DMF, RT, 2 h; c) N-methyl-4,4'-bipyridinium iodide, DMF, RT, 20 h;

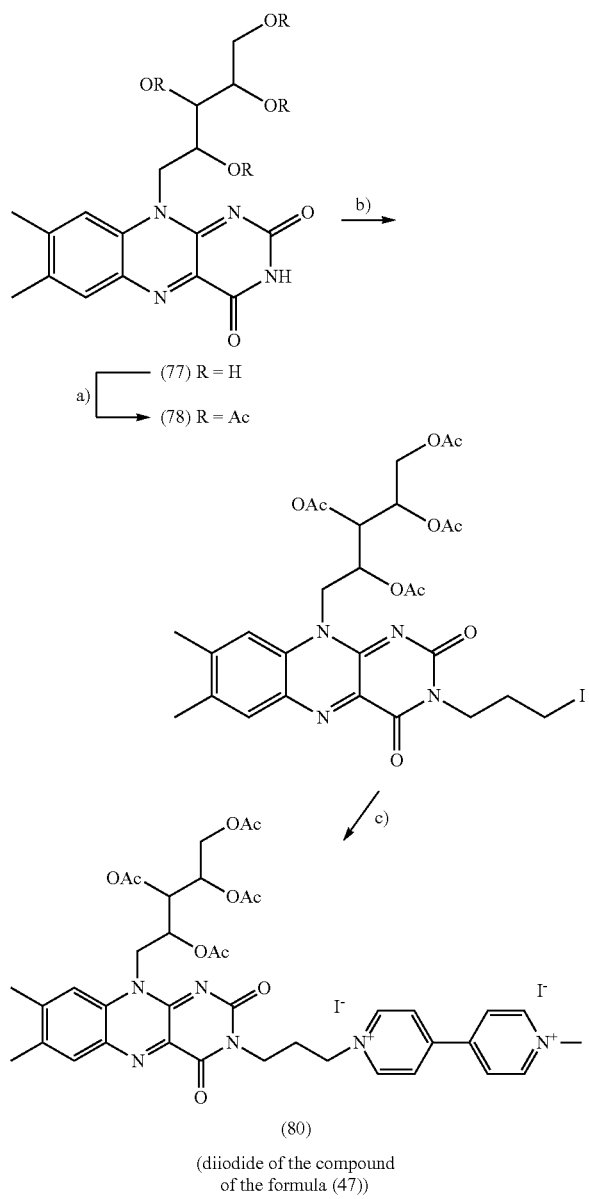

(77) R = H
(78) R = Ac

(80)
(diiodide of the compound of the formula (47))

Scheme 6: Synthesis of compound (118); reaction conditions: a) HOAc, Ac₂O, HClO₄, 50° C., 2 h; b) 1,3-diiodopropane, K₂CO₃, DMF, RT, 2 h; c) N-methyl-4,4'-bipyridinium iodide, DMF, RT, 20 h;

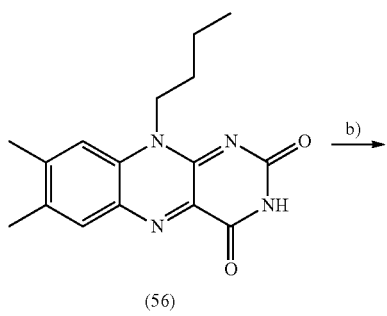

(56)

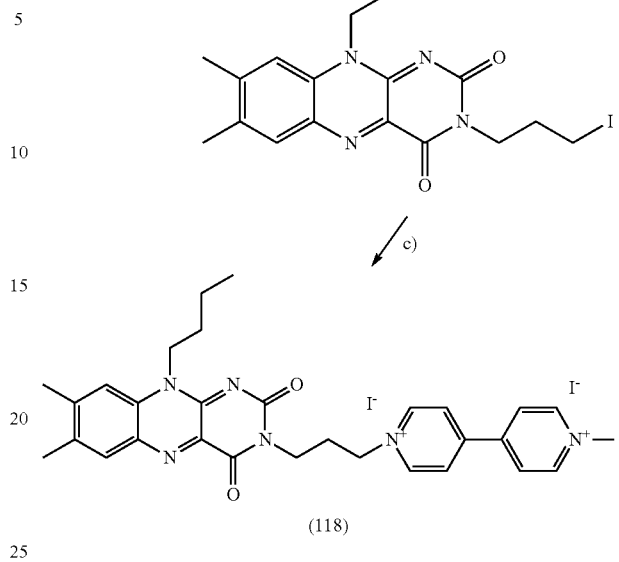

(118)

All chemicals used were purchased commercially from the usual suppliers (TCI, ABCR, Acros, Merck and Fluka) and used without further purification. Solvents were distilled before use and, if required, dried in the customary manner. Dry DMF was purchased commercially from Fluka (Taufkirchen, Germany).

Thin-layer chromatography was conducted on thin aluminum foils coated with silica gel 60 F254, from Merck (Darmstadt, Germany). Preparative thin-layer chromatography was conducted on commercially available glass plates coated with silica gel 60 (20 cm×20 cm, Carl Roth GmbH & Co. KG, Karlsruhe, Germany)). The compounds were detected by UV light ($\lambda$=254 nm, 333 nm) and some were detected with the naked eye or stained with ninhydrin. Chromatography was conducted with silica gel (0.060-0.200) from Acros (Waltham, USA).

NMR spectra were measured on a Bruker Avance 300 spectrometer (300 MHz [$^1$H NMR], 75 MHz [$^{13}$C NMR]) (Bruker Corporation, Billerica, USA).

All chemical shifts are reported in $\delta$ [ppm] relative to the external standard (tetramethylsilane, TMS). The coupling constants are each reported in Hz; characterization of the signals: s=singlet, d=doublet, t=triplet, m=multiplet, dd=doublet of doublets, br=broad. The integration determines the relative number of atoms. The signals in the carbon spectra are determined unambiguously by means of the DEPT method (pulse angle: 135°). Error limits: 0.01 ppm for $^1$H NMR, 0.1 ppm for $^{13}$C NMR and 0.1 Hz for coupling constants. The solvent used is stated for each spectrum.

The IR spectra were recorded on a Biorad Excalibur FTS 3000 spectrometer (Bio-Rad Laboratories GmbH, Munich, Germany).

ES-MS were measured with a ThermoQuest Finnigan TSQ 7000 spectrometer, all HR-MS were recorded on a ThermoQuest Finnigan MAT 95 (each from Thermo Fisher Scientific Inc, Waltham, USA) spectrometer, and argon served as the ionizing gas for FAB.

Melting points were determined with the aid of the Büchi SMP-20 melting point measuring instrument (Büchi Labortechnik GmbH, Essen, Germany) using a glass capillary.

All UV/Vis spectra were recorded with a Varian Cary 50 Bio UV/VIS spectrometer, and fluorescence spectra with a Varian Cary Eclipse spectrometer (each from Agilent Technologies, Santa Clara, USA).

The solvents for absorption and emission measurements were purchased in specific spectroscopic purity from Acros or Baker, and Uvasol from Merck. Millipore water (18 MΩ, Milli $Q_{Plus}$) was used for all measurements.

2-N-tert-butyloxycarbonylaminoethyl bromide[i] 1,2-dinitro-4,5-dimethylbenzene (51)[ii], butyl(4,5-dimethyl-2-nitrophenyl)amine (52) and 10-butyl-7,8-dimethyl-10H-benzo[g]pteridine-2,4-dione (56)[iii], N-[2-({[(tert-butyl)oxy]carbonyl}amino)ethyl]-4,5-dimethyl-2-nitro-aniline, riboflavin tetraacetate[iv], $N^1,N^2$-bis(tert-butoxycarbonyl)diethylenetriamine[v] and $N^1,N^2,N^3,N^4$-tetra(tert-butoxycarbonyl)tetraethylenepentamine[vi], N-methyl-4,4'-bipyridinium iodide[vii], 2,3,4-triacetoxy-1-[3-(3-iodopropyl)-7,8-dimethyl-2,4-dioxo-3,4-dihydro-2H-benzo[g]pteridin-10-ylmethyl]butyl acetate (79)[viii], and also 3,10-bis[2'-(tert-butyloxycarbonylamino)eth-1'-yl]-7,8-dimethylbenzo[g]-pteridine-2,4-dione and 3,10-bis(2'-aminoeth-1'-yl)-7,8-dimethylbenzo[g]pteridine-2,4-dione hydrochloride (65)[ix], were prepared by literature methods:

[i] N. Sakai, D. Gerard, S. Matile, J. Am. Chem. Soc. 2001, 123, 2517-2524.
[ii] a) A. Monge, J. A. Palop, A. López de Cerain, V. Senador, F. J. Martinez-Crespo, Y. Sainz, S. Narro, E. Garcia, C. de Miguel, M. Gonzalez, E. Hamilton, A. J. Barker, E. D. Clarke, D. T. Greenhow, J. Med. Chem. 1995, 38, 1786-1792; b) T. Sugaya, K. Nobuyuki, A. Sakaguchi, S. Tomioka, Synthesis 1995, 1257-1262; c) R. R. Holmes, R. P. Bayer, J. Am. Chem. Soc. 1960, 82, 3454-3456.
[iii] O. Wiest, Ch. B. Harrison, N. J. Saettel, R. Cibulka, M. Sax, B. König, J. Org. Chem. 2004, 69, 8183-8185
[iv] McCormick, D. B. J. Heterocycl. Chem. 1970, 7, 447-450.
[v] C. Moura, R. F. Vitor, L. Maria, A. Paulo, I. C. Santos, I. Santos, Dalton Trans., 2006, 5630-5640
[vi] S. Srinivasachari, K. M. Fichter, Th. M. Reineke, J. Am. Chem. Soc. 2008, 130, 4618-4627
[vii] Y. Xiao, L. Chu, Y. Sanakis, P. Liu, J. Am. Chem. Soc. 2009, 131, 9931-9933
[viii] A. Barthel, L. Trieschmann, D. Strohl, R. Kluge, G. Bohm, Rene Csuk, Arch. Pharm. Chem. Life Sci. 2009, 342, 445-452
[ix] J. Svoboda, H. Schmaderer, B. König, Chem. Eur. J. 2008, 14, 1854-1865

Bromocholine hydrobromide was purchased with a purity of >98% from TCI Deutschland GmbH (Eschborn, Germany) and used without further purification.

General Method I): Conversion of 1,2-dinitro-4,5-dimethylbenzene to Substituted 4,5-dimethyl-2-nitroanilines 1,2-Dinitro-4,5-dimethylbenzene (3.92 g, 20 mmol) and the respective amine specified in table 1 (100 mmol) were refluxed in dry ethanol (100 mL) and freshly distilled triethylamine (50 mL) at oil bath temperature 90° C. under nitrogen for 2 days. After cooling to room temperature, the solvent mixture was drawn off under reduced pressure and the residue was dried.

TABLE 1

| | | Amines used |
|---|---|---|
| Example | Target compound | Amine used |
| — | (52) | $H_2NCH_2CH_2CH_2CH_3$ |
| Ia) | (53) | $H_2NCH_2CH_2N(CH_3)_2$ |
| Ib) | (54) | $H_2NCH_2CH_2NH(Boc)CH_2CH_2NHBoc$ |
| Ic) | (55) | $H_2NCH_2CH_2(NH(Boc)CH_2CH_2)_3NHBoc$ |
| Id) | (150) | $H_2NCH_2CH_2(NH(Boc)CH_2CH_2)_2NHBoc$ |

Ia) N'-(4,5-dimethyl-2-nitrophenyl)-N,N-dimethyl-ethane-1,2-diamine (53)

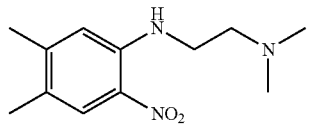

The crude product was recrystallized from ethanol. This gives 2.99 g of orange crystal needles (63% of theory, 126 mmol).
$^1$H NMR (300 MHz, CDCl$_3$): δ [ppm]=2.17 (s, 3H), 2.26 (s, 3H), 2.32 (s, 6H), 2.71 (t, 2H, J=544 Hz), 3.32 (m, 2H), 6.61 (s, 1H), 7.91 (s, 1H), 8.19 (bs, 1H); —MS (Cl-MS, NH$_3$): m/z (%)=238.1 (100, (MH$^+$)); —MW=237.30 g/mol—MF=C$_{12}$H$_{19}$N$_3$O$_2$ Ib) (2-{tert-butoxycarbonyl-[2-(4,5-dimethyl-2-nitrophenylamino)ethyl]amino}-ethyl)carbamic acid tert-butyl ester (54)

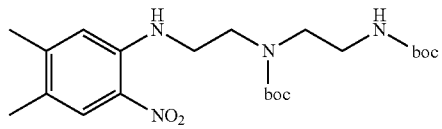

The crude product was purified by column chromatography on silica gel with ethyl acetate/petroleum ether 1:4, which gave an orange solid. (6.97 g, 77% of theory, 15.4 mmol).
$^1$H NMR (300 MHz, CDCl$_3$): δ [ppm]=1.43 (s, 9H), 1.45 (s, 9H), 2.18 (s, 3H), 2.27 (s, 3H), 3.23 (m, 2H), 3.32 (m, 2H), 3.48 (m, 2H), 3.53 (app. d, 2H), 4.78 (bs, 1H), 6.69 (m, 1H), 7.90 (s, 1H), 8.03 (m, 1H); —MS (ESI-MS, H$_2$O/MeOH+0.1% TFA): m/z (%)=453.1 (100, (MH$^+$)); —MW=452.56 g/mol—MF=C$_{22}$H$_{36}$N$_4$O$_6$ Ic) {2-[tert-butoxycarbonyl-(2-tert-butoxycarbonylaminoethyl)amino]ethyl}-(2-{tert-butoxycarbonyl-[2-(4, 5-dimethyl-2-nitrophenylamino)ethyl]amino}ethyl)-carbamic acid tert-butyl ester (55)

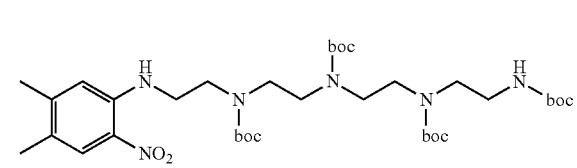

The crude product was purified by column chromatography on silica gel with ethyl acetate/petroleum ether 1:6, and a yellow/orange solid was obtained (9.01 g, 61% of theory, 12.2 mmol).

$^1$H NMR (300 MHz, CDCl$_3$): δ [ppm]=1.40 (s, 9H), 1.41 (s, 9H), 1.43 (s, 9H), 1.45 (s, 9H), 2.17 (s, 3H), 2.26 (s, 3H), 3.21-3.39 (m, 10H), 3.41-3.59 (m, 6H), 4.72 (bs, 1H), 4.80 (bs, 1H), 4.96-5.03 (m, 2H), 6.70 (m, 1H), 7.89 (s, 1H), 8.05 (m, 1H); —MS (ESI-MS, H$_2$O/MeOH+0.1% TFA): m/z (%)=739.1 (100, (MH$^+$)); —MW=738.93 g/mol—MF=C$_{32}$H$_{62}$N$_6$O$_{10}$ Id) {2-[tert-butoxycarbonylamino]ethyl}-(2-{tert-butoxycarbonyl-[2-(4,5-dimethyl-2-nitrophenylamino)ethyl]amino}ethyl)carbamic acid tert-butyl ester (150)

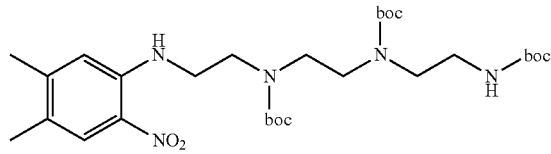

The crude product was purified by column chromatography on silica gel with ethyl acetate/petroleum ether 1:6, and a yellow/orange solid was obtained (6.58 g, 55% of theory, 11.0 mmol).

$^1$H NMR (300 MHz, CDCl$_3$): δ [ppm]=1.41 (s, 9H), 1.42 (s, 9H), 1.43 (s, 9H), 2.18 (s, 3H), 2.25 (s, 3H), 3.20-3.37 (m, 8H), 3.42-3.57 (m, 4H), 4.71 (bs, 1H), 6.72 (m, 1H), 7.88 (s, 1H), 8.03 (m, 1H); —MS (ESI-MS, H$_2$O/MeOH+0.1% TFA): m/z (%)=596.1 (100, (MH$^+$)); —MW=595.61 g/mol—MF=C$_{29}$H$_{49}$N$_5$O$_8$ General Method II): Conversion of Substituted 2-nitroanilines to the Corresponding Monosubstituted 10H-benzo[g]pteridine-2,4-dione Derivatives The respective 2-nitroaniline (53) to (55) and (150) obtained above in Ia) to Id) (10 mmol) was dissolved in acetic acid (100 mL). Palladium on activated carbon (100 mg, 10% Pd) was added and the mixture was stirred at hydrogen pressure 20 bar in an autoclave at room temperature for 14 h. The colorless solution was filtered into a Schlenk flask with a nitrogen atmosphere, and alloxane monohydrate (4.00 g, 25 mmol) and boric acid (15.50 g, 250 mmol) were added. The flask was wrapped in aluminum foil and the mixture was stirred in the dark under nitrogen at room temperature for 2 days. The orange/yellow suspension was diluted with water (200 mL) and extracted four times with dichloromethane (150 mL each time). The combined organic phases were washed with water (100 mL), dried over magnesium sulfate and concentrated by rotary evaporation.

IIa) 10-(2-dimethylaminoethyl)-7,8-dimethyl-10H-benzo[g]pteridine-2,4-dione (57)

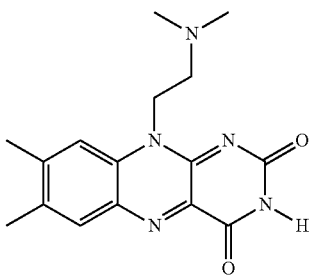 [SMILES: Cc1cc2nc3c(=O)[nH]c(=O)nc-3n(CCN(C)C)c2cc1C]

The residue was purified by column chromatography on silica gel with ethyl acetate/methanol 20:1→5:2. Orange solid (2.22 g, 7.07 mmol, 71% of theory).

$^1$H NMR (300 MHz, DMSO-d6): δ [ppm]=2.34 (s, 3H), 2.43 (s, 3H), 2.91 (s, 6H), 3.39 (m, 2H), 4.61 (m, 2H), 7.52 (s, 1H), 7.78 (s, 1H), 11.38 (s, 1H); —MS (ESI-MS, H$_2$O/MeOH+0.1% TFA): m/z (%)=314.0 (100, (MH$^+$)); —MW=313.36 g/mol—MF=C$_{16}$H$_{19}$N$_5$O$_2$ IIb) (2-{tert-butoxycarbonyl-[2-(7,8-dimethyl-2,4-dioxo-3,4-dihydro-2H-benzo[g]pteridin-10-yl)ethyl]amino}ethyl)carbamic acid tert-butyl ester (58)

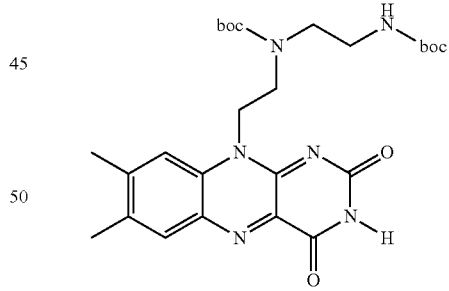

The residue was purified by column chromatography on silica gel with dichloromethane/methanol 95:5. The product is an orange solid (3.51 g, 6.64 mmol, 66% of theory).

$^1$H NMR (300 MHz, CDCl$_3$): δ [ppm]=1.42 (s, 9H), 1.43 (s, 9H), 2.38 (s, 3H), 2.51 (s, 3H), 3.19 (m, 2H), 3.30 (m, 2H), 3.48-3.76 (m, 4H), 5.02 (bs, 1H), 7.78 (s, 1H), 7.92 (s, 1H), 9.81 (s, 1H); —MS (ESI-MS, H$_2$O/MeOH+0.1% TFA): m/z (%)=529.0 (100, (MH$^+$)); —MW=528.61 g/mol—MF=C$_{26}$H$_{36}$N$_6$O$_6$ IIc) {2-[tert-butoxycarbonyl-(2-tert-butoxycarbonylaminoethyl)amino]ethyl}-(2-{tert-butoxycarbonyl[2-(7,8-dimethyl-2,4-dioxo-3,4-dihydro-2H-benzo[g]pteridin-10-yl)ethyl]amino}ethyl)carbamic acid tert-butyl ester (59)

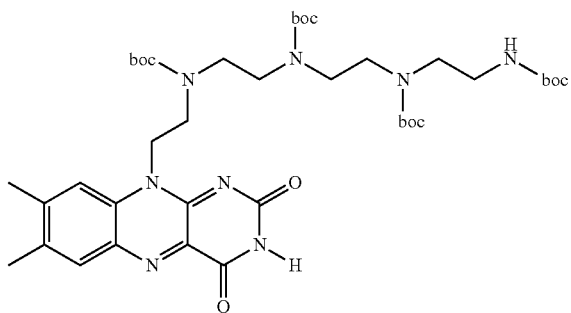

The residue was purified by column chromatography on silica gel with dichloromethane/methanol 95:5. Orange solid (4.30 g, 5.28 mmol, 53% of theory).

$^1$H NMR (300 MHz, CDCl$_3$): δ [ppm]=1.36-1.53 (m, 36H), 2.39 (s, 3H), 2.50 (s, 3H), 3.10-3.50 (m, 14H), 3.55-3.75 (m, 2H), 5.07 (bs, 1H), 7.80 (s, 1H), 7.96 (s, 1H), 9.73 (s, 1H); —MS (ESI-MS, H$_2$O/MeOH+0.1% TFA): m/z (%)=815.1 (100, (MH$^+$)); —MW=814.99 g/mol— MF=C$_{40}$H$_{62}$N$_8$O$_{10}$ IId) {2-(tert-butoxycarbonylaminoethyl}-(2-{tert-butoxycarbonyl-[2-(7,8-dimethyl-2,4-dioxo-3,4-dihydro-2H-benzo[g]pteridin-10-yl)ethyl]amino}ethyl)carbamic acid tert-butyl ester (151)

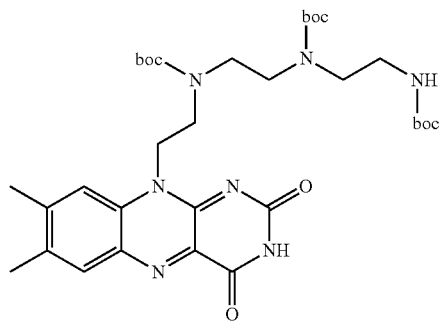

The residue was purified by column chromatography on silica gel with dichloromethane/methanol 95:5. Yellow/orange solid (3.28 g, 4.88 mmol, 49% of theory).

$^1$H NMR (300 MHz, CDCl$_3$): δ [ppm]=1.33-1.51 (m, 27H), 2.38 (s, 3H), 2.52 (s, 3H), 3.12-3.48 (m, 10H), 3.53-3.76 (m, 2H), 5.04 (bs, 1H), 7.82 (s, 1H), 7.95 (s, 1H), 9.71 (s, 1H); —MS (ESI-MS, H$_2$O/MeOH+0.1% TFA): m/z (%)=815.1 (100, (MH$^+$)); —MW=671.8 g/mol— MF=C$_{33}$H$_{49}$N$_7$O$_8$ General Method III): Deprotection of Boc-Protected Flavin Derivatives The respective flavin (2.0 mmol) was dissolved in dichloromethane (100 mL), HCl in diethyl ether (10 mL) was added dropwise and the reaction mixture was stirred in the dark with exclusion of moisture overnight. The precipitate was filtered off with suction, washed with diethyl ether and dried.

IIIa) (2-aminoethyl)-[2-(7,8-dimethyl-2,4-dioxo-3,4-dihydro-2H-benzo[g]pteridin-10-yl)ethyl]amine dihydrochloride (63)

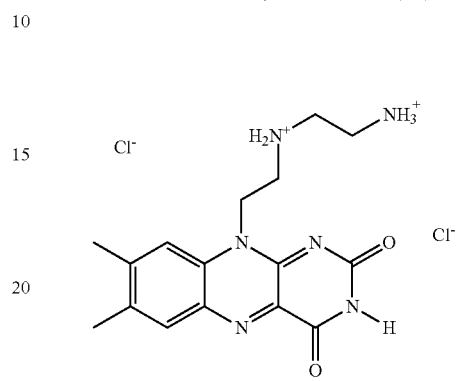

The flavin (58) obtained in IIb) was deprotected by general method III) and a light brown solid (0.79 g, 1.97 mmol, 98% of theory) was obtained.

IR (neat); ν [cm$^{-1}$]=3440 (m), 1714 (s), 1616 (s), 1584 (s), 1544 (s), 1459 (m), 1346 (m), 1252 (s), 1194 (m), 1024 (w), 931 (w), 876 (w), 809 (w), 772 (w); —MS (ESI-MS, H$_2$O/MeOH+0.1% TFA): m/z (%)=330.1 (47, (MH$^+$)), 165.0 (100, (M+2H$^+$)$^{2+}$); —MW=330.39+2×35.45 g/mol— MF=C$_{16}$H$_{22}$N$_6$O$_2$Cl$_2$ IIIb) 10-(2-{2-[2-(2-aminoethylamino)ethylamino]ethylamino}ethyl)-7,8-dimethyl-10H-benzo[g]pteridine-2,4-dione tetrahydrochloride (14)

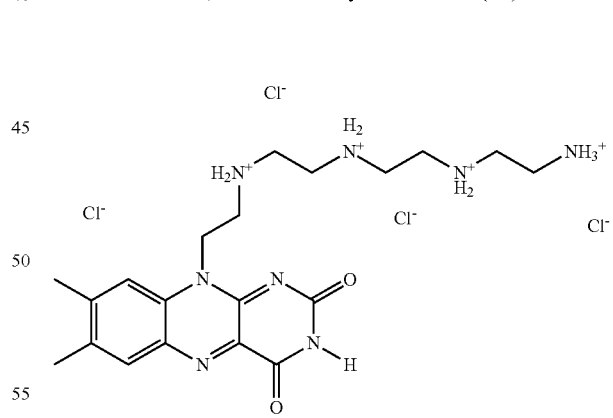

The flavin (59) obtained in IIc) was deprotected by general method III) and a light brown solid (0.97 g, 1.71 mmol, 86% of theory) was obtained.

IR (neat); ν [cm$^{-1}$]=3440 (m), 1713 (s), 1618 (s), 1583 (s), 1541 (s), 1458 (m), 1344 (m), 1256 (s), 1192 (m), 1023 (w), 932 (w), 878 (w), 808 (w), 771 (w); —MS (ESI-MS, H$_2$O/MeOH+0.1% TFA): m/z (%)=418.1 (63, (MH$^+$)), 209.0 (100, (M+2H$^+$)$^{2+}$); —MW=418.55+4×35.45 g/mol— MF=C$_{20}$H$_{34}$N$_8$O$_2$Cl$_4$ IIId) 10-(2-{2-[2-ethylamino]ethylamino}ethyl)-7,8-dimethyl-10H-benzo[g]pteridine-2,4-dione trihydrochloride (152)

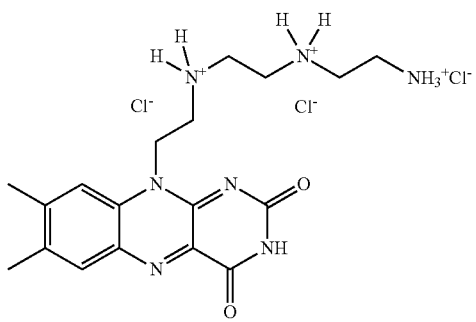

The flavin (151) obtained in IId) was deprotected by general method III) and an orange/brown solid (0.81 g, 1.40 mmol, 70% of theory) was obtained.

IR (neat); v [cm$^{-1}$]=3442 (m), 1711 (s), 1616 (s), 1584 (s), 1542 (s), 1458 (m), 1346 (m), 1258 (s), 1193 (m), 1024 (w), 932 (w), 877 (w), 806 (w), 772 (w); —MS (ESI-MS, H$_2$O/MeOH+0.1% TFA): m/z (%)=474.1 (49, (MH$^+$)), 237.0 (100, (M+2H$^+$)$^{2+}$); —MW=474.47+3×35.45 g/mol—MF=C$_{18}$H$_{28}$N$_7$O$_2$Cl$_3$ IV) [2-(10-butyl-7,8-dimethyl-2,4-dioxo-4,10-dihydro-2H-benzo[g]pteridin-3-yl)-ethyl]trimethylammonium bromide (60)

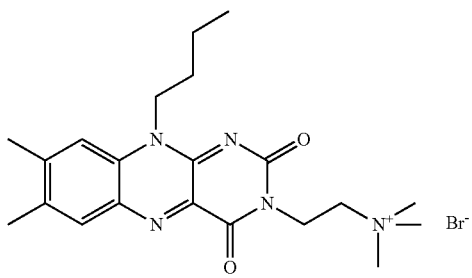

Flavin (56) (310 mg, 1.0 mmol) was dissolved in dry DMF (20 mL), cesium carbonate (1.63 g, 5 mmol) and bromocholine hydrobromide (0.5 g, 2.0 mmol) were added, and the mixture was stirred at room temperature in the dark for 1 d. Bromocholine hydrobromide (0.5 g, 2.0 mmol) was again added and the mixture was stirred at room temperature in the dark for a further day. The DMF was drawn off and the residue was suspended in chloroform/methanol 6:1 (50 mL). The suspension was filtered and the filtrate was concentrated to dryness. The crude product was purified by preparative thin-layer chromatography on silica gel (CHCl$_3$/MeOH—4:1) and purified by recrystallization from water.

Yield: 161 mg of an orange solid (0.347 mmol, 35% of theory)

R$_f$=0.1 (CHCl$_3$:MeOH—4:1)

$^1$H NMR (300 MHz, DMSO-d6): δ [ppm]=0.97 (t, 3H, J=7.3 Hz), 1.48 (m, 2H), 1.70 (m, 2H), 2.41 (s, 3H), 2.51 (s, 3H), 3.14-3.35 (m, 8H), 3.95 (t, 2H, J=6 Hz), 4.56 (t, 2H, J=7.8 Hz), 7.77 (s, 1H), 7.89 (s, 1H); —MS (ESI-MS, H$_2$O/MeOH+0.1% TFA): m/z (%)=384.1 (100, (M$^+$)); —MW=384.51+79.90 g/mol—MF=C$_{21}$H$_{30}$N$_5$O$_2$Br V) [10-butyl-3-(2-trimethylammoniumethyl)-7-methyl-2,4-dioxo-2,3,4,10-tetrahydrobenzo[g]pteridin-8-ylmethyl]triethylammonium dibromide (62)

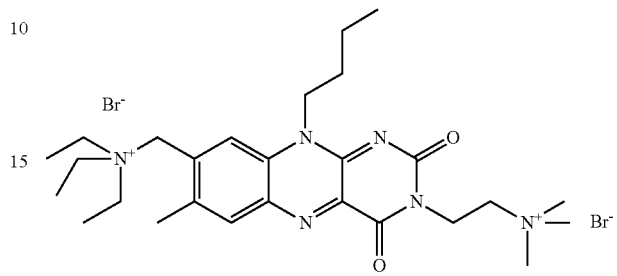

[2-(10-Butyl-7,8-dimethyl-2,4-dioxo-4,10-dihydro-2H-benzo[g]pteridin-3-yl)ethyl]-trimethylammonium bromide (60) (140 mg, 0.3 mmol) was suspended in 15 ml of dioxane. The mixture was brought to reflux temperature, dibenzoyl peroxide (10 mg in a little dioxane) was added, and 0.80 g of dioxane dibromide (3.0 mmol) in 5 mL of dioxane was added dropwise. The mixture was refluxed for 30 min and cooled to room temperature, and the solvent was drawn off under reduced pressure.

The crude 8α-bromoflavin (61) was dissolved in DMF (10 mL), the solution was degassed and triethylamine (0.60 g, 0.76 mL, 6.0 mmol) was added dropwise over 5 min. The mixture was stirred in the dark at 50° C. under N$_2$ overnight. After cooling to room temperature, the reaction mixture was added dropwise to 200 mL of ice-cold diethyl ether, and the crude product was filtered off, washed with diethyl ether and dried under reduced pressure. The residue was purified by chromatography on RP-18 gel with MeCN/water 9:1→4:1. For further purification, the product was recrystallized from water.

A brown solid (31 mg, 0.048 mmol, 16% of theory) was obtained.

MS (ESI-MS, H$_2$O/MeOH+0.1% TFA): m/z (%)=484.1 (37, (M$^+$)), 242.0 (100, (M$^{2+}$)); —MW=484.69+2×79.90 g/mol—MF=C$_{27}$H$_{44}$N$_6$O$_2$Br$_2$ VI) 3,10-bis(2-trimethylammoniumethyl)-7,8-dimethyl-10H-benzo[g]pteridine-2,4-dione dibromide (68)

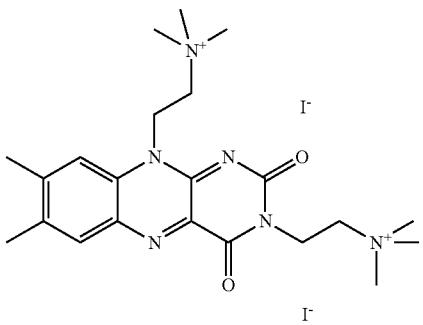

3,10-bis(2'-Aminoeth-1'-yl)-7,8-dimethylbenzo[g]pteridine-2,4-dione hydrochloride (65) (400 mg, 1.0 mmol) was dissolved in dry DMF (20 mL), cesium carbonate (1.32 g, 4.0 mmol) and methyl iodide (1.42 g, 10.0 mmol) were added and the mixture was stirred in the dark at room temperature for 20 h. The suspension was diluted with chloroform (100 mL) and washed with water (30 mL). The organic phase was dried over magnesium sulfate and the solvents were drawn off under reduced pressure. The crude product was purified by preparative thin-layer chromatography on silica gel (CHCl$_3$/MeOH—4:1).

Yield: 404 mg of an orange solid (0.61 mmol, 61% of theory)

$^1$H NMR (300 MHz, DMSO-d6): δ [ppm]=2.42 (s, 3H), 2.54 (s, 3H), 3.10-3.42 (m, 16H), 4.15 (d, 2H, J=5.7 Hz), 4.93 (d, 2H, J=6.4 Hz), 7.96 (s, 1H), 8.32 (s, 1H); —MS (ESI-MS, H$_2$O/MeOH+0.1% TFA): m/z (%)=414.1 (48, (M$^+$)), 207.0 (100, (M$^{2+}$)); —MW=414.56+2×126.90 g/mol—MF=C$_{22}$H$_{34}$N$_6$O$_2$I$_2$ VII) 3-(2-trimethylammoniumethyl)-10-{2-[(2-trimethylammoniumethyl)dimethyl-ammonium]ethyl}-7,8-dimethyl-10H-benzo[g]pteridine-2,4-dione tribromide (71)

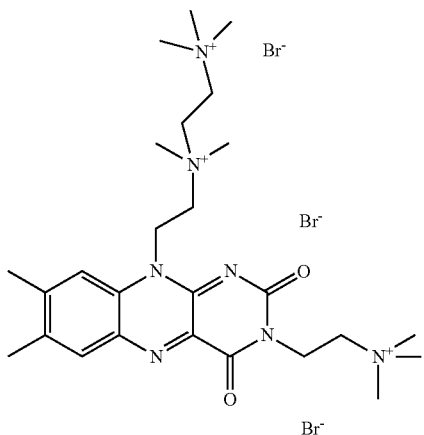

The flavin (57) obtained in IIa) (300 mg, 1.0 mmol) was dissolved in dry DMF (20 mL), cesium carbonate (1.96 g, 6 mmol) and bromocholine hydrobromide (1.0 g, 4.0 mmol) were added, and the mixture was stirred at room temperature in the dark for 1 d. Bromocholine hydrobromide (0.5 g, 2.0 mmol) was again added and the mixture was stirred at room temperature in the dark for a further day. The DMF was drawn off and the residue was suspended in chloroform/methanol 3:1 (50 mL). The suspension was filtered and the filtrate was concentrated to dryness. The residue was purified by chromatography on RP-18 gel with MeCN/water 9:1→4:1. For further purification, the product was recrystallized from water.

Yield: 213 mg of an orange solid (0.293 mmol, 29% of theory)

MS (ESI-MS, H$_2$O/MeOH+0.1% TFA): m/z (%)=486.1 (11, (M$^+$)), 243.0 (100, (M$^{2+}$)), 162.0 (7, (M$^{3+}$)); —MW=486.69+3×79.90 g/mol—MF=C$_{26}$H$_{44}$N$_7$O$_2$Br$_3$ VIII) (2-tert-butoxycarbonylaminoethyl)-{2-[3-(2-tert-butoxycarbonylaminoethyl)-7,8-dimethyl-2,4-dioxo-3,4-dihydro-2H-benzo[g]pteridin-10-yl]ethyl}dimethyl-ammonium bromide (69)

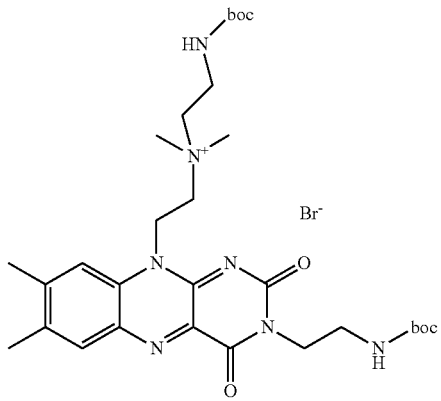

The flavin (57) obtained in IIa) (300 mg, 1.0 mmol) was dissolved in dry DMF (20 mL), and potassium carbonate (1.4 g, 10 mmol) and potassium iodide (1.1 g, 6 mmol) were added. After stirring at room temperature for 20 minutes, 2-(tert-butyloxycarbonylamino)ethyl bromide (1.15 g, 5 mmol) in DMF (5 mL) were added dropwise and the mixture was stirred in the dark at room temperature for 1 d. 2-(tert-Butyloxycarbonylamino)ethyl bromide (0.58 g, 2.5 mmol) was again added and the mixture was stirred at room temperature in the dark for a further day. The DMF was drawn off and the residue was dissolved in dichloromethane (200 mL). It was washed successively with aqueous sodium hydrogencarbonate solution (5%, 50 mL) and water (60 mL), dried over MgSO$_4$ and concentrated by rotary evaporation. The residue was purified by preparative thin-layer chromatography on silica gel with chloroform/methanol 6:1.

Yield: 301 mg of an orange solid (0.442 mmol, 44% of theory)

MS (ESI-MS, H$_2$O/MeOH+0.1% TFA): m/z (%)=600.1 (100, (M$^+$)); —MW=600.74+79.90 g/mol—MF=C$_{30}$H$_{46}$N$_7$O$_6$Br IX) (2-aminoethyl)-{2-[3-(2-aminoethyl)-7,8-dimethyl-2,4-dioxo-3,4-dihydro-2H-benzo[g]pteridin-10-yl]ethyl}dimethylammonium chloride dihydrochloride (70)

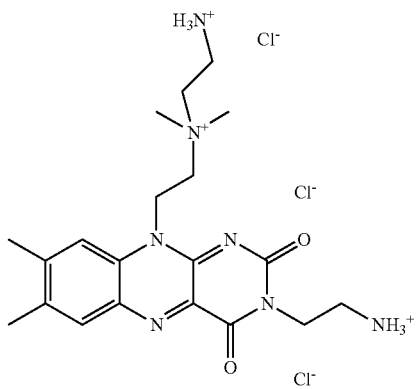 [SMILES: Cc1cc2nc3c(=O)n(CC[NH3+])c(=O)nc-3n(CC[N+](C)(C)CC[NH3+])c2cc1C ; [Cl-] ; [Cl-] ; [Cl-]]

The flavin (69) obtained in VIII) was deprotected by general method III and 0.93 g of a light brown solid (1.83 mmol, 92% of theory) was obtained.

MS (ESI-MS, H$_2$O/MeOH+0.1% TFA): m/z (%)=402.1 (16, (MH$^+$)), 201.0 (100, ((M+2H$^+$)$^{2+}$)), 134.0 (4, ((M+3H$^+$)$^{3+}$)); —MW=402.52+3×35.45 g/mol— MF=C$_{20}$H$_{32}$N$_7$O$_2$Cl$_3$ X) [3,10-bis(2-aminoethyl)-7-methyl-2,4-dioxo-2,3,4,10-tetrahydro-benzo[g]pteridin-8-ylmethyl]triethylammonium bromide dihydrochloride (67)

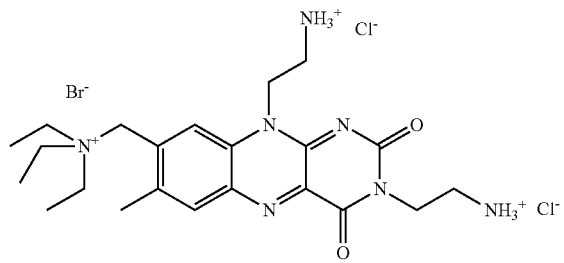 [SMILES: CC[N+](CC)(CC)Cc1cc2c(cc1C)nc1c(=O)n(CC[NH3+])c(=O)nc-1n2CC[NH3+] ; [Br-] ; [Cl-] ; [Cl-]]

3,10-bis(2'-Aminoeth-1'-yl)-7,8-dimethylbenzo[g]pteridine-2,4-dione hydrochloride (65) (400 mg, 1.0 mmol) was suspended in 25 ml of dioxane. The mixture was brought to reflux temperature, dibenzoyl peroxide (20 mg in a little dioxane) was added, and 0.80 g of dioxane dibromide (3.0 mmol) in 5 mL of dioxane was added dropwise. The mixture was refluxed for 30 min and cooled to room temperature, and the solvent was drawn off under reduced pressure.

The crude 8α-bromoflavin (66) was dissolved in DMF (10 mL), the solution was degassed and triethylamine (1.01 g, 1.26 mL, 10.0 mmol) was added dropwise over 5 min. The mixture was stirred in the dark at 50° C. under N$_2$ overnight. After cooling to room temperature, the reaction mixture was added dropwise to 200 mL of ice-cold diethyl ether, and the crude product was filtered off, washed with diethyl ether and dried under reduced pressure. The residue was purified by chromatography on RP-18 gel with MeCN/water 9:1→4:1. For further purification, the product was recrystallized from water.

A brown solid (53 mg, 0.091 mmol, 9% of theory) was obtained.

MS (ESI-MS, H$_2$O/MeOH+0.1% TFA): m/z (%)=430.1 (12, (MH$^+$)), 215.0 (100, ((M+2H$^+$)$^{2+}$)), 143.2 (2, ((M+3H$^+$)$^{3+}$)); —MW=430.58+79.90+2×35.45 g/mol— MF=C$_{22}$H$_{36}$N$_7$O$_2$BrCl$_2$ XI) 1-{3-[7,8-dimethyl-2,4-dioxo-10-(2,3,4,5-tetraacetoxypentyl)-4,10-dihydro-2H-benzo[g]pteridin-3-yl]propyl}methyl-[4,4']bipyridinyl-1-ium diiodide (80)

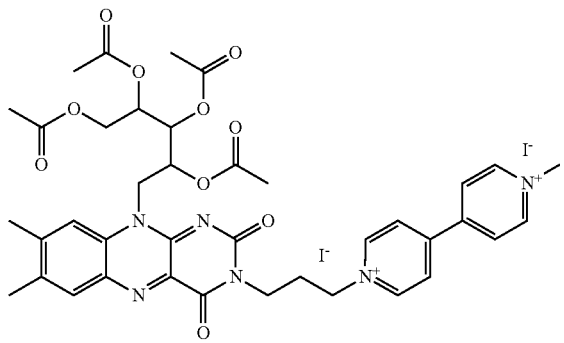

2,3,4-Triacetoxy-1-[3-(3-iodopropyl)-7,8-dimethyl-2,4-dioxo-3,4-dihydro-2H-benzo[g]pteridin-10-ylmethyl]butyl acetate (79) (0.75 g, 1.05 mmol) was stirred with N-methyl-4,4'-bipyridinium iodide (356 mg, 1.2 mmol) and NaHCO$_3$ (0.1 g, 1.2 mmol) in DMF (10 mL) in a nitrogen atmosphere in the dark at 50° C. for 24 h. The solvent was drawn off under reduced pressure and the residue was purified by preparative thin-layer chromatography (CHCl$_3$/MeOH 6:1).

This gives 312 mg of a light brown solid (0.34 mmol, 33% of theory).

$^1$H NMR (300 MHz, MeOD): δ [ppm]=1.71 (s, 3H), 2.02 (s, 3H), 2.21 (s, 3H), 2.26 (s, 3H), 2.41 (s, 3H), 2.49 (m, 2H), 2.51 (s, 3H), 4.26 (s, 3H), 4.18-4.30 (m, 3H), 4.50 (m, 1H), 4.89 (m, 2H), 5.18 (m, 2H), 5.46 (m, 1H), 5.53 (m, 1H), 5.66 (m, 1H), 7.86 (s, 1H), 7.91 (s, 1H), 8.21 (d, J=5.6 Hz, 2H), 8.98 (d, J=5.6 Hz, 2H), 9.24 (d, J=5.6 Hz, 2H), 9.59 (d, J=5.6 Hz, 2H); —MS (ESI-MS, H$_2$O/MeOH+0.1% TFA): m/z (%)=756.1 (56, (M$^+$)), 378.0 (100, (M$^{2+}$)); —MW=756.82+2×126.90—MF=C$_{39}$H$_{44}$N$_6$O$_{10}$I$_2$ General Method XII): Esterification of Riboflavin with Amino Acids Riboflavin (72) (1.88 g, 5 mmol) was dissolved in dry DMF (50 mL) while heating to 80° C. After cooling to room temperature, the respective amino acid specified (100 mmol) was added, followed by DMAP (1.22 g, 10 mmol), triethylamine (1.01 g, 1.26 mL, 10 mmol) and DCC (2.06 g, 10 mmol). The mixture was stirred in the dark at 50° C. under N$_2$ overnight. The solvent was drawn off under reduced pressure, and the residue was dissolved in chloroform (200 mL). The solution was washed with aqueous sodium hydrogencarbonate solution (5%, 100 mL), water (100 mL) and sat. aqueous sodium chloride solution (100 mL), dried over MgSO$_4$ and concentrated by rotary evaporation. The crude product was purified by column chromatography on silica gel with dichloromethane/methanol 20:1.

XIIa) tert-butoxycarbonylaminoacetic acid 2,3,4-tris-(2-tert-butoxycarbonylamino-acetoxy)-5-(7,8-dimethyl-2,4-dioxo-3,4-dihydro-2H-benzo[g]pteridin-10-yl)-pentyl ester (73)

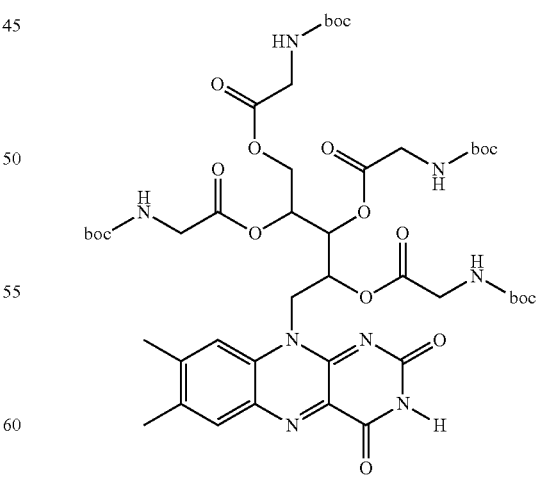

N-Boc-Glycine (3.48 g, 20 mmol) was reacted with riboflavin (72) according to general method XII), and 3.92 g of a light brown solid (3.90 mmol, 78% of theory) were obtained.

$^1$H NMR (300 MHz, CDCl$_3$): δ [ppm]=1.39 (s, 9H), 1.40 (s, 9H), 1.41 (s, 9H), 1.43 (s, 9H), 2.41 (s, 3H), 2.52 (s, 3H), 3.48-3.56 (m, 3H), 3.81-3.90 (m, 3H), 3.93-4.32 (m, 5H), 4.45 (m, 1H), 4.60-5.30 (m, 2H), 4.90 (m, 1H), 5.45-5.68 (m, 2H), 5.73 (m, 1H), 6.11 (bs, 1H), 7.63 (s, 1H), 7.88 (s, 1H), 8.96 (bs, 1H); —MS (ESI-MS, H$_2$O/MeOH+0.1% TFA): m/z (%)=1005.5 (100, (MH$^+$)); —MW=1005.05 g/mol—MF=C$_{45}$H$_{64}$N$_8$O$_{18}$ XIIb) 2,6-bis-tert-butoxycarbonylaminohexanoic acid 2,3,4-tris(2,6-bis-tert-butoxycarbonylaminohexanoxy)-5-(7, 8-dimethyl-2,4-dioxo-3,4-dihydro-2H-benzo[g]pteridin-10-yl) pentyl ester (74)

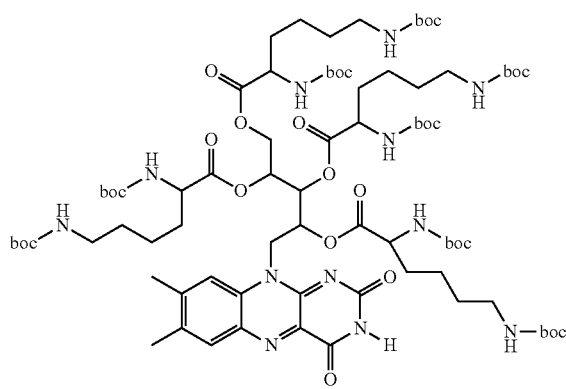

The reaction of α,ε-di-Boc-L-lysine (6.84 g, 20 mmol) with riboflavin (72) according to general method XII) gave 5.17 g of a light brown solid (3.06 mmol, 61% of theory).
$^1$H NMR (300 MHz, CDCl$_3$): δ [ppm]=1.36-1.52 (m, 72H), 1.21-1.42 (m, 16H), 1.44-1.86 (m, 16H), 2.40 (s, 3H), 2.53 (s, 3H), 2.98-3.06 (m, 4H), 3.41 (m, 1H), 3.61 (m, 3H), 3.93-4.32 (m, 3H), 4.43 (m, 1H), 4.60-5.30 (m, 2H), 4.86 (m, 1H), 5.11 (m, 2H), 5.58 (m, 1H), 7.61 (s, 1H), 7.90 (s, 1H), 8.94 (bs, 1H); —MS (ESI-MS, H$_2$O/MeOH+0.1% TFA): m/z (%)=1707.3 (61, (M+NH$_{4+}$)), 1690.2 (100, (MH$^+$)), 845.8 (88, (M+2H$^+$)$^{2+}$); —MW=1690.02 g/mol—MF=C$_{81}$H$_{132}$N$_{12}$O$_{26}$ XIII) aminoacetic acid 2,3,4-tris(2-aminoacetoxy)-5-(7,8-dimethyl-2,4-dioxo-3,4-dihydro-2H-benzo[g]pteridin-10-yl)pentyl ester tetrahydrochloride (75)

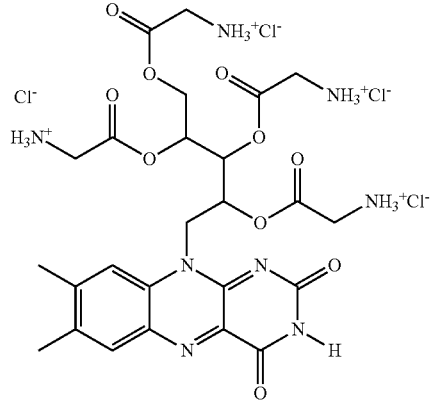

The flavin (73) obtained in XIIa) was deprotected by general method III) and 1.44 g of a light brown solid (1.69 mmol, 85% of theory) were obtained.
MS (ESI-MS, H$_2$O/MeOH+0.1% TFA): m/z (%)=605.5 (36, (MH$^+$)), 303.3 (100, (M+2H$^+$)$^{2+}$), 202.4 (41, (M+3H$^+$)$^3$); —MW=608.61+4×35.45 g/mol—MF=C$_{25}$H$_{36}$N$_8$O$_{10}$Cl$_4$ XIV) 2,6-bisaminohexanoic acid 2,3,4-tris-(2,6-bisaminohexanoxy)-5-(7,8-dimethyl-2,4-dioxo-3,4-dihydro-2H-benzo[g]pteridin-10-yl)pentyl ester octahydrochloride (76)

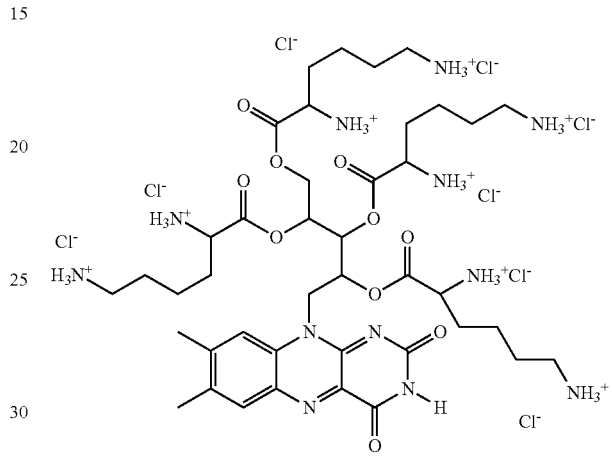

The flavin (74) obtained in XIIb) was deprotected by general method III) and 1.49 g of a brown solid (1.26 mmol, 63% of theory) were obtained.
MS (ESI-MS, H$_2$O/MeOH+0.1% TFA): m/z (%)=898.2 (15, (MH$^+$)), 449.5 (100, (M+2H$^+$)$^{2+}$), 300.1 (9, (M+3H$^+$)$^{3+}$); —MW=897.14+8×35.45 g/mol—MF=C$_{41}$H$_{76}$N$_{12}$O$_{10}$Cl$_8$ XV) 1-{3-[7,8-dimethyl-2,4-dioxo-10-(butyl)-4,10-dihydro-2H-benzo[g]pteridin-3-yl]-propyl}methyl-[4,4']bipyridinyl-1-ium diiodide (118)

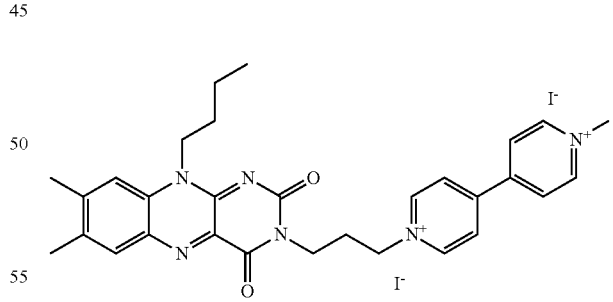

3-(10-Butyl-7,8-dimethyl-2,4-dioxo-4, 10-dihydro-2H-benzo[g]pteridin-3-yl)propyl iodide (xx) (0.51 g, 1.05 mmol) was stirred with N-methyl-4,4'-bipyridinium iodide (356 mg, 1.2 mmol) and NaHCO$_3$ (0.1 g, 1.2 mmol) in DMF (10 mL) in a nitrogen atmosphere in the dark at 50° C. for 24 h. The solvent was drawn off under reduced pressure and the residue was purified by preparative thin-layer chromatography (CHCl$_3$/MeOH 6:1).
This gives 351 mg of an orange solid (0.34 mmol, 45% of theory).

$^1$H NMR (300 MHz, MeOD): δ [ppm]=0.92 (t, 3H), 1.46 (m, 2H), 1.72 (m, 2H), 2.32 (m, 2H), 2.47 (s, 3H), 2.56 (s, 3H), 3.96 (m, 2H), 4.16-4.32 (m, 3H), 4.51 (m, 1H), 4.86 (m, 2H), 5.16 (m, 2H), 5.48 (m, 1H), 5.52 (m, 1H), 5.64 (m, 1H), 7.84 (s, 1H), 7.92 (s, 1H), 8.22 (d, J=5.6 Hz, 2H), 8.97 (d, J=5.6 Hz, 2H), 9.23 (d, J=5.6 Hz, 2H), 9.59 (d, J=5.6 Hz, 2H); —MS (ESI-MS, H$_2$O/MeOH+0.1% TFA): m/z (%)=510.1 (19, (M$^+$)), 255.0 (100, (M$^{2+}$)); —MW=510.6+2×126.90—MF=C$_{30}$H$_{34}$N$_6$O$_2$I$_2$ Example 2) Phototoxicity Experiments a) Production of the Test Plates and Bacterial Strains A sample of the bacterial strain *Staphylococcus aureus* (ATCC number: 25923) or *Escherichia coli* (ATCC number: 25922) was taken from a cryogenically frozen culture, isolated on Müller-Hinton agar plates and cultivated under aerobic conditions at 37° C. in an overnight culture. Thereafter, 5 ml of Müller-Hinton liquid medium were inoculated with a smear of the bacterial culture (single colony) and incubated at 37° C. overnight. The bacterial suspension thus obtained was centrifuged at 2500 rpm for 10 min and the bacterial pellet obtained was resuspended in 5 ml of sterile PBS. The optical density of the bacterial suspension for the phototoxicity tests was OD$_{600\ nm}$=0.6, which corresponds to a bacteria count of ~1-8×10$^{8-12}$ bacteria per ml. The biochemical analysis and resistance determination of the bacteria were conducted with the VITEK2 system according to the M100-S14 guidelines from the NCCLS (2004).

To check sensitivity of medically significant pathogens against antibiotics and sulfonamides, in accordance with the NCCLS guidelines, Müller-Hinton media were used (Deutsche Gesellschaft für Hygiene und Mikrobiologie (DGHM), Institute of Hygiene and Microbiology, University of Bonn, Germany):
a) Müller-Hinton broth (Oxoid, Wesel, Germany)
2.0 g/l beef, dried infusion from 300 g, 17.5 g/l casein hydrolyzate,
1.5 g/l starch, pH: 7.4+0.2
b) Müller-Hinton agar (Oxoid, Wesel, Germany)
2.0 g/l beef, dried infusion from 300 g, 17.5 g/l casein hydrolyzate,
1.5 g/l starch, pH: 7.4+0.2
13 g/l agar-agar b) Procedure for the Phototoxicity Test:

200 μl of a bacterial suspension (bacterial density: 10$^8$-10$^{12}$/ml) were incubated with 200 μl of each of various concentrations of the photosensitizers to be tested at room temperature for 10 min or 30 min. Thereafter, the bacteria were washed twice with distilled water and resuspended in 200 μl of distilled water, and the entire volume was transferred to a 96-well microtiter plate and then irradiated. The photosensitizers used were dissolved in distilled water and various dilution series were prepared (0 μM, 1 μM, 10 μM, 100 μM).

For sensitization, the Omnicure Series 2000 lamp (Photonics Solutions Inc., Edinburgh, UK) was used, which emits light from a range from 390 nm to 500 nm and has emission maxima E$_{max}$ at 405 nm and 436 nm. The power applied in each case was 50 mW/cm$^2$.

Irradiated and unirradiated samples were used as controls. Likewise run were bacterial suspensions incubated only with photosensitizer (dark control).

The determination of the colony-forming units (CFU) per ml was conducted by the method published by Miles and Misra (Miles, A A; Misra, S S, Irwin, J O (1938 November). "The estimation of the bactericidal power of the blood.". The *Journal of hygiene* 38 (6): 732-49). For this purpose, serial dilutions from 10$^{-2}$ to 10$^{-9}$ of the corresponding bacterial suspension were prepared. 3×20 μl of each of the corresponding bacterial dilutions were then dripped onto Müller-Hinton plates and incubated at 37° C. for 24 h. Thereafter, the number of surviving colony-forming units (CFU) was determined. Each of the experiments was repeated three times.

c) Result of the Phototoxicity Experiments:

The results of the phototoxicity experiments are shown in FIGS. 1-11.

FIGS. 1-12 show the logarithmic decreases in the CFU/ml 24 h after irradiation and the corresponding controls (only irradiated bacteria; bacteria incubated with photosensitizer but not irradiated; untreated bacteria) for the respective photosensitizer specified.

Each of the colony-forming units (CFU) per ml reported is the median from three experiments.

FIG. 1 shows the effect of flavin FL-08 (diiodide of the compound having the formula (47)) on *E. coli* and *S. aureus*.

Figure 1A:
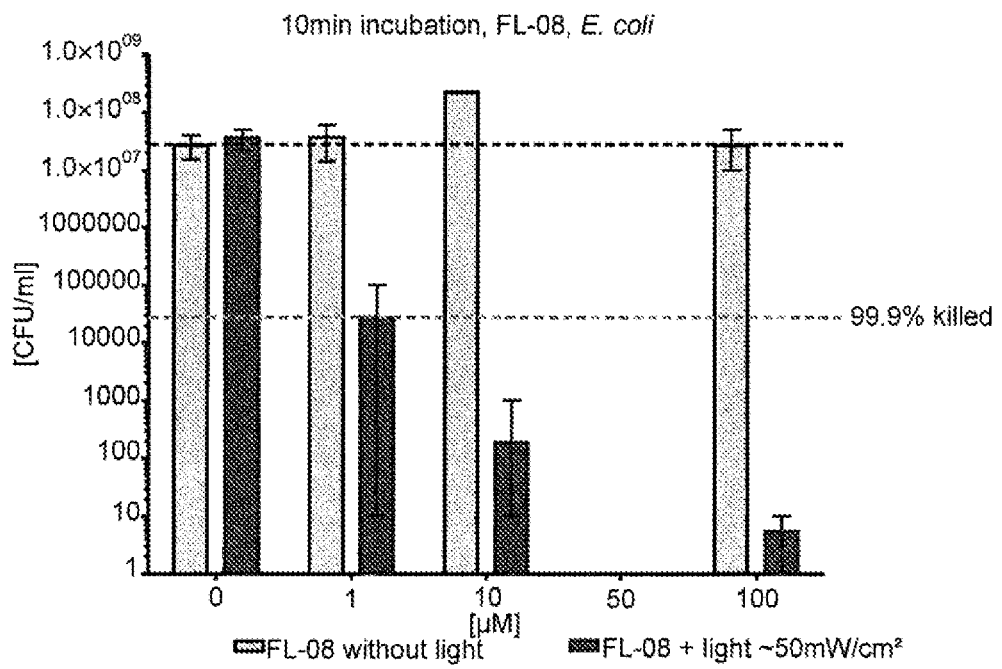
FIG. 1a) shows the results of incubation of *Escherichia coli* samples with FL-08 for 10 minutes.

FIG. 1a: *E. coli* samples were incubated with various concentrations (0 μM, 1 μM, 10 μM, 100 μM) of flavin FL-08 for 10 min. Subsequently, the samples were either irradiated at 50 mW/cm$^2$ (210 sec; 10.5 J/cm$^2$) (dark gray bar) or not irradiated (light gray bar). After 24 h, the surviving colonies were counted (CFU/ml). The black line indicates the dark control reference (0 μM flavin FL-08, no light). The dotted line marked "99.9% killed" indicates a decrease in the CFU/ml by 3 log$_{10}$ stages; this corresponds to a decrease by 99.9% ("antibacterial action"). N=3; median CFU/ml±SEM.

Figure 1B:
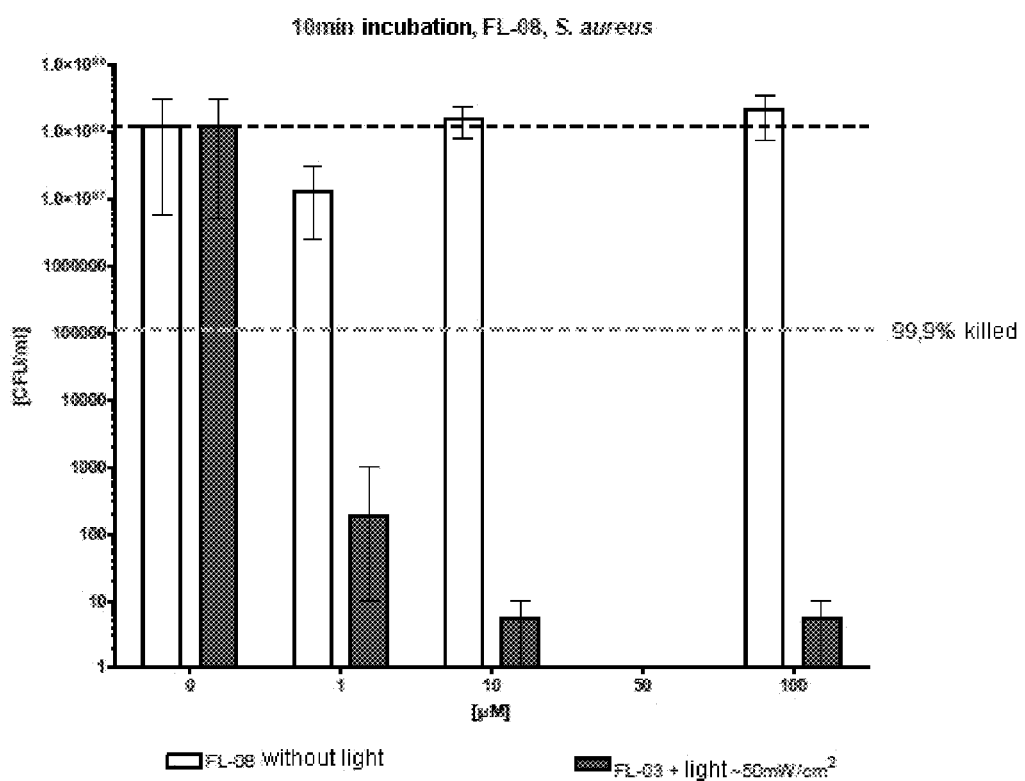
FIG. 1b) shows the results of incubation of *Staphylococcus aureus* samples with FL-08 for 10 minutes.

FIG. 1b: *S. aureus* samples were incubated with various concentrations (0 μM, 1 μM, 10 μM, 100 μM) of flavin FL-08 for 10 min. Subsequently, the samples were either irradiated at 50 mW/cm$^2$ (210 sec; 10.5 J/cm$^2$) (dark gray bar) or not irradiated (white bar). After 24 h, the surviving colonies were counted (CFU/ml). The black line indicates the dark control reference (0 μM flavin FL-08, no light). The dotted line marked "99.9% killed" indicates a decrease in the CFU/ml by 3 log$_{10}$ stages; this corresponds to a decrease by 99.9% ("antibacterial action"). N=3; median CFU/ml±SEM.

Figure 2:
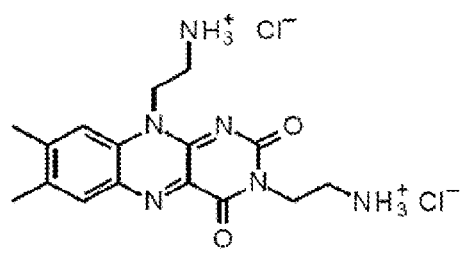
FIG. 2 shows the structural formula of Flavin FL-02.

FIG. 2 shows the effect of flavin FL-02 (dichloride of the compound having the formula (20)) on *E. coli* and *S. aureus*.

Figure 2A:
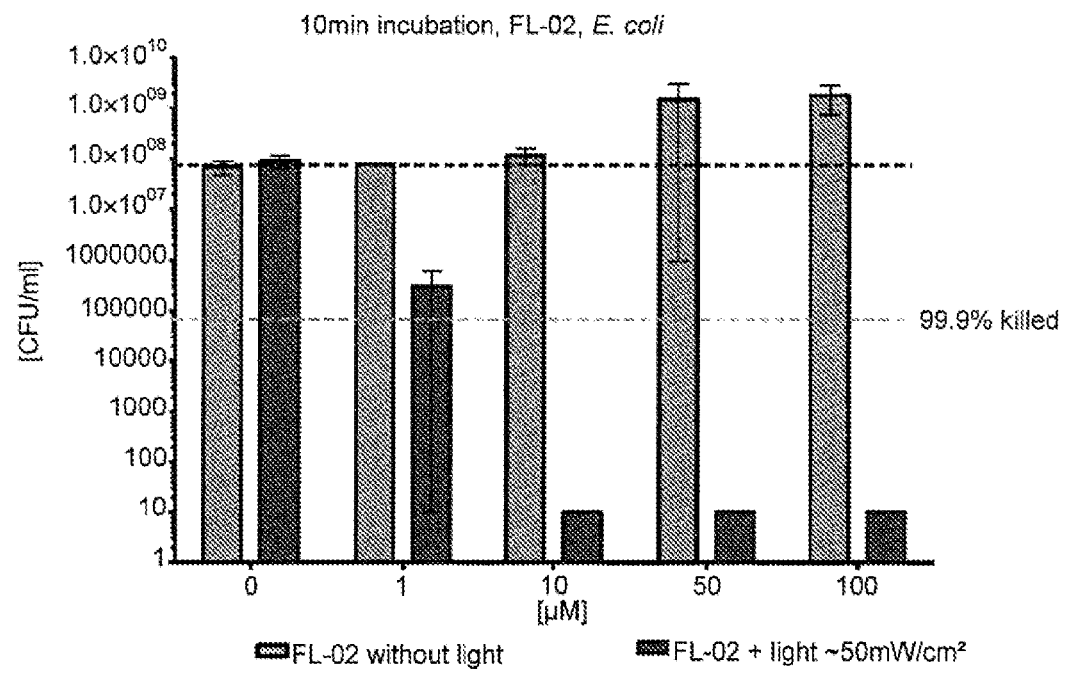
FIG. 2a) shows the results of incubation of *Escherichia coli* samples with FL-02 for 10 minutes.

FIG. 2a: *E. coli* samples were incubated with various concentrations (0 μM, 1 μM, 10 μM, 50 μM, 100 μM) of flavin FL-02 for 10 min. Subsequently, the samples were either irradiated at 50 mW/cm$^2$ (210 sec; 10.5 J/cm$^2$) (dark gray bar) or not irradiated (light gray bar). After 24 h, the surviving colonies were counted (CFU/ml). The black line indicates the dark control reference (0 μM flavin FL-02, no light). The dotted line marked "99.9% killed" indicates a decrease in the CFU/ml by 3 log$_{10}$ stages; this corresponds to a decrease by 99.9% ("antibacterial action"). N=3; median CFU/ml±SEM.

Figure 2B:
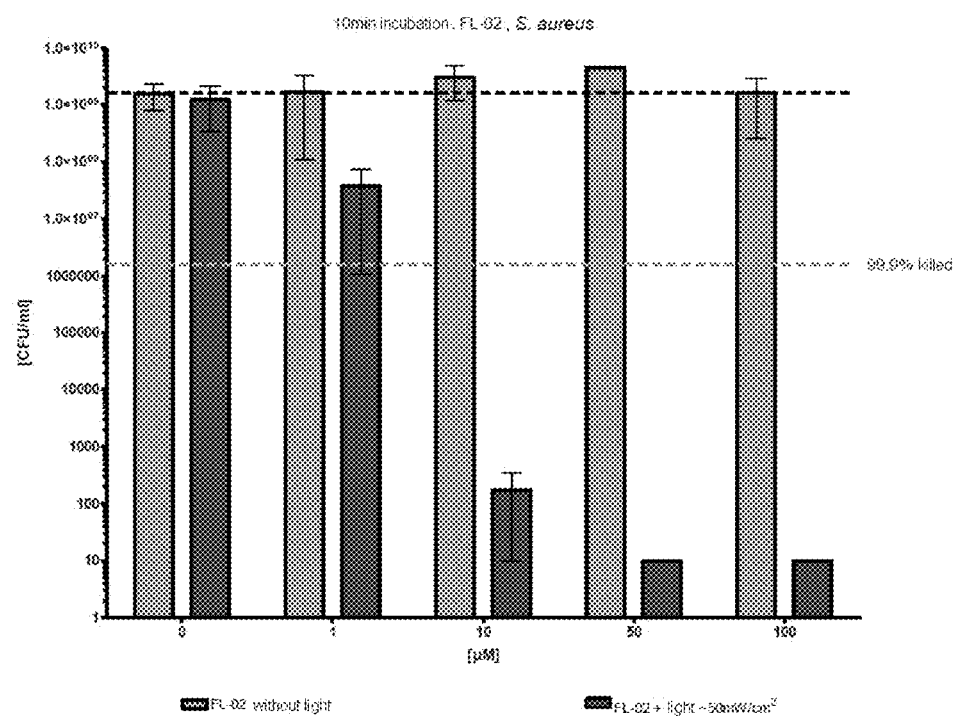
FIG. 2b) shows the results of incubation of *Staphylococcus aureus* samples with FL-02 for 10 minutes.

FIG. 2b: *S. aureus* samples were incubated with various concentrations (0 μM, 1 μM, 10 μM, 50 μM, 100 μM) of flavin FL-02 for 10 min. Subsequently, the samples were either irradiated at 50 mW/cm$^2$ (210 sec; 10.5 J/cm$^2$) (dark gray bar) or not irradiated (light gray bar). After 24 h, the surviving colonies were counted (CFU/ml). The black line indicates the dark control reference (0 μM flavin FL-02, no light). The dotted line marked "99.9% killed" indicates a decrease in the CFU/ml by 3 log$_{10}$ stages; this corresponds to a decrease by 99.9% ("antibacterial action"). N=3; median CFU/ml±SEM.

Figure 3:
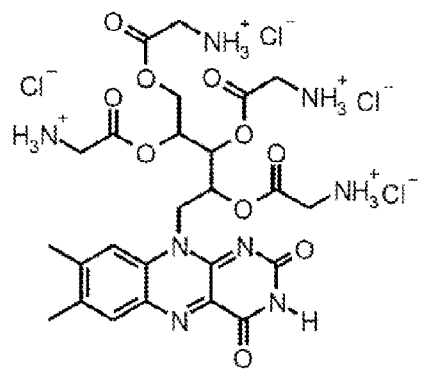
FIG. 3 shows the structural formula of Flavin FL-06.

FIG. 3 shows the effect of flavin FL-06 (iodide of the compound having the formula (37)) on *E. coli* and *S. aureus*.

Figure 3A:
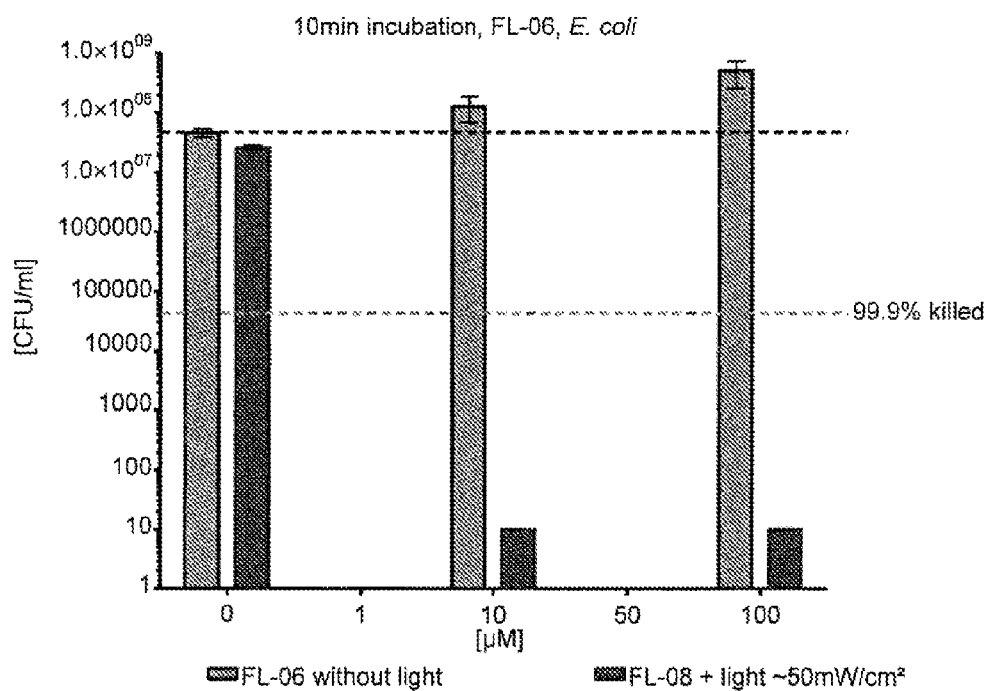
FIG. 3a) shows the results of incubation of *Escherichia coli* samples with FL-06 for 10 minutes.

FIG. 3a: *E. coli* samples were incubated with various concentrations (0 µM, 10 µM, 100 µM) of flavin FL-06 for 10 min. Subsequently, the samples were either irradiated at 50 mW/cm$^2$ (210 sec; 10.5 J/cm$^2$) (dark gray bar) or not irradiated (light gray bar). After 24 h, the surviving colonies were counted (CFU/ml). The black line indicates the dark control reference (0 µM flavin FL-06, no light). The dotted line marked "99.9% killed" indicates a decrease in the CFU/ml by 3 log$_{10}$ stages; this corresponds to a decrease by 99.9% ("antibacterial action"). N=3; median CFU/ml±SEM.

Figure 3B:
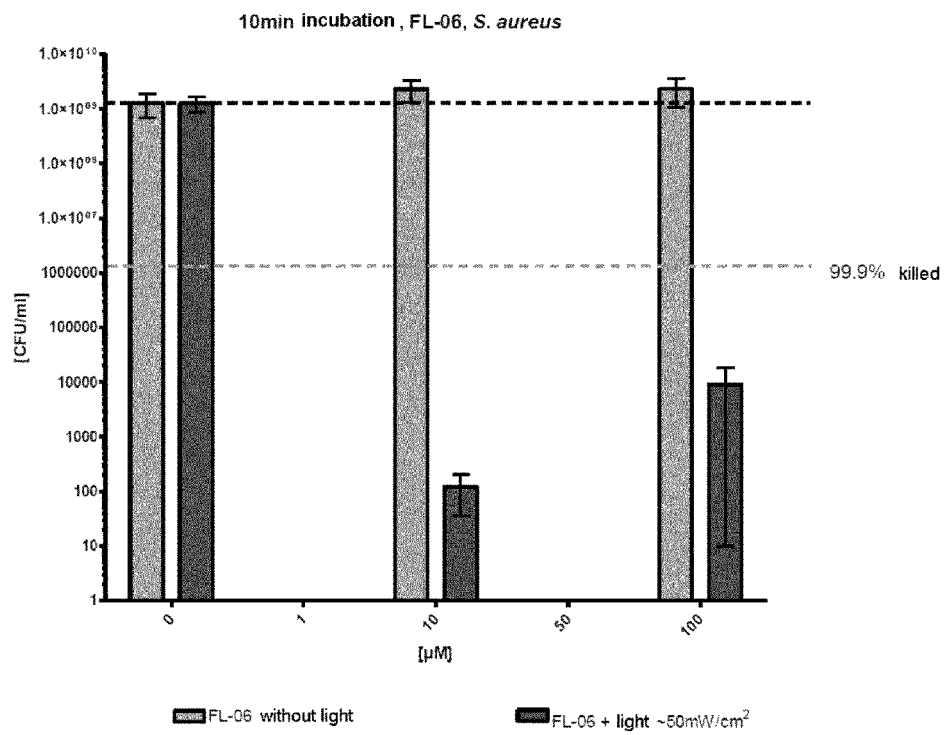
FIG. 3b) shows the results of incubation of *Staphylococcus aureus* samples with FL-06 for 10 minutes.

FIG. 3b: *S. aureus* samples were incubated with various concentrations (0 µM, 10 µM, 100 µM) of flavin FL-06 for 10 min. Subsequently, the samples were either irradiated at 50 mW/cm$^2$ (210 sec; 10.5 J/cm$^2$) (dark gray bar) or not irradiated (light gray bar). After 24 h, the surviving colonies were counted (CFU/ml). The black line indicates the dark control reference (0 µM flavin FL-06, no light). The dotted line marked "99.9% killed" indicates a decrease in the CFU/ml by 3 log$_{10}$ stages; this corresponds to a decrease by 99.9% ("antibacterial action"). N=3; median CFU/ml±SEM.

Figure 4:
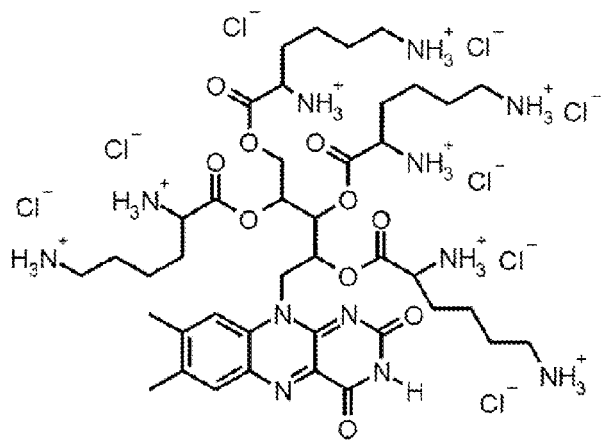
FIG. 4 shows the structural formula of Flavin FL-07.

FIG. 4 shows the effect of flavin FL-07 (octachloride of the compound having the formula (49)) on *E. coli* and *S. aureus*.

Figure 4A:
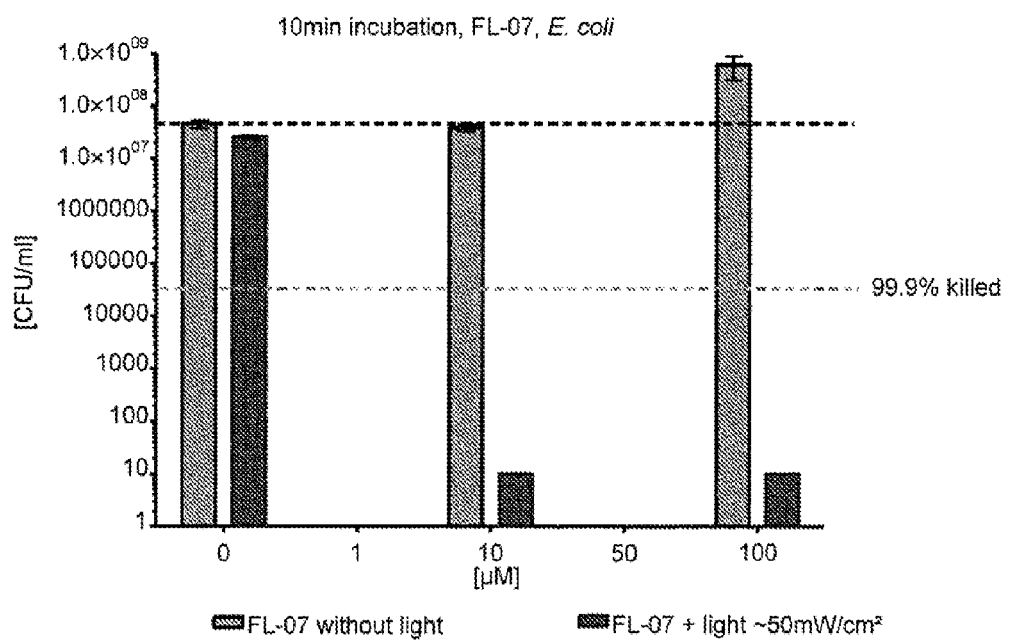
FIG. 4a) shows the results of incubation of *Escherichia coli* samples with FL-07 for 10 minutes.

FIG. 4a: *E. coli* samples were incubated with various concentrations (0 µM, 10 µM, 100 µM) of flavin FL-07 for 10 min. Subsequently, the samples were either irradiated at 50 mW/cm$^2$ (210 sec; 10.5 J/cm$^2$) (dark gray bar) or not irradiated (light gray bar). After 24 h, the surviving colonies were counted (CFU/ml). The black line indicates the dark control reference (0 µM flavin FL-07, no light). The dotted line marked "99.9% killed" indicates a decrease in the CFU/ml by 3 log$_{10}$ stages; this corresponds to a decrease by 99.9% ("antibacterial action"). N=3; median CFU/ml±SEM.

Figure 4B:
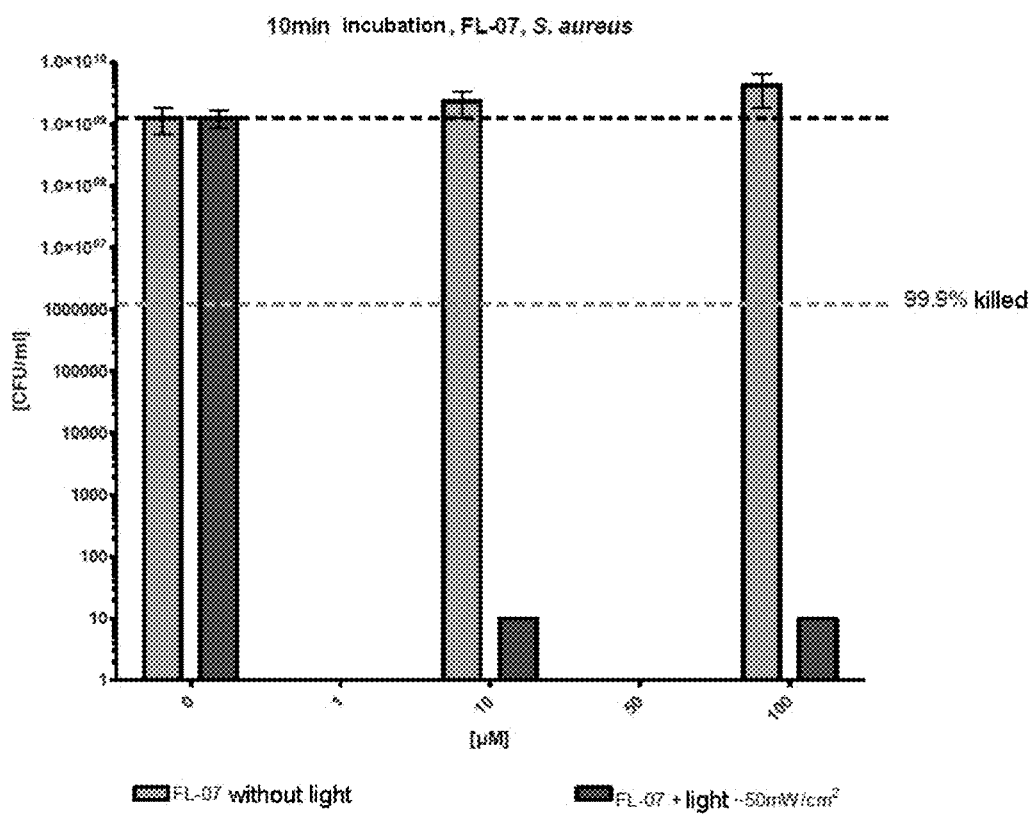
FIG. 4b) shows the results of incubation of *Staphylococcus aureus* samples with FL-07 for 10 minutes.

FIG. 4b: *S. aureus* samples were incubated with various concentrations (0 µM, 10 µM, 100 µM) of flavin FL-07 for 10 min. Subsequently, the samples were either irradiated at 50 mW/cm$^2$ (210 sec; 10.5 J/cm$^2$) (dark gray bar) or not irradiated (light gray bar). After 24 h, the surviving colonies were counted (CFU/ml). The black line indicates the dark control reference (0 µM flavin FL-07, no light). The dotted line marked "99.9% killed" indicates a decrease in the CFU/ml by 3 log$_{10}$ stages; this corresponds to a decrease by 99.9% ("antibacterial action"). N=3; median CFU/ml±SEM.

Figure 5:
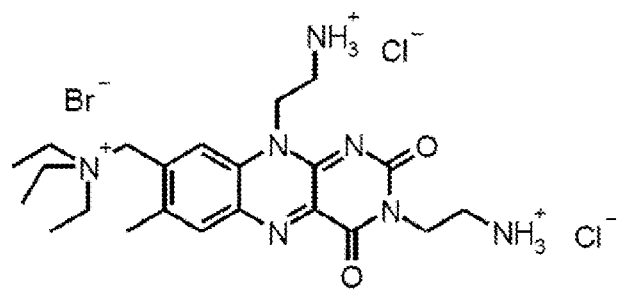
FIG. 5 shows the structural formula of Flavin FL-13.

FIG. 5 shows the effect of flavin FL-13 (bromide dichloride of the compound having the formula (41)) on *E. coli* and *S. aureus*.

Figure 5A:
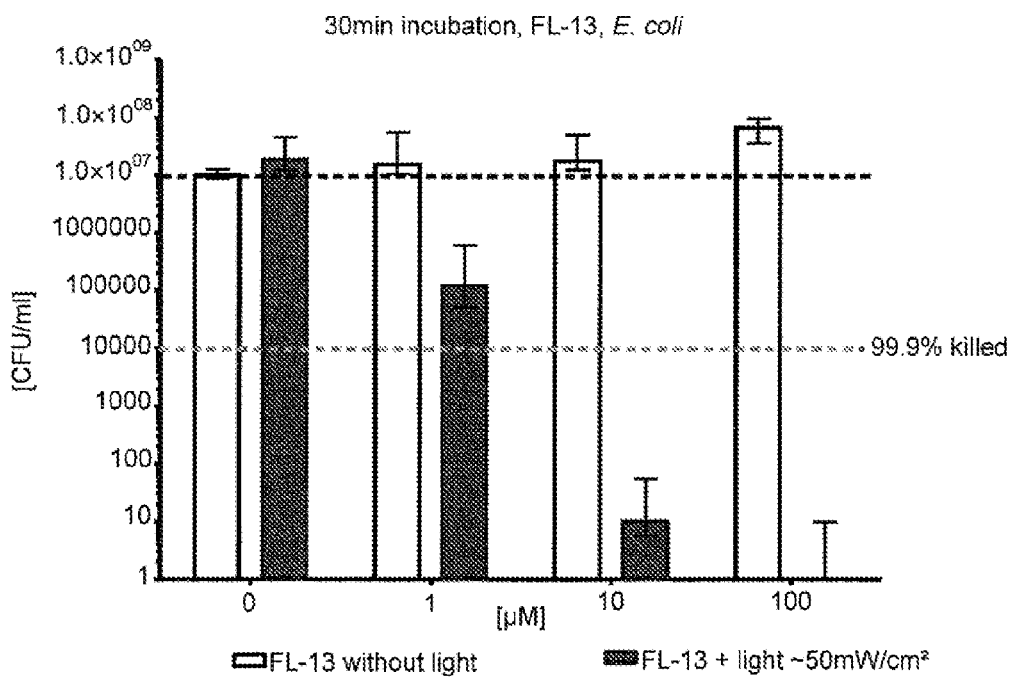
FIG. 5a) shows the results of incubation of *Escherichia coli* samples with FL-13 for 30 minutes.

FIG. 5a: *E. coli* samples were incubated with various concentrations (0 µM, 1 µM, 10 µM, 100 µM) of flavin FL-13 for 30 min. Subsequently, the samples were either irradiated at 50 mW/cm$^2$ (210 sec; 10.5 J/cm$^2$) (dark gray bar) or not irradiated (white bar). After 24 h, the surviving colonies were counted (CFU/ml). The black line indicates the dark control reference (0 µM flavin FL-13, no light). The dotted line marked "99.9% killed" indicates a decrease in the CFU/ml by 3 log$_{10}$ stages; this corresponds to a decrease by 99.9% ("antibacterial action"). N=3; median CFU/ml±SEM.

FIG. 5b: *S. aureus* samples were incubated with various concentrations (0 µM, 1 µM, 10 µM, 100 µM) of flavin FL-13 for 30 min. Subsequently, the samples were either irradiated at 50 mW/cm$^2$ (210 sec; 10.5 J/cm$^2$) (dark gray bar) or not irradiated (white bar). After 24 h, the surviving colonies were counted (CFU/ml). The black line indicates the dark control reference (0 µM flavin FL-13, no light). The dotted line marked "99.9% killed" indicates a decrease in the CFU/ml by 3 log$_{10}$ stages; this corresponds to a decrease by 99.9% ("antibacterial action"). N=3; median CFU/ml±SEM.

Figure 6:
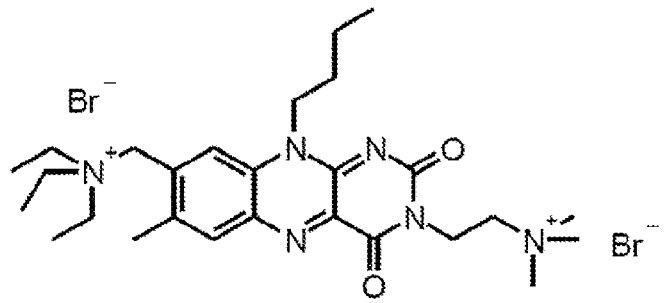
FIG. 6 shows the structural formula of Flavin FL-15.

FIG. 6 shows the effect of flavin FL-15 (dibromide of the compound having the formula (42)) on *E. coli* and *S. aureus*.

Figure 6A:
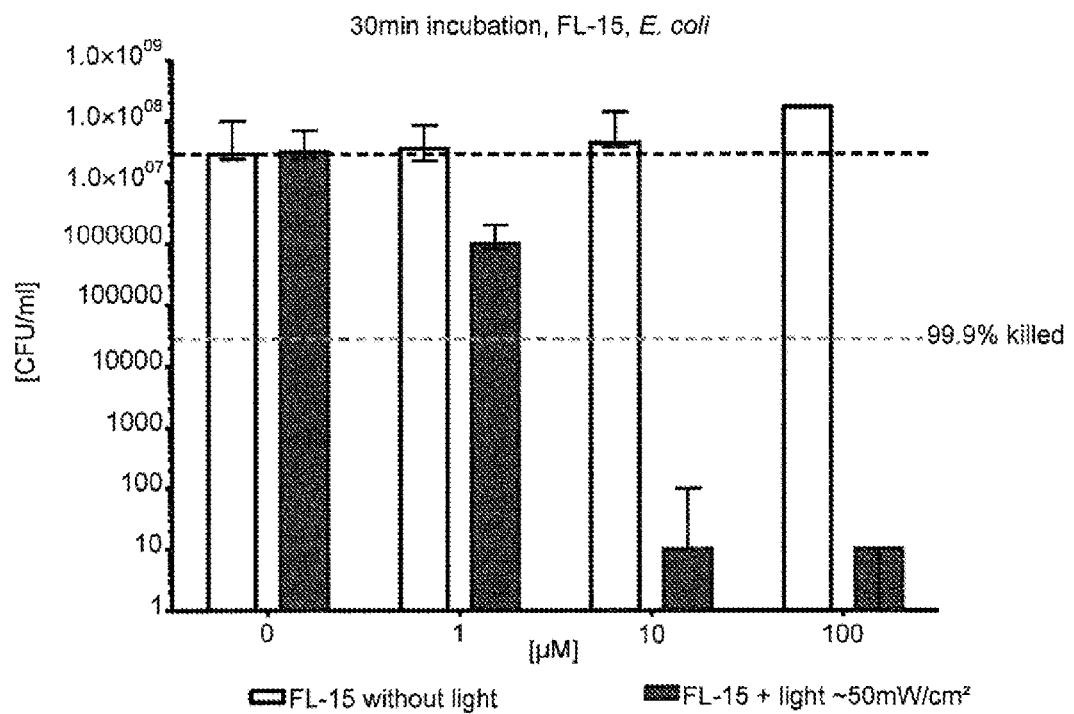
FIG. 6a) shows the results of incubation of *Escherichia coli* samples with FL-15 for 30 minutes.

FIG. 6a: *E. coli* samples were incubated with various concentrations (0 µM, 1 µM, 10 µM, 100 µM) of flavin FL-15 for 30 min. Subsequently, the samples were either irradiated at 50 mW/cm$^2$ (210 sec; 10.5 J/cm$^2$) (dark gray bar) or not irradiated (white bar). After 24 h, the surviving colonies were counted (CFU/ml). The black line indicates the dark control reference (0 µM flavin FL-15, no light). The dotted line marked "99.9% killed" indicates a decrease in the CFU/ml by 3 log$_{10}$ stages; this corresponds to a decrease by 99.9% ("antibacterial action"). N=3; median CFU/ml±SEM.

Figure 6B:
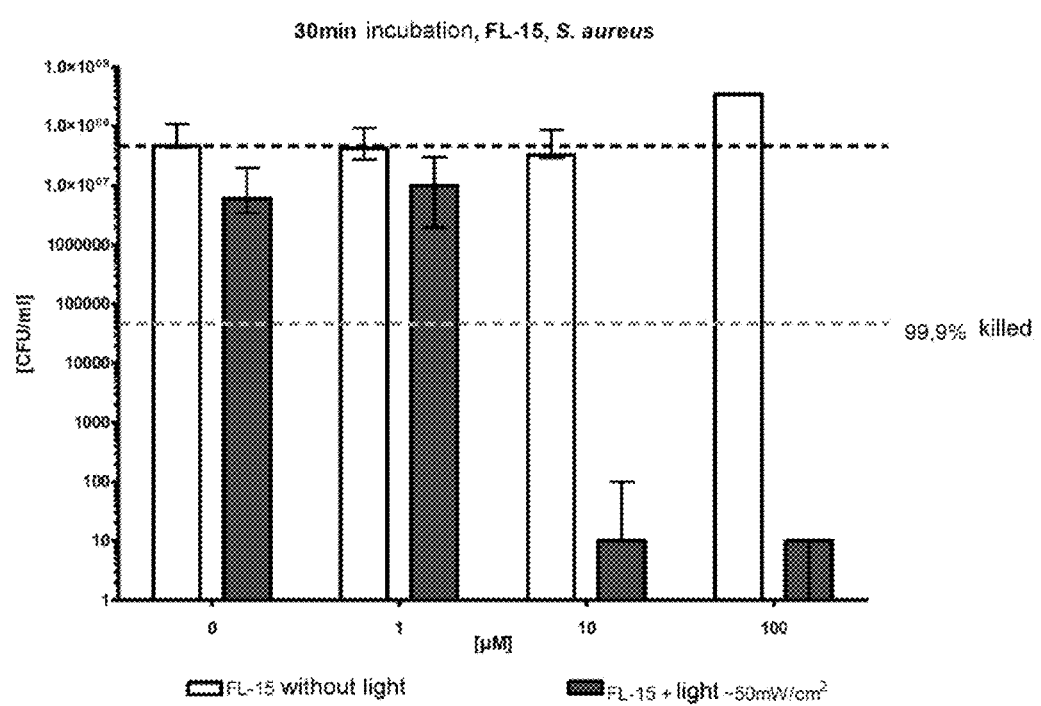
FIG. 6b) shows the results of incubation of *Staphylococcus aureus* samples with FL-15 for 30 minutes.

FIG. 6b: *S. aureus* samples were incubated with various concentrations (0 µM, 1 µM, 10 µM, 100 µM) of flavin FL-15 for 30 min. Subsequently, the samples were either irradiated at 50 mW/cm$^2$ (210 sec; 10.5 J/cm$^2$) (dark gray bar) or not irradiated (white bar). After 24 h, the surviving colonies were counted (CFU/ml). The black line indicates the dark control reference (0 µM flavin FL-15, no light). The dotted line marked "99.9% killed" indicates a decrease in the CFU/ml by 3 log$_{10}$ stages; this corresponds to a decrease by 99.9% ("antibacterial action"). N=3; median CFU/ml±SEM.

Figure 7:
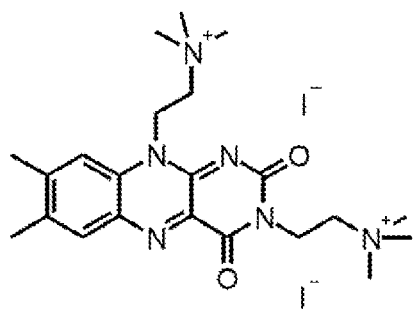
FIG. 7 shows the structural formula of Flavin FL-17.

FIG. 7 shows the effect of flavin FL-17 (diiodide of the compound having the formula (40)) on *E. coli* and *S. aureus*.

Figure 7A:
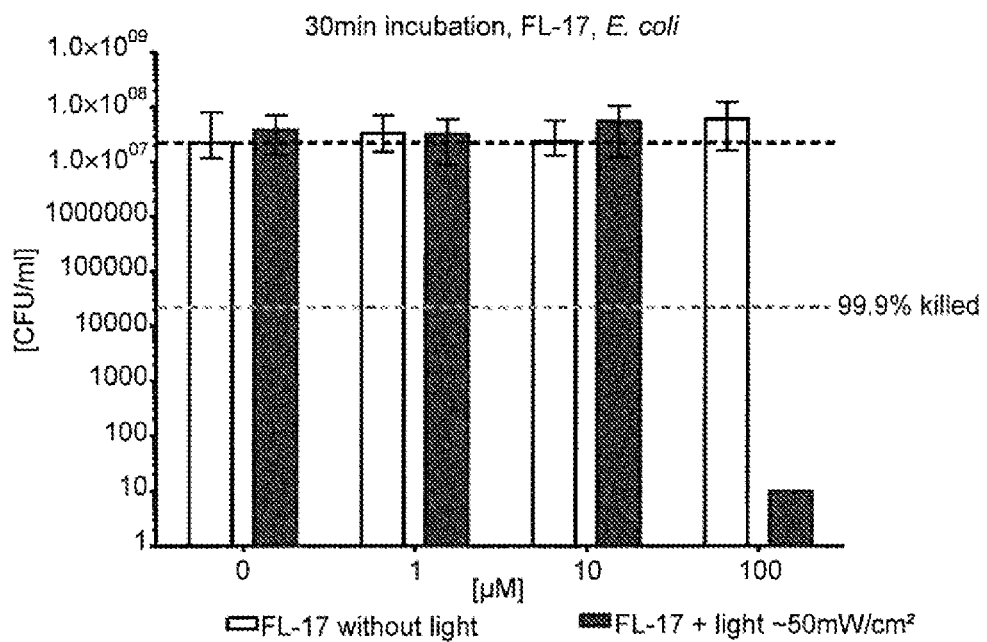
FIG. 7a) shows the results of incubation of *Escherichia coli* samples with FL-17 for 30 minutes.

FIG. 7a: *E. coli* samples were incubated with various concentrations (0 µM, 1 µM, 10 µM, 100 µM) of flavin FL-17 for 30 min. Subsequently, the samples were either irradiated at 50 mW/cm$^2$ (210 sec; 10.5 J/cm$^2$) (dark gray bar) or not irradiated (white bar). After 24 h, the surviving colonies were counted (CFU/ml). The black line indicates the dark control reference (0 µM flavin FL-17, no light). The dotted line marked "99.9% killed" indicates a decrease in the CFU/ml by 3 log$_{10}$ stages; this corresponds to a decrease by 99.9% ("antibacterial action"). N=3; median CFU/ml±SEM.

Figure 7B:
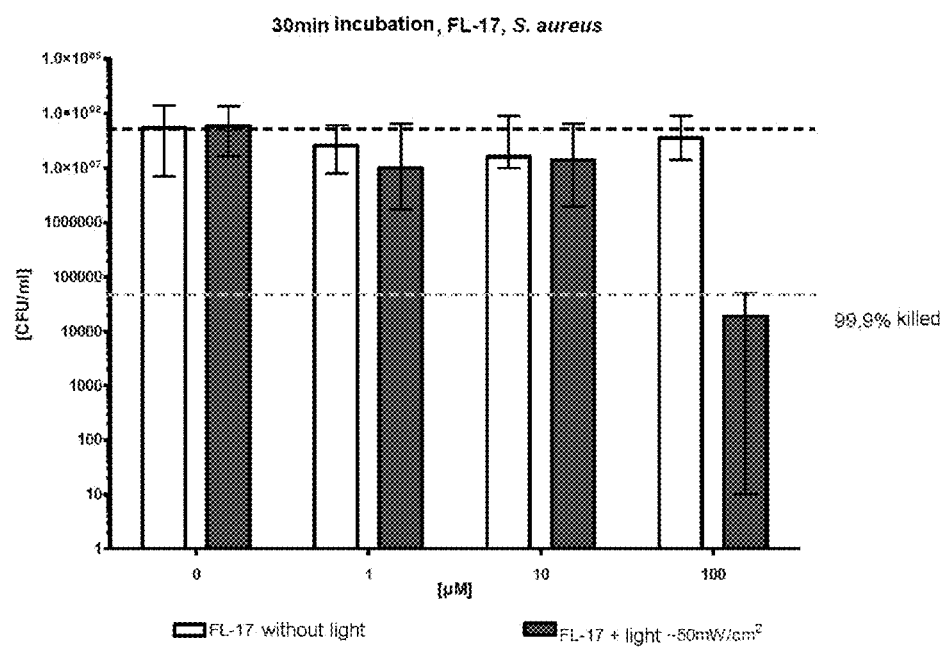
FIG. 7b) shows the results of incubation of *Staphylococcus aureus* samples with FL-17 for 30 minutes.

FIG. 7b: *S. aureus* samples were incubated with various concentrations (0 µM, 1 µM, 10 µM, 100 µM) of flavin FL-17 for 30 min. Subsequently, the samples were either irradiated at 50 mW/cm$^2$ (210 sec; 10.5 J/cm$^2$) (dark gray bar) or not irradiated (white bar). After 24 h, the surviving colonies were counted (CFU/ml). The black line indicates the dark control reference (0 µM flavin FL-17, no light). The dotted line marked "99.9% killed" indicates a decrease in the CFU/ml by 3 log$_{10}$ stages; this corresponds to a decrease by 99.9% ("antibacterial action"). N=3; median CFU/ml±SEM.

Figure 8:
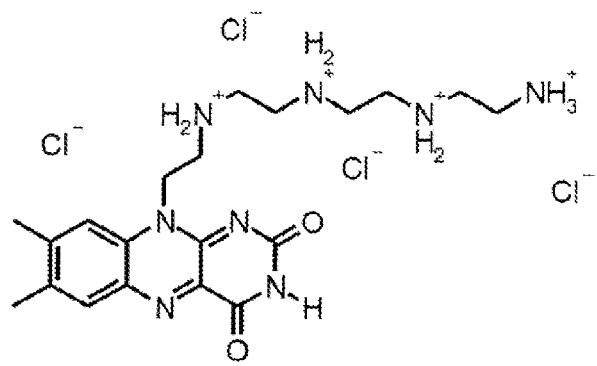
FIG. 8 shows the structural formula of Flavin FL-21.

FIG. 8 shows the effect of flavin FL-21 (iodide of the compound having the formula (46)) on *E. coli* and *S. aureus*.

Figure 8A:
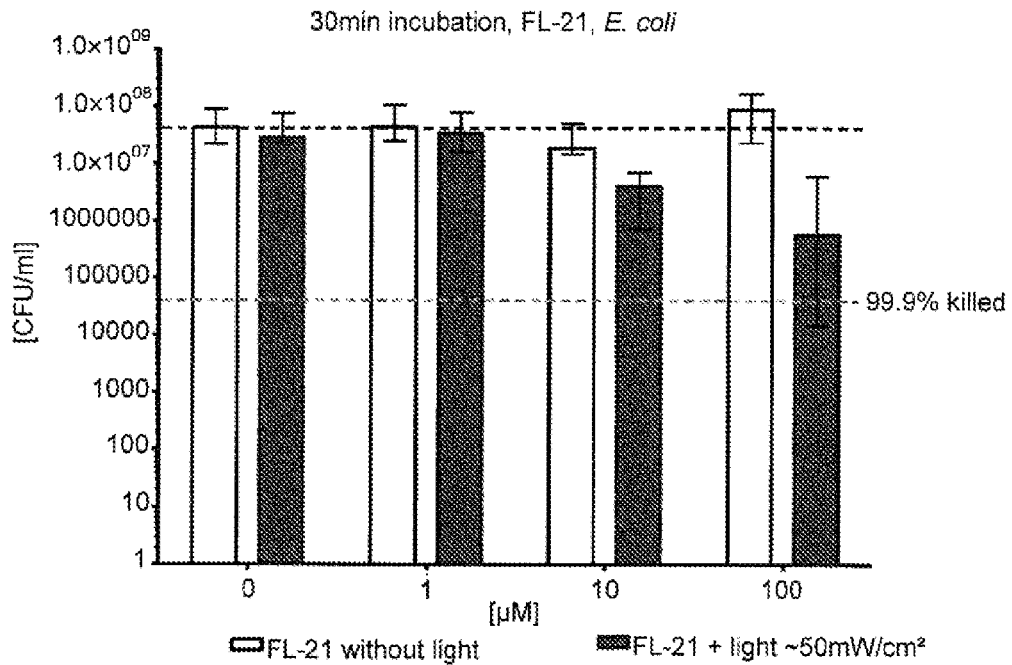
FIG. 8a) shows the results of incubation of *Escherichia coli* samples with FL-21 for 30 minutes.

FIG. 8a: *E. coli* samples were incubated with various concentrations (0 µM, 1 µM, 10 µM, 100 µM) of flavin FL-21 for 30 min. Subsequently, the samples were either irradiated at 50 mW/cm$^2$ (210 sec; 10.5 J/cm$^2$) (dark gray bar) or not irradiated (white bar). After 24 h, the surviving colonies were counted (CFU/ml). The black line indicates the dark control reference (0 µM flavin FL-21, no light). The dotted line marked "99.9% killed" indicates a decrease in the CFU/ml by 3 log$_{10}$ stages; this corresponds to a decrease by 99.9% ("antibacterial action"). N=3; median CFU/ml±SEM.

Figure 8B:
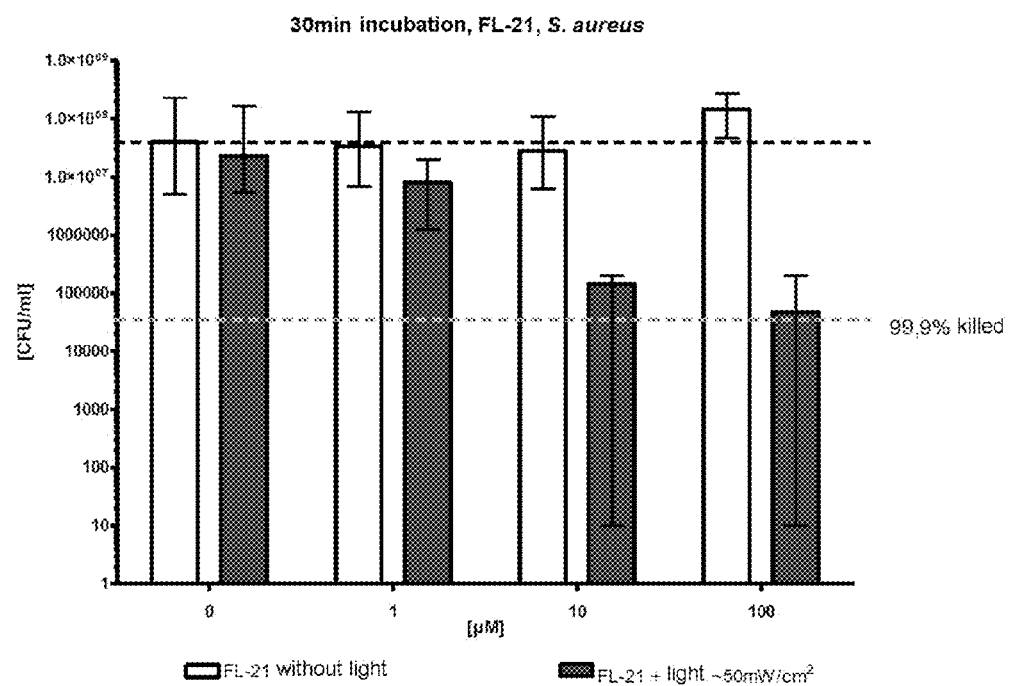
FIG. 8b) shows the results of incubation of *Staphylococcus aureus* samples with FL-21 for 30 minutes.

FIG. 8b: *S. aureus* samples were incubated with various concentrations (0 µM, 1 µM, 10 µM, 100 µM) of flavin FL-21 for 30 min. Subsequently, the samples were either irradiated at 50 mW/cm$^2$ (210 sec; 10.5 J/cm$^2$) (dark gray bar) or not irradiated (white bar). After 24 h, the surviving colonies were counted (CFU/ml). The black line indicates the dark control reference (0 µM flavin FL-21, no light). The dotted line marked "99.9% killed" indicates a decrease in the CFU/ml by 3 log$_{10}$ stages; this corresponds to a decrease by 99.9% ("antibacterial action"). N=3; median CFU/ml±SEM.

Figure 9:
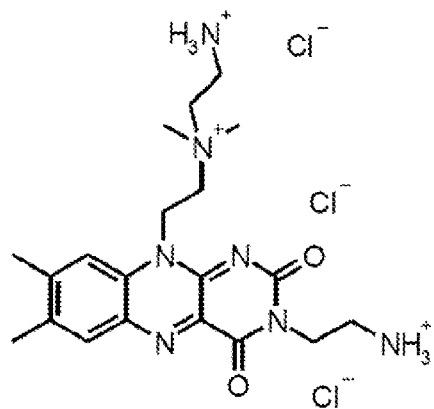
FIG. 9 shows the structural formula of Flavin FL-24.

FIG. 9 shows the effect of flavin FL-24 (trichloride of the compound having the formula (44)) on E. coli and S. aureus.

Figure 9A:
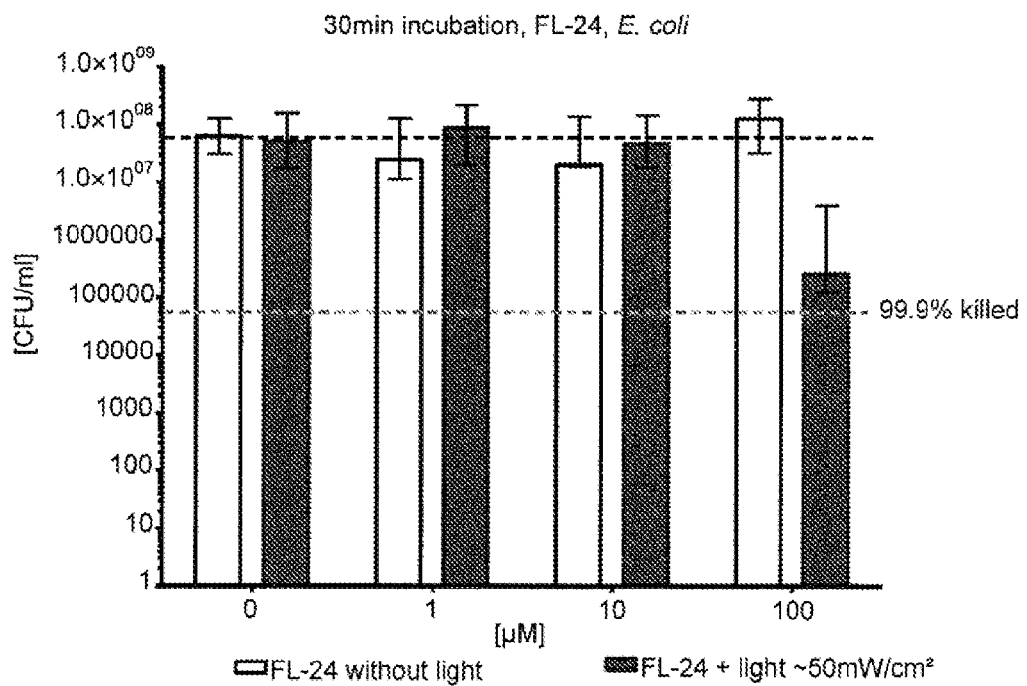
FIG. 9a) shows the results of incubation of *Escherichia coli* samples with FL-24 for 30 minutes.

FIG. 9a: E. coli samples were incubated with various concentrations (0 µM, 1 µM, 10 µM, 100 µM) of flavin FL-24 for 30 min. Subsequently, the samples were either irradiated at 50 mW/cm$^2$ (210 sec; 10.5 J/cm$^2$) (dark gray bar) or not irradiated (white bar). After 24 h, the surviving colonies were counted (CFU/ml). The black line indicates the dark control reference (0 µM flavin FL-24, no light). The dotted line marked "99.9% killed" indicates a decrease in the CFU/ml by 3 $\log_{10}$ stages; this corresponds to a decrease by 99.9% ("antibacterial action"). N=3; median CFU/ml±SEM.

Figure 9B:
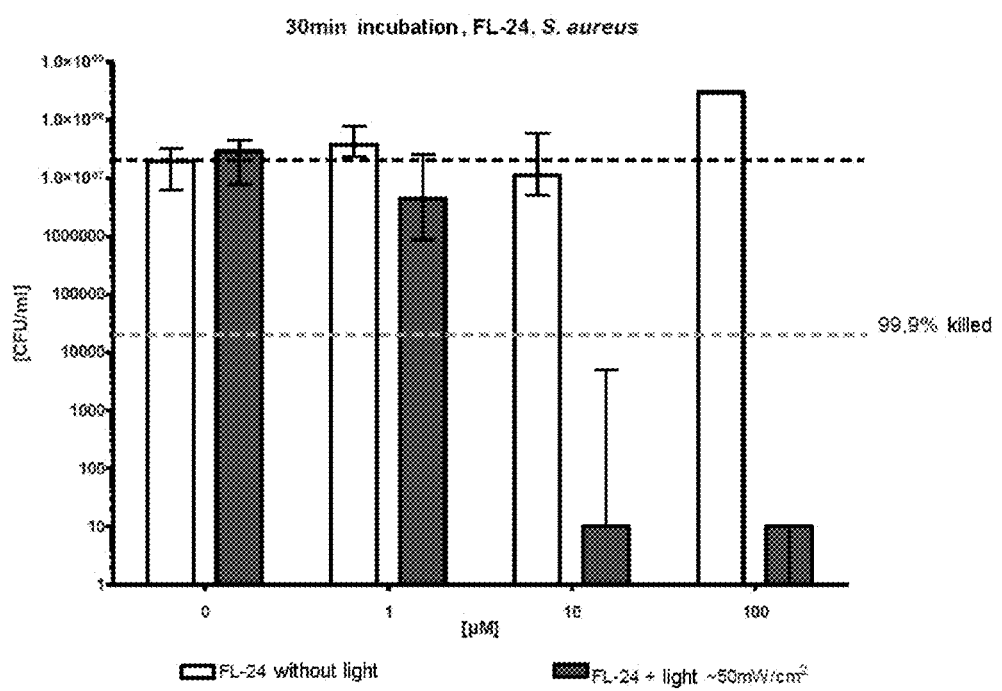
FIG. 9b) shows the results of incubation of *Staphylococcus aureus* samples with FL-24 for 30 minutes.

FIG. 9b: S. aureus samples were incubated with various concentrations (0 µM, 1 µM, 10 µM, 100 µM) of flavin FL-24 for 30 min. Subsequently, the samples were either irradiated at 50 mW/cm$^2$ (210 sec; 10.5 J/cm$^2$) (dark gray bar) or not irradiated (white bar). After 24 h, the surviving colonies were counted (CFU/ml). The black line indicates the dark control reference (0 µM flavin FL-24, no light). The dotted line marked "99.9% killed" indicates a decrease in the CFU/ml by 3 $\log_{10}$ stages; this corresponds to a decrease by 99.9% ("antibacterial action"). N=3; median CFU/ml±SEM.

Figure 10:
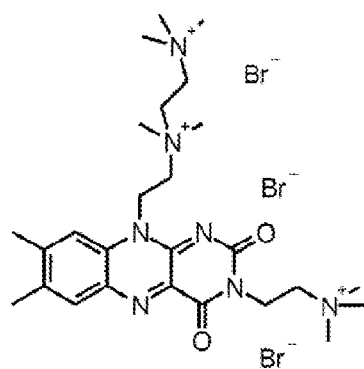
FIG. 10 shows the structural formula of Flavin FL-26.

FIG. 10 shows the effect of flavin FL-26 (tribromide of the compound having the formula (43)) on E. coli and S. aureus.

Figure 10A:
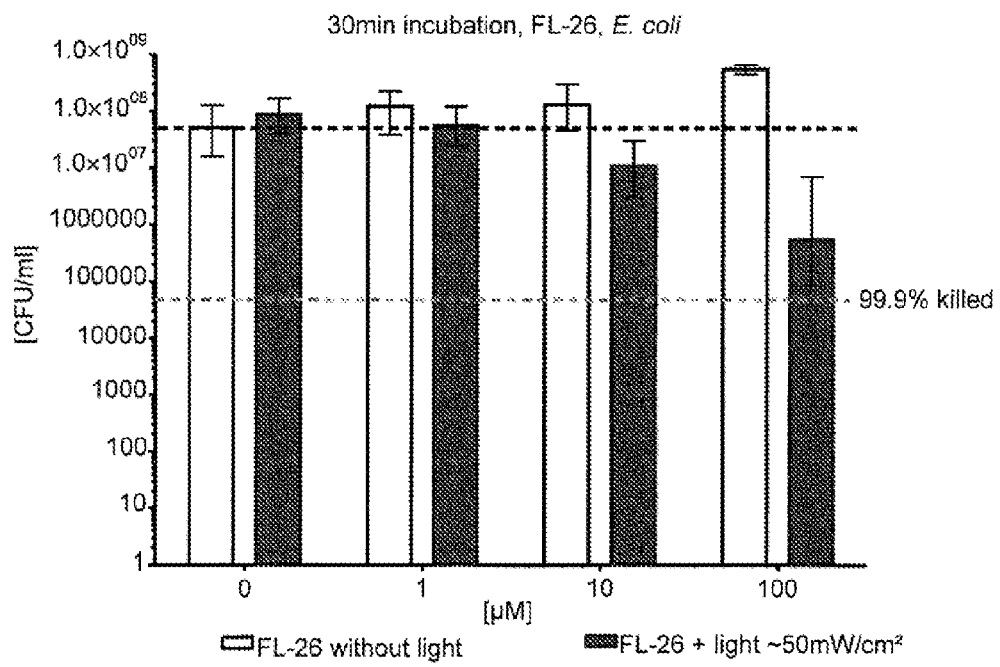
FIG. 10a) shows the results of incubation of *Escherichia coli* samples with FL-26 for 30 minutes.

FIG. 10a: E. coli samples were incubated with various concentrations (0 µM, 1 µM, 10 µM, 100 µM) of flavin FL-26 for 30 min. Subsequently, the samples were either irradiated at 50 mW/cm$^2$ (210 sec; 10.5 J/cm$^2$) (dark gray bar) or not irradiated (white bar). After 24 h, the surviving colonies were counted (CFU/ml). The black line indicates the dark control reference (0 µM flavin FL-26, no light). The dotted line marked "99.9% killed" indicates a decrease in the CFU/ml by 3 $\log_{10}$ stages; this corresponds to a decrease by 99.9% ("antibacterial action"). N=3; median CFU/ml±SEM.

Figure 10B:
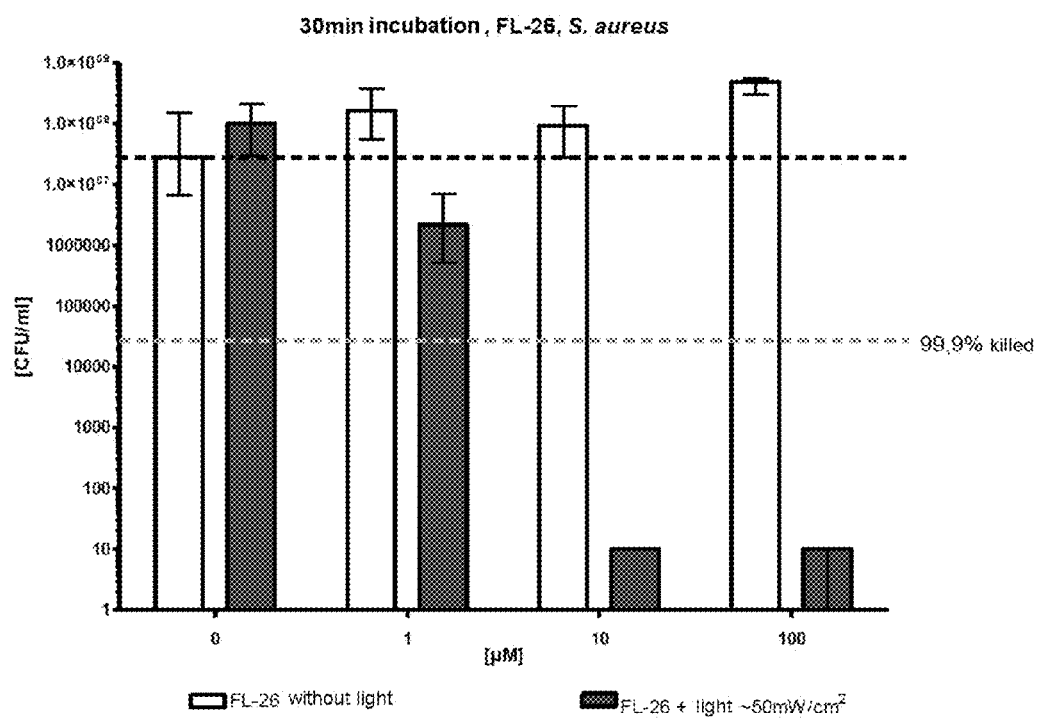
FIG. 10b) shows the results of incubation of *Staphylococcus aureus* samples with FL-26 for 30 minutes.

FIG. 10b: S. aureus samples were incubated with various concentrations (0 µM, 1 µM, 10 µM, 100 µM) of flavin FL-26 for 30 min. Subsequently, the samples were either irradiated at 50 mW/cm$^2$ (210 sec; 10.5 J/cm$^2$) (dark gray bar) or not irradiated (white bar). After 24 h, the surviving colonies were counted (CFU/ml). The black line indicates the dark control reference (0 µM flavin FL-26, no light). The dotted line marked "99.9% killed" indicates a decrease in the CFU/ml by 3 $\log_{10}$ stages; this corresponds to a decrease by 99.9% ("antibacterial action"). N=3; median CFU/ml±SEM.

Figure 11:
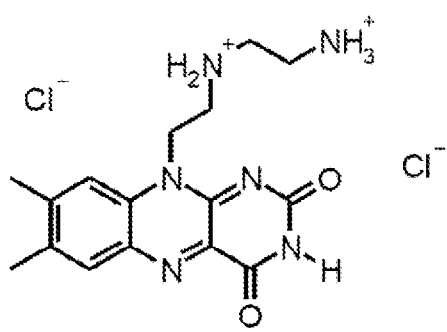
FIG. 11 shows the structural formula of Flavin FL-27.

FIG. 11 shows the effect of flavin FL-27 (dichloride of the compound having the formula (45)) on E. coli and S. aureus.

Figure 11A:
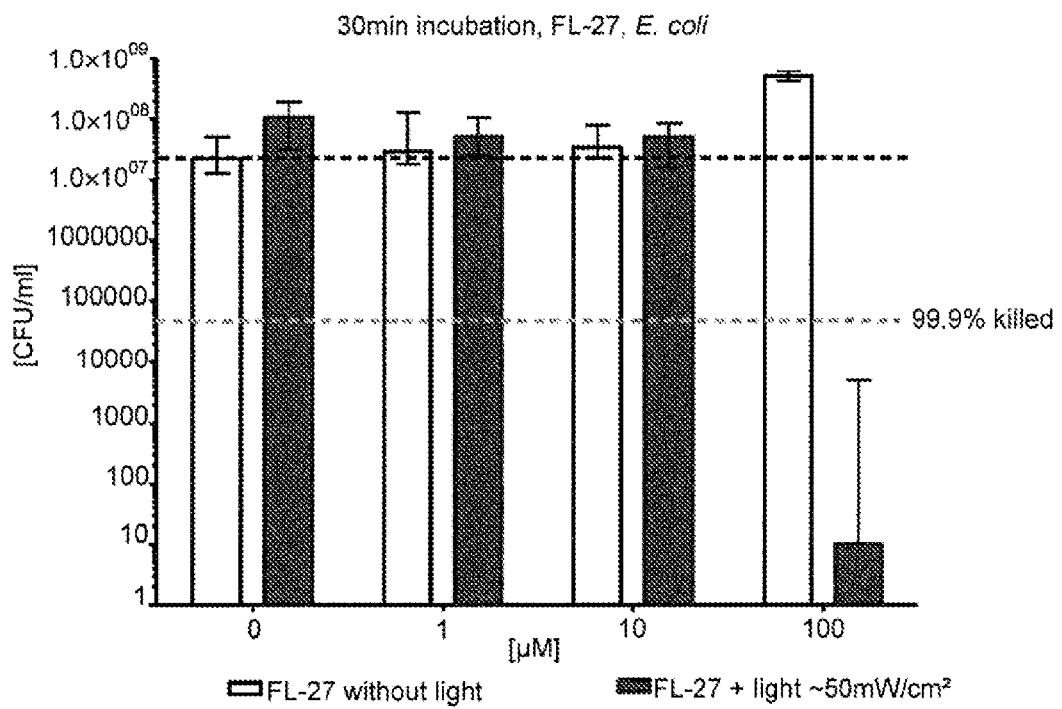
FIG. 11a) shows the results of incubation of *Escherichia coli* samples with FL-27 for 30 minutes.

FIG. 11a: E. coli samples were incubated with various concentrations (0 µM, 1 µM, 10 µM, 100 µM) of flavin FL-27 for 30 min. Subsequently, the samples were either irradiated at 50 mW/cm$^2$ (210 sec; 10.5 J/cm$^2$) (dark gray bar) or not irradiated (white bar). After 24 h, the surviving colonies were counted (CFU/ml). The black line indicates the dark control reference (0 µM flavin FL-27, no light). The dotted line marked "99.9% killed" indicates a decrease in the CFU/ml by 3 $\log_{10}$ stages; this corresponds to a decrease by 99.9% ("antibacterial action"). N=3; median CFU/ml±SEM.

Figure 11B:
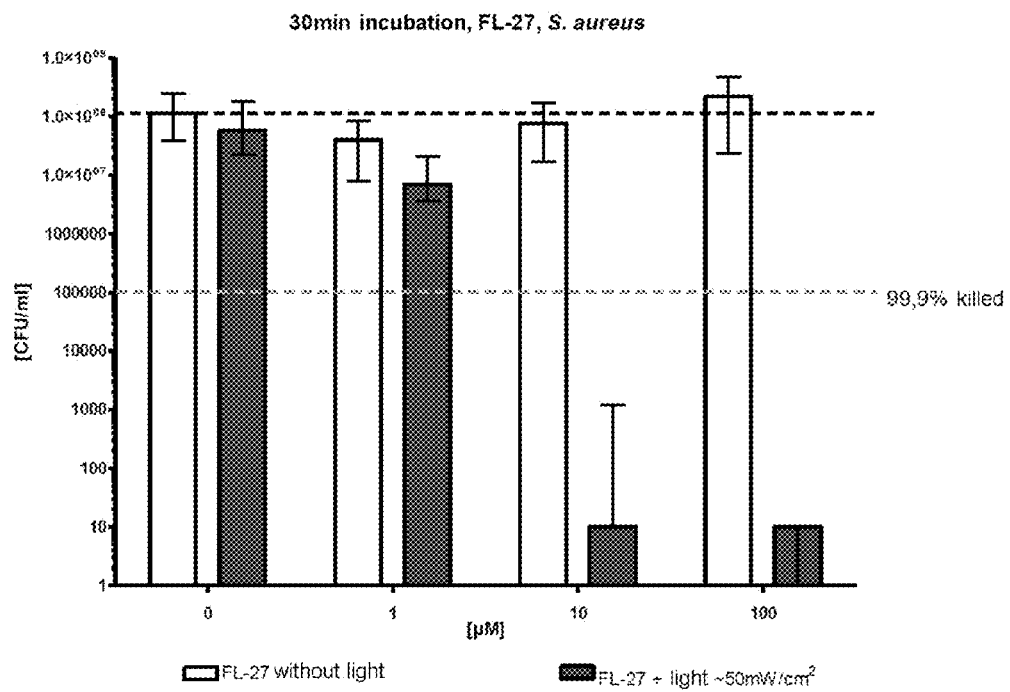
FIG. 11b) shows the results of incubation of *Staphylococcus aureus* samples with FL-27 for 30 minutes.

FIG. 11b: S. aureus samples were incubated with various concentrations (0 µM, 1 µM, 10 µM, 100 µM) of flavin FL-27 for 30 min. Subsequently, the samples were either irradiated at 50 mW/cm$^2$ (210 sec; 10.5 J/cm$^2$) (dark gray bar) or not irradiated (white bar). After 24 h, the surviving colonies were counted (CFU/ml). The black line indicates the dark control reference (0 µM flavin FL-27, no light). The dotted line marked "99.9% killed" indicates a decrease in the CFU/ml by 3 $\log_{10}$ stages; this corresponds to a decrease by 99.9% ("antibacterial action"). N=3; median CFU/ml±SEM.

Figure 12:
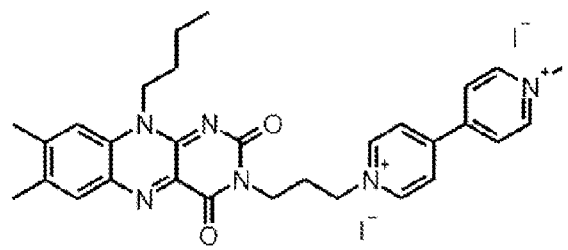
FIG. 12 shows the structural formula of Flavin FL-08b.

FIG. 12 shows the effect of flavin FL-27 (dichloride of the compound having the formula (51)) on E. coli and S. aureus.

Figure 12A:
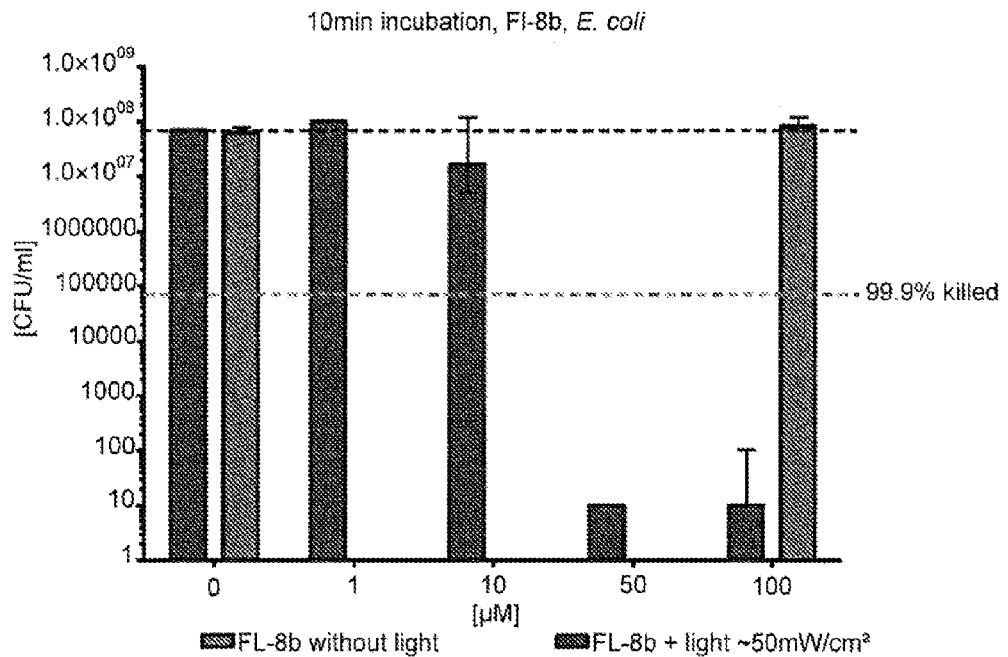
FIG. 12a) shows the results of incubation of *Escherichia coli* samples with FL-8b for 10 minutes.

FIG. 12a: E. coli was incubated with various concentrations of FL-08b [µM] for 10 min, then the samples were irradiated at 50 mW/cm$^2$ (210 sec; 10.5 J/cm$^2$). 24 h later, the surviving colonies were counted (CFU/ml). Gray bar: dark control without light. Red bar: incubated with photosensitizer and irradiated. The black line indicates the dark control reference (no photosensitizer incubation, no light). The green line indicates a decrease in the CFU/ml by 3 log 10 stages; this corresponds to a decrease by 99.9% ("antibacterial action"). N=3; median CFU/ml±SEM.

FIG. 12b: S. aureus was incubated with various concentrations of FL-08b [µM] for 10 min, then the samples were irradiated at 50 mW/cm$^2$ (210 sec; 10.5 J/cm$^2$). 24 h later, the surviving colonies were counted (CFU/ml). Gray bar: dark control without light. Red bar: incubated with photosensitizer and irradiated. The black line indicates the dark control reference (no photosensitizer incubation, no light). The green line indicates a decrease in the CFU/ml by 3 log 10 stages; this corresponds to a decrease by 99.9% ("antibacterial action"). N=3; median CFU/ml±SEM.

As apparent from FIGS. 1-12, irradiation of the microorganisms used Staphylococcus aureus (S. aureus) and Escherichia coli (E. coli) at a light dose of 10.5 J/cm$^2$ with blue light (390 nm-500 nm) in the absence of a photosensitizer (0 µM of the respective flavin) has no influence on the number of surviving microorganisms in comparison to the unexposed control.

In addition, the results shown in FIGS. 1-12 show that the incubation (10 min or 30 min) of the respective photosensitizer with the microorganisms without subsequent exposure likewise has only a small influence, if any, on the number of surviving microorganisms. As apparent from FIGS. 1-12, there is a decrease in the CFU/ml and hence inactivation of E. coli and S. aureus after incubation (10 min or 30 min) of the microorganisms as a function of the concentration used of the respective photosensitizers, and subsequent irradiation with a light dose of 10.5 J/cm$^2$.

The effectiveness of phototoxicity with respect to bacteria after irradiation was defined according to the following guidelines for hand hygiene in the health sector (Boyce, J. M., and D. Pittet. 2002. Guideline for Hand Hygiene in Health-Care Settings: recommendations of the Healthcare Infection Control Practices Advisory Committee and the HICPAC/SHEA/APIC/IDSA Hand Hygiene Task Force. Infect Control Hosp Epidemiol 23: p. 3-40):

reduction in the CFU/ml by 1 $\log_{10}$ stage ≙ 90% effectiveness reduction in the CFU/ml by 3 $\log_{10}$ stages ≙ 99.9% effectiveness reduction in the CFU/ml by 5 $\log_{10}$ stages ≙ 99.999% effectiveness For effective inactivation, the decrease of ≥3 $\log_{10}$ stages can therefore be adopted, and S. aureus and E. coli were chosen as examples of representatives from the group of the Gram-positive and Gram-negative bacteria (see Boyce J. M and D. Pittet 2009).

The concentration required to achieve a reduction by ≥3 $\log_{10}$ stages is shown in table 2.

TABLE 2

Summary of photodynamic inactivation

| Photosensitizer | Required concentration [µM] to achieve a reduction by ≥3log$_{10}$ stages (decrease by 99.9%), irradiation at 10.5 J/cm$^2$ | |
|---|---|---|
| | E. coli | S. aureus |
| FL-02 | 10 | 10 |
| FL-06 | 10 | 10 |
| FL-07 | 10 | 10 |
| FL-08 | 1 | 1 |
| FL-08b | 50 | 10 |
| FL-13 | 10 | 10 |
| FL-15 | 10 | 10 |
| FL-17 | 100 | 100 |
| FL-21 | >100(*) | 100 |
| FL-24 | >100(*) | 10 |
| FL-26 | >100(*) | 10 |
| FL-27 | 100 | 10 |

(*)to date, only a reduction of less than 3-log$_{10}$ stages has been achieved (99%), at a concentration of 100 µM with subsequent irradiation

What is claimed is:
1. A compound having the formula (1):

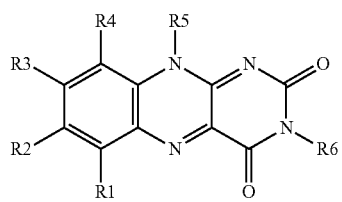

(1)

where I) only 1 R1, R2, R3, or R4 radical is an organic radical having:
a) at least two uncharged, protonatable nitrogen atoms not bonded directly to the isoalloxazine ring, or
b) at least two positively charged nitrogen atoms not bonded directly to the isoalloxazine ring,
and where each of the R1, R2, R3 and R4 radicals which is not an organic radical having a) at least two uncharged, protonatable nitrogen atoms not bonded directly to the isoalloxazine ring, or b) at least two positively charged nitrogen atoms not bonded directly to the isoalloxazine ring, is the same or different and is independently hydrogen, halogen, hydroxyl, thiol, nitro, carboxylate, aldehyde having 1 to 20 carbon atoms, ketone having 2 to 20 carbon atoms, O-alkyl having 1 to 20 carbon atoms, S-alkyl having 1 to 20 carbon atoms, O-alkenyl having 2 to 20 carbon atoms, S-alkenyl having 2 to 20 carbon atoms, O-aryl having 5 to 20 carbon atoms, S-aryl having 5 to 20 carbon atoms, carboxylic ester having 1 to 20 carbon atoms, carboxamide having 1 to 20 carbon atoms, thioester having 1 to 20 carbon atoms, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms or heteroaryl having 4 to 20 carbon atoms, which does not contain any nitrogen atoms, and
where each of the R5 and R6 radicals is the same or different and is independently hydrogen, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms or heteroaryl having 4 to 20 carbon atoms, which does not contain any nitrogen atoms, or wherein R5 can be acyclic polyol radical selected from the group consisting of arabityl, ribityl, xylityl, erythrityl, threityl, lactityl, mannityl and sorbityl, or an ether, ester or acetal thereof with the proviso that the R3 radical is not an aminomethyl radical, where the nitrogen atom may be unsubstituted or substituted, and excluding compounds in which the R1, R4 and R6 radicals are hydrogen, the R2 radical is hydrogen, alkyl having 1 to 8 carbon atoms or cycloalkyl having 3 to 7 carbon atoms, the R3 radical is hydrogen, halogen, alkyl having 1 to 8 carbon atoms, O-alkyl having 1 to 8 carbon atoms or a heterocyclic radical having 4 to 7 carbon atoms, and the R5 radical is an alkyl radical which has 1 to 8 carbon atoms and is substituted by at least by a radical of the formula $—N(R^{35})(R^{36})$ or a radical of the formula $—OR^{35}$, where the $R^{35}$ radical is a radical of the formula $—C_{1-8}alkyl(amine)-OR^{37}$ or a 7,8-dimethylisoalloxazin-10-yl-$C_{1-8}$alkyl radical and where the $R^{36}$ radical is hydrogen or a radical of the formula $—C_{1-8}$alkyl, which may be unsubstituted or substituted, and where the $R^{37}$ radical is hydrogen, aryl having 6 to 7 carbon atoms or alkyl which may be unsubstituted or substituted and has 1 to 8 carbon atoms, and additionally excluding compounds in which the R1 and R4 radicals are hydrogen, the R6 radical is hydrogen or a radical having the general formula $—C_{1-4}alkyl-OC(O)CH_3$, the R2 radical is hydrogen or alkyl having 1 to 8 carbon atoms and the R5 radical is a radical having the general formula $—C_{1-6}alkyl-N(R^{31})—C_{0-3}alkyl-(R^{32})$, where $R^{31}$ is hydrogen or a radical having the formula $—C_{1-4}alkyl$ and where $R^{32}$ is a radical having the formula $—C_{1-4}alkyl-N(R^{33})(R^{34})$, a radical having the formula $—C_{0-4}alkyl-aryl$, a radical having the formula $—C_{0-4}alkylheterocycloalkyl$ or a radical having the formula $—C_{0-4}alkylheteroaryl$, and where the $R^{33}$ and $R^{34}$ radicals are each independently hydrogen or $—C_{1-4}alkyl$, and excluding 10-butyl-7,8-dimethyl-3-[2-oxo-2-(1,4,7,10-tetrazacyclododec-1-yl)ethyl]benzo[g]pteridine-2,4-dione and 10-[2-(2-methoxyethoxy)ethyl]-7,8-dimethyl-3-[2-oxo-2-(1,4,7,10-tetrazacyclododec-1-yl)ethyl]benzo[g]pteridine-2,4-dione, or where II) only 1 R1, R2, R3, or R4 radical is an organic radical having:
a) at least one uncharged, protonatable nitrogen atom not bonded directly to the isoalloxazine ring, and
b) at least one positively charged nitrogen atom not bonded directly to the isoalloxazine ring, wherein the organic radical having
a) at least one uncharged protonatable nitrogen atom not bound directly to the isoalloxazine ring, and
b) at least one positively charged nitrogen atom not bonded directly to the isoalloxazine ring, is a radical of the formula (2), (3) or (4):

 (2)

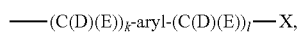 (3)

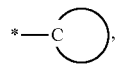 (4)

where h is an integer from 1 to 20 and k and 1 are each independently an integer from 0 to 6, and where D and E are each independently hydrogen, halogen, hydroxyl, O—$R^{(VIII)}$ where $R^{(VIII)}$ is methyl, ethyl, n-propyl, n-butyl, phenyl or benzyl, O—C(=O)—$R^{(IX)}$ where R(IX) is hydrogen, methyl, ethyl, n-propyl, n-butyl, phenyl or benzyl, or thiol and where X is an organic radical containing at least one selected from the group consisting of a) at least one uncharged, protonatable nitrogen atom and b) at least one positively charged nitrogen atom, and the aryl radical is a substituted or unsubstituted aromatic system having 5 to 20 carbon atoms or a substituted or unsubstituted heteroaromatic system which does not contain any nitrogen atom and has 4 to 20 carbon atoms, and where the radical having the formula (4) is a heteroaromatic system which is bonded to the isoalloxazine ring via a carbon atom of the heteroaromatic system and which contains at least one selected from the group consisting of a) at least one uncharged, protonatable nitrogen atom and b) at least one positively charged nitrogen atom and where each of the R1, R2, R3 and R4 radicals which is not an organic radical having a) at least one uncharged, protonatable nitrogen atom not bonded directly to the isoalloxazine ring, or b) at least one positively charged nitrogen atom not bonded directly to the isoalloxazine ring, is the same or different and is independently hydrogen, halogen, hydroxyl, thiol, nitro, carboxylate, aldehyde having 1 to 20 carbon atoms, ketone having 2 to 20 carbon atoms, O-alkyl having 1 to 20 carbon atoms, S-alkyl having 1 to 20 carbon atoms, O-alkenyl having 2 to 20 carbon atoms, S-alkenyl having 2 to 20 carbon atoms, O-aryl having 5 to 20 carbon atoms, S-aryl having 5 to 20 carbon atoms, carboxylic ester having 1 to 20 carbon atoms, carboxamide having 1 to 20 carbon atoms, thioester having 1 to 20 carbon atoms, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms or heteroaryl having 4 to 20 carbon atoms, which does not contain any nitrogen atoms, or where each of the R5 and R6 radicals is the same or different and is independently hydrogen, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms or heteroaryl having 4 to 20 carbon atoms, which does not contain any nitrogen atoms, or wherein R5 can be acyclic polyol radical selected from the group consisting of arabityl, ribityl, xylityl, erythrityl, threityl, lactityl, mannityl and sorbityl, or an ether, ester or acetal thereof or where III) at least 2 R1, R2, R3, or R4 radicals are an organic radical having at least one selected from the group consisting of:

a) at least one uncharged, protonatable nitrogen atom not bonded directly to the isoalloxazine ring, and b) at least one positively charged, preferably quaternary, nitrogen atom not bonded directly to the isoalloxazine ring, and where each of the R1, R2, R3 and R4 radicals which is not an organic radical having a) at least one uncharged, protonatable nitrogen atom not bonded directly to the isoalloxazine ring, or b) at least one positively charged nitrogen atom not bonded directly to the isoalloxazine ring, is the same or different and is independently hydrogen, halogen, hydroxyl, thiol, nitro, carboxylate, aldehyde having 1 to 20 carbon atoms, ketone having 2 to 20 carbon atoms, O-alkyl having 1 to 20 carbon atoms, S-alkyl having 1 to 20 carbon atoms, O-alkenyl having 2 to 20 carbon atoms, S-alkenyl having 2 to 20 carbon atoms, O-aryl having 5 to 20 carbon atoms, S-aryl having 5 to 20 carbon atoms, carboxylic ester having 1 to 20 carbon atoms, carboxamide having 1 to 20 carbon atoms, thioester having 1 to 20 carbon atoms, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms or heteroaryl having 4 to 20 carbon atoms, which does not contain any nitrogen atoms, and where each of the R5 and R6 radicals is the same or different and is independently hydrogen, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms or heteroaryl having 4 to 20 carbon atoms, which does not contain any nitrogen atoms, or wherein R5 can be acyclic polyol radical selected from the group consisting of arabityl, ribityl, xylityl, erythrityl, threityl, lactityl, mannityl and sorbityl, or an ether, ester or acetal thereof and excluding the compound having the formula (20):

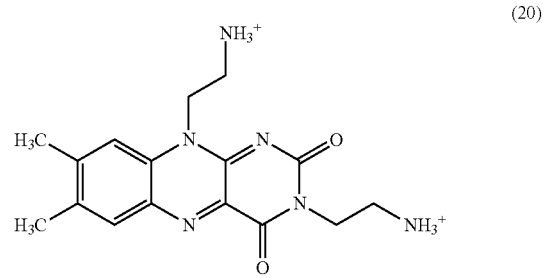 [SMILES: Cc1cc2nc3c(=O)n(CC[NH3+])c(=O)nc-3n(CC[NH3+])c2cc1C] (20)

and wherein in variants I), II) and III) of the compound of formula (1), the alkyl radicals and alkenyl radicals may be straight-chain or branched and be either unsubstituted or substituted by at least one radical selected from the group consisting of hydroxyl, sulfanyl, alkyloxy, alkylsulfanyl, alkanoyloxy, amino, alkylamino having 1 to 4 carbon atoms, dialkylamino having 2 to 8 carbon atoms, trialkylammonio having 3 to 12 carbon atoms, and guanidine.

2. The compound as claimed in claim 1, where the R1 and R4 radicals, which may each independently be the same or different, are hydrogen or methyl, and where R2 and R3 radicals are an organic radical of the general formula —(C(D)(E))$_h$-X or —(C(D)(E))$_k$-aryl-(C(D)(E))$_l$-X, where X is an organic radical containing at least one selected from the group consisting of
a) at least one uncharged, protonatable nitrogen atom and
b) one positively charged nitrogen atom.

3. The compound as claimed in claim 1, where X is a radical of the general formula (2):

(2)

where A is an oxygen or sulfur atom and where n is an integer from 1 to 8 and m is an integer from 0 to 100, and where B is a radical of the formula (3a), (3b), (4a), (4b), (5a) or (5b):

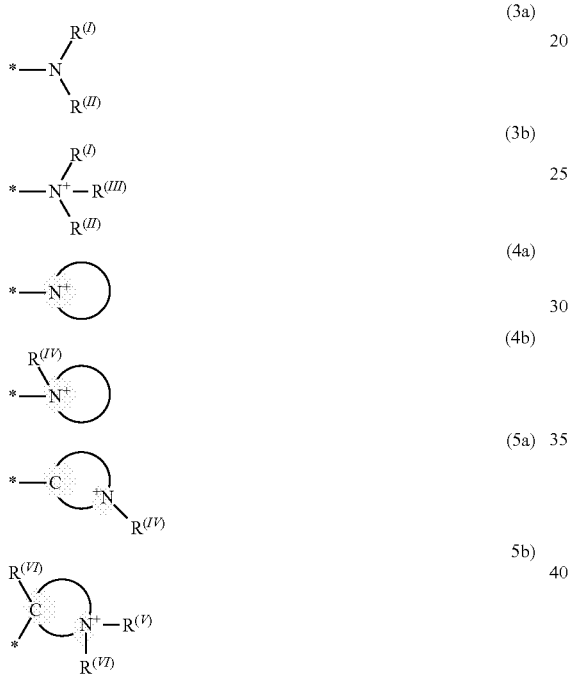

and where the $R^{(I)}$ radical is an aryl radical having 5 to 20 carbon atoms, a heterocyclic radical having 5 to 20 carbon atoms, an alkyl radical, which may be straight-chain or branched, having 1 to 20 carbon atoms, an alkenyl radical, which may be straight-chain or branched, having 2 to 20 carbon atoms, a hydroxyalkyl radical, which may be straight-chain or branched, having 1 to 20 carbon atoms, an ether radical, which may be straight-chain or branched, having 2 to 20 carbon atoms, a thioether radical, which may be straight-chain or branched, having 2 to 20 carbon atoms, or an alkylamino radical, which may be straight-chain or branched, having 1 to 20 carbon atoms, where each of the $R^{(II)}$, $R^{(III)}$, $R^{(IV)}$, $R^{(V)}$ and $R^{(VI)}$ radicals is independently hydrogen, an aryl radical having 5 to 20 carbon atoms, a heterocyclic radical having 5 to 20 carbon atoms, an alkyl radical, which may be straight-chain or branched, having 1 to 20 carbon atoms, an alkenyl radical, which may be straight-chain or branched, having 2 to 20 carbon atoms, a hydroxyalkyl radical, which may be straight-chain or branched, having 1 to 20 carbon atoms, an ether radical, which may be straight-chain or branched, having 2 to 20 carbon atoms, a thioether radical, which may be straight-chain or branched, having 2 to 20 carbon atoms, or an alkylamino radical, which may be straight-chain or branched, having 1 to 20 carbon atoms and where each of the aforementioned aryl radicals, heterocyclic radicals, alkyl radicals, alkenyl radicals, hydroxyalkyl radicals, ether radicals, thioether radicals and alkylamino radicals is substituted at least by one selected from the group consisting of amino radical(s) and alkylamino radical(s), which may be straight-chain or branched, having 1 to 20 carbon atoms, and where the radical having the formula (4a) and the radical having the formula (5a):

is a substituted or unsubstituted heterocyclic radical having 5 to 7 ring atoms including 2 to 4 nitrogen atoms and at least 1 carbon atom and optionally 1 or 2 oxygen or sulfur atoms, where 1 nitrogen atom forms a double bond, and where the radical having the formula (4b) and the radical having the formula (5b):

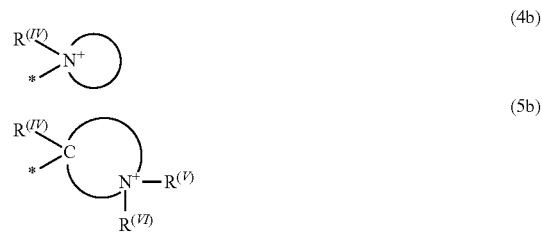

is a substituted or unsubstituted heterocyclic radical having 5 to 7 ring atoms including 2 to 4 nitrogen atoms and at least 1 carbon atom and optionally 1 or 2 oxygen or sulfur atoms.

4. The compound as claimed in claim 1, where the organic radical having:
a) at least two uncharged, protonatable nitrogen atoms not bonded directly to the isoalloxazine ring, or
b) at least two positively charged nitrogen atoms not bonded directly to the isoalloxazine ring, is in each case selected from the radicals of the formulae (30a) to (36)

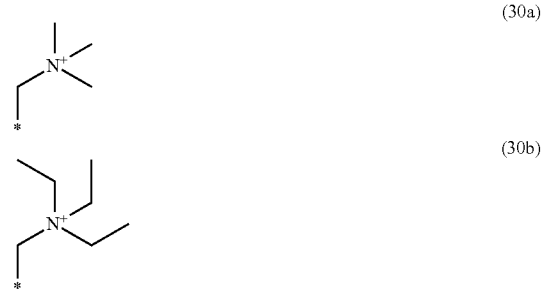

(31a) 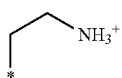

(31b) 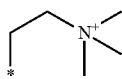

(32a) 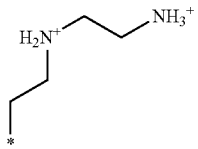

(32b) 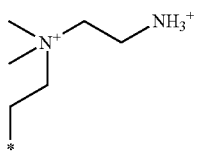

(32c) 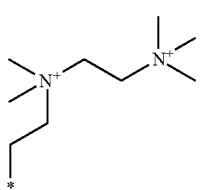

(33a) 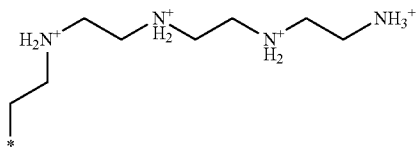

(33b) 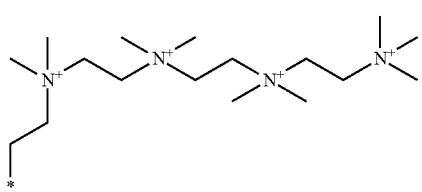

(34a) 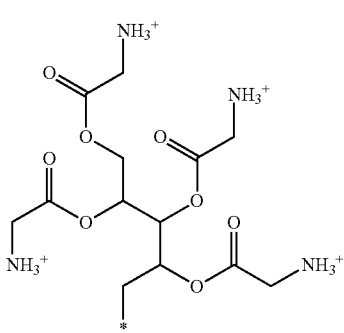

(34b) 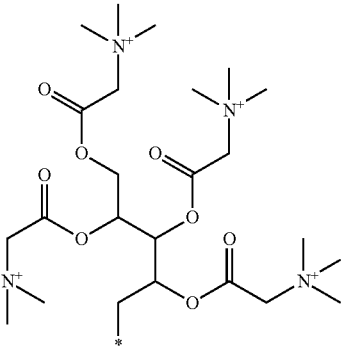

(35a) 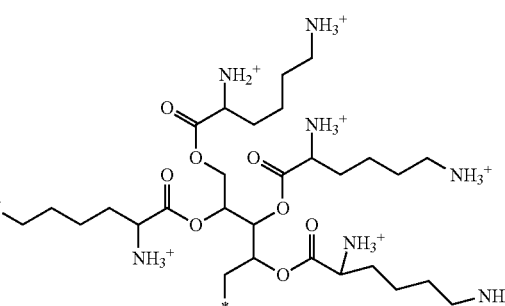

(35b) 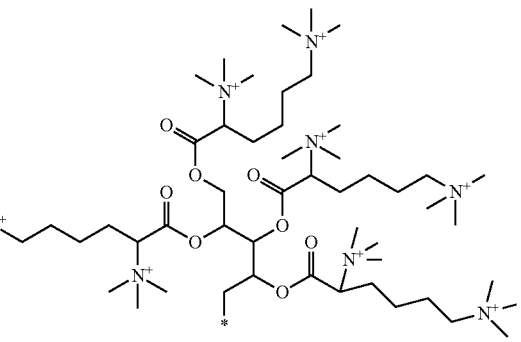

(36) 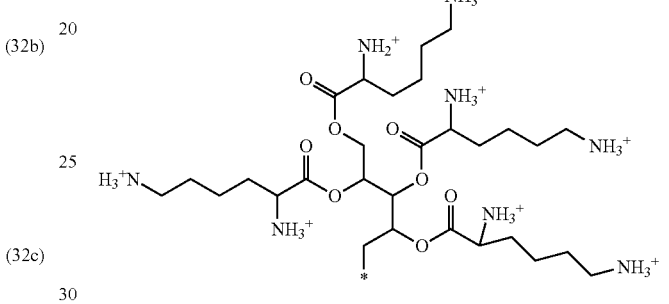

5. A pharmaceutical composition comprising at least one compound as claimed in claim 1 or at least one selected from the group consisting of a pharmacologically acceptable salt, an ester and a complex thereof and at least one pharmacologically acceptable excipient.

6. A coated article, wherein the surface of the article comprises at least one compound as claimed in claim 1.

7. A process for preparing a compound of claim 1, wherein the process comprises the following steps:

(A) reducing a substituted nitroaniline of the formula (9) to a substituted o-phenylenediamine of the formula (10)

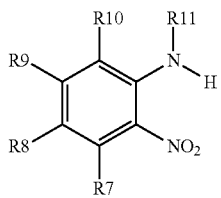

(9)

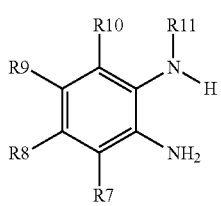

(10)

where each of the R7 to R10 radicals is the same or different and is independently hydrogen, halogen, hydroxyl, thiol, nitro, carboxylate, aldehyde having 1 to 20 carbon atoms, ketone having 2 to 20 carbon atoms, O-alkyl having 1 to 20 carbon atoms, S-alkyl having 1 to 20 carbon atoms, O-alkenyl having 2 to 20 carbon atoms, S-alkenyl having 2 to 20 carbon atoms, O-aryl having 5 to 20 carbon atoms, S-aryl having 5 to 20 carbon atoms, carboxylic ester having 1 to 20 carbon atoms, carboxamide having 1 to 20 carbon atoms, thioester having 1 to 20 carbon atoms, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms, heteroaryl which does not contain any nitrogen atom and has 4 to 20 carbon atoms, —$(C(D)(E))_h$-OH, —$(C(D)(E))_h$-aryl-$(C(D)(E))_j$-OH or an organic radical containing at least one selected from the group consisting of a) at least one uncharged, protonatable nitrogen atom not bonded directly to the isoalloxazine ring, and b) at least one positively charged nitrogen atom not bonded directly to the isoalloxazine ring, and where the R11 radical is hydrogen, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms, heteroaryl which does not contain any nitrogen atom and has 4 to 20 carbon atoms, —$(C(D)(E))_h$-OH, —$(C(D)(E))_h$-aryl-$(C(D)(E))_j$-OH or an organic radical containing at least one selected from the group consisting of a) at least one uncharged, protonatable nitrogen atom not bonded directly to the isoalloxazine ring, and b) at least one positively charged nitrogen atom not bonded directly to the isoalloxazine ring, and (B) condensing the substituted o-phenylenediamine of the formula (10) obtained in step (A) with alloxane or the hydrate thereof to obtain a compound having the formula (11):

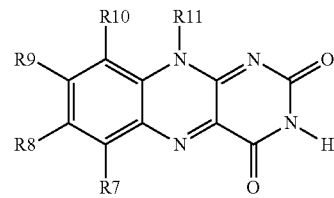

(11)

(C) optionally reacting the compound of the formula (11) obtained in step (B) with an alkylating agent of the general formula T-alkyl, T-alkenyl, T-cycloalkyl, T-cycloalkenyl, T-$(C(D)(E))_h$-OH, T-$(C(D)(E))_k$-aryl-$(C(D)(E))_j$-OH, T-aryl, T-$(C(D)(E))_h$-X or T-$(C(D)(E))_k$-aryl-$(C(D)(E))_j$-X, where the T radical is hydrogen, chlorine, bromine, iodine, p-toluenesulfonyl (OTs), methanesulfonyl (OMs), OH or $R_2S^+$, where each R may independently be the same or different to obtain a compound having the formula (12):

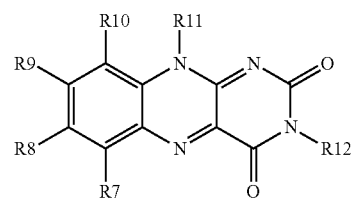

(12)

where the R12 radical is hydrogen, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms, heteroaryl which has 4 to 20 carbon atoms and does not contain any nitrogen atom, —$(C(D)(E))_h$-OH, —$(C(D)(E))_k$-aryl-$(C(D)(E))_j$-OH or an organic radical containing at least one selected from the group consisting of a) at least one uncharged, protonatable nitrogen atom not bonded directly to the isoalloxazine ring, and b) at least one positively charged nitrogen atom not bonded directly to the isoalloxazine ring, and (D) optionally reacting the compound of the formula (11) obtained in step (B) or the compound of the formula (12) obtained in step (C) with tosyl chloride, mesyl chloride or iodine, optionally in the presence of a catalyst, and subsequently with an organic compound containing at least one selected from the group consisting of at least one uncharged, protonatable nitrogen atom and b) at least one positively charged nitrogen atom, when at least 1 R7, R8, R9, R10, R11 or R12 radical is —$(C(D)(E))_h$-OH or —$(C(D)(E))_k$-aryl-$(C(D)(E))_j$-OH, to obtain the 10H-benzo[g]pteridine-2,4-dione derivative of the formula (1), with the proviso that at least 2 RE R2, R3, R4, R5 or R6 radicals are an organic radical having at least one selected from the group consisting of:

a) at least one uncharged, protonatable nitrogen atom not bonded directly to the isoalloxazine ring, and b) at least one positively charged nitrogen atom not bonded directly to the isoalloxazine ring, and where each h is an integer from 1 to 20 and k, l are each independently an integer from 0 to 6, where D and E are each independently hydrogen, halogen, hydroxyl, O—$R^{(VIII)}$ where $R^{(VIII)}$ is methyl, ethyl, n-propyl, n-butyl, phenyl or benzyl, O—C(=O)—R$^{(IX)}$ where R(IX) is hydrogen, methyl, ethyl, n-propyl, n-butyl, phenyl or benzyl, or thiol, and where each X is an organic radical having at least one selected from the group consisting of a) at least one uncharged, protonatable nitrogen atom not bonded directly to the isoalloxazine ring, and b) at least one positively charged nitrogen atom not bonded directly to the isoalloxazine ring, and each aryl is a substituted or unsubstituted aromatic system having 5 to 20 carbon atoms or a substituted or unsubstituted heteroaromatic system which does not contain any nitrogen atom and has 4 to 20 carbon atoms.

8. A process for preparing a compound as claimed in claim 1, wherein the process comprises the following steps:
(A) condensing an amine having the formula R11-NH$_2$ with a chlorouracil derivative of the formula (13), optionally in the presence of a catalyst to obtain a compound having the formula (14):

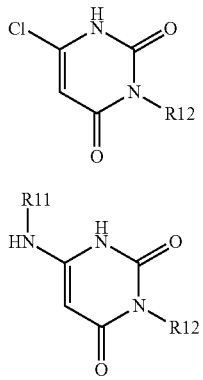

where each of the R11 and R12 radicals is the same or different and is independently hydrogen, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms, heteroaryl which does not contain any nitrogen atom and has 4 to 20 carbon atoms, —(C(D)(E))$_h$-OH, —(C(D)(E))$_k$-aryl-(C(D)(E))$_l$-OH or an organic radical containing at least one selected from the group consisting of a) at least one uncharged, protonatable nitrogen atom not bonded directly to the isoalloxazine ring, and b) at least one positively charged nitrogen atom not bonded directly to the isoalloxazine ring, (B) reacting the compound of the formula (14) obtained in step (A) with a nitroso compound of the formula (15) to obtain a compound of the formula (12):

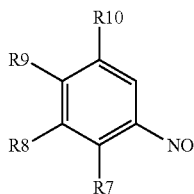

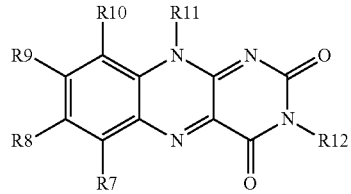

where each of the R7 to R10 radicals, which may independently be the same or different, is hydrogen, halogen, hydroxyl, thiol, nitro, carboxylate, aldehyde having 1 to 20 carbon atoms, ketone having 2 to 20 carbon atoms, O-alkyl having 1 to 20 carbon atoms, S-alkyl having 1 to 20 carbon atoms, O-alkenyl having 2 to 20 carbon atoms, S-alkenyl having 2 to 20 carbon atoms, O-aryl having 5 to 20 carbon atoms, S-aryl having 5 to 20 carbon atoms, carboxylic ester having 1 to 20 carbon atoms, carboxamide having 1 to 20 carbon atoms, thioester having 1 to 20 carbon atoms, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms, heteroaryl which does not contain any nitrogen atom and has 4 to 20 carbon atoms, —(C(D)(E))$_h$-OH, —(C(D)(E))$_k$-aryl-(C(D)(E))$_l$-OH or an organic radical containing at least one selected from the group consisting of a) at least one uncharged, protonatable nitrogen atom not bonded directly to the isoalloxazine ring, and b) at least one positively charged nitrogen atom not bonded directly to the isoalloxazine ring, and (C) optionally reacting the compound of the formula (12) obtained in step (B) with tosyl chloride, mesyl chloride or iodine, optionally in the presence of a catalyst, and subsequently with an organic compound containing at least one tertiary nitrogen atom has been reacted, when at least 1 R7, R8, R9, R10, R11 or R12 radical is —(C(D)(E))$_h$-OH or
—(C(D)(E))$_k$-aryl-(C(D)(E))$_l$-OH, to obtain the 10H-benzo[g]pteridine-2,4-dione derivative of the formula (1)
with the proviso that at least 2 R1, R2, R3, R4, R5 or R6 radicals are an organic radical having at least one selected from the group consisting of:
a) at least one uncharged, protonatable nitrogen atom not bonded directly to the isoalloxazine ring, and
b) at least one positively charged nitrogen atom not bonded directly to the isoalloxazine ring, and where each h is an integer from 1 to 20 and k, l are each independently an integer from 0 to 6, where D and E are each independently hydrogen, halogen, hydroxyl, O—R$^{(VIII)}$ where R$^{(VIII)}$ is methyl, ethyl, n-propyl, n-butyl, phenyl or benzyl, O—C(=O)—R$^{(IX)}$ where R(IX) is hydrogen, methyl, ethyl, n-propyl, n-butyl, phenyl or benzyl, or thiol, and where each X is an organic radical having at least one selected from the group consisting of a) at least one uncharged, protonatable nitrogen atom not bonded directly to the isoalloxazine ring, and b) at least one positively charged nitrogen atom not bonded directly to the isoalloxazine ring, and each aryl is a substituted or unsubstituted aromatic system having 5 to 20 carbon atoms or a substituted or unsubstituted heteroaromatic system which does not contain any nitrogen atom and has 4 to 20 carbon atoms.

9. A process for preparing a compound as claimed in claim 1, wherein the process comprises the following steps:

(A) preparing a substituted aniline having the formula (122a) or (122b) by (a) peptide coupling/reduction to an aniline having the formula (121) or (b) reductive amination of an aniline having the formula (121) with aldehydes or (c) Pd-catalyzed coupling of a halide of the formula (124) to an amines of the formula R11-NH₂ or (d) Pd-catalyzed coupling of an amine of the formula (120) to a halide of the formula R11-NH₂

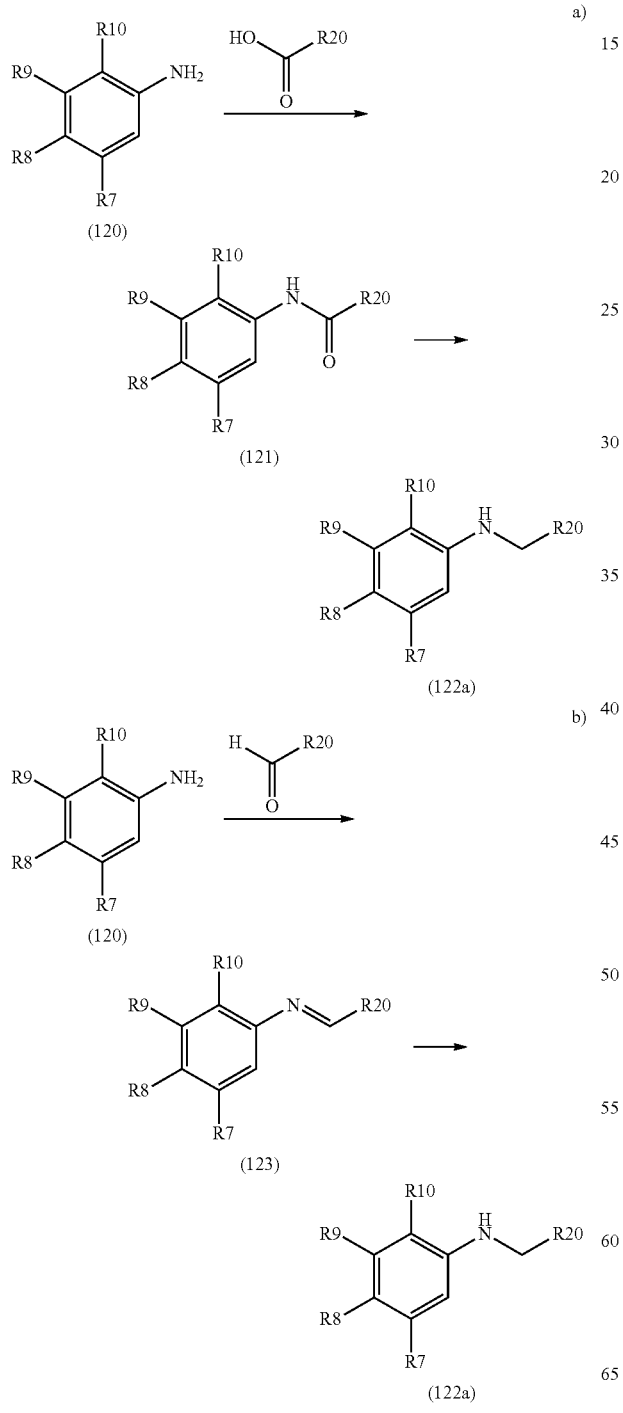

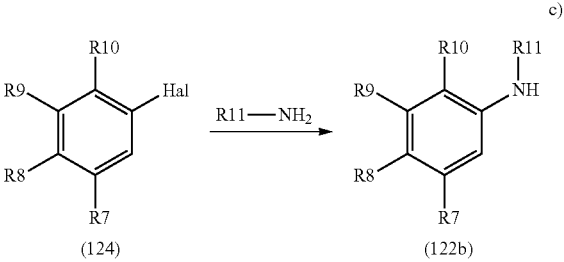

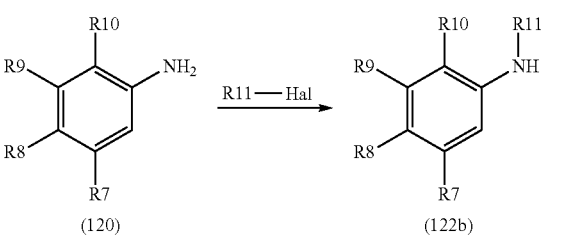

where each of the R7 to R10 radicals, which may independently be the same or different, is hydrogen, halogen, hydroxyl, thiol, nitro, carboxylate, aldehyde having 1 to 20 carbon atoms, ketone having 2 to 20 carbon atoms, O-alkyl having 1 to 20 carbon atoms, S-alkyl having 1 to 20 carbon atoms, O-alkenyl having 2 to 20 carbon atoms, S-alkenyl having 2 to 20 carbon atoms, O-aryl having 5 to 20 carbon atoms, S-aryl having 5 to 20 carbon atoms, carboxylic ester having 1 to 20 carbon atoms, carboxamide having 1 to 20 carbon atoms, thioester having 1 to 20 carbon atoms, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms, heteroaryl which does not contain any nitrogen atom and has 4 to 20 carbon atoms, $-(C(D)(E))_h\text{-OH}$, $-(C(D)(E))_k\text{-aryl-}(C(D)(E))_l\text{-OH}$ or an organic radical containing at least one selected from the group consisting of a) at least one uncharged, protonatable nitrogen atom not bonded directly to the isoalloxazine ring, and b) at least one positively charged nitrogen atom not bonded directly to the isoalloxazine ring, and where the R11 radical is hydrogen, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms, heteroaryl which does not contain any nitrogen atom and has 4 to 20 carbon atoms, $-(C(D)(E))_h\text{-OH}$, $-(C(D)(E))_k\text{-aryl-}(C(D)(E))_l\text{-OH}$ or an organic radical containing at least one selected from the group consisting of a) at least one uncharged, protonatable nitrogen atom not bonded directly to the isoalloxazine ring, and b) at least one positively charged nitrogen atom not bonded directly to the isoalloxazine ring, and where the R20 radical is hydrogen, alkyl having 1 to 19 carbon atoms, alkenyl having 2 to 19 carbon atoms, ether having 1 to 19 carbon atoms, thioether having 1 to 19 carbon atoms, cycloalkyl having 3 to 19 carbon atoms, cycloalkenyl having 3 to 19 carbon atoms, aryl having 5 to 19 carbon atoms, heteroaryl which has 4 to 19 carbon atoms and does not contain any nitrogen atoms, $-(C(D)(E))_{h-1}\text{-OH}$, $-(C(D)(E))_{k-1}\text{-aryl-}(C(D)(E))_{l-1}\text{-OH}$ or an organic radical containing at least one selected from the group consisting of a) at least one uncharged, protonatable nitrogen atom not bonded directly to the isoalloxazine ring, and b) at least one positively charged nitrogen atom not bonded directly to the isoalloxazine ring, and
where the Hal radical is fluorine, chlorine, bromine or iodine,
(B) reacting the substituted aniline having the formula (122a) obtained in step (A) with violuric acid to obtain a compound of the formula (11z):

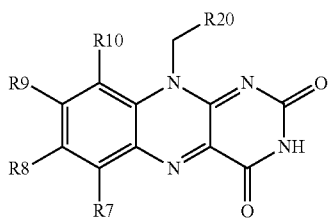

(11z)

or
reacting the substituted aniline having the formula (122b) obtained in step (A) with violuric acid to obtain a compound of the formula (11):

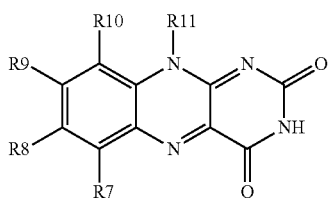

(11)

(C) optionally reacting the compound of the formula (11z) obtained in step (B) with tosyl chloride, mesyl chloride or iodine, optionally in the presence of a catalyst, and subsequently with an organic compound containing at least one tertiary nitrogen atom is reacted, when at least 1 R7, R8, R9, R10, R11 or R20 radical is —C(D)(E))$_h$-OH or —(C(D)(E))$_k$-aryl-(C(D)(E))$_l$-OH, to obtain the 10H-benzo[g]pteridine-2,4-dione derivative of the formula (12z):

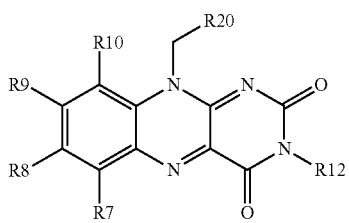

(12z)

where D and E are each independently hydrogen, halogen, hydroxyl, O—R$^{(VIII)}$ where R$^{(VIII)}$ is methyl, ethyl, n-propyl, n-butyl, phenyl or benzyl, O—C(=O)—R$^{(IX)}$ where R(IX) is hydrogen, methyl, ethyl, n-propyl, n-butyl, phenyl or benzyl, or thiol
or
reacting the compound of the formula (11) obtained in step (B) with tosyl chloride, mesyl chloride or iodine, optionally in the presence of a catalyst, and subsequently with an organic compound containing at least one tertiary nitrogen atom is reacted, when at least 1 R7, R8, R9, R10, R11 or R20 radical is —C(D)(E))$_h$-OH or —(C(D)(E))$_k$-aryl-(C(D)(E))$_l$-OH, to obtain the 10H-benzo[g]pteridine-2,4-dione derivative of the formula (12):

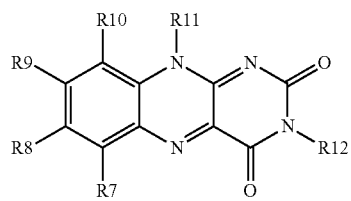

(12)

where D and E are each independently hydrogen, halogen, hydroxyl, O—R$^{(VIII)}$ where R$^{(VIII)}$ is methyl, ethyl, n-propyl, n-butyl, phenyl or benzyl, O—C(=O)—R$^{(IX)}$ where R(IX) is hydrogen, methyl, ethyl, n-propyl, n-butyl, phenyl or benzyl, or thiol and
with the proviso that
I) only 1 R1, R2, R3, R4, R5 or R6 radical is an organic radical having:
a) at least two uncharged, protonatable nitrogen atoms not bonded directly to the isoalloxazine ring, or
b) at least two positively charged nitrogen atoms not bonded directly to the isoalloxazine ring, or
II) only 1 R1, R2, R3, R4, R5 or R6 radical is an organic radical having:
a) at least one uncharged, protonatable nitrogen atom(s) not bonded directly to the isoalloxazine ring, and
b) at least one positively charged nitrogen atom(s) not bonded directly to the isoalloxazine ring,
or
III) at least 2 R1, R2, R3, R4, R5 or R6 radicals are an organic radical having:
a) at least one uncharged, protonatable nitrogen atom(s) not bonded directly to the isoalloxazine ring, and
b) at least one positively charged nitrogen atom(s) not bonded directly to the isoalloxazine ring.

10. A method for inactivating microorganisms located on or within a subject in need of such inactivation, said method comprising applying upon said subject a compound of the claim 1.

11. The compound according to claim 1, wherein at least one positively charged nitrogen atom not bonded directly to the isoalloxazine ring is a quaternary nitrogen atom.

12. The compound according to claim 1, wherein said at least one positively charged nitrogen atom not bonded directly to the isoalloxazine ring is a quaternary nitrogen atom.

13. The compound according to claim 1, wherein the halogen is selected from the group consisting of chlorine, bromine, iodine and fluorine.

14. The compound according to claim 1, wherein D and E are each independently hydrogen or hydroxyl.

15. The compound according to claim 3, wherein each of said aryl radicals, heterocyclic radicals, alkyl radicals, alkenyl radicals, hydroxyalkyl radicals, ether radicals, thioether radicals and alkylamino radicals is substituted by one selected from the group consisting of at least two, at least three, at least four and at least five, of said amino radicals and/or alkyl amino radicals.

16. The compound according to claim 4, wherein said at least two positively charged nitrogen atoms are quaternary nitrogen atoms.

17. The process according to claim 7, wherein each R is selected from the group consisting of methyl, ethyl, propyl and butyl.

18. The process according to claim 7, wherein the halogen is selected from the group consisting of chlorine, bromine, iodine and fluorine.

19. The process according to claim 7, wherein D and E are each independently hydrogen or hydroxyl.

20. The process according to claim 8, wherein the catalyst is a Lewis acid or a Brønsted acid.

21. The process according to claim 8 wherein the halogen is selected from the group consisting of chlorine, bromine, iodine and fluorine.

22. The process according to claim 8, wherein D and E are each independently hydrogen or hydroxyl.

23. The process according to claim 9, wherein the halogen is selected from the group consisting of chlorine, bromine, iodine and fluorine.

24. The process according to claim 9, wherein D and E are each independently hydrogen or hydroxyl.

25. The process according to claim 9, wherein the positively charged nitrogen atoms not bonded directly to the isoalloxazine ring are quaternary nitrogen atoms.

26. The process according to claim 9, wherein one selected from at least two, at least three, at least four and at least five, uncharged protonatable nitrogen atoms are not bonded directly to the isoalloxazine ring.

27. The process according to claim 9, wherein one selected from at least two, at least three, at least four and at least five positively charged nitrogen atoms are not bonded directly to the isoalloxazine ring.

28. The method according to claim 10, wherein the inactivation of microorganisms is a photodynamic inactivation.

29. The method according to claim 10, wherein the microorganisms are selected from the group consisting of viruses, archaea, bacteria, bacterial spores, fungi, fungal spores, protozoa, algae and blood-transmissible parasites.

30. The method according to claim 10, wherein said photosensitizer compound is applied upon said subject in at least one selected from the group consisting of the cleaning of teeth, dentures, and dental braces, prophylaxis, and treatment of a disorder of at least one of dental tissue and of the poridontium.

31. The method according to claim 10, wherein said photosensitizer is applied upon said subject in at least one selected from the group consisting of prophylaxis and treatment of an infectious skin disease.

32. A method for inactivating microorganisms located on or within an object, said method comprising applying to said object a compound of claim 1 during at least one of surface cleaning and coating of said object.

33. The method according to claim 32, wherein the object is selected from the group consisting of medical products, food and drink packaging and hygiene articles.

34. The method according to claim 32, wherein the microorganisms are selected from the group consisting of viruses, archaea, bacteria, bacterial spores, fungi, fungal spores, protozoa, algae and blood-transmissible parasites.

35. A method for inactivating microorganisms in a liquid, said method comprising introducing in said liquid a compound of claim 1.

36. The method according to claim 35, wherein said liquid is water, blood, an aqueous formulation, or an emulsion paint.

37. The method according to claim 35, wherein the microorganisms are selected from the group consisting of viruses, archaea, bacteria, bacterial spores, fungi, fungal spores, protozoa, algae and blood-transmissible parasites.

* * * * *